(12) United States Patent
Arnold et al.

(10) Patent No.: US 7,855,213 B2
(45) Date of Patent: Dec. 21, 2010

(54) COMPOUNDS

(75) Inventors: James Arnold, Wilmington, DE (US); Phil Edwards, Wilmington, DE (US); Mark Sylvester, Wilmington, DE (US); Stefan Berg, Södertälje (SE); Jörg Holenz, Södertälje (SE); Annika Kers, Södertälje (SE); Karin Kolmodin, Södertälje (SE); Laszlo Rakos, Södertälje (SE); Liselotte Öhberg, Södertälje (SE); Rotticci Didier, Södertälje (SE); Gianni Chessari, Cambridge (GB); Miles Congreve, Cambridge (GB); Christopher Murray, Cambridge (GB); Sahil Patel, Cambridge (GB)

(73) Assignees: AstraZeneca AB, Sodertalje (SE); Astex Therapeutics Ltd., Cambridge (GB)

( * ) Notice: Subject to any disclaimer, the term of this patent is extended or adjusted under 35 U.S.C. 154(b) by 155 days.

(21) Appl. No.: 11/762,487

(22) Filed: Jun. 13, 2007

(65) Prior Publication Data
US 2008/0171771 A1  Jul. 17, 2008

Related U.S. Application Data

(60) Provisional application No. 60/815,800, filed on Jun. 22, 2006, provisional application No. 60/818,557, filed on Jul. 5, 2006, provisional application No. 60/891,242, filed on Feb. 23, 2007.

(51) Int. Cl.
*A61K 31/506* (2006.01)
*C07D 403/02* (2006.01)

(52) U.S. Cl. .................. 514/256; 544/333

(58) Field of Classification Search .......... 514/339, 514/416; 548/471; 546/277.1
See application file for complete search history.

(56) References Cited

U.S. PATENT DOCUMENTS

| | | | |
|---|---|---|---|
| 4,605,642 A | 8/1986 | Rivier et al. | |
| 5,063,245 A | 11/1991 | Abreu et al. | |
| 5,877,399 A | 3/1999 | Hsiao et al. | |
| 5,942,400 A | 8/1999 | Anderson et al. | |
| 6,211,235 B1 | 4/2001 | Wu et al. | |
| 6,221,667 B1 | 4/2001 | Reiner et al. | |
| 6,245,884 B1 | 6/2001 | Hook | |
| 6,245,964 B1 | 6/2001 | McLonlogue et al. | |
| 7,629,356 B2 | 12/2009 | Chessari et al. | |
| 2005/0282825 A1 | 12/2005 | Malamas et al. | |
| 2005/0282826 A1 | 12/2005 | Malamas et al. | |
| 2006/0281729 A1 | 12/2006 | Iserloh et al. | |
| 2006/0287294 A1 | 12/2006 | Zhu et al. | |
| 2007/0004730 A1 | 1/2007 | Zhou et al. | |
| 2007/0004786 A1 | 1/2007 | Malamas et al. | |
| 2007/0049589 A1 | 3/2007 | Thompson, III et al. | |
| 2007/0099875 A1 | 5/2007 | Zhu et al. | |
| 2007/0099898 A1 | 5/2007 | Zhu et al. | |
| 2008/0287462 A1 | 11/2008 | Chessari et al. | |

FOREIGN PATENT DOCUMENTS

| | | |
|---|---|---|
| EP | 686673 A1 | 6/1995 |
| EP | 742217 A1 | 5/1996 |
| EP | 0855444 A2 | 7/1998 |
| WO | 9534563 A1 | 12/1995 |
| WO | 99/11643 A1 | 3/1999 |
| WO | 0017369 A2 | 3/2000 |
| WO | 0047618 A2 | 8/2000 |
| WO | 0058479 A1 | 10/2000 |
| WO | 0077030 A1 | 12/2000 |
| WO | 0100663 A2 | 1/2001 |
| WO | 0100665 A2 | 1/2001 |
| WO | 0123533 A2 | 4/2001 |
| WO | 0129563 A1 | 4/2001 |
| WO | 0202505 A2 | 1/2002 |
| WO | 0202506 A2 | 1/2002 |
| WO | 0202512 A2 | 1/2002 |
| WO | 0202518 A2 | 1/2002 |
| WO | 0202520 A2 | 1/2002 |
| WO | 0214264 A2 | 2/2002 |
| WO | 0225276 A1 | 3/2002 |
| WO | 2005058311 A1 | 6/2005 |
| WO | 2005097767 A1 | 10/2005 |
| WO | 2005123672 A2 | 12/2005 |
| WO | 2006009655 A1 | 1/2006 |
| WO | 2006/020879 | 2/2006 |
| WO | 2006034419 A2 | 3/2006 |
| WO | 2006041404 A1 | 4/2006 |
| WO | 2006041405 A1 | 4/2006 |
| WO | 2006065204 A1 | 6/2006 |

(Continued)

OTHER PUBLICATIONS

Vippagunta et al., Crystalline solids, 2001, Advanced Drug Delivery Reviews, 48, pp. 3 and 18.*

(Continued)

*Primary Examiner*—Kamal A Saeed
*Assistant Examiner*—Kristin Bianchi
(74) *Attorney, Agent, or Firm*—David Gryte

(57) ABSTRACT

This invention relates to novel compounds having the structural formula I below:

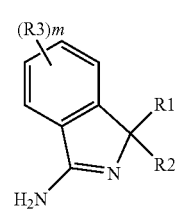

and to their pharmaceutically acceptable salt, compositions and methods of use. These novel compounds provide a treatment or prophylaxis of cognitive impairment, Alzheimer Disease, neurodegeneration and dementia.

16 Claims, No Drawings

FOREIGN PATENT DOCUMENTS

| | | |
|---|---|---|
| WO | 2006065277 A2 | 6/2006 |
| WO | 2006/076284 A2 | 7/2006 |
| WO | 2006/099379 A2 | 9/2006 |
| WO | 2006/138217 A1 | 12/2006 |
| WO | 2006/138264 A2 | 12/2006 |
| WO | 2006/138265 A2 | 12/2006 |
| WO | 2006/138266 A2 | 12/2006 |
| WO | 2006138230 A2 | 12/2006 |
| WO | 2007/011810 A1 | 1/2007 |
| WO | 2007011833 A2 | 1/2007 |
| WO | 2007/049532 A1 | 5/2007 |
| WO | 2007/058602 A2 | 5/2007 |
| WO | 2007058580 A1 | 5/2007 |
| WO | 2007058581 A1 | 5/2007 |
| WO | 2007058582 A1 | 5/2007 |
| WO | 2007058583 A2 | 5/2007 |
| WO | 2007058601 A1 | 5/2007 |
| WO | 2007058602 A2 | 5/2007 |
| WO | 20007073284 A1 | 6/2007 |
| WO | 2007114771 A1 | 10/2007 |
| WO | 2007120096 A1 | 10/2007 |
| WO | 2007/146225 A2 | 12/2007 |
| WO | 2007/149033 A1 | 12/2007 |
| WO | 2007145568 A1 | 12/2007 |
| WO | 2007145569 A1 | 12/2007 |
| WO | 2007145570 A1 | 12/2007 |
| WO | 2007145571 A1 | 12/2007 |
| WO | 2008063114 A1 | 5/2008 |
| WO | 2008076043 A1 | 6/2008 |
| WO | 2008076044 A1 | 6/2008 |
| WO | 2008076045 A1 | 6/2008 |
| WO | 2008076046 A1 | 6/2008 |
| WO | 2008150217 A1 | 12/2008 |
| WO | 2009005470 A1 | 1/2009 |
| WO | 2009005471 A1 | 1/2009 |
| WO | 2010056194 A1 | 5/2010 |
| WO | 2010056195 A1 | 5/2010 |
| WO | 2010056196 A1 | 5/2010 |

OTHER PUBLICATIONS

Von Angerer, S. "Product class 12: pyrimidines", Science of Synthesis, 2004, 16, 379-572.
Blanchard, Barbara; PNAS, Oct. 2004, 101 (40), 14326-14332.
Barrett, P et al, J. Chem. Soc., 1939, 1809-20.
Bartlett, R et al, J. Chem. Soc. Section C., 1969, 1, 129-33.
Sawanishi et al, Chemical & Pharmaceutical Bulletin, 1985, 33 (10), 4564-71.
Siling, S et al, Doklady Akademii Nauk SSSR, 1988, 299 (3), 633-5.
De Strooper, Bart et al., A Firm Base for Drug Development, Dec. 1999, Nature 402, 1999, 471-472.
Yankner B A., New Clues to Alzheimer's Disease: Unraveling the Roles of Anyloid and Tau, Nature Medicine, 1996, 2(8), 850-852.
Office action dated Mar. 19, 2009 received in co pending U.S. Appl. No. 12/120,736.
Dorwald F. Z. Side Reactions in Organic Synthesis, A Guide to Successful Synthesis Design, Weinheim: Wiley-VCH Verlag GmBH & Co, KgaA, 2005, Preface.
Hussain et al., 1999, Mol Cell Neurosci. Dec 14(6), 419-427.
Jordan V. C., Nature Reviews, Mar. 2, 2003: 205-213.
Lin et. al, 2000, PNAS, 97(4), 1456-1460.
Owens M.J., Pharm Rev vol. 43, pp. 425-473 (1991).
Oyama et al., 1994, J Neurochem, 62(3), 1062-1066.
Sinha et. al., 1999, Nature 402(6761), 537-540.
Vassar et. al., 1999, Science, 286(5440), 735-741.
Vippagunta et al. Crystalline Solids, 2001, Advanced Drug Delivery Reviews, 48, pp. 3 and 18.
Yan et. al, 1999, Nature 402(6761), 533-537.
Yankner, 1996, Nature Medicine, 2(8), 850-852.
U.S. Appl. No. 12/618,088 dated 2009.
U.S. Appl. No. 12/618,114 dated 2009.
U.S. Appl. No. 12/618,212 dated 2009.

* cited by examiner

COMPOUNDS

PRIORITY CLAIM TO RELATED PATENT APPLICATIONS

This patent claims priority to U.S. Provisional Patent Application Nos. 60/815,800 (filed 22 Jun. 2006); 60/818,557 (filed 5 Jul. 2006); and 60/891,242 (filed 23 Feb. 2007). The entire text of each of the above-referenced patent applications is incorporated by reference into this Patent.

FIELD OF THE INVENTION

The present invention relates to novel compounds, their pharmaceutical compositions. In addition, the present invention relates to therapeutic methods for the treatment and/or prevention of Aβ-related pathologies such as Downs syndrome and β-amyloid angiopathy, such as but not limited to cerebral amyloid angiopathy, hereditary cerebral hemorrhage, disorders associated with cognitive impairment, such as but not limited to MCI ("mild cognitive impairment"), Alzheimer Disease, memory loss, attention deficit symptoms associated with Alzheimer disease, neurodegeneration associated with diseases such as Alzheimer disease or dementia including dementia of mixed vascular and degenerative origin, pre-senile dementia, senile dementia and dementia associated with Parkinson's disease, progressive supranuclear palsy or cortical basal degeneration.

BACKGROUND OF THE INVENTION

Several groups have identified and isolated aspartate proteinases that have β-secretase activity (Hussain et al., 1999; Lin et. al, 2000; Yan et. al, 1999; Sinha et. al., 1999 and Vassar et. al., 1999). β-secretase is also known in the literature as Asp2 (Yan et. al, 1999), Beta site APP Cleaving Enzyme (BACE) (Vassar et. al., 1999) or memapsin-2 (Lin et al., 2000). BACE was identified using a number of experimental approaches such as EST database analysis (Hussain et al. 1999); expression cloning (Vassar et al. 1999); identification of human homologs from public databases of predicted *C. elegans* proteins (Yan et al. 1999) and finally utilizing an inhibitor to purify the protein from human brain (Sinha et al. 1999). Thus, five groups employing three different experimental approaches led to the identification of the same enzyme, making a strong case that BACE is a β-secretase.

BACE was found to be a pepsin-like aspartic proteinase, the mature enzyme consisting of the N-terminal catalytic domain, a transmembrane domain, and a small cytoplasmic domain. BACE has an optimum activity at pH 4.0-5.0 (Vassar et al, 1999)) and is inhibited weakly by standard pepsin inhibitors such as pepstatin. It has been shown that the catalytic domain minus the transmembrane and cytoplasmic domain has activity against substrate peptides (Lin et al, 2000). BACE is a membrane bound type 1 protein that is synthesized as a partially active proenzyme, and is abundantly expressed in brain tissue. It is thought to represent the major β-secretase activity, and is considered to be the rate-limiting step in the production of amyloid-β-protein (Aβ). It is thus of special interest in the pathology of Alzheimer's disease, and in the development of drugs as a treatment for Alzheimer's disease.

Aβ or amyloid-β-protein is the major constituent of the brain plaques which are characteristic of Alzheimer's disease (De Strooper et al, 1999). Aβ is a 39-42 residue peptide formed by the specific cleavage of a class I transmembrane protein called APP, or amyloid precursor protein. Aβ-secretase activity cleaves this protein between residues Met671 and Asp672 (numbering of 770aa isoform of APP) to form the N-terminus of Aβ. A second cleavage of the peptide is associated with γ-secretase to form the C-terminus of the Aβ peptide.

Alzheimer's disease (AD) is estimated to afflict more than 20 million people worldwide and is believed to be the most common form of dementia. Alzheimer's disease is a progressive dementia in which massive deposits of aggregated protein breakdown products—amyloid plaques and neurofibrillary tangles accumulate in the brain. The amyloid plaques are thought to be responsible for the mental decline seen in Alzheimer's patients.

The likelihood of developing Alzheimer's disease increases with age, and as the aging population of the developed world increases, this disease becomes a greater and greater problem. In addition to this, there is a familial link to Alzheimer's disease and consequently any individuals possessing the double mutation of APP known as the Swedish mutation (in which the mutated APP forms a considerably improved substrate for BACE) have a much greater chance of developing AD, and also of developing it at an early age (see also U.S. Pat. No. 6,245,964 and U.S. Pat. No. 5,877,399 pertaining to transgenic rodents comprising APP-Swedish). Consequently, there is also a strong need for developing a compound that can be used in a prophylactic fashion for these individuals.

The gene encoding APP is found on chromosome 21, which is also the chromosome found as an extra copy in Down's syndrome. Down's syndrome patients tend to acquire Alzheimer's disease at an early age, with almost all those over 40 years of age showing Alzheimer's-type pathology (Oyama et al., 1994). This is thought to be due to the extra copy of the APP gene found in these patients, which leads to overexpression of APP and therefore to increased levels of APPβ causing the high prevalence of Alzheimer's disease seen in this population. Thus, inhibitors of BACE could be useful in reducing Alzheimer's-type pathology in Down's syndrome patients.

Drugs that reduce or block BACE activity should therefore reduce Aβ levels and levels of fragments of Aβ in the brain, or elsewhere where Aβ or fragments thereof deposit, and thus slow the formation of amyloid plaques and the progression of AD or other maladies involving deposition of Aβ or fragments thereof (Yankner, 1996; De Strooper and Konig, 1999). BACE is therefore an important candidate for the development of drugs as a treatment and/or prophylaxis of Aβ-related pathologies such as Downs syndrome and β-amyloid angiopathy, such as but not limited to cerebral amyloid angiopathy, hereditary cerebral hemorrhage, disorders associated with cognitive impairment, such as but not limited to MCI ("mild cognitive impairment"), Alzheimer Disease, memory loss, attention deficit symptoms associated with Alzheimer disease, neurodegeneration associated with diseases such as Alzheimer disease or dementia including dementia of mixed vascular and degenerative origin, pre-senile dementia, senile dementia and dementia associated with Parkinson's disease, progressive supranuclear palsy or cortical basal degeneration.

It would therefore be useful to inhibit the deposition of Aβ and portions thereof by inhibiting BACE through inhibitors such as the compounds provided herein.

The therapeutic potential of inhibiting the deposition of Aβ has motivated many groups to isolate and characterize secretase enzymes and to identify their potential inhibitors (see, e.g., WO01/23533 A2, EP0855444, WO00/17369, WO00/58479, WO00/47618, WO00/77030, WO01/00665, WO01/00663, WO01/29563, WO02/25276, U.S. Pat. No. 5,942,400, U.S. Pat. No. 6,245,884, U.S. Pat. No. 6,221,667, U.S. Pat. No. 6,211,235, WO02/02505, WO02/02506, WO02/02512, WO02/02518, WO02/02520, WO02/14264, WO05/058311, WO05/097767, WO06/041404, WO06/041405, WO06/0065204, WO06/0065277, US2006287294, WO06/138265, US20050282826, US20050282825, US20060281729, WO06/138217, WO06/138230, WO06/138264, WO06/138265, WO06/138266, WO06/099379, WO06/076284, US20070004786, US20070004730, WO07/011833, WO07/011810, US20070099875, US20070099898, WO07/049, 532).

The compounds of the present invention show beneficial properties compared to the potential inhibitors known in the art, e.g. improved hERG selectivity.

DISCLOSURE OF THE INVENTION

Provided herein are novel compounds of structural formula I:

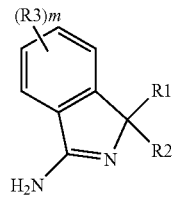

wherein
$R^1$ is selected from hydrogen, nitro, cyano, -Q-$C_{1-6}$alkyl, -Q-$C_{2-6}$alkenyl, -Q-$C_{2-6}$alkynyl, -Q-$C_{3-6}$cycloalkyl, -Q-$C_{5-7}$cycloalkenyl, -Q-$C_{1-6}$alkyl$C_{3-6}$cycloalkyl, -Q-aryl, -Q-heteroaryl, -Q-$C_{1-6}$alkylaryl, -Q-$C_{1-6}$alkylheteroaryl, -Q-heterocyclyl and -Q-$C_{1-6}$alkylheterocyclyl, wherein said -Q-$C_{1-6}$alkyl, -Q-$C_{2-6}$alkenyl, -Q-$C_{2-6}$alkynyl, -Q-$C_{3-6}$cycloalkyl, -Q-$C_{5-7}$cycloalkenyl, -Q-$C_{1-6}$alkyl$C_{3-6}$cycloalkyl, -Q-aryl, -Q-heteroaryl, -Q-$C_{1-6}$alkylaryl, -Q-$C_{1-6}$alkylheteroaryl, -Q-heterocyclyl, or -Q-$C_{1-6}$alkylheterocyclyl is optionally substituted by one, two or three $R^7$;
$R^2$ is $(C(R^4)(R^5))_nR^6$, $C_{2-4}$alkenyl$R^6$, $C_{2-4}$alkynyl$R^6$, $C_{5-7}$cycloalkenyl$R^6$, nitro or cyano and if n>1 then each $C(R^4)(R^5)$ is independent of the others;
$R^3$ is independently selected from hydrogen, halogen, $C_{1-6}$alkyl, $C_{3-6}$alkenyl, $C_{3-6}$alkynyl, $C_{3-6}$cycloalkyl, $C_{5-7}$cycloalkenyl, aryl, heteroaryl, heterocyclyl, $C_{1-6}$alkyl$C_{3-6}$cycloalkyl, $C_{1-6}$alkylaryl, $C_{1-6}$alkylheteroaryl and $C_{1-6}$alkylheterocyclyl, wherein said $C_{1-6}$alkyl, $C_{3-6}$alkenyl, $C_{3-6}$alkynyl, $C_{3-6}$cycloalkyl, $C_{5-7}$cycloalkenyl, aryl, heteroaryl, heterocyclyl, $C_{1-6}$alkyl$C_{3-6}$cycloalkyl, $C_{1-6}$alkylaryl, $C_{1-6}$alkylheteroaryl or $C_{1-6}$alkylheterocyclyl is optionally substituted with one, two or three A;
-Q- is a direct bond, —CONH—, —CO—, —CON($C_{1-6}$alkyl)-, —CON($C_{3-6}$cycloalkyl)-, —SO—, —$SO_2$—, —$SO_2$NH—, —$SO_2$N($C_{1-6}$alkyl)-, —$SO_2$N($C_{3-6}$cycloalkyl)-, —$NHSO_2$—, —N($C_{1-6}$alkyl)$SO_2$—, —NHCO—, —N($C_{1-6}$alkyl)CO—, —N($C_{3-6}$cycloalkyl)CO— or —N($C_{3-6}$cycloalkyl)$SO_2$—;
$R^4$ and $R^5$ are independently selected from hydrogen, $C_{1-6}$alkyl, cyano, halo or nitro; or $R^4$ and $R^5$ together form oxo, $C_{3-6}$cycloalkyl or heterocyclyl;
$R^6$ is selected from methyl, $C_{3-6}$cycloalkyl, heterocyclyl, aryl and heteroaryl, wherein said methyl, $C_{3-6}$cycloalkyl, heterocyclyl, aryl or heteroaryl is optionally substituted with between one and four $R^7$, and wherein any of the individual aryl or groups may be optionally fused with a 4, 5, 6 or 7 membered cycloalkyl, cycloalkenyl or heterocyclyl group to form a bicyclic ring system where the bicyclic ring system is optionally substituted with between one and four A;
$R^7$ is independently selected from halogen, nitro, CHO, $C_{0-6}$alkylCN, $OC_{1-6}$alkylCN, $C_{0-6}$alkylOR$^8$, $OC_{2-6}$alkylOR$^8$, hydroxy, fluoromethyl, difluoromethyl, trifluoromethyl, fluoromethoxy, difluoromethoxy, trifluoromethoxy, $C_{0-6}$alkylNR$^8$R$^9$, $OC_{2-6}$alkylNR$^8$R$^9$, $OC_{2-6}$alkylOC$_{2-6}$alkylNR$^8$R$^9$, NR$^8$OR$^9$, $C_{0-6}$alkylCO$_2$R$^8$, $OC_{1-6}$alkylCO$_2$R$^8$, $C_{0-6}$alkylCONR$^8$R$^9$, $OC_{1-6}$alkylCONR$^8$R$^9$, $OC_{2-6}$alkylNR$^8$(CO)R$^9$, $C_{0-6}$alkylNR$^8$(CO)R$^9$, O(CO)NR$^8$R$^9$, NR$^8$(CO)OR$^9$, NR$^8$(CO)NR$^8$R$^9$, O(CO)OR$^8$, O(CO)R$^8$, $C_{0-6}$alkylCOR$^8$, $OC_{1-6}$alkylCOR$^8$, NR$^8$(CO)(CO)R$^8$, NR$^8$(CO)(CO)NR$^8$R$^9$, $C_{0-6}$alkylSR$^8$, $C_{0-6}$alkyl(SO$_2$)NR$^8$R$^9$, $OC_{1-6}$alkylNR$^8$(SO$_2$)R$^9$, $OC_{0-6}$alkyl(SO$_2$)NR$^8$R$^9$, $C_{0-6}$alkyl(SO)NR$^8$R$^9$, $OC_{1-6}$alkyl(SO)NR$^8$R$^9$, OSO$_2$R$^8$, SO$_3$R$^8$, $C_{0-6}$alkylNR$^8$(SO$_2$)NR$^8$R$^9$, $C_{0-6}$alkylNR$^8$(SO)R$^9$, $OC_{2-6}$alkylNR$^8$(SO)R$^8$, $OC_{1-6}$alkylSO$_2$R$^8$, $C_{1-6}$alkylSO$_2$R$^8$, $C_{0-6}$alkylSOR$^8$, $C_{1-6}$alkyl, $C_{2-6}$alkenyl, $C_{2-6}$alkynyl, $C_{0-6}$alkylC$_{3-6}$cycloalkyl, $C_{0-6}$alkylaryl, $C_{0-6}$alkylheteroaryl, $C_{0-6}$alkylheterocyclyl and $OC_{2-6}$alkylheterocyclyl, wherein said $C_{1-6}$alkyl, $C_{2-6}$alkenyl, $C_{2-6}$alkynyl, $C_{0-6}$alkylC$_{3-6}$cycloalkyl, $C_{0-6}$alkylaryl, $C_{0-6}$alkylheteroaryl, $C_{0-6}$alkylheterocyclyl or $OC_{2-6}$alkylheterocyclyl is optionally substituted by one or more $R^{14}$, and wherein any of the individual aryl or heteroaryl groups may be optionally fused with a 4, 5, 6 or 7 membered cycloalkyl, cycloalkenyl or heterocyclyl group to form a bicyclic ring system where the bicyclic ring system is optionally substituted with between one and four A with the proviso that said bicyclic ring system is not an indane, benzo[1,3]dioxole or 2,3-dihydrobenzo[1,4]-dioxine ring system;
$R^{14}$ is selected from halogen, nitro, CHO, $C_{0-6}$alkylCN, $OC_{1-6}$alkylCN, $C_{0-6}$alkylOR$^8$, $OC_{1-6}$alkylOR$^8$, fluoromethyl, difluoromethyl, trifluoromethyl, fluoromethoxy, difluoromethoxy, trifluoromethoxy, $C_{0-6}$alkylNR$^8$R$^9$, $OC_{2-6}$alkylNR$^8$R$^9$, $OC_{2-6}$alkylOC$_{2-6}$alkylNR$^8$R$^9$, NR$^8$OR$^9$, $C_{0-6}$alkylCO$_2$R$^8$, $OC_{1-6}$alkylCO$_2$R$^8$, $C_{0-6}$alkylCONR$^8$R$^9$, $OC_{1-6}$alkylCONR$^8$R$^9$, $OC_{2-6}$alkylNR$^8$(CO)R$^9$, $C_{0-6}$alkylNR$^8$(CO)R$^9$, O(CO)NR$^8$R$^9$, NR$^8$(CO)OR$^9$, NR$^8$(CO)NR$^8$R$^9$, O(CO)OR$^8$, O(CO)R$^8$, $C_{0-6}$alkylCOR$^8$, $OC_{1-6}$alkylCOR$^8$, NR$^8$(CO)(CO)R$^8$, NR$^8$(CO)(CO)NR$^8$R$^9$, $C_{0-6}$alkylSR$^8$, $C_{0-6}$alkyl(SO$_2$)NR$^8$R$^9$, $OC_{2-6}$alkylNR$^8$(SO$_2$)R$^9$, $OC_{0-6}$alkyl(SO$_2$)NR$^8$R$^9$, $C_{0-6}$alkyl(SO)NR$^8$R$^9$, $OC_{1-6}$alkyl(SO)NR$^8$R$^9$, OSO$_2$R$^8$, SO$_3$R$^8$, $C_{0-6}$alkylNR$^8$(SO$_2$)NR$^8$R$^9$, $C_{0-6}$alkylNR$^8$(SO)R$^9$, $OC_{2-6}$alkylNR$^8$(SO)R$^8$, $OC_{1-6}$alkylSO$_2$R$^8$, $C_{1-6}$alkylSO$_2$R$^8$, $C_{0-6}$alkylSOR$^8$, $C_{1-6}$alkyl, $C_{2-6}$alkenyl, $C_{2-6}$alkynyl, $C_{0-6}$alkylC$_{3-6}$cycloalkyl, $C_{0-6}$alkylaryl, $C_{0-6}$alkylheteroaryl, $C_{0-6}$alkylheterocyclyl and $OC_{2-6}$alkylheterocyclyl, wherein said is $C_{1-6}$alkyl, $C_{2-6}$alkenyl, $C_{2-6}$alkynyl, $C_{0-6}$alkylC$_{3-6}$cycloalkyl, $C_{0-6}$alkylaryl, $C_{0-6}$alkylheteroaryl, $C_{0-6}$alkylheterocyclyl or $OC_{2-6}$alkylheterocyclyl is optionally substituted by between one and four A;
$R^8$ and $R^9$ are independently selected from hydrogen and $C_{1-6}$alkyl, $C_{2-6}$alkenyl, $C_{2-6}$alkynyl, fluoromethyl, difluoromethyl, trifluoromethyl, fluoromethoxy, difluoromethoxy, trifluoromethoxy, $C_{0-6}$alkylC$_{3-6}$cycloalkyl, $C_{0-6}$alkylaryl, $C_{0-6}$alkylheteroaryl, $C_{0-6}$alkylheterocyclyl and $C_{1-6}$alkylNR$^{10}$R$^{11}$, wherein said $C_{1-6}$alkyl, $C_{2-6}$alkenyl, $C_{2-6}$alkynyl, $C_{0-6}$alkylC$_{3-6}$cycloalkyl, $C_{0-6}$alkylaryl, C$_{0-6}$alkylheteroaryl or C$_{0-6}$alkylheterocyclyl is optionally substituted by between one and four A; or R$^8$ and R$^9$ may together form a 4 to 6 membered heterocyclic ring containing one or more heteroatoms selected from N, O or S that is optionally substituted by A; whenever two R$^8$ groups occur in the structure then they may optionally together form a 5 or 6 membered heterocyclic ring containing one or more heteroatoms selected from N, O or S, that is optionally substituted by A;

R$^{10}$ and R$^{11}$ are independently selected from hydrogen, C$_{1-6}$alkyl, C$_{3-6}$alkenyl, C$_{3-6}$alkynyl, C$_{0-6}$alkylC$_{3-6}$cycloalkyl, C$_{0-6}$alkylaryl, C$_{0-6}$alkylheterocyclyl and C$_{0-6}$alkylheteroaryl, wherein said C$_{1-6}$alkyl, C$_{3-6}$alkenyl, C$_{3-6}$alkynyl, C$_{0-6}$alkylC$_{3-6}$cycloalkyl, C$_{0-6}$alkylaryl, C$_{0-6}$alkylheteroaryl or C$_{0-6}$alkylheterocyclyl is optionally substituted by A; or R$^{10}$ and R$^{11}$ may together form a 4 to 6 membered heterocyclic ring containing one or more heteroatoms selected from N, O or S optionally substituted by A;

m is 0, 1, 2 or 3;

n is 0, 1, 2 or 3;

A is selected from oxo, halogen, nitro, CN, OR$^{12}$, C$_{1-6}$alkyl, C$_{2-6}$alkenyl, C$_{2-6}$alkynyl, C$_{0-6}$alkylaryl, C$_{0-6}$alkylheteroaryl, C$_{0-6}$alkylC$_{3-6}$cycloalkyl, C$_{0-6}$alkylheterocyclyl, fluoromethyl, difluoromethyl, trifluoromethyl, fluoromethoxy, difluoromethoxy, trifluoromethoxy, OC$_{2-6}$alkylNR$^{12}$R$^{13}$, NR$^{12}$R$^{13}$, CONR$^{12}$R$^{13}$, NR$^{12}$(CO)R$^{13}$, O(CO)C$_{1-6}$alkyl, (CO)OC$_{1-6}$alkyl, COR$^{12}$, (SO$_2$)NR$^{12}$R$^{13}$, NSO$_2$R$^{12}$, SO$_2$R$^{12}$, SOR$^{12}$, (CO)C$_{1-6}$alkylNR$^{12}$R$^{13}$, (SO$_2$)C$_{1-6}$alkylNR$^{12}$R$^{13}$, OSO$_2$R$^{12}$ and SO$_3$R$^{12}$ wherein said C$_{1-6}$alkyl, C$_{2-6}$alkenyl, C$_{2-6}$alkynyl, C$_{0-6}$alkylaryl, C$_{0-6}$alkylheteroaryl, C$_{0-6}$alkylheterocyclyl or C$_{0-6}$alkylC$_{3-6}$cycloalkyl, is optionally substituted with halo, OSO$_2$R$^{12}$, SO$_3$R$^{12}$, nitro, cyano, OR$^{12}$, C$_{1-6}$alkyl, fluoromethyl, difluoromethyl, trifluoromethyl, fluoromethoxy, difluoromethoxy or trifluoromethoxy;

R$^{12}$ and R$^{13}$ are independently selected from hydrogen, C$_{1-6}$alkyl, C$_{3-6}$cycloalkyl, aryl, heteroaryl and heterocyclyl, wherein said C$_{1-6}$alkyl, C$_{3-6}$cycloalkyl, aryl, heteroaryl or heterocyclyl is optionally substituted by one, two or three hydroxy, cyano, halo or C$_{1-3}$alkyloxy; or R$^{12}$ and R$^{13}$ may together form a 4 to 6 membered heterocyclic ring containing one or more heteroatoms selected from N, O or S optionally substituted by hydroxy, C$_{1-3}$alkyloxy, cyano or halo;

as a free base or a pharmaceutically acceptable salt, solvate or solvate of a salt thereof.

In another aspect of the invention, there is provided a compound of formula I:

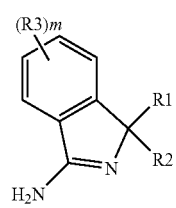

I wherein

R$^1$ is selected from hydrogen, nitro, cyano, -Q-C$_{1-6}$alkyl, -Q-C$_{2-6}$alkenyl, -Q-C$_{2-6}$alkynyl, -Q-C$_{3-6}$cycloalkyl, -Q-C$_{5-7}$cycloalkenyl, -Q-C$_{1-6}$alkylC$_{3-6}$cycloalkyl, -Q-aryl, -Q-heteroaryl, -Q-C$_{1-6}$alkylaryl, -Q-C$_{1-6}$alkylheteroaryl, -Q-heterocyclyl, and -Q-C$_{1-6}$alkylheterocyclyl, wherein said -Q-C$_{1-6}$alkyl, -Q-C$_{2-6}$alkenyl, -Q-C$_{2-6}$alkynyl, -Q-C$_{3-6}$cycloalkyl, -Q-C$_{5-7}$cycloalkenyl, -Q-C$_{1-6}$alkylC$_{3-6}$cycloalkyl, -Q-aryl, -Q-heteroaryl, -Q-C$_{1-6}$alkylaryl, -Q-C$_{1-6}$alkylheteroaryl, -Q-heterocyclyl, or -Q-C$_{1-6}$alkylheterocyclyl is optionally substituted by one, two or three R$^7$;

R$^2$ is (C(R$^4$)(R$^5$))$_n$R$^6$, C$_{2-4}$alkenylR$^6$, C$_{2-4}$alkynylR$^6$, C$_{5-7}$cycloalkenylR$^6$, nitro or cyano and if n>1 then each C(R$^4$)(R$^5$) is independent of the others;

R$^3$ is independently selected from hydrogen, halogen, C$_{1-6}$alkyl, C$_{3-6}$alkenyl, C$_{3-6}$alkynyl, C$_{3-6}$cycloalkyl, C$_{5-7}$cycloalkenyl, aryl, heteroaryl, heterocyclyl, C$_{1-6}$alkylC$_{3-6}$cycloalkyl, C$_{1-6}$alkylaryl, C$_{1-6}$alkylheteroaryl and C$_{1-6}$alkylheterocyclyl, wherein said C$_{1-6}$alkyl, C$_{3-6}$alkenyl, C$_{3-6}$alkynyl, C$_{3-6}$cycloalkyl, C$_{5-7}$cycloalkenyl, aryl, heteroaryl, heterocyclyl, C$_{1-6}$alkylC$_{3-6}$cycloalkyl, C$_{1-6}$alkylaryl, C$_{1-6}$alkylheteroaryl or C$_{1-6}$alkylheterocyclyl is optionally substituted with one, two or three A;

-Q- is a direct bond, —CONH—, —CO—, —CON(C$_{1-6}$alkyl)-, —CON(C$_{3-6}$cycloalkyl)-, —SO—, —SO$_2$—, —SO$_2$NH—, —SO$_2$N(C$_{1-6}$alkyl)-, —SO$_2$N(C$_{3-6}$cycloalkyl)-, —NHSO$_2$—, —N(C$_{1-6}$alkyl)SO$_2$—, —NHCO—, —N(C$_{1-6}$alkyl)CO—, —N(C$_{3-6}$cycloalkyl)CO— or —N(C$_{3-6}$cycloalkyl)SO$_2$—;

R$^4$ and R$^5$ are independently selected from hydrogen, C$_{1-6}$alkyl, cyano, halo or nitro; or R$^4$ and R$^5$ together form oxo, C$_{3-6}$cycloalkyl or heterocyclyl;

R$^6$ is selected from methyl, C$_{3-6}$cycloalkyl, heterocyclyl, aryl and heteroaryl wherein each of said methyl, C$_{3-6}$cycloalkyl, heterocyclyl, aryl or heteroaryl is optionally substituted with between one and four R$^7$, and wherein any of the individual aryl or heteroaryl groups may be optionally fused with a 4, 5, 6 or 7 membered cycloalkyl, cycloalkenyl or 3-methyl-3-phenylisoindolin-1-imine;

3'-(3-methyl-2,3-dihydro-1H-isoindol-1-yl)biphenyl-3-carbonitrile;

3-(3'methoxybiphenyl-3-yl)-3-methylisoindolin-1-imine;

3-(3'chlorobiphenyl-3-yl)-3-methylisoindolin-1-imine; and 3-methyl-3-(3-pyridin-3-ylphenyl)isoindolin-1-imine;

as a free base or a pharmaceutically acceptable salt, solvate or solvate of a salt thereof.

In another aspect of the invention, there is provided a compound of formula I, wherein R$^8$ and R$^9$ are independently selected from hydrogen, C$_{1-6}$alkyl, C$_{2-6}$alkenyl, C$_{2-6}$alkynyl, fluoromethyl, difluoromethyl, trifluoromethyl, fluoromethoxy, difluoromethoxy, trifluoromethoxy, C$_{0-6}$alkylC$_{3-6}$cycloalkyl, C$_{0-6}$alkylaryl, C$_{0-6}$alkylheteroaryl, C$_{0-6}$alkylheterocyclyl and C$_{1-6}$alkylNR$^{10}$R$^{11}$, wherein said C$_{1-6}$alkyl, C$_{2-6}$alkenyl, C$_{2-6}$alkynyl, C$_{0-6}$alkylC$_{3-6}$cycloalkyl, C$_{0-6}$alkylaryl, C$_{0-6}$alkylheteroaryl or C$_{0-6}$alkylheterocyclyl is optionally substituted by A; or R$^8$ and R$^9$ may together form a 4 to 6 membered heterocyclic ring containing one or more heteroatoms selected from N, O or S that is optionally substituted by A; whenever two R$^8$ groups occur in the structure then they may optionally together form a 5 or 6 membered heterocyclic ring containing one or more heteroatoms selected from N, O or S, that is optionally substituted by A.

In another aspect of the invention, there is provided a compound of formula I, wherein $R^1$ is selected from -Q-aryl and -Q-heteroaryl, wherein said -Q-aryl or -Q-heteroaryl is optionally substituted by one, two or three $R^7$;

$R^2$ is $(C(R^4)(R^5))_n R^6$, and if n>1 then each $C(R^4)(R^5)$ is independent of the others;

$R^3$ is independently selected from hydrogen, halogen, $C_{1-6}$alkyl, $C_{3-6}$alkenyl, $C_{3-6}$alkynyl, $C_{3-6}$cycloalkyl, $C_{5-7}$cycloalkenyl, aryl, heteroaryl, heterocyclyl, $C_{1-6}$alkyl$C_{3-6}$cycloalkyl, $C_{1-6}$alkylaryl, $C_{1-6}$alkylheteroaryl or $C_{1-6}$alkylheterocyclyl, wherein the $C_{1-6}$alkyl, $C_{3-6}$alkenyl, $C_{3-6}$alkynyl, $C_{3-6}$cycloalkyl, $C_{5-7}$cycloalkenyl, aryl, heteroaryl, heterocyclyl, $C_{1-6}$alkyl$C_{3-6}$cycloalkyl, $C_{1-6}$alkylaryl, $C_{1-6}$alkylheteroaryl or $C_{1-6}$alkylheterocyclyl is optionally substituted with one, two or three A;

-Q- is a direct bond;

heterocyclyl group to form a bicyclic ring system where the bicyclic ring system is optionally substituted with between one and four A;

$R^7$ is independently selected from halogen, nitro, CHO, $C_{0-6}$alkylCN, $OC_{1-6}$alkylCN, $C_{0-6}$alkylOR$^8$, $OC_{2-6}$alkylOR$^8$, hydroxy, fluoromethyl, difluoromethyl, trifluoromethyl, fluoromethoxy, difluoromethoxy, trifluoromethoxy, $C_{0-6}$alkylNR$^8$R$^9$, $OC_{2-6}$alkylNR$^8$R$^9$, $OC_{2-6}$alkylOC$_{2-6}$alkylNR$^8$R$^9$, NR$^8$OR$^9$, $C_{0-6}$alkylCO$_2$R$^8$, $OC_{1-6}$alkylCO$_2$R$^8$, $C_{0-6}$alkylCONR$^8$R$^9$, $OC_{1-6}$alkylCONR$^8$R$^9$, $OC_{2-6}$alkylNR$^8$(CO)R$^9$, $C_{0-6}$alkylNR$^8$(CO)R$^9$, O(CO)NR$^8$R$^9$, NR$^8$(CO)OR$^9$, NR$^8$(CO)NR$^8$R$^9$, O(CO)OR$^8$, O(CO)R$^8$, $C_{0-6}$alkylCOR$^8$, $OC_{1-6}$alkylCOR$^8$, NR$^8$(CO)(CO)R$^8$, NR$^8$(CO)(CO)NR$^8$R$^9$, $C_{0-6}$alkylSR$^8$, $C_{0-6}$alkyl(SO$_2$)NR$^8$R$^9$, $OC_{1-6}$alkylNR$^8$(SO$_2$)R$^9$, $OC_{0-6}$alkyl(SO$_2$)NR$^8$R$^9$, $C_{0-6}$alkyl(SO)NR$^8$R$^9$, $OC_{1-6}$alkyl(SO)NR$^8$R$^9$, OSO$_2$R$^8$, SO$_3$R$^8$, $C_{0-6}$alkylNR$^8$(SO$_2$)NR$^8$R$^9$, $C_{0-6}$alkylNR$^8$(SO)R$^9$, $OC_{2-6}$alkylNR$^8$(SO)R$^8$, $OC_{1-6}$alkylSO$_2$R$^8$, $C_{1-6}$alkylSO$_2$R$^8$, $C_{0-6}$alkylSOR$^8$, $C_{1-6}$alkyl, $C_{2-6}$alkenyl, $C_{2-6}$alkynyl, $C_{0-6}$alkylC$_{3-6}$cycloalkyl, $C_{0-6}$alkylaryl, $C_{0-6}$alkylheteroaryl, $C_{0-6}$alkylheterocyclyl, and $OC_{2-6}$alkylheterocyclyl, wherein any $C_{1-6}$alkyl, $C_{2-6}$alkenyl, $C_{2-6}$alkynyl, $C_{0-6}$alkylC$_{3-6}$cycloalkyl, $C_{0-6}$alkylaryl, $C_{0-6}$alkylheteroaryl, $C_{0-6}$alkylheterocyclyl or $OC_{2-6}$alkylheterocyclyl is optionally substituted by one or more $R^{14}$, and wherein any of the individual aryl or heteroaryl groups may be optionally fused with a 4, 5, 6 or 7 membered cycloalkyl, cycloalkenyl or heterocyclyl group to form a bicyclic ring system where the bicyclic ring system is optionally substituted with between one and four A; with the proviso that said bicyclic ring system is not an indane, benzo[1,3]dioxole or 2,3-dihydrobenzo[1,4]-dioxine ring system;

$R^{14}$ is selected from halogen, nitro, CHO, $C_{0-6}$alkylCN, $OC_{1-6}$alkylCN, $C_{0-6}$alkylOR$^8$, $OC_{1-6}$alkylOR$^8$, fluoromethyl, difluoromethyl, trifluoromethyl, fluoromethoxy, difluoromethoxy, trifluoromethoxy, $C_{0-6}$alkylNR$^8$R$^9$, $OC_{2-6}$alkylNR$^8$R$^9$, $OC_{2-6}$alkylOC$_{2-6}$alkylNR$^8$R$^9$, NR$^8$OR$^9$, $C_{0-6}$alkylCO$_2$R$^8$, $OC_{1-6}$alkylCO$_2$R$^8$, $C_{0-6}$alkylCONR$^8$R$^9$, $OC_{1-6}$alkylCONR$^8$R$^9$, $OC_{2-6}$alkylNR$^8$(CO)R$^9$, $C_{0-6}$alkylNR$^8$(CO)R$^9$, O(CO)NR$^8$R$^9$, NR$^8$(CO)OR$^9$, NR$^8$(CO)NR$^8$R$^9$, O(CO)OR$^8$, O(CO)R$^8$, $C_{0-6}$alkylCOR$^8$, $OC_{1-6}$alkylCOR$^8$, NR$^8$(CO)(CO)R$^8$, NR$^8$(CO)(CO)NR$^8$R$^9$, $C_{0-6}$alkylSR$^8$, $C_{0-6}$alkyl(SO$_2$)NR$^8$R$^9$, $OC_{2-6}$alkylNR$^8$(SO$_2$)R$^9$, $OC_{0-6}$alkyl(SO$_2$)NR$^8$R$^9$, $C_{0-6}$alkyl(SO)NR$^8$R$^9$, $OC_{1-6}$alkyl(SO)NR$^8$R$^9$, OSO$_2$R$^8$, SO$_3$R$^8$, $C_{0-6}$alkylNR$^8$(SO$_2$)NR$^8$R$^9$, $C_{0-6}$alkylNR$^8$(SO)R$^9$, $OC_{2-6}$alkylNR$^8$(SO)R$^8$, $OC_{1-6}$alkylSO$_2$R$^8$, $C_{1-6}$alkylSO$_2$R$^8$, $C_{0-6}$alkylSOR$^8$, $C_{1-6}$alkyl, $C_{2-6}$alkenyl, $C_{2-6}$alkynyl, $C_{0-6}$alkylC$_{3-6}$cycloalkyl, $C_{0-6}$alkylaryl, $C_{0-6}$alkylheteroaryl, $C_{0-6}$alkylheterocyclyl and $OC_{2-6}$alkylheterocyclyl wherein any $C_{1-6}$alkyl, $C_{2-6}$alkenyl, $C_{2-6}$alkynyl, $C_{0-6}$alkylC$_{3-6}$cycloalkyl, $C_{0-6}$alkylaryl, $C_{0-6}$alkylheteroaryl, $C_{0-6}$alkylheterocyclyl or $OC_{2-6}$alkylheterocyclyl is optionally substituted by between one and four A;

$R^8$ and $R^9$ are independently selected from hydrogen, $C_{1-6}$alkyl, $C_{2-6}$alkenyl, $C_{2-6}$alkynyl, fluoromethyl, difluoromethyl, trifluoromethyl, fluoromethoxy, difluoromethoxy, trifluoromethoxy, $C_{0-6}$alkylC$_{3-6}$cycloalkyl, $C_{0-6}$alkylaryl, $C_{0-6}$alkylheteroaryl, $C_{0-6}$alkylheterocyclyl and $C_{1-6}$alkylNR$^{10}$R$^{11}$, wherein said $C_{1-6}$alkyl, $C_{2-6}$alkenyl, $C_{2-6}$alkynyl, $C_{0-6}$alkylC$_{3-6}$cycloalkyl, $C_{0-6}$alkylaryl, $C_{0-6}$alkylheteroaryl or $C_{0-6}$alkylheterocyclyl is optionally substituted by between one and four A; or $R^8$ and $R^9$ may together form a 4 to 6 membered heterocyclic ring containing one or more heteroatoms selected from N, O or S that is optionally substituted by A; whenever two $R^8$ groups occur in the structure then they may optionally together form a 5 or 6 membered heterocyclic ring containing one or more heteroatoms selected from N, O or S, that is optionally substituted by A;

$R^{10}$ and $R^{11}$ are independently selected from hydrogen, $C_{1-6}$alkyl, $C_{3-6}$alkenyl, $C_{3-6}$alkynyl, $C_{0-6}$alkylC$_{3-6}$cycloalkyl, $C_{0-6}$alkylaryl, $C_{0-6}$alkylheterocyclyl and $C_{0-6}$alkylheteroaryl, wherein said $C_{1-6}$alkyl, $C_{3-6}$alkenyl, $C_{3-6}$alkynyl, $C_{0-6}$alkylC$_{3-6}$cycloalkyl, $C_{0-6}$alkylaryl, $C_{0-6}$alkylheteroaryl or $C_{0-6}$alkylheterocyclyl is optionally substituted by A; or $R^{10}$ and $R^{11}$ may together form a 4 to 6 membered heterocyclic ring containing one or more heteroatoms selected from N, O or S optionally substituted by A;

m is 0, 1, 2 or 3;

n is 0, 1, 2 or 3;

A is independently selected from oxo, halogen, nitro, CN, OR$^{12}$, $C_{1-6}$alkyl, $C_{2-6}$alkenyl, $C_{2-6}$alkynyl, $C_{0-6}$alkylaryl, $C_{0-6}$alkylheteroaryl, $C_{0-6}$alkylC$_{3-6}$cycloalkyl, $C_{0-6}$alkylheterocyclyl, fluoromethyl, difluoromethyl, trifluoromethyl, fluoromethoxy, difluoromethoxy, trifluoromethoxy, $OC_{2-6}$alkylNR$^{12}$R$^{13}$, NR$^{12}$R$^{13}$, CONR$^{12}$R$^{13}$, NR$^{12}$(CO)R$^{13}$, O(CO)C$_{1-6}$alkyl, (CO)OC$_{1-6}$alkyl, COR$^{12}$, (SO$_2$)NR$^{12}$R$^{13}$, NSO$_2$R$^{12}$, SO$_2$R$^{12}$, SOR$^{12}$, (CO)C$_{1-6}$alkylNR$^{12}$R$^{13}$, (SO$_2$)C$_{1-6}$alkylNR$^{12}$R$^{13}$, OSO$_2$R$^{12}$ and SO$_3$R$^{12}$, wherein said $C_{1-6}$alkyl, $C_{2-6}$alkenyl, $C_{2-6}$alkynyl, $C_{0-6}$alkylaryl, $C_{0-6}$alkylheteroaryl, $C_{0-6}$alkylheterocyclyl or $C_{0-6}$alkylC$_{3-6}$cycloalkyl is optionally substituted with halo, OSO$_2$R$^{12}$, SO$_3$R$^{12}$, nitro, cyano, OR$^{12}$, $C_{1-6}$alkyl, fluoromethyl, difluoromethyl, trifluoromethyl, fluoromethoxy, difluoromethoxy or trifluoromethoxy;

$R^{12}$ and $R^{13}$ are independently selected from hydrogen, $C_{1-6}$alkyl, $C_{3-6}$cycloalkyl, aryl, heteroaryl and heterocyclyl, wherein said $C_{1-6}$alkyl, $C_{3-6}$cycloalkyl, aryl, heteroaryl or heterocyclyl is optionally substituted by one, two or three hydroxy, cyano, halo or $C_{1-3}$alkyloxy; or $R^{12}$ and $R^{13}$ may together form a 4 to 6 membered heterocyclic ring containing one or more heteroatoms selected from N, O or S optionally substituted by hydroxy, $C_{1-3}$alkyloxy, cyano or halo;

provided that the following compounds are excluded:

3-amino-1-cyano-N-phenyl-1H-isoindole-1-carboxamide;

3-amino-1-(1H-benzimidazol-2-yl)-1H-isoindole-1-carbonitrile;

4,4'-(3-amino-1H-isoindole-1,1-diyl)diphenol;

1-phenyl-1H-isoindol-3-amine;

1-methyl-1H-isoindol-3-amine;

1,1-dimethyl-1H-isoindol-3-amine;
2-[3-amino-1-(4-hydroxyphenyl)-1H-isoindol-1-yl]phenol;

as a free base or a pharmaceutically acceptable salt, solvate or solvate of a salt thereof.

In another aspect of the invention, there is provided a compound of formula I:

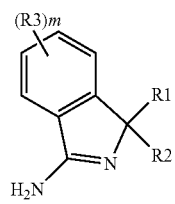

wherein $R^1$ is selected from hydrogen, nitro, cyano, -Q-$C_{1-6}$alkyl, -Q-$C_{2-6}$alkenyl, -Q-$C_{2-6}$alkynyl, -Q-$C_{3-6}$cycloalkyl, -Q-$C_{5-7}$cycloalkenyl, -Q-$C_{1-6}$alkyl$C_{3-6}$cycloalkyl, -Q-aryl, -Q-heteroaryl, -Q-$C_{1-6}$alkylaryl, -Q-$C_{1-6}$alkylheteroaryl, -Q-heterocyclyl and -Q-$C_{1-6}$alkylheterocyclyl, wherein said -Q-$C_{1-6}$alkyl, -Q-$C_{2-6}$alkenyl, -Q-$C_{2-6}$alkynyl, -Q-$C_{3-6}$cycloalkyl, -Q-$C_{5-7}$cycloalkenyl, -Q-$C_{1-6}$alkyl$C_{3-6}$cycloalkyl, -Q-aryl, -Q-heteroaryl, -Q-$C_{1-6}$alkylaryl, -Q-$C_{1-6}$alkylheteroaryl, -Q-heterocyclyl or -Q-$C_{1-6}$alkylheterocyclyl is optionally substituted by one, two or three $R^7$;

$R^2$ is $(C(R^4)(R^5))_nR^6$, $C_{2-4}$alkenyl$R^6$, $C_{2-4}$alkynyl$R^6$, $C_{5-7}$cycloalkenyl$R^6$, nitro or cyano and if n>1 then each $C(R^4)(R^5)$ is independent of the others;

$R^3$ is independently selected from hydrogen, halogen, $C_{1-6}$alkyl, $C_{3-6}$alkenyl, $C_{3-6}$alkynyl, $C_{3-6}$cycloalkyl, $C_{5-7}$cycloalkenyl, aryl, heteroaryl, heterocyclyl, $C_{1-6}$alkyl$C_{3-6}$cycloalkyl, $C_{1-6}$alkylaryl, $C_{1-6}$alkylheteroaryl and $C_{1-6}$alkylheterocyclyl, wherein said $C_{1-6}$alkyl, $C_{3-6}$alkenyl, $C_{3-6}$alkynyl, $C_{3-6}$cycloalkyl, $C_{5-7}$cycloalkenyl, aryl, heteroaryl, heterocyclyl, $C_{1-6}$alkyl$C_{3-6}$cycloalkyl, $C_{1-6}$alkylaryl, $C_{1-6}$alkylheteroaryl or $C_{1-6}$alkylheterocyclyl is optionally substituted with one, two or three A;

-Q- is a direct bond, —CONH—, —CO—, —CON($C_{1-6}$alkyl)-, —CON($C_{3-6}$cycloalkyl)-, —SO—, —SO$_2$—, —SO$_2$NH—, —SO$_2$N($C_{1-6}$alkyl)-, —SO$_2$N($C_{3-6}$cycloalkyl)-, —NHSO$_2$—, —N($C_{1-6}$alkyl)SO$_2$—, —NHCO—, —N($C_{1-6}$alkyl)CO—, —N($C_{3-6}$cycloalkyl)CO— or —N($C_{3-6}$cycloalkyl)SO$_2$—;

$R^4$ and $R^5$ are independently selected from hydrogen, $C_{1-6}$alkyl, cyano, halo and nitro; or $R^4$ and $R^5$ together form oxo, $C_{3-6}$cycloalkyl or heterocyclyl;

$R^6$ is selected from methyl, $C_{3-6}$cycloalkyl, heterocyclyl, aryl and heteroaryl, wherein said methyl, $C_{3-6}$cycloalkyl, heterocyclyl, aryl or heteroaryl is optionally substituted with between one and four $R^7$, and wherein any of the individual aryl or heteroaryl groups may be optionally fused with a 4, 5, 6 or 7 membered cycloalkyl, cycloalkenyl or heterocyclyl group to form a bicyclic ring system where the bicyclic ring system is optionally substituted with between one and four A;

$R^7$ is independently selected from halogen, nitro, CHO, $C_{0-6}$alkylCN, O$C_{1-6}$alkylCN, $C_{0-6}$alkylOR$^8$, O$C_{2-6}$alkylOR$^8$, hydroxy, fluoromethyl, difluoromethyl, trifluoromethyl, fluoromethoxy, difluoromethoxy, trifluoromethoxy, $C_{0-6}$alkylNR$^8$R$^9$, O$C_{2-6}$alkylNR$^8$R$^9$, O$C_{2-6}$alkylO$C_{2-6}$alkylNR$^8$R$^9$, NR$^8$OR$^9$, $C_{0-6}$alkylCO$_2$R$^8$, O$C_{1-6}$alkylCO$_2$R$^8$, $C_{0-6}$alkylCONR$^8$R$^9$, O$C_{1-6}$alkylCONR$^8$R$^9$, O$C_{2-6}$alkylNR$^8$(CO)R$^9$, $C_{0-6}$alkylNR$^8$(CO)R$^9$, O(CO)NR$^8$R$^9$, NR$^8$(CO)OR$^9$, NR$^8$(CO)NR$^8$R$^9$, O(CO)OR$^8$, $C_{0-6}$alkylCOR$^8$, O$C_{1-6}$alkylCOR$^8$, NR$^8$(CO)(CO)R$^8$, NR$^8$(CO)(CO)NR$^8$R$^9$, $C_{0-6}$alkylSR$^8$, $C_{0-6}$alkyl(SO$_2$)NR$^8$R$^9$, O$C_{1-6}$alkylNR$^8$(SO$_2$)R$^9$, O$C_{0-6}$alkyl(SO$_2$)NR$^8$R$^9$, $C_{0-6}$alkyl(SO)NR$^8$R$^9$, O$C_{1-6}$alkyl(SO)NR$^8$R$^9$, OSO$_2$R$^8$, SO$_3$R$^8$, $C_{0-6}$alkylNR$^8$(SO$_2$)NR$^8$R$^9$, $C_{0-6}$alkylNR$^8$(SO)R$^9$, O$C_{2-6}$alkylNR$^8$(SO)R$^8$, O$C_{1-6}$alkylSO$_2$R$^8$, $C_{1-6}$alkylSO$_2$R$^8$, $C_{0-6}$alkylSOR$^8$, $C_{1-6}$alkyl, $C_{2-6}$alkenyl, $C_{2-6}$alkynyl, $C_{0-6}$alkyl$C_{3-6}$cycloalkyl, $C_{0-6}$alkylaryl, $C_{0-6}$alkylheteroaryl, $C_{0-6}$alkylheterocyclyl and O$C_{2-6}$alkylheterocyclyl, wherein said $C_{1-6}$alkyl, $C_{2-6}$alkenyl, $C_{2-6}$alkynyl, $C_{0-6}$alkyl$C_{3-6}$cycloalkyl, $C_{0-6}$alkylaryl, $C_{0-6}$alkylheteroaryl, $C_{0-6}$alkylheterocyclyl or O$C_{2-6}$alkylheterocyclyl is optionally substituted by one or more $R^{14}$, and wherein any of the individual aryl or heteroaryl groups may be optionally fused with a 4, 5, 6 or 7 membered cycloalkyl, cycloalkenyl or heterocyclyl group to form a bicyclic ring system where the bicyclic ring system is optionally substituted with between one and four A with the proviso that said bicyclic ring system is not an indane, benzo[1,3]dioxole or 2,3-dihydrobenzo[1,4]-dioxine ring system;

$R^{14}$ is selected from halogen, nitro, CHO, $C_{0-6}$alkylCN, O$C_{1-6}$alkylCN, $C_{0-6}$alkylOR$^8$, O$C_{1-6}$alkylOR$^8$, fluoromethyl, difluoromethyl, trifluoromethyl, fluoromethoxy, difluoromethoxy, trifluoromethoxy, $C_{0-6}$alkylNR$^8$R$^9$, O$C_{2-6}$alkylNR$^8$R$^9$, O$C_{2-6}$alkylO$C_{2-6}$alkylNR$^8$R$^9$, NR$^8$OR$^9$, $C_{0-6}$alkylCO$_2$R$^8$, O$C_{1-6}$alkylCO$_2$R$^8$, $C_{0-6}$alkylCONR$^8$R$^9$, O$C_{1-6}$alkylCONR$^8$R$^9$, O$C_{2-6}$alkylNR$^8$(CO)R$^9$, $C_{0-6}$alkylNR$^8$(CO)R$^9$, O(CO)NR$^8$R$^9$, NR$^8$(CO)OR$^9$, NR$^8$(CO)NR$^8$R$^9$, O(CO)OR$^8$, O(CO)R$^8$, $C_{0-6}$alkylCOR$^8$, O$C_{1-6}$alkylCOR$^8$, NR$^8$(CO)(CO)R$^8$, NR$^8$(CO)(CO)NR$^8$R$^9$, $C_{0-6}$alkylSR$^8$, $C_{0-6}$alkyl(SO$_2$)NR$^8$R$^9$, O$C_{2-6}$alkylNR$^8$(SO$_2$)R$^9$, O$C_{0-6}$alkyl(SO$_2$)NR$^8$R$^9$, $C_{0-6}$alkyl(SO)NR$^8$R$^9$, O$C_{1-6}$alkyl(SO)NR$^8$R$^9$, OSO$_2$R$^8$, SO$_3$R$^8$, $C_{0-6}$alkylNR$^8$(SO$_2$)NR$^8$R$^9$, $C_{0-6}$alkylNR$^8$(SO)R$^9$, O$C_{2-6}$alkylNR$^8$(SO)R$^8$, O$C_{1-6}$alkylSO$_2$R$^8$, $C_{1-6}$alkylSO$_2$R$^8$, $C_{0-6}$alkylSOR$^8$, $C_{1-6}$alkyl, $C_{2-6}$alkenyl, $C_{2-6}$alkynyl, $C_{0-6}$alkyl$C_{3-6}$cycloalkyl, $C_{0-6}$alkylaryl, $C_{0-6}$alkylheteroaryl, $C_{0-6}$alkylheterocyclyl and O$C_{2-6}$alkylheterocyclyl, wherein said $C_{1-6}$alkyl, $C_{2-6}$alkenyl, $C_{2-6}$alkynyl, $C_{0-6}$alkyl$C_{3-6}$cycloalkyl, $C_{0-6}$alkylaryl, $C_{0-6}$alkylheteroaryl, $C_{0-6}$alkylheterocyclyl or O$C_{2-6}$alkylheterocyclyl is optionally substituted by between one and four A;

$R^8$ and $R^9$ are independently selected from hydrogen, $C_{1-6}$alkyl, $C_{2-6}$alkenyl, $C_{2-6}$alkynyl, fluoromethyl, difluoromethyl, trifluoromethyl, fluoromethoxy, difluoromethoxy, trifluoromethoxy, $C_{0-6}$alkyl$C_{3-6}$cycloalkyl, $C_{0-6}$alkylaryl, $C_{0-6}$alkylheteroaryl, $C_{0-6}$alkylheterocyclyl and $C_{1-6}$alkylNR$^{10}$R$^{11}$, wherein said $C_{1-6}$alkyl, $C_{2-6}$alkenyl, $C_{2-6}$alkynyl, $C_{0-6}$alkyl$C_{3-6}$cycloalkyl, $C_{0-6}$alkylaryl, $C_{0-6}$alkylheteroaryl or $C_{0-6}$alkylheterocyclyl is optionally substituted by between one and four A; or $R^8$ and $R^9$ may together form a 4 to 6 membered heterocyclic ring containing one or more heteroatoms selected from N, O or S that is optionally substituted by A; whenever two $R^8$ groups occur in the structure then they may optionally together form a 5 or 6 membered heterocyclic ring containing one or more heteroatoms selected from N, O or S, that is optionally substituted by A;

$R^{10}$ and $R^{11}$ are independently selected from hydrogen, $C_{1-6}$alkyl, $C_{3-6}$alkenyl, $C_{3-6}$alkynyl, $C_{0-6}$alkyl$C_{3-6}$cycloalkyl, $C_{0-6}$alkylaryl, $C_{0-6}$alkylheterocyclyl and $C_{0-6}$alkylheteroaryl, wherein said $C_{1-6}$alkyl, $C_{3-6}$alkenyl, $C_{3-6}$alkynyl, $C_{0-6}$alkyl$C_{3-6}$cycloalkyl, $C_{0-6}$alkylaryl, $C_{0-6}$alkylheteroaryl or $C_{0-6}$alkylheterocyclyl is optionally substituted by A; or $R^{10}$ and $R^{11}$ may together form a 4 to 6 membered heterocyclic ring containing one or more heteroatoms selected from N, O or S optionally substituted by A;

m is 0, 1, 2 or 3;

n is 0, 1, 2 or 3;

A is independently selected from oxo, halogen, nitro, CN, $OR^{12}$, $C_{1-6}$alkyl, $C_{2-6}$alkenyl, $C_{2-6}$alkynyl, $C_{0-6}$alkylaryl, $C_{0-6}$alkylheteroaryl, $C_{0-6}$alkyl$C_{3-6}$cycloalkyl, $C_{0-6}$alkylheterocyclyl, fluoromethyl, difluoromethyl, trifluoromethyl, fluoromethoxy, difluoromethoxy, trifluoromethoxy, $OC_{2-6}$alkyl$NR^{12}R^{13}$, $NR^{12}R^{13}$, $CONR^{12}R^{13}$, $NR^{12}(CO)R^{13}$, $O(CO)C_{1-6}$alkyl, $(CO)OC_{1-6}$alkyl, $COR^{12}$, $(SO_2)NR^{12}R^{13}$, $NSO_2R^{12}$, $SO_2R^{12}$, $SOR^{12}$, $(CO)C_{1-6}$alkyl$NR^{12}R^{13}$, $(SO_2)C_{1-6}$alkyl$NR^{12}R^{13}$, $OSO_2R^{12}$ and $SO_3R^{12}$, wherein said $C_{1-6}$alkyl, $C_{2-6}$alkenyl, $C_{2-6}$alkynyl, $C_{0-6}$alkylaryl, $C_{0-6}$alkylheteroaryl, $C_{0-6}$alkylheterocyclyl or $C_{0-6}$alkyl$C_{3-6}$cycloalkyl is optionally substituted with halo, $OSO_2R^{12}$, $SO_3R^{12}$, nitro, cyano, $OR^{12}$, $C_{1-6}$alkyl, fluoromethyl, difluoromethyl, trifluoromethyl, fluoromethoxy, difluoromethoxy or trifluoromethoxy;

$R^{12}$ and $R^{13}$ are independently selected from hydrogen, $C_{1-6}$alkyl, $C_{3-6}$cycloalkyl, aryl, heteroaryl and heterocyclyl, wherein said $C_{1-6}$alkyl, $C_{3-6}$cycloalkyl, aryl, heteroaryl or heterocyclyl is optionally substituted by one, two or three hydroxy, cyano, halo or $C_{1-3}$alkyloxy; or $R^{12}$ and $R^{13}$ may together form a 4 to 6 membered heterocyclic ring containing one or more heteroatoms selected from N, O or S optionally substituted by hydroxy, $C_{1-3}$alkyloxy, cyano or halo;

provided that the following compounds are excluded:
3-amino-1-cyano-N-phenyl-1H-isoindole-1-carboxamide;
3-amino-1-(1H-benzimidazol-2-yl)-1H-isoindole-1-carbonitrile;
4,4'-(3-amino-1H-isoindole-1,1-diyl)diphenol;
1-phenyl-1H-isoindol-3-amine;
1-methyl-1H-isoindol-3-amine;
1,1-dimethyl-1H-isoindol-3-amine;
2-[3-amino-1-(4-hydroxyphenyl)-1H-isoindol-1-yl]phenol; and provided that the following compounds are excluded:
$R^4$ and $R^5$ are independently selected from hydrogen, $C_{1-6}$alkyl, cyano, halo or nitro; or $R^4$ and $R^5$ together form oxo, $C_{3-6}$cycloalkyl or heterocyclyl;

$R^6$ is selected from aryl or heteroaryl wherein each of the said aryl or heteroaryl is optionally substituted with between one and four $R^7$, and wherein any of the individual aryl or heteroaryl groups may be optionally fused with a 4, 5, 6 or 7 membered cycloalkyl, cycloalkenyl or heterocyclyl group to form a bicyclic ring system;

$R^7$ is independently selected from halogen, $C_{0-6}$alkyl$OR^8$, hydroxy, $OSO_2R^8$, $C_{1-6}$alkyl, $C_{0-6}$alkylaryl and $C_{0-6}$alkylheteroaryl, wherein any $C_{1-6}$alkyl, $C_{0-6}$alkylaryl and $C_{0-6}$alkylheteroaryl may be optionally substituted by one or more $R^{14}$;

$R^{14}$ is selected from halogen, $OSO_2R^8$ and $C_{0-6}$alkyl$OR^8$, $R^8$ is independently selected from hydrogen, $C_{1-6}$alkyl and trifluoromethyl, as a free base or a pharmaceutically acceptable salt, solvate or solvate of a salt thereof.

In another aspect, the present invention provides pharmaceutical compositions comprising is as active ingredient a therapeutically effective amount of a compound of formula I in association with pharmaceutically acceptable excipients, carriers or diluents.

In another aspect, the present invention provides a compound described herein or a pharmaceutically acceptable salt thereof, for use as a medicament.

In yet another aspect, the present invention provides a compound described herein or a pharmaceutically acceptable salt thereof, for use in treating or preventing an Aβ-related pathology.

In yet another aspect, the present invention provides a compound described herein or a pharmaceutically acceptable salt thereof, for use in treating or preventing an Aβ-related pathology wherein said Aβ-related pathology is Downs syndrome, a β-amyloid angiopathy, cerebral amyloid angiopathy, hereditary cerebral hemorrhage, a disorder associated with cognitive impairment, MCI ("mild cognitive impairment"), Alzheimer Disease, memory loss, attention deficit symptoms associated with Alzheimer disease, neurodegeneration associated with Alzheimer disease, dementia of mixed vascular origin, dementia of degenerative origin, pre-senile dementia, senile dementia, dementia associated with Parkinson's disease, progressive supranuclear palsy or cortical basal degeneration.

In yet another aspect, the present invention provides a compound described herein in the manufacture of a medicament for treating or preventing an Aβ-related pathology.

In yet another aspect, the present invention provides a compound described herein in the manufacture of a medicament for treating or preventing an Aβ-related pathology, wherein said Aβ-related pathology is Downs syndrome, a β-amyloid angiopathy, cerebral amyloid angiopathy, hereditary cerebral hemorrhage, a disorder associated with cognitive impairment, MCI ("mild cognitive impairment"), Alzheimer Disease, memory loss, attention deficit symptoms associated with Alzheimer disease, neurodegeneration associated with Alzheimer disease, dementia of mixed vascular origin, dementia of degenerative origin, pre-senile dementia, senile dementia, dementia associated with Parkinson's disease, progressive supranuclear palsy or cortical basal degeneration.

In yet another aspect, the present invention provides methods of inhibiting activity of BACE comprising contacting said BACE with a compound of Formula I.

In yet another aspect, the present invention provides methods of treating or preventing an Aβ-related pathology in a mammal, comprising administering to the patient a therapeutically effective amount of a compound of Formula I.

Said methods can also be methods of treating or preventing an Aβ-related pathology in a mammal, comprising administering to the patient a therapeutically effective amount of a compound of formula I and at least one cognitive enhancing agent, memory enhancing agent, anti-inflammatory agent or choline esterase inhibitor.

Said methods can also be methods of treating or preventing an Aβ-related pathology in a mammal, comprising administering to the patient a therapeutically effective amount of a compound of formula I in combination with an atypical antipsychotic agent.

Said methods refer to a mammal and said mammal may be a human.

Said Aβ-related pathology may be selected from Downs syndrome, a β-amyloid angiopathy, cerebral amyloid angiopathy, hereditary cerebral hemorrhage, a disorder associated with cognitive impairment, MCI ("mild cognitive impairment"), Alzheimer Disease, memory loss, attention deficit symptoms associated with Alzheimer disease, neurodegeneration associated with Alzheimer disease, dementia of mixed vascular origin, dementia of degenerative origin, pre-senile dementia, senile dementia, dementia associated with Parkinson's disease, progressive supranuclear palsy and cortical basal degeneration.

Cognitive enhancing agents, memory enhancing agents and choline esterase inhibitors includes, but not limited to, onepezil (Aricept), galantamine (Reminyl or Razadyne), rivastigmine (Exelon), tacrine (Cognex) and memantine (Namenda, Axura or Ebixa)

Atypical antipsychotic agents includes, but not limited to, olanzapine (marketed as Zyprexa), aripiprazole (marketed as Abilify), risperidone (marketed as Risperdal), quetiapine (marketed as Seroquel), clozapine (marketed as Clozaril), ziprasidone (marketed as Geodon) and olanzapine/fluoxetine (marketed as Symbyax).

In another aspect of the invention, the compounds of the present invention are represented by a method for the prophylaxis of Aβ-related pathologies comprising administering to a human a therapeutically effective amount of a compound of formula I or a pharmaceutically acceptable salt, thereof as defined herein.

In another aspect of the invention, the present invention provides that the mammal or human being treated with a compound of the invention has been diagnosed with a particular disease or disorder, such as those described herein. In these cases, the mammal or human being treated is in need of such treatment. Diagnosis, however, need not be previously performed.

In another aspect of the invention, there is provided a compound of formula I, wherein
$R^1$ is -Q-aryl, wherein said -Q-aryl is optionally substituted by one, two or three $R^7$;
$R^2$ is $(C(R^4)(R^5))_n R^6$;
-Q- is a direct bond;
$R^6$ is aryl wherein said aryl is optionally substituted with between one and four $R^7$, and wherein the individual aryl group may be optionally fused with a 4, 5, 6 or 7 membered heterocyclyl group to form a bicyclic ring system;
$R^7$ is independently selected from halogen, $C_{0-6}$alkylOR$^8$, hydroxy, OSO$_2$R$^8$, $C_{1-6}$alkyl, $C_{0-6}$alkylaryl and $C_{0-6}$alkylheteroaryl, wherein any $C_{1-6}$alkyl, $C_{0-6}$alkylaryl and $C_{0-6}$alkylheteroaryl may be optionally substituted by one or more $R^{14}$;
$R^{14}$ is selected from halogen, OSO$_2$R$^8$ and $C_{0-6}$alkylOR$^8$,
$R^8$ is independently selected from hydrogen, $C_{1-6}$alkyl and trifluoromethyl;
m is 0;
n is 0;

as a free base or a pharmaceutically acceptable salt, solvate or solvate of a salt thereof.

In another aspect of the invention, there is provided a compound of formula I, wherein
$R^1$ is selected from -Q-aryl and -Q-heteroaryl, wherein said -Q-aryl or -Q-heteroaryl is optionally substituted by one, two or three $R^7$;
$R^2$ is $(C(R^4)(R^5))_n R^6$;
$R^3$ is halogen;
-Q- is a direct bond;
$R^6$ is selected from aryl and heteroaryl wherein said aryl or heteroaryl is optionally substituted with between one and four $R^7$;
$R^7$ is independently selected from halogen, $C_{0-6}$alkylCN, $C_{0-6}$alkylOR$^8$, trifluoromethyl, trifluoromethoxy, $C_{0-6}$alkylaryl and $C_{0-6}$alkylheteroaryl, wherein said $C_{0-6}$alkylaryl or $C_{0-6}$alkylheteroaryl is optionally substituted by one or more $R^{14}$;
$R^{14}$ is selected from halogen, CHO, $C_{0-6}$alkylCN, $C_{0-6}$alkylOR$^8$, $C_{0-6}$alkylCONR$^8$R$^9$, (CO)R$^9$ and $C_{1-6}$alkyl;
$R^8$ and $R^9$ are independently selected from hydrogen, $C_{1-6}$alkyl;
m is 0 or 1; and
n is 0.

In another aspect of the invention, there is provided a compound of formula I, wherein
$R^1$ is -Q-$C_{1-6}$alkyl;
$R^2$ is $(C(R^4)(R^5))_n R^6$;
-Q- is a direct bond;
$R^6$ is aryl, said aryl optionally being substituted with between one or two $R^7$;
$R^7$ is independently selected from halogen, $C_{0-6}$alkylCN, $C_{0-6}$alkylOR$^8$, $C_{0-6}$alkylaryl and $C_{0-6}$alkylheteroaryl, wherein said $C_{0-6}$alkylaryl or $C_{0-6}$alkylheteroaryl is optionally substituted by one or more $R^{14}$;
$R^{14}$ is selected from halogen, $C_{0-6}$alkylCN and $C_{0-6}$alkylOR$^8$;
$R^8$ is $C_{1-6}$alkyl;
m is 0; and
n is 0.

In another aspect of the invention, there is provided a compound of formula I, wherein
$R^1$ is -Q-aryl substituted by one or two $R^7$;
$R^2$ is $(C(R^4)(R^5))_n R^6$;
-Q- is a direct bond;
$R^6$ is selected from aryl and heteroaryl wherein said aryl or heteroaryl is optionally substituted with between one and four $R^7$;
$R^7$ is independently selected from halogen, trifluoromethyl, OSO$_2$R$^8$, $C_{0-6}$alkylOR$^8$, $C_{1-6}$alkyl, $C_{0-6}$alkylaryl and $C_{0-6}$alkylheteroaryl, wherein any $C_{0-6}$alkylaryl or $C_{0-6}$alkylheteroaryl is optionally substituted by one or more $R^{14}$;
$R^{14}$ is selected from halogen, $C_{0-6}$alkylCN and $C_{0-6}$alkylOR$^8$;
$R^8$ is selected from $C_{1-6}$alkyl, trifluoromethyl, $C_{0-6}$alkylaryl and $C_{0-6}$alkylheteroaryl, wherein said $C_{0-6}$alkylaryl or $C_{0-6}$alkylheteroaryl or $C_{0-6}$alkylheterocyclyl is optionally substituted by between one and four A;
m is 0;
n is 0;
A is selected halogen and $C_{1-6}$alkyl.

In another aspect of the invention, there is provided a compound of formula I, wherein
$R^1$ is -Q-aryl substituted by one or two $R^7$;
$R^2$ is $(C(R^4)(R^5))_n R^6$;
-Q- is a direct bond;
$R^6$ is aryl substituted with between one and four $R^7$;
$R^7$ is independently selected from halogen, OSO$_2$R$^8$, $C_{0-6}$alkylOR$^8$, $C_{1-6}$alkyl, $C_{0-6}$alkylaryl and $C_{0-6}$alkylheteroaryl, wherein any $C_{0-6}$alkylaryl or $C_{0-6}$alkylheteroaryl is optionally substituted by one or more $R^{14}$;
$R^{14}$ is selected from halogen, $C_{0-6}$alkylCN and $C_{0-6}$alkylOR$^8$;
$R^8$ is selected from $C_{1-6}$alkyl, trifluoromethyl, $C_{0-6}$alkylaryl and $C_{0-6}$alkylheteroaryl, wherein said $C_{0-6}$alkylaryl or $C_{0-6}$alkylheteroaryl or $C_{0-6}$alkylheterocyclyl is optionally substituted by between one and four A;
m is 0;
n is 0;
A is selected halogen and $C_{1-6}$alkyl.

In another aspect of the invention, there is provided a compound of formula I, wherein $R^1$ is -Q-aryl substituted by one or two $R^7$;
$R^2$ is $(C(R^4)(R^5))_n R^6$;
-Q- is a direct bond;
$R^6$ is heteroaryl, optionally substituted with between one and four $R^7$;
$R^7$ is independently selected from halogen, $OSO_2R^8$, $C_{0-6}$alkyl$OR^8$, $C_{1-6}$alkyl, $C_{0-6}$alkylaryl and $C_{0-6}$alkylheteroaryl, wherein any $C_{0-6}$alkylaryl or $C_{0-6}$alkylheteroaryl is optionally substituted by one or more $R^{14}$;
$R^{14}$ is selected from halogen, $C_{0-6}$alkylCN and $C_{0-6}$alkylOR$^8$;
$R^8$ is selected from $C_{1-6}$alkyl, trifluoromethyl, $C_{0-6}$alkylaryl and $C_{0-6}$alkylheteroaryl, wherein said $C_{0-6}$alkylaryl or $C_{0-6}$alkylheteroaryl or $C_{0-6}$alkylheterocyclyl is optionally substituted by between one and four A;
m is 0;
n is 0;
A is selected halogen and $C_{1-6}$alkyl.

In another aspect of the invention, there is provided a compound of formula I, selected from:
3,3-Diphenyl-3H-isoindol-1-ylamine;
3-(3'-Methoxy-biphenyl-3-yl)-3-(4-methoxy-phenyl)-3H-isoindol-1-ylamine trifluoroacetate;
Trifluoro-methanesulfonic acid 5-[3-amino-1-(4-methoxy-phenyl)-1H-isoindol-1-yl]-3'-methoxy-biphenyl-2-yl ester trifluoroacetate;
5-[3-Amino-1-(4-methoxy-phenyl)-1H-isoindol-1-yl]-3'-methoxy-biphenyl-2-ol trifluoroacetate;
4,4'-(3-amino-isoindole-1,1-diyl)-bis-phenol;
4-[3-Amino-1-(4-methoxy-phenyl)-1H-isoindol-1-yl]-2-pyridin-3-yl-phenol trifluoroacetate;
4-[3-Amino-1-(4-methoxy-phenyl)-1H-isoindol-1-yl]-2-pyrimidin-5-yl-phenol trifluoroacetate;
3-(4-Methoxy-phenyl)-3-(3-pyridin-3-yl-phenyl)-3H-isoindol-1-ylamine trifluoroacetate;
3-[3-(2-Fluoro-pyridin-3-yl)-phenyl]-3-(4-methoxy-phenyl)-3H-isoindol-1-ylamine trifluoroacetate;
3-(3-Bromo-phenyl)-3-(4-methoxy-phenyl)-3H-isoindol-1-ylamine;
3-(4-Methoxy-phenyl)-3-[3-(5-methoxy-pyridin-3-yl)-phenyl]-3H-isoindol-1-ylamine trifluoroacetate;
3-(4-Methoxy-phenyl)-3-(3-pyrimidin-5-yl-phenyl)-3H-isoindol-1-ylamine trifluoroacetate;
Methanesulfonic acid 3'-[3-amino-1-(4-methoxy-phenyl)-1H-isoindol-1-yl]-5-methoxy-biphenyl-3-yl ester trifluoroacetate;
3-(2,3-Dihydrobenzo[b][1,4]dioxin-6-yl)-3-(3-(2-fluoropyridin-3-yl)phenyl)-3H-isoindol-1-amine trifluoroacetate;
3-(2,3-Dihydrobenzo[b][1,4]dioxin-6-yl)-3-(3-(5-methoxypyridin-3-yl)phenyl)-3H-isoindol-1-amine trifluoroacetate;
3-(2,3-Dihydrobenzo[b][1,4]dioxin-6-yl)-3-(3-(pyridin-3-yl)phenyl)-3H-isoindol-1-amine trifluoroacetate;
3-(2,3-Dihydrobenzo[b][1,4]dioxin-6-yl)-3-(3-(pyrimidin-5-yl)phenyl)-3H-isoindol-1-amine trifluoroacetate;
3-(3'-Methoxy-biphenyl-3-yl)-3-(4-methoxy-3-methyl-phenyl)-3H-isoindol-1-ylamine trifluoroacetate;
3-(4-Methoxy-3-methyl-phenyl)-3-[3-(5-methoxy-pyridin-3-yl)-phenyl]-3H-isoindol-1-ylamine trifluoroacetate;
3-(4-Methoxy-3-methyl-phenyl)-3-(3-pyridin-3-yl-phenyl)-3H-isoindol-1-ylamine trifluoroacetate;
3-(4-Methoxy-3-methyl-phenyl)-3-(3-pyrimidin-5-yl-phenyl)-3H-isoindol-1-ylamine trifluoroacetate;
3-[3-(2-Fluoro-pyridin-3-yl)-phenyl]-3-(4-methoxy-3-methyl-phenyl)-3H-isoindol-1-ylamine trifluoroacetate;
Methanesulfonic acid 3'-[3-amino-1-(4-methoxy-3-methyl-phenyl)-1H-isoindol-1-yl]-5-methoxy-biphenyl-3-yl ester trifluoroacetate;
5'-(3-Amino-1-(2,3-dihydrobenzo[b][1,4]dioxin-6-yl)-1H-isoindol-1-yl)-5-methoxybiphenyl-3-yl methanesulfonate trifluoroacetate;
3-(2,3-Dihydrobenzo[b][1,4]dioxin-6-yl)-3-(3'-methoxybiphenyl-3-yl)-3H-isoindol-1-amine trifluoroacetate;
3-Benzo[1,3]dioxol-5-yl-3-(3-pyridin-3-yl)-3H-isoindol-1-ylamine trifluoroacetate;
3-Benzo[1,3]dioxol-5-yl-3-(3-bromophenyl)-3H-isoindol-1-ylamine;
3-Benzo[1,3]dioxol-5-yl-3-(3-pyrimidin-5-ylphenyl)-3H-isoindol-1-ylamine trifluoroacetate;
3-Benzo[1,3]dioxol-5-yl-3-[3-(2-fluoropyridin-3-yl)-phenyl]-3H-isoindol-1-ylamine trifluoroacetate;
3-Benzo[1,3]dioxol-5-yl-3-[3-(5-methoxypyridin-3-yl)-phenyl]3H isoindol-1-ylamine trifluoroacetate;
as a free base or a pharmaceutically acceptable salt, solvate or solvate of a salt thereof.

In another aspect of the invention, there is provided a compound of formula I, selected from:
3-Benzo[1,3]dioxol-5-yl-3-(3'-methoxy-biphenyl-3-yl)-3H-isoindol-1-ylamine trifluoroacetate;
Methanesulfonic acid 3'-(3-amino-1-benzo[1,3]dioxol-5-yl-1H-isoindol-1-yl)-5-methoxy-biphenyl-3-yl ester trifluoroacetate;
Methanesulfonic acid 4-[3-amino-1-(3-pyridin-3-yl-phenyl)-1H-isoindol-1-yl]-phenyl ester trifluoroacetate;
Methanesulfonic acid 4-[3-amino-1-(3-bromo-phenyl)-1H-isoindol-1-yl]-phenyl ester trifluoroacetate;
Methanesulfonic acid 4-{3-amino-1-[3-(2-fluoro-pyridin-3-yl)-phenyl]-1H-isoindol-1-yl}-phenyl ester trifluoroacetate;
Methanesulfonic acid 4-[3-amino-1-(3-pyrimidin-5-yl-phenyl)-1H-isoindol-1-yl]-phenyl ester trifluoroacetate;
Methanesulfonic acid 4-{3-amino-1-[3-(5-methoxy-pyridin-3-yl)-phenyl]-1H-isoindol-1-yl}-phenyl ester trifluoroacetate;
Methanesulfonic acid 4-[3-amino-1-(3'-methoxy-biphenyl-3-yl)-1H-isoindol-1-yl]-phenyl ester trifluoroacetate;
Methanesulfonic acid 4-[3-amino-1-(5'-methanesulfonyloxy-3'-methoxy-biphenyl-3-yl)-1H-isoindol-1-yl]-phenyl ester trifluoroacetate;
3-[3-(2-Fluoro-pyridin-3-yl)-phenyl]-3-pyridin-4-yl-3H-isoindol-1-ylamine trifluoroacetate;
3-Pyridin-4-yl-3-(3-pyridin-3-yl-phenyl)-3H-isoindol-1-ylamine trifluoroacetate;
3-Pyridin-4-yl-3-(3-pyrimidin-5-yl-phenyl)-3H-isoindol-1-ylamine trifluoroacetate;
3-[3-(5-Methoxy-pyridin-3-yl)-phenyl]-3-pyridin-4-yl-3H-isoindol-1-ylamine trifluoroacetate;
3-(3'-Methoxy-biphenyl-3-yl)-3-pyridin-4-yl-3H-isoindol-1-ylamine trifluoroacetate;
3-{3-[3-Amino-1-(4-methoxyphenyl)-1H-isoindol-1-yl]phenyl}thiophene-2-carbaldehyde 1.5 acetate;
4-[3-Amino-1-(3-bromophenyl)-1H-isoindol-1-yl]benzonitrile;
1-[3-(1-Isobutyl-1H-pyrazol-4-yl)phenyl]-1-(4-methoxyphenyl)-1H-isoindol-3-amine 0.5 acetate;
1-(4-Methoxyphenyl)-1-[3-(5-methyl-2-furyl)phenyl]-1H-isoindol-3-amine 0.5 acetate;
3'-[3-Amino-1-(4-methoxyphenyl)-1H-isoindol-1-yl]biphenyl-2-carboxamide 0.5 acetate;
1-[3-(5-Fluoropyridin-3-yl)phenyl]-1-[4-(trifluoromethoxy)phenyl]-1H-isoindol-3-amine 0.75 acetate;

1-(3-Pyrimidin-5-ylphenyl)-1-[4-(trifluoromethoxy)phenyl]-1H-isoindol-3-amine 0.25 acetate;
4-[3-Amino-1-(3-pyrimidin-5-ylphenyl)-1H-isoindol-1-yl]benzonitrile 0.25 acetate;
1-[3-(5-Fluoropyridin-3-yl)phenyl]-1-[4-(trifluoromethyl)phenyl]-1H-isoindol-3-amine 0.25 acetate;
1-(3-Pyrimidin-5-ylphenyl)-1-[4-(trifluoromethyl)phenyl]-1H-isoindol-3-amine 0.25 acetate;
3-[3-(3-Amino-1-pyridin-4-yl-1H-isoindol-1-yl)phenyl]thiophene-2-carbaldehyde;
1-[3-(1-Isobutyl-1H-pyrazol-4-yl)phenyl]-1-pyridin-4-yl-1H-isoindol-3-amine 0.25 acetate;
1-[3-(5-Methyl-2-furyl)phenyl]-1-pyridin-4-yl-1H-isoindol-3-amine acetate;
3'-(3-Amino-1-pyridin-4-yl-1H-isoindol-1-yl)biphenyl-2-carboxamide 0.25 acetate;
4-{3-Amino-1-[3-(2-fluoropyridin-3-yl)phenyl]-1H-isoindol-1-yl}benzonitrile;
1-[3-(2-Fluoropyridin-3-yl)phenyl]-1-[4-(trifluoromethyl)phenyl]-1H-isoindol-3-amine;
1-[3-(5-Fluoropyridin-3-yl)phenyl]-1-pyridin-4-yl-1H-isoindol-3-amine 0.75 acetate;
1-(4-Fluoro-3-pyrimidin-5-ylphenyl)-1-pyridin-4-yl-1H-isoindol-3-amine 0.5 acetate;
1-[4-Fluoro-3-(5-fluoropyridin-3-yl)phenyl]-1-pyridin-4-yl-1H-isoindol-3-amine 0.75 acetate;
1-(3-Fluoropyridin-4-yl)-1-[3-(5-fluoropyridin-3-yl)phenyl]-1H-isoindol-3-amine 0.5 acetate;
1-(3-Fluoropyridin-4-yl)-1-(3-pyrimidin-5-ylphenyl)-1H-isoindol-3-amine 1.25 acetate;
1-(3-Fluoropyridin-4-yl)-1-[3-(2-fluoropyridin-3-yl)phenyl]-1H-isoindol-3-amine 1.25 acetate;
1-(3-Fluoropyridin-4-yl)-1-(4-fluoro-3-pyrimidin-5-ylphenyl)-1H-isoindol-3-amine 1.25 acetate;
1-[4-Fluoro-3-(5-fluoropyridin-3-yl)phenyl]-1-(3-fluoropyridin-4-yl)-1H-isoindol-3-amine 1.5 acetate;
1-[4-Fluoro-3-(2-fluoropyridin-3-yl)phenyl]-1-(3-fluoropyridin-4-yl)-1H-isoindol-3-amine 1.5 acetate;
5-[3-(3-Amino-1-pyridin-4-yl-1H-isoindol-1-yl)phenyl]nicotinonitrile acetate;
6-Fluoro-1-(4-methoxyphenyl)-1-(3-pyrimidin-5-ylphenyl)-1H-isoindol-3-amine;
6-Fluoro-1-(4-methoxyphenyl)-1-(3-pyridin-3-ylphenyl)-1H-isoindol-3-amine;
6-Fluoro-1-(3'-methoxybiphenyl-3-yl)-1-(4-methoxyphenyl)-1H-isoindol-3-amine;
6-Fluoro-1-(4-methoxyphenyl)-1-[3-(5-methoxypyridin-3-yl)phenyl]-1H-isoindol-3-amine;
6-Fluoro-1-pyridin-4-yl-1-(3-pyridin-3-ylphenyl)-1H-isoindol-3-amine;
6-Fluoro-1-pyridin-4-yl-1-(3-pyrimidin-5-ylphenyl)-1H-isoindol-3-amine;
6-Fluoro-1-[3-(5-methoxypyridin-3-yl)phenyl]-1-pyridin-4-yl-1H-isoindol-3-amine;
6-Fluoro-1-[3-(2-fluoropyridin-3-yl)phenyl]-1-pyridin-4-yl-1H-isoindol-3-amine;
1-(3',5'-Dichlorobiphenyl-3-yl)-1-(4-methoxyphenyl)-1H-isoindol-3-amine acetate;
3'-(3-Amino-1-cyclopropyl-1H-isoindol-1-yl)-5-methoxybiphenyl-2-carbonitrile acetate;
1-Cyclopropyl-1-(3-pyrimidin-5-ylphenyl)-1H-isoindol-3-amine acetate;
3'-(3-Amino-1-methyl-1H-isoindol-1-yl)-5-methoxybiphenyl-2-carbonitrile acetate;
1-(3',5'-Dichlorobiphenyl-3-yl)-1-methyl-1H-isoindol-3-amine hydrochloride;
1-Methyl-1-(3-pyrimidin-5-ylphenyl)-1H-isoindol-3-amine acetate;
1-[3-(2-Fluoropyridin-3-yl)phenyl]-1-methyl-1H-isoindol-3-amine acetate;
1-Isopropyl-1-(3-pyrimidin-5-ylphenyl)-1H-isoindol-3-amine acetate; and
1-[3-(5-Fluoropyridin-3-yl)phenyl]-1-methyl-1H-isoindol-3-amine acetate;

as a free base or a pharmaceutically acceptable salt, solvate or solvate of a salt thereof.

In another aspect of the invention, there is provided a compound of formula I, selected from:
1-(2'-Fluoro-5'-methoxybiphenyl-3-yl)-1-(3-fluoropyridin-4-yl)-1H-isoindol-3-amine;
1-(2'-Fluoro-3'-methoxybiphenyl-3-yl)-1-(3-fluoropyridin-4-yl)-1H-isoindol-3-amine;
1-(2',6-Difluoro-3'-methoxybiphenyl-3-yl)-1-(3-fluoropyridin-4-yl)-1H-isoindol-3-amine;
5-{3-[3-Amino-1-(3-fluoropyridin-4-yl)-1H-isoindol-1-yl]phenyl}nicotinonitrile;
1-(2'-Fluoro-5'-methoxybiphenyl-3-yl)-1-pyridin-4-yl-1H-isoindol-3-amine;
1-(2'-Fluoro-3'-methoxybiphenyl-3-yl)-1-pyridin-4-yl-1H-isoindol-3-amine;
1-[4-Fluoro-3-(2-fluoropyridin-3-yl)phenyl]-1-pyridin-4-yl-1H-isoindol-3-amine;
1-[3-(2-Fluoropyridin-3-yl)phenyl]-1-(2-methoxypyrimidin-5-yl)-1H-isoindol-3-amine;
1-(2-Methoxypyrimidin-5-yl)-1-(3-pyrimidin-5-ylphenyl)-1H-isoindol-3-amine;
1-(2'-Fluoro-3'-methoxybiphenyl-3-yl)-1-(2-methoxypyrimidin-5-yl)-1H-isoindol-3-amine;
1-(2-Ethylpyridin-4-yl)-1-(3-pyrimidin-5-ylphenyl)-1H-isoindol-3-amine;
1-(2-Ethylpyridin-4-yl)-1-[3-(2-fluoropyridin-3-yl)phenyl]-1H-isoindol-3-amine;
1-(2-Isopropylpyridin-4-yl)-1-(3-pyrimidin-5-ylphenyl)-1H-isoindol-3-amine;
1-[3-(2-Fluoropyridin-3-yl)phenyl]-1-(2-isopropylpyridin-4-yl)-1H-isoindol-3-amine;
1-(2-Fluoropyridin-4-yl)-1-[3-(2-fluoropyridin-3-yl)phenyl]-1H-isoindol-3-amine;
1-[3-(2-Fluoropyridin-3-yl)phenyl]-1-(2-methoxypyridin-4-yl)-1H-isoindol-3-amine;
1-(2-Chloropyridin-4-yl)-1-[3-(2-fluoropyridin-3-yl)phenyl]-1H-isoindol-3-amine;
1-(2-Chloropyridin-4-yl)-1-(3-pyrimidin-5-ylphenyl)-1H-isoindol-3-amine;
1-(5-Fluoropyridin-3-yl)-1-[3-(2-fluoropyridin-3-yl)phenyl]-1H-isoindol-3-amine;
1-(5-Fluoropyridin-3-yl)-1-(3-pyrimidin-5-ylphenyl)-1H-isoindol-3-amine;
1-(4-Fluoro-3-pyrimidin-5-ylphenyl)-1-(4-methoxy-3-methylphenyl)-1H-isoindol-3-amine;
1-[4-Fluoro-3-(2-fluoropyridin-3-yl)phenyl]-1-(4-methoxy-3-methylphenyl)-1H-isoindol-3-amine;
6-Chloro-1-pyridin-4-yl-1-(3-pyrimidin-5-ylphenyl)-1H-isoindol-3-amine;
1-(3-Pyrimidin-5-ylphenyl)-1-[6-(trifluoromethyl)pyridin-3-yl]-1H-isoindol-3-amine 0.66 acetate;
3-[3-Amino-1-(2,6-dichloropyridin-4-yl)-1H-isoindol-1-yl]phenyl 5-chloro-1,3-dimethyl-1H-pyrazole-4-sulfonate;
3-[3-Amino-1-(2,6-dichloropyridin-4-yl)-1H-isoindol-1-yl]phenyl 6-chloroimidazo[2,1-b][1,3]thiazole-5-sulfonate;
3-[3-Amino-1-(2,6-dichloropyridin-4-yl)-1H-isoindol-1-yl]phenyl 2,6-difluorobenzenesulfonate;

3-[3-Amino-1-(4-fluoro-3-pyrimidin-5-ylphenyl)-1H-isoindol-1-yl]phenyl trifluoromethanesulfonate;
3-[3-Amino-1-(4-fluoro-3-pyrimidin-5-ylphenyl)-1H-isoindol-1-yl]phenyl trifluoromethanesulfonate; and
4-[3-Amino-1-(4-fluoro-3-pyrimidin-5-ylphenyl)-1H-isoindol-1-yl]phenyl trifluoromethanesulfonate;

as a free base or a pharmaceutically acceptable salt, solvate or solvate of a salt thereof.

Some compounds of formula may have stereogenic centres and/or geometric isomeric centres (E- and Z-isomers), and it is to be understood that the invention encompasses all such optical isomers, enantiomers, diastereoisomers, atropisomers and geometric isomers.

The present invention relates to the use of compounds of formula I as hereinbefore defined as well as to the salts thereof. Salts for use in pharmaceutical compositions will be pharmaceutically acceptable salts, but other salts may be useful in the production of the compounds of formula I.

It is to be understood that the present invention relates to any and all tautomeric forms of the compounds of formula I.

Compounds of the invention can be used as medicaments. In some embodiments, the present invention provides compounds of formula I, or pharmaceutically acceptable salts, tautomers or in vivo-hydrolysable precursors thereof, for use as medicaments. In some embodiments, the present invention provides compounds described here in for use as medicaments for treating or preventing an Aβ-related pathology. In some further embodiments, the Aβ-related pathology is Downs syndrome, a β-amyloid angiopathy, cerebral amyloid angiopathy, hereditary cerebral hemorrhage, a disorder associated with cognitive impairment, MCI ("mild cognitive impairment"), Alzheimer Disease, memory loss, attention deficit symptoms associated with Alzheimer disease, neurodegeneration associated with Alzheimer disease, dementia of mixed vascular origin, dementia of degenerative origin, pre-senile dementia, senile dementia, dementia associated with Parkinson's disease, progressive supranuclear palsy or cortical basal degeneration.

In some embodiments, the present invention provides use of compounds of formula I or pharmaceutically acceptable salts, tautomers or in vivo-hydrolysable precursors thereof, in the manufacture of a medicament for the treatment or prophylaxis of Aβ-related pathologies. In some further embodiments, the Aβ-related pathologies include such as Downs syndrome and β-amyloid angiopathy, such as but not limited to cerebral amyloid angiopathy, hereditary cerebral hemorrhage, disorders associated with cognitive impairment, such as but not limited to MCI ("mild cognitive impairment"), Alzheimer Disease, memory loss, attention deficit symptoms associated with Alzheimer disease, neurodegeneration associated with diseases such as Alzheimer disease or dementia including dementia of mixed vascular and degenerative origin, pre-senile dementia, senile dementia and dementia associated with Parkinson's disease, progressive supranuclear palsy or cortical basal degeneration.

In some embodiments, the present invention provides a method of inhibiting activity of BACE comprising contacting the BACE with a compound of the present invention. BACE is thought to represent the major β-secretase activity, and is considered to be the rate-limiting step in the production of amyloid-β-protein (Aβ). Thus, inhibiting BACE through inhibitors such as the compounds provided herein would be useful to inhibit the deposition of Aβ and portions thereof. Because the deposition of Aβ and portions thereof is linked to diseases such Alzheimer Disease, BACE is an important candidate for the development of drugs as a treatment and/or prophylaxis of Aβ-related pathologies such as Downs syndrome and β-amyloid angiopathy, such as but not limited to cerebral amyloid angiopathy, hereditary cerebral hemorrhage, disorders associated with cognitive impairment, such as but not limited to MCI ("mild cognitive impairment"), Alzheimer Disease, memory loss, attention deficit symptoms associated with Alzheimer disease, neurodegeneration associated with diseases such as Alzheimer disease or dementia including dementia of mixed vascular and degenerative origin, pre-senile dementia, senile dementia and dementia associated with Parkinson's disease, progressive supranuclear palsy or cortical basal degeneration.

In some embodiments, the present invention provides a method for the treatment of Aβ-related pathologies such as Downs syndrome and β-amyloid angiopathy, such as but not limited to cerebral amyloid angiopathy, hereditary cerebral hemorrhage, disorders associated with cognitive impairment, such as but not limited to MCI ("mild cognitive impairment"), Alzheimer Disease, memory loss, attention deficit symptoms associated with Alzheimer disease, neurodegeneration associated with diseases such as Alzheimer disease or dementia including dementia of mixed vascular and degenerative origin, pre-senile dementia, senile dementia and dementia associated with Parkinson's disease, progressive supranuclear palsy or cortical basal degeneration, comprising administering to a mammal (including human) a therapeutically effective amount of a compound of formula I, or a pharmaceutically acceptable salt, tautomer or in vivo-hydrolysable precursor thereof.

In some embodiments, the present invention provides a method for the prophylaxis of Aβ-related pathologies such as Downs syndrome and β-amyloid angiopathy, such as but not limited to cerebral amyloid angiopathy, hereditary cerebral hemorrhage, disorders associated with cognitive impairment, such as but not limited to MCI ("mild cognitive impairment"), Alzheimer Disease, memory loss, attention deficit symptoms associated with Alzheimer disease, neurodegeneration associated with diseases such as Alzheimer disease or dementia including dementia of mixed vascular and degenerative origin, pre-senile dementia, senile dementia and dementia associated with Parkinson's disease, progressive supranuclear palsy or cortical basal degeneration comprising administering to a mammal (including human) a therapeutically effective amount of a compound of formula Ia or a pharmaceutically acceptable salt, tautomer or in vivo-hydrolysable precursors.

In some embodiments, the present invention provides a method of treating or preventing Aβ-related pathologies such as Downs syndrome and β-amyloid angiopathy, such as but not limited to cerebral amyloid angiopathy, hereditary cerebral hemorrhage, disorders associated with cognitive impairment, such as but not limited to MCI ("mild cognitive impairment"), Alzheimer Disease, memory loss, attention deficit symptoms associated with Alzheimer disease, neurodegeneration associated with diseases such as Alzheimer disease or dementia including dementia of mixed vascular and degenerative origin, pre-senile dementia, senile dementia and dementia associated with Parkinson's disease, progressive supranuclear palsy or cortical basal degeneration by administering to a mammal (including human) a compound of formula I or a pharmaceutically acceptable salt, tautomer or in vivo-hydrolysable precursors and a cognitive and/or memory enhancing agent.

In some embodiments, the present invention provides a method of treating or preventing Aβ-related pathologies such as Downs syndrome and β-amyloid angiopathy, such as but not limited to cerebral amyloid angiopathy, hereditary cerebral hemorrhage, disorders associated with cognitive impairment, such as but not limited to MCI ("mild cognitive impairment"), Alzheimer Disease, memory loss, attention deficit symptoms associated with Alzheimer disease, neurodegeneration associated with diseases such as Alzheimer disease or dementia including dementia of mixed vascular and degenerative origin, pre-senile dementia, senile dementia and dementia associated with Parkinson's disease, progressive supranuclear palsy or cortical basal degeneration by administering to a mammal (including human) a compound of formula I or a pharmaceutically acceptable salt, tautomer or in vivo-hydrolysable precursors thereof wherein constituent members are provided herein, and a choline esterase inhibitor or anti-inflammatory agent.

In some embodiments, the present invention provides a method of treating or preventing Aβ-related pathologies such as Downs syndrome and β-amyloid angiopathy, such as but not limited to cerebral amyloid angiopathy, hereditary cerebral hemorrhage, disorders associated with cognitive impairment, such as but not limited to MCI ("mild cognitive impairment"), Alzheimer Disease, memory loss, attention deficit symptoms associated with Alzheimer disease, neurodegeneration associated with diseases such as Alzheimer disease or dementia including dementia of mixed vascular and degenerative origin, pre-senile dementia, senile dementia and dementia associated with Parkinson's disease, progressive supranuclear palsy or cortical basal degeneration, or any other disease, disorder, or condition described herein, by administering to a mammal (including human) a compound of the present invention and an atypical antipsychotic agent. Atypical antipsychotic agents includes, but not limited to, Olanzapine (marketed as Zyprexa), Aripiprazole (marketed as Abilify), Risperidone (marketed as Risperdal), Quetiapine (marketed as Seroquel), Clozapine (marketed as Clozaril), Ziprasidone (marketed as Geodon) and Olanzapine/Fluoxetine (marketed as Symbyax).

In some embodiments, the mammal or human being treated with a compound of the invention has been diagnosed with a particular disease or disorder, such as those described herein. In these cases, the mammal or human being treated is in need of such treatment. Diagnosis, however, need not be previously performed.

The present invention also includes pharmaceutical compositions which contain, as the active ingredient, one or more of the compounds of the invention herein together with at least one pharmaceutically acceptable carrier, diluent or excipient.

The definitions set forth in this application are intended to clarify terms used throughout this application. The term "herein" means the entire application.

A variety of compounds in the present invention may exist in particular geometric or stereoisomeric forms. The present invention takes into account all such compounds, including cis- and trans isomers, R- and S-enantiomers, diastereomers, (D)-isomers, (L)-isomers, the racemic mixtures thereof, and other mixtures thereof, as being covered within the scope of this invention. Additional asymmetric carbon atoms may be present in a substituent such as an alkyl group. All such isomers, as well as mixtures thereof, are intended to be included in this invention. The compounds herein described may have asymmetric centers. Compounds of the present invention containing an asymmetrically substituted atom may be isolated in optically active or racemic forms. It is well known in the art how to prepare optically active forms, such as by resolution of racemic forms, by synthesis from optically active starting materials, or synthesis using optically active reagents. When required, separation of the racemic material can be achieved by methods known in the art. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents, positions of substituents and/or variables are permissible only if such combinations result in stable compounds.

As used herein, "alkyl", "alkylenyl" or "alkylene" used alone or as a suffix or prefix, is intended to include both branched and straight-chain saturated aliphatic hydrocarbon groups having from 1 to 12 carbon atoms or if a specified number of carbon atoms is provided then that specific number would be intended. For example "$C_{1-6}$alkyl" denotes alkyl having 1, 2, 3, 4, 5 or 6 carbon atoms. Examples of alkyl include, but are not limited to, methyl, ethyl, n-propyl, i-propyl, n-butyl, i-butyl, sec-butyl, t-butyl, pentyl, and hexyl. As used herein, "$C_{1-3}$alkyl", whether a terminal substituent or an alkylene (or alkylenyl) group linking two substituents, is understood to specifically include both branched and straight-chain methyl, ethyl, and propyl.

As used herein, "alkenyl" refers to an alkyl group having one or more double carbon-carbon bonds. Example alkenyl groups include ethenyl, propenyl, cyclohexenyl, and the like. The term "alkenylenyl" refers to a divalent linking alkenyl group.

As used herein, "alkynyl" refers to an alkyl group having one or more triple carbon-carbon bonds. Example alkynyl groups include ethynyl, propynyl, and the like. The term "alkynylenyl" refers to a divalent linking alkynyl group.

As used herein, "aromatic" refers to hydrocarbyl groups having one or more polyunsaturated carbon rings having aromatic characters, (e.g., 4n+2 delocalized electrons) and comprising up to about 14 carbon atoms.

As used herein, the term "aryl" refers to an aromatic ring structure made up of from 5 to 14 carbon atoms. Ring structures containing 5, 6, 7 and 8 carbon atoms would be single-ring aromatic groups, for example, phenyl. Ring structures containing 8, 9, 10, 11, 12, 13, or 14 would be a polycyclic moiety in which at least one carbon is common to any two adjoining rings therein (for example, the rings are "fused rings"), for example naphthyl. The aromatic ring can be substituted at one or more ring positions with such substituents as described above. The term "aryl" also includes polycyclic ring systems having two or more cyclic rings in which two or more carbons are common to two adjoining rings (the rings are "fused rings") wherein at least one of the rings is aromatic, for example, the other cyclic rings can be cycloalkyls, cycloalkenyls or cycloalkynyls. The terms ortho, meta and para apply to 1,2-, 1,3- and 1,4-disubstituted benzenes, respectively. For example, the names 1,2-dimethylbenzene and ortho-dimethylbenzene are synonymous.

As used herein, "cycloalkyl" refers to non-aromatic cyclic hydrocarbons including cyclized alkyl, alkenyl, and alkynyl groups, having the specified number of carbon atoms.

Cycloalkyl groups can include mono- or polycyclic (e.g., having 2, 3 or 4 fused or bridged rings) groups. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (i.e., having a bond in common with) to the cycloalkyl ring, for example, benzo derivatives of cyclopentane (i.e., indanyl), cyclopentene, cyclohexane, and the like. The term "cycloalkyl" further includes saturated ring groups, having the specified number of carbon atoms. These may include fused or bridged polycyclic systems. Preferred cycloalkyls have from 3 to 10 carbon atoms in their ring structure, and more preferably have 3, 4, 5, and 6 carbons in the ring structure. For example, "$C_{3-6}$ cycloalkyl" denotes such groups as cyclopropyl, cyclobutyl, cyclopentyl, or cyclohexyl.

As used herein, "cycloalkenyl" refers to ring-containing hydrocarbyl groups having at least one carbon-carbon double bond in the ring, and having from 3 to 12 carbons atoms.

As used herein, "halo" or "halogen" refers to fluoro, chloro, bromo, and iodo.

"Counterion" is used to represent a small, negatively or positively charged species such as chloride ($Cl^-$), bromide ($Br^-$), hydroxide ($OH^-$), acetate ($CH_3COO^-$), sulfate ($SO_4^{2-}$), tosylate ($CH_3$-phenyl-$SO_3^-$), benezensulfonate (phenyl-$SO_3^-$), sodium ion ($Na^+$), potassium ($K^+$), ammonium ($NH_4^-$), and the like.

As used herein, the term "heterocyclyl" or "heterocyclic" or "heterocycle" refers to a ring-containing monovalent and divalent structures having one or more heteroatoms, independently selected from N, O and S, as part of the ring structure and comprising from 3 to 20 atoms in the rings, more preferably 3- to 7-membered rings. The number of ring-forming atoms in heterocyclyl are given in ranges herein. For example, $C_{5-10}$ heterocyclyl refers to a ring structure comprising from 5 to 10 ring-forming atoms wherein at least one of the ring-forming atoms is N, O or S. Heterocyclic groups may be saturated or partially saturated or unsaturated, containing one or more double bonds, and heterocyclic groups may contain more than one ring as in the case of polycyclic systems.

The heterocyclic rings described herein may be substituted on carbon or on a heteroatom atom if the resulting compound is stable. If specifically noted, nitrogen in the heterocyclyl may optionally be quaternized. It is understood that when the total number of S and O atoms in the heterocyclyl exceeds 1, then these heteroatoms are not adjacent to one another.

Examples of heterocyclyls include, but are not limited to, 1H-indazole, 2-pyrrolidonyl, 2H, 6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azabicyclo, azetidine, azepane, aziridine, azocinyl, benzimidazolyl, benzodioxol, benzofuranyl, benzothiofuranyl, benzothiophenyl, benzoxazolyl, benzthiazolyl, benzotriazolyl, benzotetrazolyl, benzisoxazolyl, benzisothiazolyl, benzimidazalonyl, carbazolyl, 4aH-carbazolyl, b-carbolinyl, chromanyl, chromenyl, cinnolinyl, diazepane, decahydroquinolinyl, 2H,6H-1,5,2-dithiazinyl, dioxolane, furyl, 2,3-dihydrofuran, 2,5-dihydrofuran, dihydrofuro[2,3-b]tetrahydrofuran, furanyl, furazanyl, homopiperidinyl, imidazolidine, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxirane, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, purinyl, pyranyl, pyrrolidinyl, pyrroline, pyrrolidine, pyrazinyl, pyrazolidinyl, pyrazolinyl, pyrazolyl, pyridazinyl, pyridooxazole, pyridoimidazole, pyridothiazole, pyridinyl, N-oxide-pyridinyl, pyridyl, pyrimidinyl, pyrrolidinyl, pyrrolidinyl dione, pyrrolinyl, pyrrolyl, pyridine, quinazolinyl, quinolinyl, 4H-quinolizinyl, quinoxalinyl, quinuclidinyl, carbolinyl, tetrahydrofuranyl, tetramethylpiperidinyl, tetrahydroquinoline, tetrahydroisoquinolinyl, thiophane, thiotetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiopheneyl, thiirane, triazinyl, 1,2,3-triazolyl, 1,2,4-triazolyl, 1,2,5-triazolyl, 1,3,4-triazolyl, xanthenyl.

As used herein, "heteroaryl" refers to an aromatic heterocycle having at least one heteroatom ring member such as sulfur, oxygen, or nitrogen. Heteroaryl groups include monocyclic and polycyclic (e.g., having 2, 3 or 4 fused rings) systems. Examples of heteroaryl groups include without limitation, pyridyl (i.e., pyridinyl), pyrimidinyl, pyrazinyl, pyridazinyl, triazinyl, furyl (i.e. furanyl), quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 4 to about 14, 3 to about 7, or 5 to 6 ring-forming atoms. In some embodiments, the heteroaryl group has 1 to about 4, 1 to about 3, or 1 to 2 heteroatoms. In some embodiments, the heteroaryl group has 1 heteroatom.

As used herein, the term "heterocycloalkyl" is intended to mean a 5 to 7 member cyclic non-aromatic group containing from 1 to 3 ring heteroatoms independently selected from O, N and S. Examples of heterocycloalkyl groups include, but are not limited to, tetrahydrofuranyl, dihydrofuranyl, pyrrolidinyl, and the like. A suitable heterocycloalkyl group is tetrahydrofuranyl.

As used herein, "alkoxy" or "alkyloxy" represents an alkyl group as defined above with the indicated number of carbon atoms attached through an oxygen bridge. Examples of alkoxy include, but are not limited to, methoxy, ethoxy, n-propoxy, isopropoxy, n-butoxy, isobutoxy, t-butoxy, n-pentoxy, isopentoxy, cyclopropylmethoxy, allyloxy and propargyloxy. Similarly, "alkylthio" or "thioalkoxy" represent an alkyl group as defined above with the indicated number of carbon atoms attached through a sulphur bridge.

As used herein, the term "carbonyl" is art recognized and includes such moieties as can be represented by the general formula:

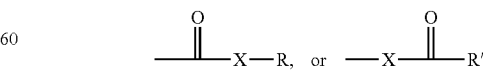

wherein X is a bond or represents an oxygen or sulfur, and R represents a hydrogen, an alkyl, an alkenyl, —$(CH_2)_m$—R" or a pharmaceutically acceptable salt, R' represents a hydrogen, an alkyl, an alkenyl or —$(CH_2)_m$—R", where m is an integer less than or equal to ten, and R" is alkyl, cycloalkyl, alkenyl, aryl, or heteroaryl. Where X is an oxygen and R and R' is not hydrogen, the formula represents an "ester". Where X is an oxygen, and R is as defined above, the moiety is referred to herein as a carboxyl group, and particularly when R' is a hydrogen, the formula represents a "carboxylic acid." Where X is oxygen, and R' is a hydrogen, the formula represents a "formate." In general, where the oxygen atom of the above formula is replaced by sulfur, the formula represents a "thiolcarbonyl" group. Where X is a sulfur and R and R' is not hydrogen, the formula represents a "thiolester." Where X is sulfur and R is hydrogen, the formula represents a "thiolcarboxylic acid." Where X is sulfur and R' is hydrogen, the formula represents a "thiolformate." On the other hand, where X is a bond, and R is not a hydrogen, the above formula represents a "ketone" group. Where X is a bond, and R is hydrogen, the above formula is represents an "aldehyde" group.

As used herein, the term "sulfonyl" refers to a moiety that can be represented by the general formula:

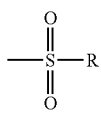

wherein R is represented by but not limited to hydrogen, alkyl, cycloalkyl, alkenyl, aryl, heteroaryl, aralkyl, or heteroaralkyl.

As used herein, some substituents are described in a combination of two or more groups. For example, the expression of "$C(=O)C_{3-9}cycloalkylR^d$" is meant to refer to a structure:

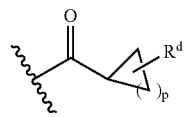

wherein p is 1, 2, 3, 4, 5, 6 or 7 (i.e., $C_{3-9}$cycloalkyl); the $C_{3-9}$cycloalkyl is substituted by $R^d$; and the point of attachment of the "$C(=O)C_{3-9}cycloalkylR^d$" is through the carbon atom of the carbonyl group, which is on the left of the expression.

As used herein, the phrase "protecting group" means temporary substituents which protect a potentially reactive functional group from undesired chemical transformations. Examples of such protecting groups include esters of carboxylic acids, silyl ethers of alcohols, and acetals and ketals of aldehydes and ketones respectively. The field of protecting group chemistry has been reviewed (Greene, T. W.; Wuts, P. G. M. *Protective Groups in Organic Synthesis,* $3^{rd}$ ed.; Wiley: New York, 1999).

As used herein, "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof (i.e., also include counterions). Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, phosphoric, and the like; and the salts prepared from organic acids such as lactic, maleic, citric, benzoic, methanesulfonic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; nonaqueous media like ether, ethyl acetate, ethanol, isopropanol, or acetonitrile can be used.

As used herein, "in vivo hydrolysable precursors" means an in vivo hydrolysable (or cleavable) ester of a compound of any of the formulas described herein that contains a carboxy or a hydroxy group. For example amino acid esters, $C_{1-6}$ alkoxymethyl esters like methoxymethyl; $C_{1-6}$alkanoyloxymethyl esters like pivaloyloxymethyl; $C_{3-8}$cycloalkoxycarbonyloxy $C_{1-6}$alkyl esters like 1-cyclohexylcarbonyloxyethyl, acetoxymethoxy, or phosphoramidic cyclic esters.

As used herein, "tautomer" means other structural isomers that exist in equilibrium resulting from the migration of a hydrogen atom. For example, keto-enol tautomerism where the resulting compound has the properties of both a ketone and an unsaturated alcohol.

As used herein "stable compound" and "stable structure" are meant to indicate a compound that is sufficiently robust to survive isolation to a useful degree of purity from a reaction mixture, and formulation into an efficacious therapeutic agent.

Compounds of the invention further include hydrates and solvates.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^2H$ (also written as D for deuterium), $^3H$ (also written as T for tritium) $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro receptor labeling and competition assays, compounds that incorporate $^3H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is understood that a "radio-labeled compound" is a compound that has incorporated at least one radionuclide. In some embodiments the radionuclide is selected from the group consisting of $^3H$, $^{14}C$, $^{125}I$, $^{35}S$ and $^{82}Br$.

The anti-dementia treatment defined herein may be applied as a sole therapy or may involve, in addition to the compound of the invention, conventional chemotherapy. Such chemotherapy may include one or more of the following categories of agents: acetyl cholinesterase inhibitors, anti-inflammatory agents, cognitive and/or memory enhancing agents or atypical antipsychotic agents.

Such conjoint treatment may be achieved by way of the simultaneous, sequential or separate dosing of the individual components of the treatment. Such combination products employ the compounds of this invention.

Compounds of the present invention may be administered orally, parenteral, buccal, vaginal, rectal, inhalation, insufflation, sublingually, intramuscularly, subcutaneously, topically, intranasally, intraperitoneally, intrathoracially, intravenously, epidurally, intrathecally, intracerebroventricularly and by injection into the joints.

The dosage will depend on the route of administration, the severity of the disease, age and weight of the patient and other factors normally considered by the attending physician, when determining the individual regimen and dosage level as the most appropriate for a particular patient.

An effective amount of a compound of the present invention for use in therapy of dementia is an amount sufficient to symptomatically relieve in a warm-blooded animal, particularly a human the symptoms of dementia, to slow the progression of dementia, or to reduce in patients with symptoms of dementia the risk of getting worse.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances, which may also act as diluents, flavoring agents, solubilizers, lubricants, suspending agents, binders, or tablet disintegrating agents; it can also be an encapsulating material.

In powders, the carrier is a finely divided solid, which is in a mixture with the finely divided active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

Suitable carriers include magnesium carbonate, magnesium stearate, talc, lactose, sugar, pectin, dextrin, starch, tragacanth, methyl cellulose, sodium carboxymethyl cellulose, a low-melting wax, cocoa butter, and the like.

In some embodiments, the present invention provides a compound of formula I or a pharmaceutically acceptable salt thereof for the therapeutic treatment (including prophylactic treatment) of mammals including humans, it is normally formulated in accordance with standard pharmaceutical practice as a pharmaceutical composition.

In addition to the compounds of the present invention, the pharmaceutical composition of this invention may also contain, or be co-administered (simultaneously or sequentially) with, one or more pharmacological agents of value in treating one or more disease conditions referred to herein.

The term composition is intended to include the formulation of the active component or a pharmaceutically acceptable salt with a pharmaceutically acceptable carrier. For example this invention may be formulated by means known in the art into the form of, for example, tablets, capsules, aqueous or oily solutions, suspensions, emulsions, creams, ointments, gels, nasal sprays, suppositories, finely divided powders or aerosols or nebulisers for inhalation, and for parenteral use (including intravenous, intramuscular or infusion) sterile aqueous or oily solutions or suspensions or sterile emulsions.

Liquid form compositions include solutions, suspensions, and emulsions. Sterile water or water-propylene glycol solutions of the active compounds may be mentioned as an example of liquid preparations suitable for parenteral administration. Liquid compositions can also be formulated in solution in aqueous polyethylene glycol solution. Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

The pharmaceutical compositions can be in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms.

Compositions may be formulated for any suitable route and means of administration. Pharmaceutically acceptable carriers or diluents include those used in formulations suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy.

For solid compositions, conventional non-toxic solid carriers include, for example, pharmaceutical grades of mannitol, lactose, cellulose, cellulose derivatives, starch, magnesium stearate, sodium saccharin, talcum, glucose, sucrose, magnesium carbonate, and the like may be used. Liquid pharmaceutically administrable compositions can, for example, be prepared by dissolving, dispersing, etc, an active compound as defined above and optional pharmaceutical adjuvants in a carrier, such as, for example, water, saline aqueous dextrose, glycerol, ethanol, and the like, to thereby form a solution or suspension. If desired, the pharmaceutical composition to be administered may also contain minor amounts of non-toxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. Actual methods of preparing such dosage forms are known, or will be apparent, to those skilled in this art; for example, see Remington's Pharmaceutical Sciences, Mack Publishing Company, Easton, Pa., 15th Edition, 1975.

The compounds of the invention may be derivatised in various ways. As used herein "derivatives" of the compounds includes salts (e.g. pharmaceutically acceptable salts), any complexes (e.g. inclusion complexes or clathrates with compounds such as cyclodextrins, or coordination complexes with metal ions such as $Mn^{2+}$ and $Zn^{2+}$), free acids or bases, polymorphic forms of the compounds, solvates (e.g. hydrates), prodrugs or lipids, coupling partners and protecting groups. By "prodrugs" is meant for example any compound that is converted in vivo into a biologically active compound.

Salts of the compounds of the invention are preferably physiologically well tolerated and non toxic. Many examples of salts are known to those skilled in the art. All such salts are within the scope of this invention, and references to compounds include the salt forms of the compounds.

Where the compounds contain an amine function, these may form quaternary ammonium salts, for example by reaction with an alkylating agent according to methods well known to the skilled person. Such quaternary ammonium compounds are within the scope of the invention.

Compounds containing an amine function may also form N-oxides. A reference herein to a compound that contains an amine function also includes the N-oxide.

Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle.

N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comma* 1977, 7, 509-514) in which the amine compound is reacted with m-chloroperoxybenzoic acid (MCPBA), for example, in an inert solvent such as dichloromethane.

Where the compounds contain chiral centres, all individual optical forms such as enantiomers, epimers and diastereoisomers, as well as racemic mixtures of the compounds are within the scope of the invention.

Compounds may exist in a number of different geometric isomeric, and tautomeric forms and references to compounds include all such forms. For the avoidance of doubt, where a compound can exist in one of several geometric isomeric or tautomeric forms and only one is specifically described or shown, all others are nevertheless embraced by the scope of this invention.

The quantity of the compound to be administered will vary for the patient being treated and will vary from about 100 ng/kg of body weight to 100 mg/kg of body weight per day and preferably will be from 10 pg/kg to 10 mg/kg per day. For instance, dosages can be readily ascertained by those skilled in the art from this disclosure and the knowledge in the art. Thus, the skilled artisan can readily determine the amount of compound and optional additives, vehicles, and/or carrier in compositions and to be administered in methods of the invention.

Compounds of the present invention have been shown to inhibit beta secretase (including BACE) activity in vitro. Inhibitors of beta secretase have been shown to be useful in blocking formation or aggregation of Aβ peptide and therefore have beneficial effects in treatment of Alzheimer's Disease and other neurodegenerative diseases associated with elevated levels and/or deposition of Aβ peptide. Therefore, it is believed that the compounds of the present invention may be used for the treatment of Alzheimer disease and disease associated with dementia Hence, compounds of the present invention and their salts are expected to be active against age-related diseases such as Alzheimer, as well as other Aβ related pathologies such as Downs syndrome and β-amyloid angiopathy. It is expected that the compounds of the present invention would most likely be used as single agents but could also be used in combination with a broad range of cognition deficit enhancement agents.

Methods of Preparation

The present invention also relates to processes for preparing the compound of formula I as a free base or a pharmaceutically acceptable salt thereof. Throughout the following description of such processes it is understood that, where appropriate, suitable protecting groups will be added to, and subsequently removed from the various reactants and intermediates in a manner that will be readily understood by one skilled in the art of organic synthesis. Conventional procedures for using such protecting groups as well as examples of suitable protecting groups are for example described in "Protective Groups in Organic Synthesis", T. W. Greene, P. G. M Wutz, Wiley-Interscience, New York, 1999. It is understood that microwaves can be used for the heating of reaction mixtures.

EXAMPLES

General Methods

General procedures for making the compounds of the invention is as follows:

The invention will now be illustrated by the following non-limiting examples, in which, unless stated otherwise:

Temperatures are given in degrees Celsius (° C.); unless otherwise stated, operations were carried out at room or ambient temperature, that is, at a temperature in the range of 18-25° C.;

Organic solutions were dried over anhydrous magnesium sulfate; evaporation of solvent was carried out using a rotary evaporator under reduced pressure (600-4000 Pascals; 4.5-30 mm Hg) with a bath temperature of up to 60° C.;

Chromatography means flash chromatography on silica gel; thin layer chromatography (TLC) was carried out on silica gel plates;

In general, the course of reactions was followed by TLC or HPLC and reaction times are given for illustration only;

Melting points are uncorrected and (dec) indicate decomposition;

Final products had satisfactory proton nuclear magnetic resonance (NMR) spectra;

When given, NMR data is in the form of delta values for major diagnostic protons, given in parts per million (ppm) relative to tetramethylsilane (TMS) as an internal standard, determined at 300-500 MHz using deuterated chloroform (CDCl$_3$), dimethylsulphoxide (d$_6$-DMSO) or dimethylsulphoxide/TFA (d$_6$-DMSO/TFA) as solvent; conventional abbreviations for signal shape are used; for AB spectra the directly observed shifts are reported; coupling constants (J) are given in Hz; Ar designates an aromatic proton when such an assignment is made;

Reduced pressures are given as absolute pressures in pascals (Pa); elevated pressures are given as gauge pressures in bars;

Non-aqueous reactions were run under a nitrogen atmosphere

Solvent ratios are given in volume:volume (v/v) terms; and

Mass spectra (MS) were run using an automated system with atmospheric pressure chemical (APCI), electron impact (EI), atmospheric pressure photo ionisation (APPI) or electrospray (+ES) ionization. Generally, only spectra where parent masses are observed are reported. Sometimes the lowest mass major ion is reported for molecules where isotope splitting results in multiple mass spectral peaks (for example when chlorine is present).

Mass spectra were recorded using a Hewlett Packard 5988A and MicroMass Quattro-1 Mass Spectrometer and are reported as m/z for the parent molecular ion with its relative intensity.

LC-MS HPLC conditions: Column: Agilent Zorbax SB-C8 2 mm ID×50 mm Flow: 1.4 mL/min Gradient: 95% A to 90% B over 3 min. hold 1 minute ramp down to 95% A over 1 minute and hold 1 minute. Where A=2% acetonitrile in water with 0.1% formic acid and B=2% water in acetonitrile with 0.1% formic acid. UV-DAD 210-400 nm LC-MS HPLC conditions for Exact Mass data: Column: Agilent Zorbax SB-C8 2 mm ID×50 mm Flow: 1.4 mL/min Gradient: 95% A to 90% B over 11.5 min. hold 1 minute ramp down to 95% A over 1 minute and hold 1 minute. Where A=2% acetonitrile in water with 0.1% formic acid and B=2% water in acetonitrile with 0.1% formic acid. UV-DAD 210-400 nm.

Mass spectra were otherwise recorded using the following systems:

LC-MS analyses were performed on an LC-MS system consisting of a Waters Alliance 2795 HPLC, a Waters PDA 2996 diode array detector, a Sedex 75 ELS detector and a ZMD single quadrupole mass spectrometer. The mass spectrometer was equipped with an electrospray ion source (ES) operated in positive or negative ion mode. The capillary voltage was set to 3.2 kV and the cone voltage to 30 V, respectively. The mass spectrometer was scanned between m/z 100-600 by a scan time of 0.7 s. The diode array detector was scanned from 200-400 nm. The temperature of the ELS detector was adjusted to 40° C. and the pressure was set to 1.9 bar. For separation a linear gradient was applied starting at 100% A (A: 10 mM ammonium acetate in 5% acetonitrile) and ending at 100% B (B: acetonitrile). The column used was an X-Terra MS C8, 3.0 mm×50 mm, 3.5 µm (Waters) run at a flow rate of 1.0 mL/min. The column oven temperature was set to 40° C., or LC-MS analyses were performed on a LC-MS system consisting of a Waters Alliance 2795 HPLC, a Waters PDA 2996 diode array detector, a Sedex 75 ELS detector and a ZQ single quadrupole mass spectrometer. The mass spectrometer was equipped with an electrospray ion source (ES) operated in positive or negative ion mode. The capillary voltage was set to 3.2 kV and the cone voltage to 30 V, respectively. The mass spectrometer was scanned between m/z 100-700 with a scan time of 0.3 s. The diode array detector scanned from 200-400 nm. The temperature of the ELS detector was adjusted to 40° C. and the pressure was set to 1.9 bar. Separation was performed on an X-Terra MS C8, 3.0 mm×50 mm, 3.5 µm (Waters) run at a flow rate of 1 mL/min. A linear gradient was applied starting at 100% A (A: 10 mM ammonium acetate in 5% acetonitrile or 8 mM formic acid in 5% acetonitrile) ending at 100% B (B: acetonitrile). The column oven temperature was set to 40° C., or LC-MS analyses were preformed on a Water Acquity system with PDA (Waters 2996) and Waters ZQ mass spectrometer. Column; Acquity UPLC™ BEH $C_8$ 1.7 µm 2.1×50 mm. The column temperature was set to 65° C. A linear 2 min gradient from 100% A (A: 95% 0.01M ammonium acetate in MilliQ water and 5% acetonitrile) to 100% B (5% 0.01 M ammonium acetate in MilliQ water and 95% acetonitrile) was applied for LC-separation at flow rate 1.2 mL/min. The PDA was scanned from 210-350 nm and 254 nm was extracted for purity determination. The ZQ mass spectrometer was run with ES in pos/neg switching mode. The Capillary Voltage was 3 kV and the Cone Voltage was 30V or LC-MS analyses were performed on a LC-MS consisting of a Waters sample manager 2777C, a Waters 1525µ binary pump, a Waters 1500 column oven, a Waters ZQ single quadrupole mass spectrometer, a Waters PDA2996 diode array detector and a Sedex 85 ELS detector. The mass spectrometer was configured with an atmospheric pressure chemical ionisation (APCI) ion source which was further equipped with atmospheric pressure photo ionisation (APPI) device. The mass spectrometer scanned in the positive mode, switching between APCI and APPI mode. The mass range was set to m/z 120-800 using a scan time of 0.3 s. The APPI repeller and the APCI corona were set to 0.86 kV and 0.80 µA, respectively. In addition, the desolvation temperature (300° C.), desolvation gas (400 L/Hr) and cone gas (5 L/Hr) were constant for both APCI and APPI mode. Separation was performed using a Gemini column C18, 3.0 mm×50 mm, 3 µm, (Phenomenex) and run at a flow rate of 1 ml/min. A linear gradient was used starting at 100% A (A: 10 mM NH4OAc in 5% MeOH) and ending at 100% B (MeOH). The column oven temperature was set to 40° C. or LC-MS analyses were performed on a LC-MS consisting of a Waters sample manager 2777C, a Waters 1525µ binary pump, a Waters 1500 column oven, a Waters ZQ single quadrupole mass spectrometer, a Waters PDA2996 diode array detector and a Sedex 85 ELS detector. The mass spectrometer was equipped with an electrospray ion source (ES) operated in positive or negative ion mode. The mass spectrometer scanned between m/z 100-700 with a scan time of 0.3 s. The capillary voltage was set to 3.4 kV and the cone voltage was set to 30 V, respectively. The diode array detector scanned from 200-400 nm. The temperature of the ELS detector was adjusted to 40° C. and the pressure was set to 1.9 bar. For separation a linear gradient was applied starting at 100% A (A: 10 mM NH4OAc in 5% CH3CN or 8 mM HCOOH in 5% CH3CN) and ending at 100% B (B: CH3CN). The column used was a Gemini C18, 3.0 mm×50 mm, 3 µm, (Phenomenex) which was run at a flow rate of 1 ml/min. The column oven temperature was set to 40° C.

GC-MS: Compound identification was performed on a GC-MS system (GC 6890, 5973N MSD) supplied by Agilent Technologies. The column used was a VF-5 MS, ID 0.25 mm×15 m, 0.25 µm (Varian Inc.). A linear temperature gradient was applied starting at 40° C. (hold 1 min) and ending at 300° C. (hold 1 min), 25° C./minute. The mass spectrometer was equipped with a chemical ionisation (CI) ion source and the reactant gas was methane. The mass spectrometer was equipped with an electron impact (EI) ion source and the electron voltage was set to 70 eV. The mass spectrometer scanned between m/z 50-500 and the scan speed was set to 3.25 scan/s.

Preparative chromatography was run according to:

Agilent preparative reverse phase HPLC conditions: Compounds were purified using a Phenomenex Luna C18 reverse phase column (250×21 mm, 10 micron particle size). To one skilled in the art, it is appreciated that the crude samples can be dissolved in methanol, DMF, or a wide range of acetonitrile/water mixtures with and without TFA, methanol, or DMF in concentrations ranging from dilute to concentrated. All purifications were run using 220 nm wavelength for collecting fractions. Retention time ($t_R$)=min. Agilent Gradient 1 (AG1): 0% acetonitrile with 0.1% TFA 3 min, ramp 0-50% acetonitrile/water with 0.1% TFA over 12 min, hold at 50% acetonitrile/water for 3 min, 50-100% acetonitrile/water with 0.1% TFA over 7 min, flow rate of 40 ml/min. Agilent Gradient 2 (AG2): 5-100% acetonitrile/water with 0.1% TFA over 20 min, flow rate of 40 mL/min. Agilent Gradient 3 (AG3): 0% acetonitrile with 0.1% TFA 3 min, ramp 0-100% acetonitrile/water with 0.1% TFA over 25 min, flow rate of 40 ml/min or Preparative chromatography was run on Waters auto purification HPLC with a diode array detector. Column: XTerra MS C8, 19×300 mm, 10 µm. Gradient with acetonitrile/0.1 M ammonium acetate in 5% acetonitrile in MilliQ Water. Flow rate: 20 mL/min.

Alternatively, purification was achieved on a semi preparative Shimadzu LC-8A HPLC with a Shimadzu SPD-10A UV-vis.-detector equipped with a Waters Symmetry® column (C18, 5 µm, 100 mm×19 mm). Gradient with acetonitrile/0.1% trifluoroacetic acid in MilliQ Water. Flow rate: 10 mL/min. Alternatively, another column was used; Atlantis C18 19×100 mm, 5 µm column. Gradient with acetonitrile/0.1 M ammonium acetate in 5% acetonitrile in MilliQ Water. Flow rate: 15 mL/min, or Preparative-HPLC was run on a Waters FractionLynx system with a Autosampler combined Automated Fraction Collector (Waters 2767), Gradient Pump (Waters 2525), Regeneration Pump (Waters 600), Make Up Pump (Waters 515), Waters Active Splitter, Column Switch (Waters CFO), PDA (Waters 2996) and Waters ZQ mass spectrometer. Column; XBridge™ Prep C8 5 μm OBD™ 19×100 mm, with guard column; XTerra® Prep MS C8 10 μm 19×10 mm Cartridge. A gradient from 100% A (95% 0.1 M ammonium acetate in MilliQ water and 5% acetonitrile) to 100% B (100% acetonitrile) was applied for LC-separation at flow rate 25 mL/min. The PDA was scanned from 210-350 nm. The ZQ mass spectrometer was run with ES in positive mode. The Capillary Voltage was 3 kV and the Cone Voltage was 30V. Mixed triggering, UV and MS signal, determined the fraction collection.

HPLC analyses were performed on an Agilent HP1100 system consisting of a G1379A Micro Vacuum Degasser[1], a G1312A Binary Pump[2], a G1367 Well-Plate Autosampler[3], a G1316A Thermostatted Column Compartment and a G1315B Diode Array Detector. The diode array detector was scanned from 210 to 300 nm, step and peak width were set to 2 nm and 0.05 min, respectively. The column used was an X-Terra MS C8, 3.0×100 mm, 3.5 μm (Waters) run at a flow rate of 1.0 ml/min. The column oven temperature was set to 40° C. A linear gradient was applied, starting at 100% A (A: 10 mM NH$_4$OAc in 5% CH3CN) and ending at 100% B (B: CH3CN).

Normal phase chromatography conditions: Flash chromatography employed as a method for purification for selected intermediates. Isco CombiFlash Sq 16× instrument: prepackaged disposable RediSep SiO$_2$ stationary phase columns (4, 12, 40, 120 gram sizes) with gradient elution at 5-125 mL/min of selected bi-solvent mixture, UV detection (190-760 nm range) or timed collection, 0.1 mm flow cell path length or Merck Silica gel 60 (0.040-0.063 mm) was used.

$^1$H NMR spectra were recorded in the indicated deuterated solvent at 400 MHz, unless stated otherwise, using a Bruker DPX400 NMR spectrometer operating at 400 MHz equipped with a 4-nucleus probehead with Z-gradients or a Bruker av400 NMR spectrometer equipped with a 3 mm flow injection SEI$^1$H/D-$^{13}$C probehead with Z-gradients, using a BEST 215 liquid handler for sample injection. Resonance multiplicities are denoted s, d, t, q, m and br for singlet, doublet, triplet, quartet, multiplet, and broad respectively.

Microwave heating instrumentation: A Personal Chemistry Smith Synthesizer unit (monomodal, 2.45 GHz, 300 W max), a Creator, a Initiator or a Smith Synthesizer Single-mode microwave cavity producing continuous irradiation at 2450 MHz was utilized for microwave heating of reactions.

Commercial reagents were used without further purification.

Room temperature refers to 20-25° C.

Terms and abbreviations: Solvent mixture compositions are given as volume percentages or volume ratios. In cases where the NMR spectra are complex; only diagnostic signals are reported. atm: atmospheric pressure; Boc: t-butoxycarbonyl; Cbz: benzyloxycarbonyl; DCM: dichloromethane; DIPEA: diisopropylethylamine; DMF: N;N-dimethyl formamide; DMSO: dimethyl sulfoxide; Et$_2$O: diethyl ether; EtoAc: ethyl acetate; h: hour(s); HPLC: high pressure liquid chromatography; minute(s): min.; NMR: nuclear magnetic resonance; psi: pounds per square inch; TFA: trifluoroacetic acid; THF: tetrahydrofuran; ACN: acetonitrile.

Compounds have been named using ACD/Name, version 8.08, or version 9.0 software from Advanced Chemistry Development, Inc. (ACD/Labs), Toronto ON, Canada, www.acdlabs.com, 2004 and 2005; Beilstein AutoNom version 4.01, MDL Information Systems GmbH, Frankfurt Germany or ChemDraw Ultra version 9.0, software from CambridgeSoft Corporation, Cambridge, Mass., USA, www.cambridgesoft.com.

Scheme 1

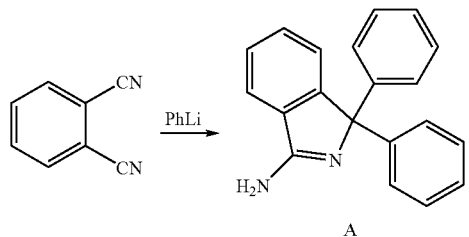

Example 1

3,3-Diphenyl-3H-isoindol-1-ylamine (Scheme #1, A)

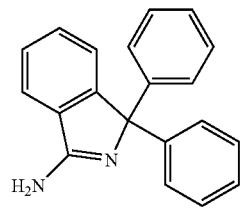

To a −78° C. cooled solution of 1,2-dicyanobenzene (200 mg, 1.56 mmol) in tetrahydrofuran (10 mL) was added 1.8 M phenyllithium in di-n-butylether (1.73 mL, 3.12 mmol). After 30 minutes the reaction was warmed to room temperature and quenched by adding water (1.5 mL) and the solvent removed under reduced pressure. The brown solid was purified by reverse-phase HPLC using acetonitrile/water as the mobile phase on a C18 column with the following gradient:

| time | % water | % acetonitrile |
| --- | --- | --- |
| 0 | 80 | 20 |
| 4 | 78 | 22 |
| 15.5 | 30 | 70 |
| 16.5 | 10 | 90 |
| 17 | 80 | 20 |
| 19 | 80 | 20 |

A second purification was required using preparative SFC using a Berger pyridyl column with a gradient of 10-35% MeOH.CO$_2$ for 8 min (RT=5.36 min) to give the title compound as a white solid (37 mg, 8%). $^1$H NMR (300 MHz, DMSO-d$_6$) δ 7.77-7.73 (m, 1 H), 7.64 (t, J=4.3 Hz, 1 H), 7.41 (dt, J=8.8, 4.9 Hz, 2H), 7.30-7.14 (m, 10 H); MS (TOF ES+) m/z 285 [M+1]$^+$; t$_R$=6.65 min. Exact Mass: Calculated 285.1392, Found 285.1315.

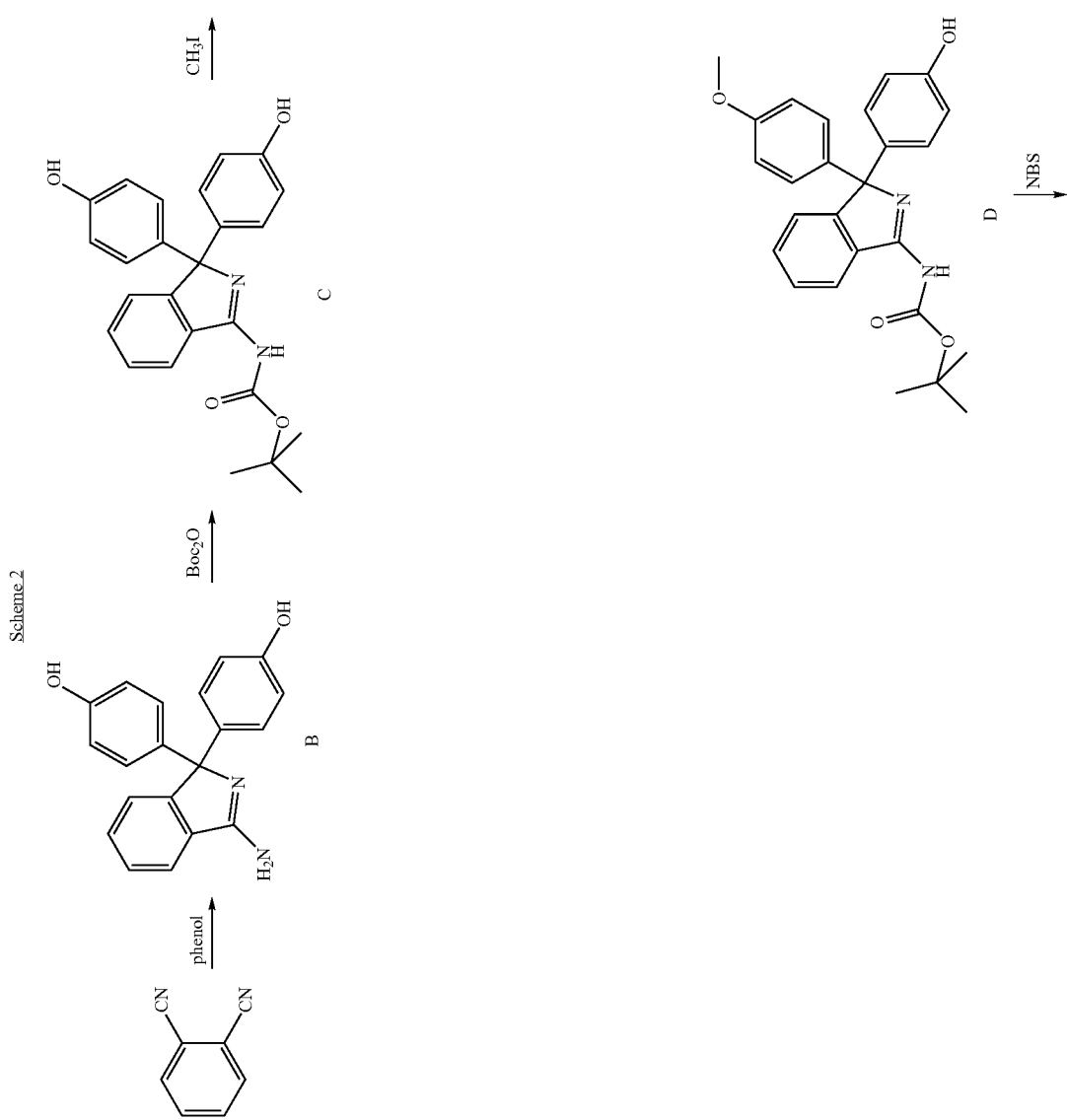

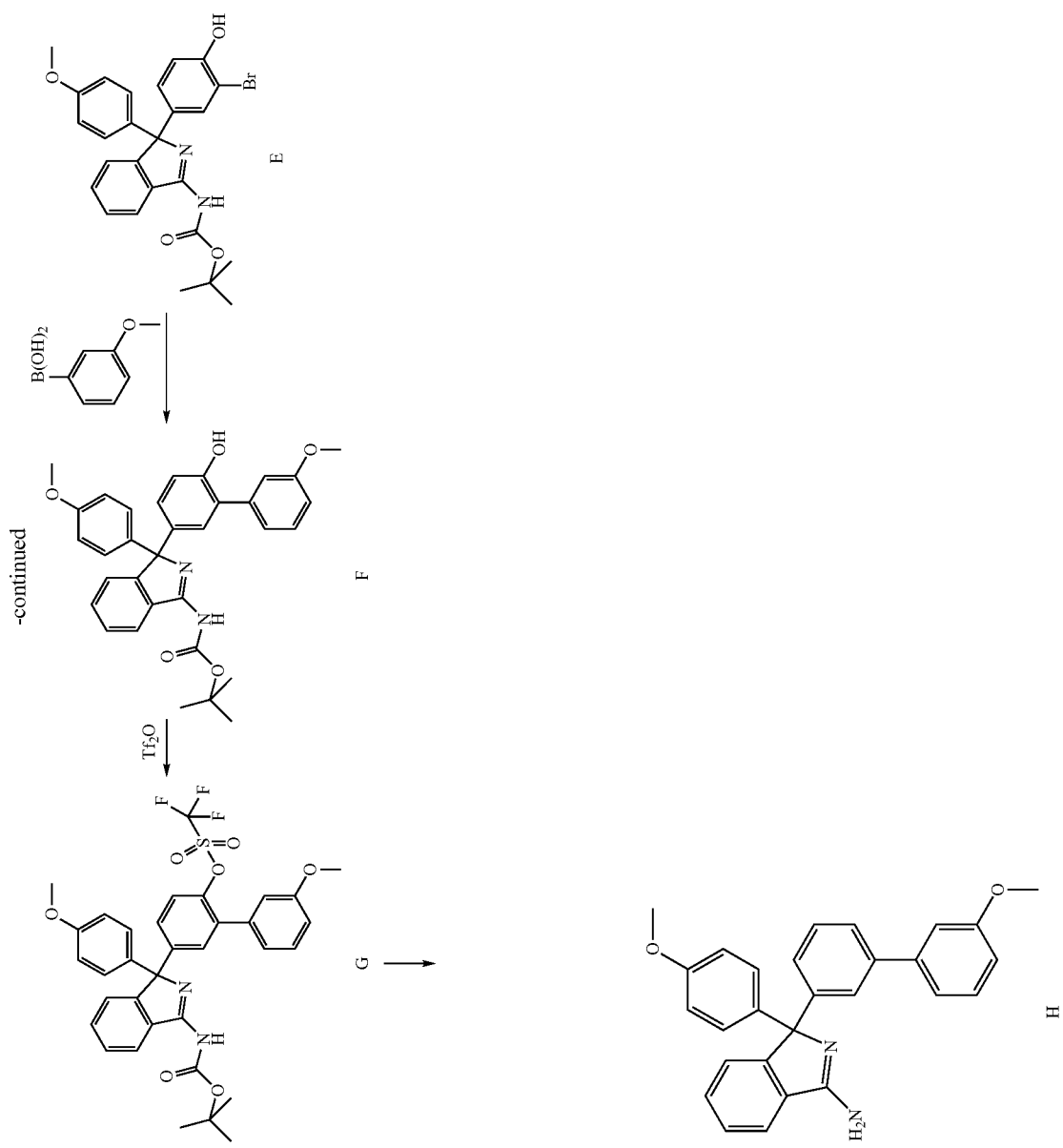

Example 2

3-(3'-Methoxy-biphenyl-3-yl)-3-(4-methoxy-phenyl)-3H-isoindol-1-ylamine trifluoroacetate (Scheme #2, H)

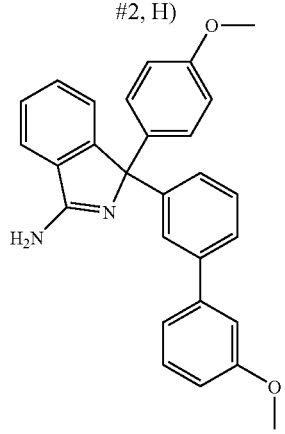

To trifluoro-methanesulfonic acid 5-[3-tert-butoxycarbonylamino-1-(4-methoxy-phenyl)-1H-isoindol-1-yl]-3'-methoxy-biphenyl-2-yl ester (Scheme #2, G) (50 mg, 0.075 mmol) was added potassium phosphate (32 mg, 0.15 mmol), dichlorobis(triphenylphosphine)palladium(II) (16 mg, 0.022 mmol), and 1,2-dimethoxyethane: water:ethanol (7:3:2, 2.0 mL). The reaction was heated in a microwave at 125° C. for 15 minutes, more dichlorobis(triphenylphosphine)palladium(II) (16 mg, 0.022 mmol) was added, and the reaction reheated at 125° C. for 15 minutes. The solvent was removed under reduced pressure and the crude material dissolved in acetonitrile/water with trifluoroacetic acid (75:25:0.1, 1.0 mL), the insoluble material was filtered off and the filtrate was purified using RP-HPLC AG1 ($t_R$=21.2 min). The combined purified fractions were lyophilized to give the title compound (9.0 mg). $^1$H NMR (300 MHz, DMSO-$d_6$/TFA-d) δ 8.33 (d, J=7.7 Hz, 1 H) 7.87 (m, 2 H), 7.22-7.13 (m, 4 H), 7.76-7.64 (m, 2 H), 7.59-7.47 (m, 2 H), 7.40-7.29 (m, 2 H), 6.97 (d, J=8.8 Hz, 3 H), 3.81 (s, 3 H), 3.76 (s, 3 H); MS (ES+) m/z 421 [M+1]$^+$; $t_R$=2.08 min.

Trifluoro-methanesulfonic acid 5-[3-tert-butoxycarbonylamino-1-(4-methoxy-phenyl)-1H-isoindol-1-yl]-3'-methoxy-biphenyl-2-yl ester (Scheme #2, G)

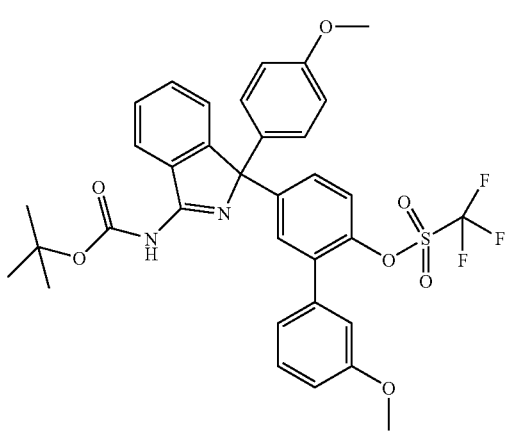

To [3-(6-hydroxy-3'-methoxy-biphenyl-3-yl)-3-(4-methoxy-phenyl)-3H-isoindol-1-yl]-carbamic acid tert-butyl ester (Scheme #2, F) (196 mg, 0.365 mmol) in an ice cold solution of dichloromethane was added pyridine (60.0 uL, 0.730 mmol) followed by trifluoromethanesulfonic anhydride (93 uL, 0.438 mmol). After stirring for 30 minutes the reaction was removed of solvent under reduced pressure and the crude mixture was purified on 20 g silica eluting with 5% acetone/dichloromethane to give the title compounds as a white solid (226 mg, 93%). $^1$H NMR (300 MHz, DMSO-$d_6$) δ 7.86 (d, J=7.5 Hz, 1 H), 7.72-7.64 (m, 2 H), 7.58-7.36 (m, 5 H), 7.28-7.20 (m, 2 H), 7.02-6.84 (m, 5 H), 3.77 (s, 3 H), 3.72 (m, 3 H), 1.49 (m, 9 H); MS (APCI+) m/z 669 [M+1]$^+$; $t_R$=2.94 min.

Example 3

Trifluoro-methanesulfonic acid 5-[3-amino-1-(4-methoxy-phenyl)-1H-isoindol-1-yl]-3'-methoxy-biphenyl-2-yl ester trifluoroacetate

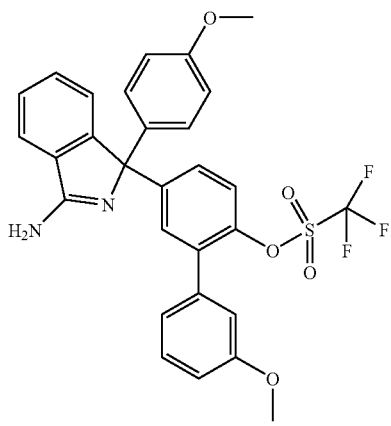

To trifluoro-methanesulfonic acid 5-[3-tert-butoxycarbonylamino-1-(4-methoxy-phenyl)-1H-isoindol-1-yl]-3'-methoxy-biphenyl-2-yl ester (Scheme #2, G) (22.5 mg, 33.6 umol) was added trifluoroacetic acidin dichloromethane (10%, 1-2 mL) and reaction stirred 60 minutes. The solvents were removed under reduced pressure and the resulting gum put under high vacuum at 50° C. over night to give the title compound as a waxy solid (22.9 mg). $^1$H NMR (300 MHz, DMSO-$d_6$) δ 8.30 (d, J=7.7 Hz, 1 H), 7.88 (q, J=8.2 Hz, 2 H), 7.77-7.71 (m, 1 H), 7.62-7.59 (m, 1 H), 7.49-7.38 (m, 3 H), 7.20-7.16 (m, 2 H), 7.05-6.96 (m, 5 H), 3.78 (s, 3 H), 3.74 (s, 3 H); MS (APCI+) m/z 569 [M+1]$^+$; $t_R$=2.64 min.

Example 4

5-[3-Amino-1-(4-methoxy-phenyl)-1H-isoindol-1-yl]-3'-methoxy-biphenyl-2-ol trifluoroacetate

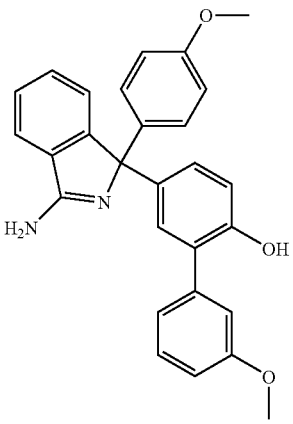

To [3-(6-hydroxy-3'-methoxy-biphenyl-3-yl)-3-(4-methoxy-phenyl)-3H-isoindol-1-yl]-carbamic acid tert-butyl ester (Scheme #2, F) (10.0 mg, 18.6 umol) was added trifluoroacetic acid in dichloromethane (10%, 1-2 mL) and reaction stirred 60 minutes. The solvents were removed under reduced pressure and the resulting gum put under high vacuum at 50° C. over night to give the title compound as a waxy solid (10.4 mg). $^1$H NMR (300 MHz, DMSO-$d_6$) δ 8.26 (d, J=7.8 Hz, 1 H), 7.85-7.67 (m, 3 H), 7.32-7.18 (m, 4 H), 7.03-6.85 (m, 8 H), 3.74 (d, J=2.7 Hz, 6 H); MS (APCI+) m/z 437 [M+1]$^+$; $t_R$=2.14 min.

[3-(6-Hydroxy-3'-methoxy-biphenyl-3-yl)-3-(4-methoxy-phenyl)-3H-isoindol-1-yl]-carbamic acid tert-butyl ester (Scheme #2, F)

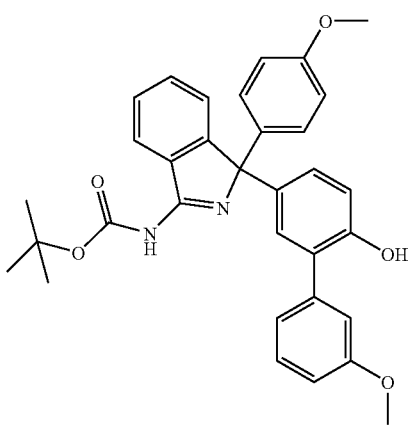

To [3-(3-bromo-4-hydroxy-phenyl)-3-(4-methoxy-phenyl)-3H-isoindol-1-yl]-carbamic acid tert-butyl ester (Scheme #2, E) (364 mg, 0.72 mmol) was added potassium phosphate (303 mg, 1.43 mmol), 3-methoxyphenylboronic acid (163 mg, 1.07 mmol), dichlorobis(triphenylphosphine) palladium(II) (50 mg, 0.072 mmol), and 1,2-dimethoxyethane: water:ethanol (7:3:2, 20 mL). The reaction was placed in a hot bath and heated to reflux. After 10 minutes additional 3-methoxyphenylboronic acid (60 mg) and dichlorobis(triphenylphosphine)palladium(II) (25 mg) were added and the reaction refluxed for 30 minutes. Ethyl acetate was added, salts filtered off, and the filtrate removed of solvent under reduced pressure. The mixture was purified three times; first using 20 g silica eluting with 5% acetone/dichloromethane, second using 20 g silica eluting with dichloromethane then 5% acetone/dichloromethane, and third using 40 g silica eluting with a gradient of hexanes to 50% ethyl acetate/hexanes. The product was removed of solvent under reduced pressure to give the title compounds as a white solid which was placed under high vacuum over night (208 mg, 54%). $^1$H NMR (300 MHz, DMSO-$d_6$/TFA-d) δ 8.62 (d, J=7.9 Hz, 1 H), 7.88 (t, J=7.6 Hz, 1 H), 7.78-7.69 (m, 2 H), 7.34-7.29 (m, 4 H), 7.10-7.02 (m, 3 H), 6.95-6.86 (m, 4 H), 3.76 (d, J=2.1 Hz, 6 H), 1.62 (s, 9 H); MS (APCI+) m/z 537 [M+1]$^+$; $t_R$=2.50 min.

Example 5

4-[3-Amino-1-(4-methoxy-phenyl)-1H-isoindol-1-yl]-2-bromo-phenol trifluoroacetate

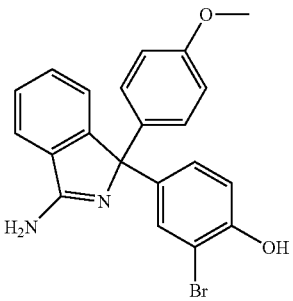

To [3-(3-bromo-4-hydroxy-phenyl)-3-(4-methoxy-phenyl)-3H-isoindol-1-yl]-carbamic acid tert-butyl ester (Scheme #2, E) (9.5 mg, 18.6 umol) was added trifluoroacetic acid in dichloromethane (10%, 1-2 mL) and reaction stirred 30 minutes. The solvents were removed under reduced pressure and the resulting gum put under high vacuum at 50° C. over night to give the title compound as a waxy solid (10.3 mg). $^1$H NMR (300 MHz, DMSO-$d_6$) δ 8.26 (d, J=7.7 Hz, 1 H), 7.83 (t, J=7.2 Hz, 1 H), 7.76-7.68 (m, 2 H), 7.30 (d, J=2.3 Hz, 1 H), 7.16 (d, J=8.8 Hz, 2 H), 7.04 (dd, J=8.5, 2.3 Hz, 1 H), 6.97-6.93 (m, 3 H), 3.75 (s, 3 H); MS (APCI+) m/z 409 [M+1]$^+$; $t_R$=1.95 min.

[3-(3-Bromo-4-hydroxy-phenyl)-3-(4-methoxy-phenyl)-3H-isoindol-1-yl]-carbamic acid tert-butyl ester (Scheme #2, E)

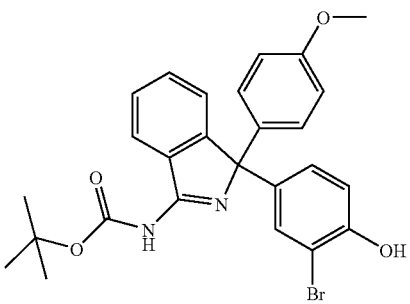

To an ice cold solution of [3-(4-hydroxy-phenyl)-3-(4-methoxy-phenyl)-3H-isoindol-1-yl]-carbamic acid tert-butyl ester (Scheme #2, D) (663 mg, 1.540 mmol) in dry chloroform was added N-bromosuccinimide (274 mg, 1.540 mmol) portion-wise over 30 minutes and the reaction stirred for 25 minutes. The solvent was removed under reduced pressure and the mixture chromatographed on 80 g silica eluting with 5% acetone in dichloromethane.

The combined purified fractions were removed of solvents under reduced pressure and placed under high vacuum overnight to give the title compound as a tan solid (390 mg, 50%).
$^1$H NMR (300 MHz, DMSO-$d_6$/TFA-d) δ 8.63 (d, J=8.0 Hz, 1 H), 7.88 (t, J=7.3 Hz, 1 H), 7.75-7.70 (m, 2 H), 7.48 (d, J=2.3 Hz, 1 H), 7.29 (d, J=8.9 Hz, 2 H), 7.07 (dd, J=8.6, 2.3 Hz, 1 H), 6.94 (dd, J=8.8, 2.4 Hz, 3 H), 3.77 (s, 3 H), 1.62 (s, 9 H); MS (APCI+) m/z 509 [M+1]$^+$; $t_R$=2.27 min.

[3-(4-Hydroxy-phenyl)-3-(4-methoxy-phenyl)-3H-isoindol-1-yl]-carbamic acid tert-butyl ester (Scheme #2, D)

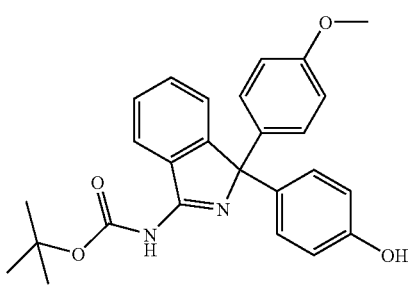

To a solution of [3,3-bis-(4-hydroxy-phenyl)-3H-isoindol-1-yl]-carbamic acid tert-butyl ester (Scheme #2, C) (5.0 g, 12.0 mmol) and cesium carbonate (3.9 mL, 12.0 mmol) in N,N-dimethyl formamide (100 mL) was added iodomethane (0.7 mL, 11.4 mmol) in N,N-dimethyl formamide (3 mL) and the mixture stirred at ambient temperature for 18 hours. The N,N-dimethyl formamide was removed under reduced pressure to yield an amber syrup. To this was added ethyl acetate (250 mL) and the mixture stirred vigorously for 0.5 h. The insolubles were filtered and the filtrate concentrated under reduced pressure to yield a tan solid. The crude compound was purified using flash chromatography (silica; 90:10 dichloromethane:ethyl acetate) to give the title compound as a white solid (2.11 g, 34%). $^1$H NMR (300 MHz, DMSO-$d_6$) δ 7.83 (d, J=7.5 Hz, 1 H), 7.64 (t, J=7.3 Hz, 1 H), 7.55-7.49 (m, 2 H), 7.16 (d, J=8.8 Hz, 2 H), 7.04 (d, J=8.6 Hz, 2 H), 6.89 (d, J=8.8 Hz, 2 H), 6.71 (d, J=8.7 Hz, 2 H), 3.71 (d, J=8.3 Hz, 3 H), 1.46 (s, 9 H); MS (APCI+) m/z 430 [M+1]$^+$; $t_R$=2.20 min.

[3,3-Bis-(4-hydroxy-phenyl)-3H-isoindol-1-yl]-carbamic acid tert-butyl ester (Scheme #2, C):

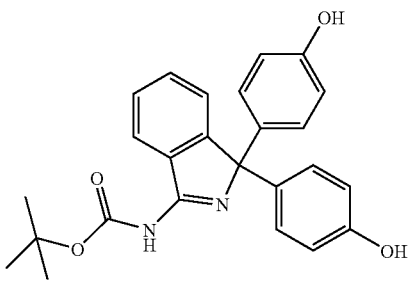

To a solution of 4,4'-(3-amino-isoindole-1,1-diyl)-bis-phenol (Scheme #2, B, Example 6) (5.0 g, 15.8 mmol) and triethylamine (6.6 mL, 47.4 mmol) in N,N-dimethyl formamide (100 mL) was added di-tert-butyl-dicarbonate (3.8 g, 17.4 mmol) and the mixture stirred at ambient temperature for 18 hours. The N,N-dimethyl formamide was removed under reduced pressure to yield an orange syrup. To this was added dichloromethane (200 mL) and the resulting precipitate was filtered to give the title compound as a pale pink solid (6.1 g, 92%). $^1$H NMR (300 MHz, DMSO-$d_6$/TFA-d) δ 8.59 (d, J=7.8 Hz, 1 H), 7.86 (t, J=7.2 Hz, 1 H), 7.68 (m, 2 H), 7.14 (d, J=8.7 Hz, 4 H), 6.75 (d, J=8.7 Hz, 4 H), 1.61 (s, 9 H); MS (APCI+) m/z 417 [M+1]$^+$; $t_R$=1.48 min.

Example 6

4,4'-(3-Amino-isoindole-1,1-diyl)-bis-phenol (Scheme #2, B)

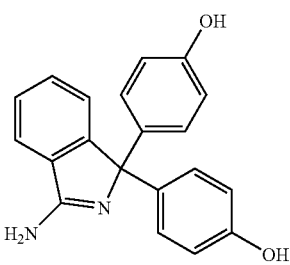

A mixture of phenol (294 g, 3.10 moles) and 1,2-dicyanobenzene (20 g, 0.16 moles) was heated to reflux at 185° C. for 3 hours. The reaction was cooled to room temperature and diluted with 2:1 ether:hexane (1.5 L). The resulting precipitate was stirred for 1 hour and filtered. The isolated filter cake was triturated with dichloromethane (0.6 L), stirred for 0.5 hour and filtered. The crude compound was purified using flash chromatography (silica; 65:30:5 dichloromethane:acetone: methanol with 0.1% NH$_4$OH, 8 L; 50:50 dichloromethane:methanol with 0.1% NH$_4$OH, 4 L; methanol with 0.1% NH$_4$OH, 1 L) to give the title compound as a pale yellow solid (9 g, 20%). $^1$H NMR (300 MHz, DMSO-$d_6$/TFA-d) δ 8.47 (d, J=7.8 Hz, 1 H), 7.91 (t, J=7.2 Hz, 1 H), 7.87 (m, 2 H), 7.25 (d, J=8.7 Hz, 4 H), 6.98 (d, J=8.7 Hz, 4 H); MS (ES+) m/z 317 [M+1]$^+$; $t_R$=1.24 min.

Examples 7-9

The following compounds were prepared using the route described above:

TABLE 1

| Ex. | Compound | Structure | NMR | m/z M + 1 (Ionization) | LC $t_R$ (min) |
|---|---|---|---|---|---|
| 7 | 4-[3-Amino-1-(4-methoxy-phenyl)-1H-isoindol-1-yl]-2-pyridin-3-yl-phenol trifluoroacetate | 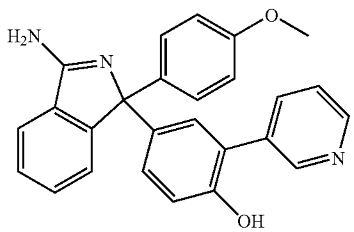 | $^1$H NMR (300 MHz, DMSO-d6) δ 8.72 (s, 1 H), 8.54 (s, 1 H), 8.27 (d, J = 7.7 Hz, 1 H), 8.00 (d, J = 7.9 Hz, 1 H), 7.86-7.80 (m, 2 H), 7.73-7.68 (m, 1 H), 7.53-7.49 (m, 1 H), 7.21-7.10 (m, 3 H), 7.01-6.92 (m, 4 H), 3.74 (s, 3 H), | 408 (APCI+) | 1.60 |
| 8 | 4-[3-Amino-1-(4-methoxy-phenyl)-1H-isoindol-1-yl]-2-pyrimidin-5-yl-phenol trifluoroacetate | 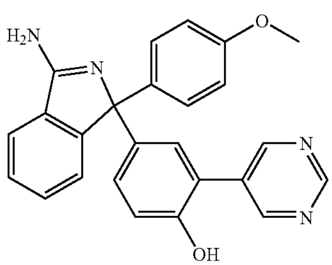 | $^1$H NMR (300 MHz, DMSO-d6) δ 9.11 (s, 1 H), 8.92 (s, 2 H), 8.26 (d, J = 7.6 Hz, 1 H), 7.83 (d, J = 3.9 Hz, 1 H), 7.73-7.66 (m, 1 H), 7.28 (d, J = 2.4 Hz, 1 H), 7.19-7.14 (m, 2 H), 7.03-6.99 (m, 2 H), 6.94 (d, J = 8.8 Hz, 2 H), 6.75 (d, J = 8.7 Hz, 1 H), 3.74 (s, 3 H). | 409 (APCI+) | 1.82 |
| 9 | 3-(4-Methoxy-phenyl)-3-(3-pyridin-3-yl-phenyl)-3H-isoindol-1-ylamine trifluoroacetate | 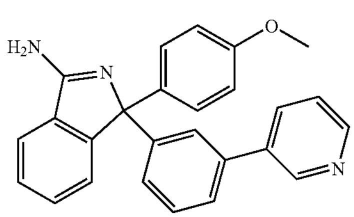 | $^1$H NMR (500 MHz, DMSO) δ 8.85 (s, 1 H), 8.60 (s, 1 H), 8.29 (d, J = 7.9 Hz, 1 H), 8.05 (d, J = 8.0 Hz, 1 H) 7.90 (d, J = 7.7 Hz, 1 H), 7.85 (t, J = 7.6 Hz, 1 H), 7.76-7.71 (m, 2 H), 7.61 (s, 1 H), 7.56-7.50 (m, 2 H), 7.37 (d, J = 7.9 Hz, 1 H), 7.17 (d, J = 8.7 Hz, 2 H), 6.96 (d, J = 8.8 Hz, 2 H), 3.74 (s, 3 H). | 392 (ES+) | 1.51 |

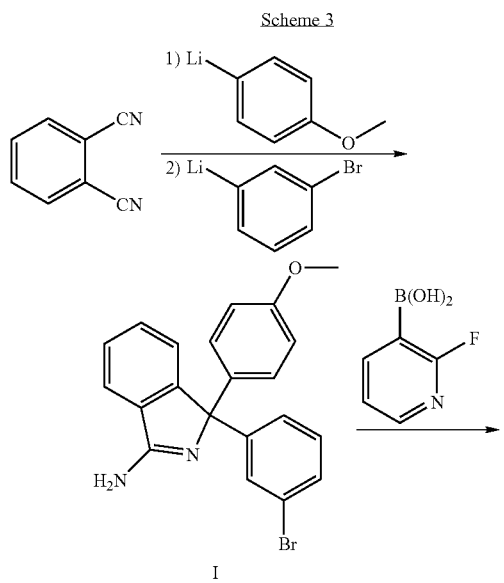

Example 10

3-[3-(2-Fluoro-pyridin-3-yl)-phenyl]-3-(4-methoxy-phenyl)-3H-isoindol-1-ylamine trifluoroacetate (Scheme #3, J)

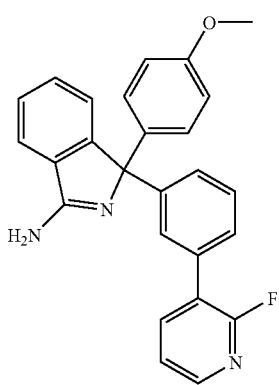

To 3-(3-bromo-phenyl)-3-(4-methoxy-phenyl)-3H-isoindol-1-ylamine (Scheme #3, I, Example 11) (50 mg, 0.13 mmol) was added potassium phosphate (81 mg, 0.38 mmol), 2-fluoropyridyl-3-boronic acid (27 mg, 0.19 mmol), dichlorobis(triphenylphosphine)palladium(II) (9 mg, 0.013 mmol), and 1,2-dimethoxyethane: water:ethanol (7:3:2, 2.0 mL). The reaction was heated in a microwave reactor at 100° C. for 15 minutes. The reaction was filtered and the filtrate was removed of solvent under reduced pressure. The resulting residue was dissolved in acetonitrile/water with trifluoroacetic acid, (75:25:0.1, 2.0 mL), and purified using RP-HPLC AG2 ($t_R$=15.2 min). The combined purified fractions were lyophilized to give the title compound (40.5 mg, 61%). $^1$H NMR (500 MHz, DMSO) δ 8.29 (d, J=7.8 Hz, 1 H), 8.25 (d, J=4.6 Hz, 1 H), 8.08-8.04 (m, 1 H), 7.84 (d, J=4.0 Hz, 2 H), 7.75-7.71 (m, 1 H), 7.64 (d, J=7.6 Hz, 1 H), 7.55 (t, J=7.8 Hz, 2 H), 7.51 (s, 1 H), 7.48-7.45 (m, 2 H), 7.38 (d, J=8.0 Hz, 1 H), 7.17 (d, J=8.9 Hz, 1 H), 6.96 (d, J=8.9 Hz, 1 H), 3.75 (s, 3 H); MS (ES+) m/z 537 [M+1]$^+$; $t_R$=2.50 min.

Example 11

3-(3-Bromo-phenyl)-3-(4-methoxy-phenyl)-3H-isoindol-1-ylamine (Scheme #3, I)

To a −78° C. cooled solution of 4-bromoanisol (489 uL, 3.90 mmol) in tetrahydrofuran (20 mL) was added 1.6 M n-butyllithium in hexanes (2.44 mL, 3.90 mmol) and the solution stirred 10 minutes. This was cannulated into a −78° C. solution of 1,2-dicyanobenzene (500 mg, 3.90 mmol) in tetrahydrofuran (20 mL). To a separate round bottom flask was added 1,3-dibromobenzene (471 uL, 3.90 mmol) and tetrahydrofuran (20 mL) and the solution cooled in a −78° C. bath. To this was added 1.6 M n-butyllithium in hexanes (2.44 mL, 3.90 mmol) and the solution stirred 10 minutes. This anion was cannulated into the 1,2-dicyanobenzene reaction and the mixture was stirred at −78° C. for 2 hours. The reaction was poured into saturated ammonium chloride (100 mL) and extracted with ethyl acetate twice. The combined organic layers were washed with aqueous saturated sodium chloride, dried over magnesium sulfate and removed of solvent under reduced pressure to give an amber oil. The amber oil was placed on a 40 g silica gel column eluted with dichloromethane/methanol (9:1) and the combined purified fractions were removed of solvent under reduced pressure to give the titled compound as a tan solid (170 mg, 11%).

$^1$H NMR (300 MHz, DMSO-$d_6$/TFA-d) δ 8.33 (d, J=7.7 Hz, 1H), 7.89-7.71 (m, 3 H), 7.60 (d, J=7.7 Hz, 1 H), 7.48 (s, 1 H), 7.41-7.29 (m, 2 H), 7.17 (d, J=8.8 Hz, 2 H), 6.97 (d, J=8.8 Hz, 2 H), 3.77 (s, 3 H); MS (ES+) m/z 393 [M+1]$^+$; $t_R$=1.89 min.

Examples 12-25

The following compounds were prepared using the route described above:

TABLE 2

| Ex | Compound | Structure | NMR | m/z M + 1 (Ionization) | LC $t_R$ (min) |
|---|---|---|---|---|---|
| 12 | 3-(4-Methoxy-phenyl)-3-[3-(5-methoxy-pyridin-3-yl)-phenyl]-3H-isoindol-1-ylamine trifluoroacetate | 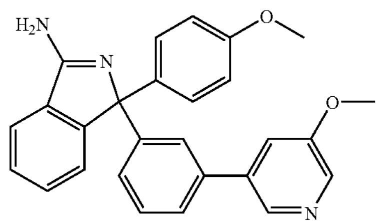 | $^1$H NMR (500 MHz, DMSO) δ 8.83-8.78 (m, 1 H), 8.74-8.68 (m, 1 H), 8.38-8.33 (m, 2 H), 7.97-7.84 (m, 3 H), 7.77-7.72 (m, 2 H), 7.63 (t, J = 7.9 Hz, 1 H), 7.53 (d, J = 7.4 Hz, 1 H), 7.16 (d, J = 8.7 Hz, 2 H), 6.96 (d, J = 8.9 Hz, 2 H), 4.07 (s, 3 H), 3.76 (s, 3 H). | 422 (ES+) | 1.72 |
| 13 | 3-(4-Methoxy-phenyl)-3-(3-pyrimidin-5-yl-phenyl)-3H-isoindol-1-ylamine trifluoroacetate | 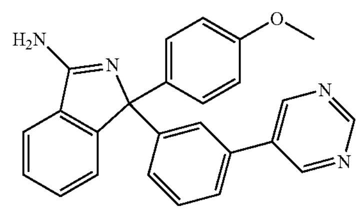 | $^1$H NMR (500 MHz, DMSO) δ 9.21 (s, 1 H), 9.11 (s, 2 H), 8.33 (d, J = 7.7 Hz, 1 H), 7.94 (d, J = 7.9 Hz, 1 H), 7.88-7.82 (m, 2 H), 7.73 (t, J = 7.5 Hz, 2 H), 7.59 (t, J = 7.9 Hz, 1 H), 7.46 (d, J = 9.0 Hz, 1 H), 7.18 (d, J = 8.8 Hz, 2 H), 6.96 (d, J = 9.0 Hz, 2 H), 3.76 (s, 3 H). | 393 (ES+) | 1.66 |
| 14 | Methanesulfonic acid 3'-[3-amino-1-(4-methoxy-phenyl)-1H-isoindol-1-yl]-5-methoxy-biphenyl-3-yl ester trifluoroacetate | 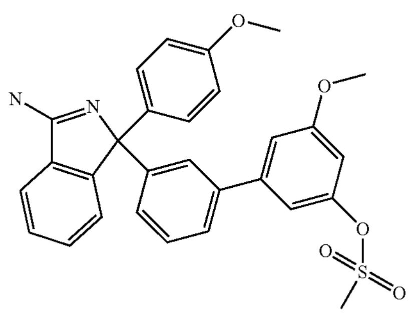 | $^1$H NMR (500 MHz, DMSO) δ 8.34 (t, J = 7.6 Hz, 1 H), 7.93-7.84 (m, 2 H), 7.75-7.71 (m, 2 H), 7.67-7.62 (m, 1 H), 7.59-7.51 (m, 3 H), 7.44-7.30 (m, 2 H), 7.20-7.15 (m, 2 H), 6.98-6.96 (m, 2 H), 3.86 (s, 3 H), 3.76 (s, 3 H), 3.41 (s, 3 H). | 515 (ES+) | 2.11 |
| 15 | 3-(2,3-Dihydrobenzo[b][1,4]dioxin-6-yl)-3-(3-(2-fluoropyridin-3-yl)phenyl)-3H-isoindol-1-amine trifluoroacetate | 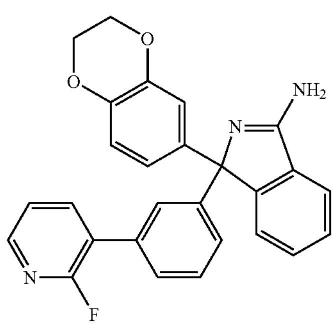 | $^1$H NMR (500 MHz, DMSO) δ 11.67 (s, 1 H), 10.01 (s, 1 H), 9.45 (s, 1 H), 8.28 (d, J = 7.5 Hz, 1 H), 8.26-8.24 (m, 1 H), 8.07 (t, J = 8.8 Hz, 1 H), 7.88-7.82 (m, 2 H), 7.73 (t, J = 7.1 Hz, 1 H), 7.63 (d, J = 7.5 Hz, 1 H), 7.55 (t, J = 7.8 Hz, 1 H), 7.51 (s, 1 H), 7.47 (t, J = 6.1 Hz, 1 H), 7.39 (d, J = 8.2 Hz, 1 H), 6.91-6.87 (m, 1 H), 6.73-6.68 (m, 2 H), 4.27-4.20 (m, 4 H). | 438 (ES+) | 1.90 |
| 16 | 3-(2,3-Dihydrobenzo[b][1,4]dioxin-6-yl)-3-(3-(5-methoxypyridin-3-yl)phenyl)-3H-isoindol-1-amine trifluoroacetate | 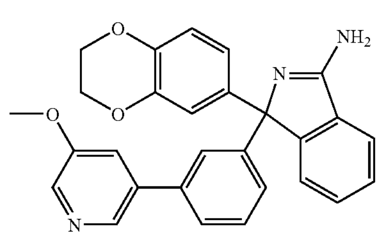 | $^1$H NMR (500 MHz, DMSO) δ 11.66 (s, 1 H), 10.01 (s, 1 H), 9.47 (s, 1 H), 8.43 (s, 1 H), 8.32 (s, 1 H), 8.28 (d, J = 2.7 Hz, 1 H), 8.28 (d, J = 8.2 Hz, 1 H), 7.93 (d, J = 8.2 Hz, 1 H), 7.85 (t, J = 7.8 Hz, 1 H), 7.76 (d, J = 8.2 Hz, 1 H), 7.73 (t, J = 7.8 Hz, 1 H), 7.62-7.60 (m, 1 H), 7.59-7.57 (m, 1 H), 7.54 (t, J = 8.0 Hz, 2 H), 7.38 (d, J = 7.8 Hz, 1 H), 6.88 (d, J = 8.9 Hz, 1 H), 6.71-6.67 (m, 2 H), 4.25-4.19 (m, 4 H), 3.90 (s, 3 H). | 450 (ES+) | 1.77 |

TABLE 2-continued

| Ex | Compound | Structure | NMR | m/z M + 1 (Ionization) | LC t$_R$ (min) |
|---|---|---|---|---|---|
| 17 | 3-(2,3-Dihydrobenzo[b][1,4]dioxin-6-yl)-3-(3-(pyridin-3-yl)phenyl)-3H-isoindol-1-amine trifluoroacetate | 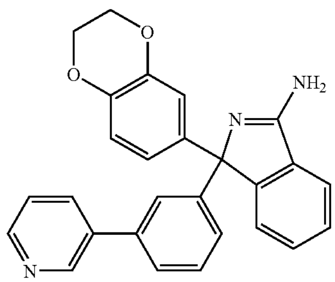 | $^1$H NMR (500 MHz, DMSO) δ 11.67 (s, 1 H), 10.00 (s, 1 H), 9.46 (s, 1 H), 8.86-8.84 (m, 1 H), 8.60 (d, J = 5.4 Hz, 1 H), 8.29 (d, J = 7.5 Hz, 1 H), 8.05 (d, J = 8.2 Hz, 1 H), 7.93 (d, J = 8.2 Hz, 1 H), 7.85 (t, J = 7.8 Hz, 1 H), 7.76-7.72 (m, 2 H), 7.61 (s, 1 H), 7.57-7.50 (m, 2 H), 7.37 (d, J = 8.2 Hz, 1 H), 6.90-6.87 (m, 1 H), 6.72-6.68 (m, 2 H), 4.25-4.19 (m, 4 H). | 420 (ES+) | 1.58 |
| 18 | 3-(2,3-Dihydrobenzo[b][1,4]dioxin-6-yl)-3-(3-(pyrimidin-5-yl)phenyl)-3H-isoindol-1-amine trifluoroacetate | 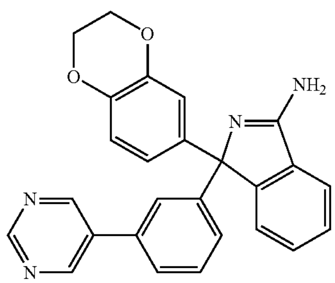 | $^1$H NMR (500 MHz, DMSO) δ 11.68 (s, 1 H), 10.02 (s, 1 H), 9.48 (s, 1 H), 9.20 (s, 1 H), 9.08 (s, 2 H), 8.29 (d, J = 7.2 Hz, 1 H), 7.95 (d, J = 7.2 Hz, 1 H), 7.87-7.80 (m, 2 H), 7.73 (t, J = 7.5 Hz, 1 H), 7.71-7.69 (m, 1 H), 7.58 (t, J = 7.5 Hz, 1 H), 7.44 (d, J = 8.8 Hz, 1 H), 6.90-6.86 (m, 1 H), 6.70-6.67 (m, 2 H), 4.25-4.18 (m, 4 H). | 421 (ES+) | 1.71 |
| 19 | 3-(3-Bromo-phenyl)-3-(4-methoxy-3-methyl-phenyl)-3H-isoindol-1-ylamine trifluoroacetate | 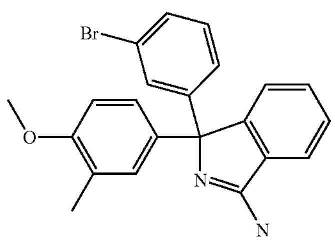 | $^1$H NMR (500 MHz, DMSO) δ 8.32 (d, J = 8.7 Hz, 1 H), 7.87-7.81 (m, 2 H), 7.75 (t, J = 7.5 Hz, 1 H), 7.60 (d, J = 7.5 Hz, 1 H), 7.45 (s, 1 H), 7.38 (t, J = 7.6 Hz, 1 H), 7.28 (d, J = 7.4 Hz, 1 H), 7.16 (m, 2 H), 6.96 (d, J = 8.7 Hz, 2 H), 3.79 (s, 3 H), 2.11 (s, 3 H). | 407 (APCI+) | 2.22 |
| 20 | 3-(3'-Methoxy-biphenyl-3-yl)-3-(4-methoxy-3-methyl-phenyl)-3H-isoindol-1-ylamine trifluoroacetate | 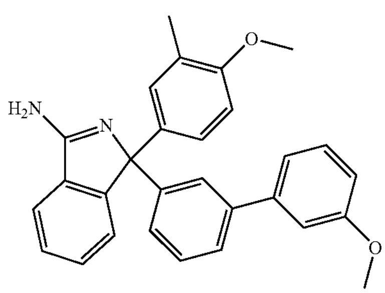 | $^1$H NMR (500 MHz, DMSO) δ 8.32 (d, J = 8.7 Hz, 1 H), 7.85 (m, 1 H), 7.77-7.63 (m, 2 H), 7.54-7.45 (m, 2 H), 7.38 (t, J = 7.6 Hz, 1 H), 7.28 (d, J = 7.4 Hz, 1 H), 7.15 (m, 2 H), 7.05 (m, 2 H), 6.96 (m, 2 H), 3.86 (s, 3 H), 3.79 (s, 3 H), 2.11 (s, 3 H). | 435 (ES+) | 2.46 |
| 21 | 3-(4-Methoxy-3-methyl-phenyl)-3-[3-(5-methoxy-pyridin-3-yl)-phenyl]-3H-isoindol-1-ylamine trifluoroacetate | 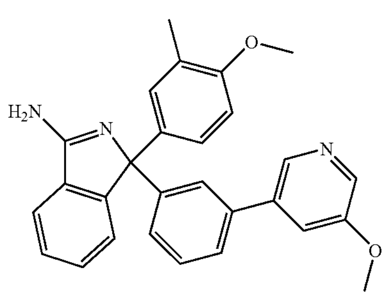 | $^1$H NMR (500 MHz, DMSO) δ 8.80 (s, 1 H), 8.68 (s, 1 H), 8.38-8.33 (m, 2 H), 7.95 (d, J = 8.7 Hz, 1 H), 7.91-7.84 (m, 2 H), 7.77-7.72 (m, 2 H), 7.63 (t, J = 7.9 Hz, 1 H), 7.51 (d, J = 7.4 Hz, 1 H), 7.09 (m, 2 H), 6.96 (d, J = 8.9 Hz, 2 H), 4.06 (s, 3 H), 3.78 (s, 3 H), 2.10 (s, 3 H). | 436 (ES+) | 1.80 |

TABLE 2-continued

| Ex | Compound | Structure | NMR | m/z M + 1 (Ionization) | LC t$_R$ (min) |
|---|---|---|---|---|---|
| 22 | 3-(4-Methoxy-3-methyl-phenyl)-3-(3-pyridin-3-yl-phenyl)-3H-isoindol-1-ylamine trifluoroacetate | 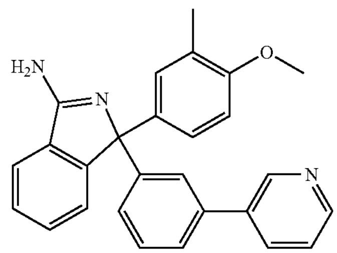 | $^1$H NMR (500 MHz, DMSO) δ 9.20 (s, 1 H), 8.95 (m, 1 H), 8.32 (d, J = 8.8 Hz, 2 H), 8.15 (m, 1 H), 7.95 (d, J = 8.7 Hz, 1 H), 7.91-7.84 (m, 2 H), 7.77-7.72 (m, 2 H), 7.63 (t, J = 7.9 Hz, 1 H), 7.51 (d, J = 7.4 Hz, 1 H), 7.02 (m, 2 H), 6.96 (d, J = 8.9 Hz, 2 H), 3.78 (s, 3 H), 2.10 (s, 3 H). | 406 (ES+) | 1.61 |
| 23 | 3-(4-Methoxy-3-methyl-phenyl)-3-(3-pyrimidin-5-yl-phenyl)-3H-isoindol-1-ylamine trifluoroacetate | 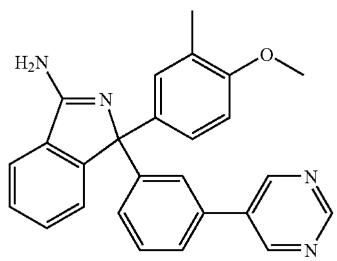 | $^1$H NMR (500 MHz, DMSO) δ 9.21 (s, 1 H), 9.10 (s, 2 H), 8.35 (d, J = 8.7 Hz, 1 H), 7.94 (d, J = 8.9 Hz, 1 H), 7.88-7.82 (m, 2 H), 7.78-7.73 (m, 2 H), 7.59 (t, J = 7.9 Hz, 1 H), 7.46 (d, J = 7.8 Hz, 1 H), 7.18 (m, 2 H), 6.96 (d, J = 9.0 Hz, 2 H), 3.78 (s, 3 H), 2.10 (s, 3 H). | 407 (ES+) | 2.04 |
| 24 | 3-[3-(2-Fluoro-pyridin-3-yl)-phenyl]-3-(4-methoxy-3-methyl-phenyl)-3H-isoindol-1-ylamine trifluoroacetate | 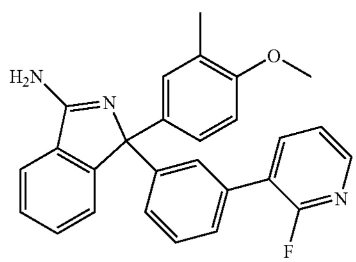 | $^1$H NMR (500 MHz, DMSO) δ 8.34 (d, J = 8.0 Hz, 1 H), 8.27 (m, 1 H), 7.84 (m, 2 H), 7.75 (m, 1 H), 7.65 (m, 1 H), 7.63 (m, 1 H), 7.58-7.51 (m, 2 H), 7.37 (d, J = 8.0 Hz, 1 H), 7.05 (m, 2 H), 6.96 (d, J = 9.5 Hz, 2 H), 3.79 (s, 3 H), 2.11 (s, 3 H). | 424 (ES+) | 2.20 |
| 25 | Methanesulfonic acid 3'-[3-amino-1-(4-methoxy-3-methyl-phenyl)-1H-isoindol-1-yl]-5-methoxy-biphenyl-3-yl ester trifluoroacetate | 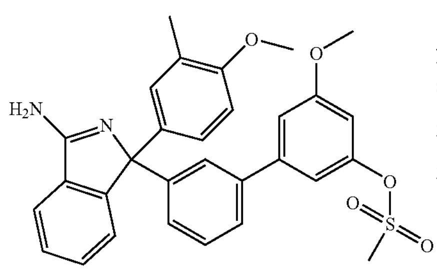 | $^1$H NMR (500 MHz, DMSO) δ 8.34 (t, J = 7.6 Hz, 1 H), 7.93-7.84 (m, 2 H), 7.75-7.71 (m, 2 H), 7.59 (s, 1 H), 7.55 (d, J = 8.0 Hz, 1 H), 7.33 (d, J = 2 H, 8.0 Hz, 1 H), 7.17 (s, 1 H), 7.15 (s, 1 H), 7.05 (m, 2 H), 6.96 (s, 1 H), 6.92 (d, J = 8.0 Hz, 1 H), 3.86 (s, 3 H), 3.79 (s, 3 H), 3.41 (s, 3 H), 2.11 (s, 3 H). | 529 (ES+) | 2.15 |
| 26 | 5'-(3-Amino-1-(2,3-dihydrobenzo[b][1,4]dioxin-6-yl)-1H-isoindol-1-yl)-5-methoxybiphenyl-3-yl methanesulfonate trifluoroacetate | 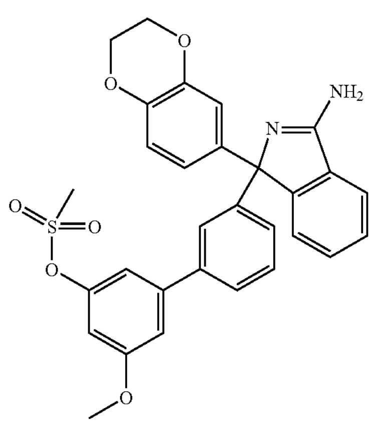 | $^1$H NMR (500 MHz, DMSO) δ 11.61 (s, 1 H), 9.99 (s, 1 H), 9.44 (s, 1 H), 8.28 (d, J = 8.2 Hz, 1 H), 7.91 (d, J = 8.2 Hz, 1 H), 7.85 (t, J = 7.7 Hz, 1 H), 7.76-7.69 (m, 2 H), 7.55 (s, 1 H), 7.51 (t, J = 7.9 Hz, 1 H), 7.34 (d, J = 7.7 Hz, 1 H), 7.14 (d, J = 15.3 Hz, 1 H), 6.97 (s, 1 H), 6.88 (d, J = 9.3 Hz, 1 H), 6.71-6.67 (m, 2 H), 4.25-4.21 (m, 4 H), 3.84 (s, 3 H), 3.41 (s, 3 H). | 543 (ES+) | 2.15 |

TABLE 2-continued

| Ex | Compound | Structure | NMR | m/z M + 1 (Ionization) | LC $t_R$ (min) |
|---|---|---|---|---|---|
| 27 | 3-(2,3-Dihydrobenzo[b][1,4]dioxin-6-yl)-3-(3'-methoxybiphenyl-3-yl)-3H-isoindol-1-amine trifluoroacetate | 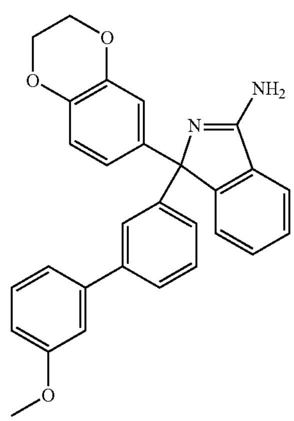 | $^1$H NMR (500 MHz, DMSO) δ 11.63 (s, 1 H), 9.98 (s, 1 H), 9.43 (s, 1 H), 8.28 (d, J = 8.2 Hz, 1 H), 8.28 (s, 1 H), 7.93-7.82 (m, 2 H), 7.73 (t, J = 7.4 Hz, 1 H), 7.68 (d, J = 7.7 Hz, 1 H), 7.52 (s, 1 H), 7.49 (t, J = 7.9 Hz, 1 H), 7.38 (t, J = 8.5 Hz, 1 H), 7.29 (d, J = 7.7 Hz, 1 H), 7.12 (s, 1 H), 6.96 (d, J = 8.8 Hz, 1 H), 6.90-6.87 (m, 1 H), 6.73-6.68 (m, 2 H), 4.22 (s, 4 H), 3.80 (s, 3 H). | 449 (ES+) | 2.20 |

The requisite boronic ester needed for Example 14, was prepared as outlined in Scheme 4:

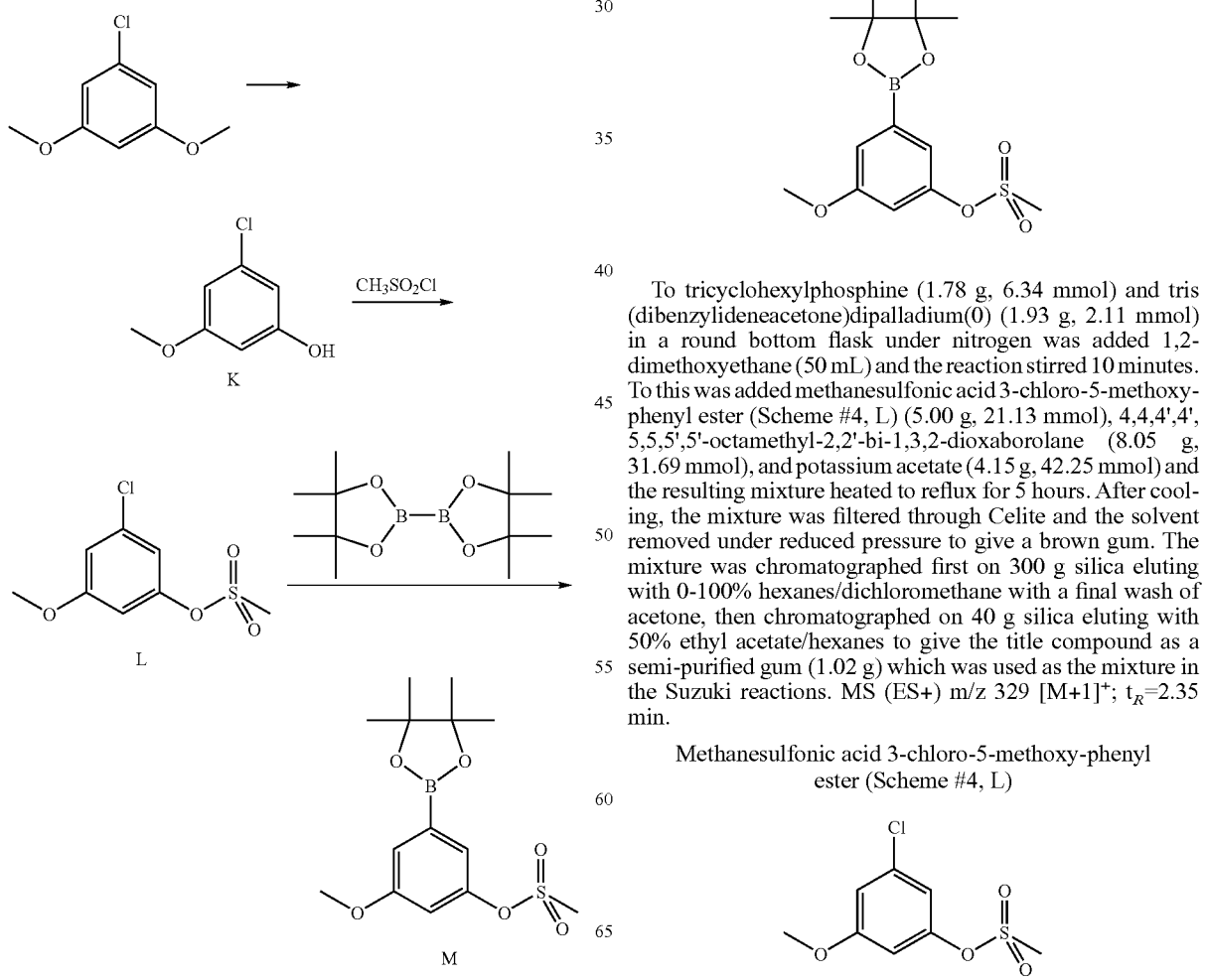

Methanesulfonic acid 3-methoxy-5-(4,4,5,5-tetramethyl-[1,3,2]dioxaborolan-2-yl)-phenyl ester (Scheme #4, M)

To tricyclohexylphosphine (1.78 g, 6.34 mmol) and tris(dibenzylideneacetone)dipalladium(0) (1.93 g, 2.11 mmol) in a round bottom flask under nitrogen was added 1,2-dimethoxyethane (50 mL) and the reaction stirred 10 minutes. To this was added methanesulfonic acid 3-chloro-5-methoxyphenyl ester (Scheme #4, L) (5.00 g, 21.13 mmol), 4,4,4',4', 5,5,5',5'-octamethyl-2,2'-bi-1,3,2-dioxaborolane (8.05 g, 31.69 mmol), and potassium acetate (4.15 g, 42.25 mmol) and the resulting mixture heated to reflux for 5 hours. After cooling, the mixture was filtered through Celite and the solvent removed under reduced pressure to give a brown gum. The mixture was chromatographed first on 300 g silica eluting with 0-100% hexanes/dichloromethane with a final wash of acetone, then chromatographed on 40 g silica eluting with 50% ethyl acetate/hexanes to give the title compound as a semi-purified gum (1.02 g) which was used as the mixture in the Suzuki reactions. MS (ES+) m/z 329 [M+1]$^+$; $t_R$=2.35 min.

Methanesulfonic acid 3-chloro-5-methoxy-phenyl ester (Scheme #4, L)

To a 0° C. solution of 3-chloro-5-methoxy-phenol (Scheme #4, K) (16.62 g, 104.80 mmol) and pyridine (12.8 mL, 157.20 mmol) in dichloromethane (150 mL) was added methanesulfonyl chloride (8.9 mL, 115.28 mmol). The reaction was warmed to room temperature and stirred 24 hours. The dichloromethane was removed under reduced pressure and the crude material partitioned between ethyl acetate and 1N hydrochloric acid. The organic layer was washed 1N hydrochloric acid (4×), aqueous saturated sodium chloride (1×), saturated potassium carbonate (3×), aqueous saturated sodium chloride (1×), dried over magnesium sulfate, and solvent removed under reduced pressure. The crude solid was crystallized overnight from dichloromethane (50 mL) and crystals filtered off, washed with dichloromethane, and placed under high vacuum to give the title compound (9.35 g, 38%). $^1$H NMR (300 MHz, DMSO-$d_6$) δ 7.09 (t, J=2.0 Hz, 1 H), 7.05 (t, J=1.9 Hz, 1 H), 6.93 (t, J=2.1 Hz, 1 H), 3.82 (s, 3 H), 3.42 (s, 3 H); MS (APCI+) m/z 237 [M+1]$^+$; $t_R$=2.28 min.

3-Chloro-5-methoxy-phenol (Scheme #4, K)

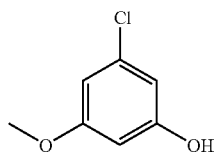

To sodium methanethiolate (12.32 g, 173.80 mmol) was added 1-methyl-2-pyrrolidine (75 mL) followed by 1-chloro-3,5-dimethoxy-benzene (20.00 g, 115.87 mmol) and the reaction heated in a 140° C. bath for 2.5 hours then stirred at room temperature over night. The 1-methyl-2-pyrrolidine was removed under reduced pressure and the material partitioned between ethyl acetate/water/1N hydrochloric acid. The organic layer was washed with twice with 1N hydrochloric acid, once with aqueous saturated sodium chloride, dried over magnesium sulfate and solvent removed under reduced pressure to give a yellowish solid. The solid was chromatographed on 400 mL plug of silica gel eluting with dichloromethane. The combined purified fractions were removed of solvent to give the title compound as a yellow solid (16.62 g, 90%). $^1$H NMR (300 MHz, DMSO-$d_6$) δ 6.43 (t, J=2.0 Hz, 1 H), 6.40 (t, J=1.9 Hz, 1 H), 6.28 (t, J=2.1 Hz, 1 H), 3.71 (s, 3 H); MS (APCI+) m/z 159 [M+1]$^+$; $t_R$=2.04 min.

Scheme 5

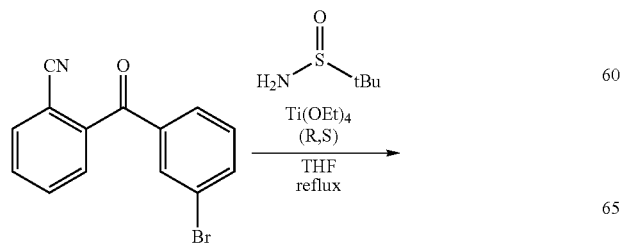

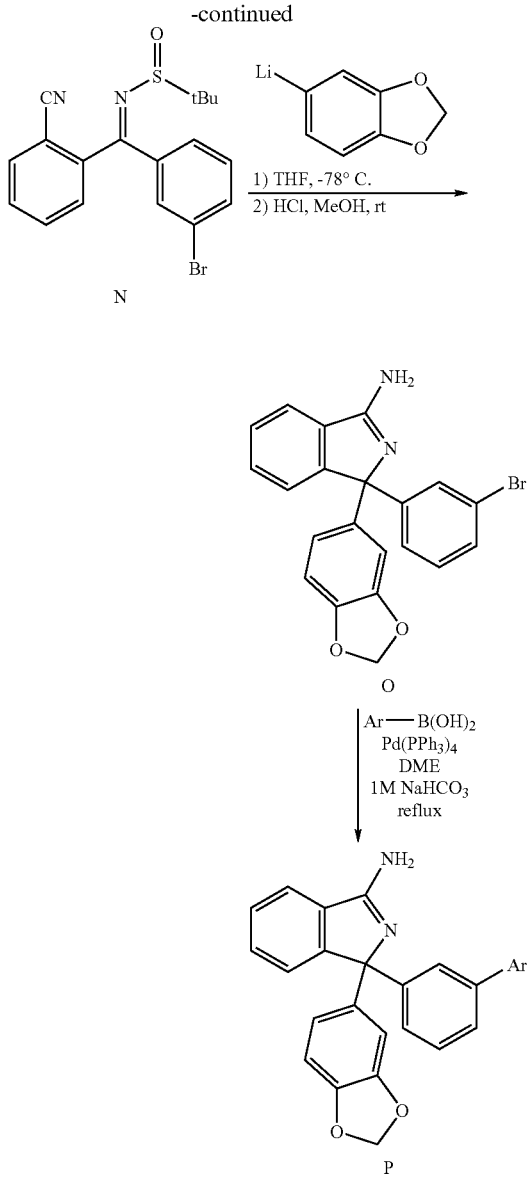

Example 28

3-Benzo[1,3]dioxol-5-yl-3-(3-pyridin-3-yl)-3H-isoindol-1-ylamine trifluoroacetate (Scheme #5, P)

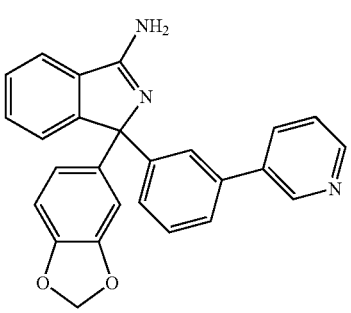

3-Benzo[1,3]dioxol-5-yl-3-(3-bromophenyl)-3H-isoindol-1-ylamine (0.060 g, 0.147 mmol) (Scheme #5, O, Example 29) and tetrakis(triphenylphosphine)palladium (0) (10 mg) were combined in ethylene glycol dimethyl ether (1.4 mL). Pyridine 3-boronic acid (0.025 g, 0.203 mmol) and 1M aqueous sodium bicarbonate solution (1.0 mL) were added, respectively. The mixture was refluxed for one hour, cooled to ambient temperature, and filtered. The filtrate was partitioned between water and ethyl acetate. The organic portion was washed (water, brine), dried (magnesium sulfate), filtered, and evaporated. The crude material was chromatographed on a silica gel flash column with 10% 2M ammonia in methanol/dichloromethane, then the partially purified material was dissolved in acetonitrile/water and purified by RP-HPLC AG2 ($t_R$=10.7 min). The combined purified fractions were lyophilized to give the title compound (0.066 g). $^1$H NMR (500 MHz, DMSO-$d_6$) δ 11.71 (s, 1 H), 10.02 (s, 1 H), 9.50 (s, 1 H), 8.86 (s, 1 H), 8.61-8.60 (m, 1 H), 8.29 (d, J=7.8 Hz, 1 H), 8.06 (d, J=8.0 Hz, 1 H), 7.94 (d, J=7.9 Hz, 1 H), 7.87-7.84 (m, 1 H), 7.76-7.72 (m, 2 H), 7.61 (s, 1 H), 7.56-7.52 (m, 2 H), 7.36 (d, J=8.0 Hz, 1 H), 6.92 (d, J=8.1 Hz, 1 H), 6.79 (s, 1 H), 6.74-6.72 (m, 1 H), 6.03 (s, 2 H); MS (APCI+) m/z 406 [M+1]$^+$; $t_R$=1.67 min.

Example 29
3-Benzo[1,3]dioxol-5-yl-3-(3-bromophenyl)-3H-isoindol-1-ylamine (Scheme #5, O)

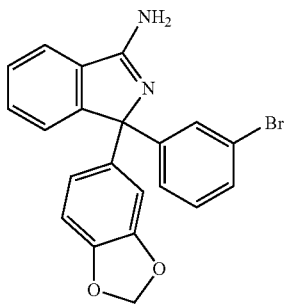

n-Butyllithium solution (1.6 M, 0.75 mL, 1.15 mmol) was added drop wise to a −78° C. solution of 4-bromo-1,2-methylenedioxybenzene (0.25 g, 1.24 mmol) in tetrahydrofuran (4.8 mL) and stirred for 30 min. A solution of N-[(3-bromophenyl)(2-cyanophenyl)methylene]-2-methylpropane-2-sulfinamide (0.400 g, 1.03 mmol) (Scheme #5, N) in tetrahydrofuran (3.0 mL) was added drop wise over 15 min and stirring continued at −78° C. for two hours. The reaction was slowly warmed to −25° C. and quenched by addition of water (5 mL). The mixture was partitioned between water and ethyl acetate. The organic portion was washed (water, brine), dried (magnesium sulfate), and concentrated to a crude oil. The oil was chromatographed on a silica gel flash column with 3:1 hexane/ethyl acetate to give the intermediate as a white gum. The gum was dissolved in methanol (10 mL), treated with 1 M hydrogen chloride in diethyl ether (2 mL), and stirred at ambient temperature for 22 hours. The reaction mixture was concentrated and the residue partitioned between aqueous sodium bicarbonate solution and dichloromethane.

The organic portion was washed (brine), dried (sodium sulfate), and evaporated. The crude material was chromatographed on a silica gel flash column with 5% 2 M ammonia in methanol/dichloromethane, then triturated with hexane to give the title compound as an off-white solid (0.300 g, 71%). $^1$H NMR (300 MHz, DMSO-$d_6$) δ 7.78-7.67 (m, 2 H), 7.47-7.37 (m, 4 H), 7.31-7.19 (m, 2 H), 6.78-6.72 (m, 5 H), 5.95 (s, 2 H); MS (APCI+) m/z 407 [M+1]$^+$; $t_R$=2.12 min.

N-[(3-bromophenyl)(2-cyanophenyl)methylene]-2-methylpropane-2-sulfinamide (Scheme #5, N)

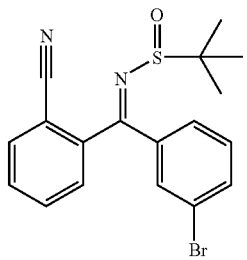

To a solution of titanium (IV) ethoxide (3.48 g, 15.3 mmol) in tetrahydrofuran (14.0 mL) was added 3-bromo-2'-cyanobenzophenone (2.00, 7.0 mmol). After stirring for two minutes, 2-methyl-2-propanesulfinamide (0.93 g, 7.68 mmol) was added. The mixture was refluxed for 13 hours and heated at 50° C. for 31 hours. After cooling to ambient temperature, the mixture was diluted with methanol (15 mL) and treated with saturated aqueous sodium bicarbonate solution (15 drops) to form a gelatinous precipitate. The material was further diluted with ethyl acetate and vacuum filtered through a pad of sodium sulfate to remove the precipitate. The filtrate was concentrated to a crude oil that was purified by flash chromatography on silica gel with 10% acetonitrile/dichloromethane and triturated with hexane/ethyl acetate to give the title compound as a yellow solid (1.81 g, 66%). $^1$H NMR (300 MHz, DMSO-$d_6$) δ 7.98 (d, J=7.7 Hz, 1 H), 7.87-7.79 (m, 2 H), 7.72-7.66 (m, 2 H), 7.64-7.43 (m, 3 H), 1.27 (s, 9 H).

Examples 30-33

Additional compounds in Table 3 were prepared according to Scheme 5 using the appropriate boronic acid starting material.

TABLE 3

| Ex | Compound | Structure | NMR | m/z M + 1 (Ionization) | LC $t_R$ (min) |
|---|---|---|---|---|---|
| 30 | 3-Benzo[1,3]dioxol-5-yl-3-(3-pyrimidin-5-ylphenyl)-3H-isoindol-1-ylamine trifluoroacetate | 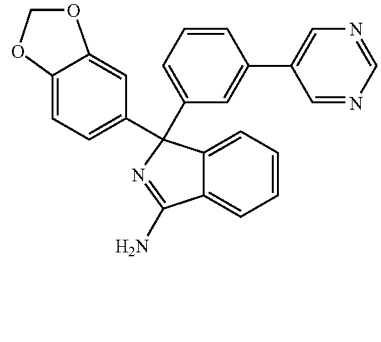 | $^1$H NMR (500 MHz, DMSO-$d_6$) δ 11.68 (s, 1 H), 10.03 (s, 1 H), 9.49 (s, 1 H), 9.20 (s, 1 H), 9.09 (s, 2 H), 8.29 (d, J = 7.8 Hz, 1 H), 7.96 (d, J = 7.8 Hz, 1 H), 7.75-7.66 (m, 2 H), 7.87-7.82 (m, 2 H), 7.60-7.57 (m, 1 H), 7.44-7.42 (m, 1 H), 6.92 (d, J = 8.3 Hz, 1 H), 6.77 (s, 1 H), 6.72-6.70 (m, 1 H), 6.03 (s, 2 H). | 407 (APCI+) | 1.80 |

TABLE 3-continued

| Ex | Compound | Structure | NMR | m/z M + 1 (Ionization) | LC t$_R$ (min) |
|---|---|---|---|---|---|
| 31 | 3-Benzo[1,3]dioxol-5-yl-3-[3-(2-fluoropyridin-3-yl)-phenyl]-3H-isoindol-1-ylamine trifluoroacetate | 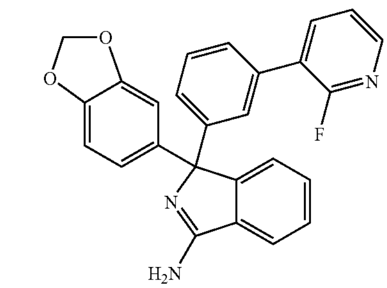 | $^1$H NMR (500 MHz, DMSO-d6) δ 11.72 (s, 1 H), 10.03 (s, 1 H), 9.50 (s, 1 H), 8.30-8.24 (m, 2 H), 8.09-8.05 (m, 1 H), 7.89-7.83 (m, 2 H), 7.75-7.72 (m, 1 H), 7.65-7.63 (m, 1 H), 7.57-7.45 (m, 3 H), 7.37 (d, J = 8.0 Hz, 1 H), 6.92 (d, J = 8.2 Hz, 1 H), 6.80 (s, 1 H), 6.73 (d, J = 8.1 Hz, 1 H), 6.04 (s, 2 H). | 424 (APCI+) | 1.98 |
| 32 | 3-Benzo[1,3]dioxol-5-yl-3-[3-(5-methoxy-pyridin-3-yl)-phenyl]3H isoindol-1-ylamine trifluoroacetate | 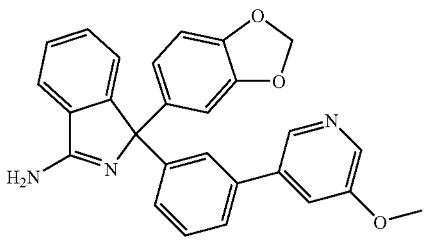 | $^1$H NMR (500 MHz, DMSO-d$_6$) δ 11.70 (s, 1 H), 10.02 (s, 1 H), 9.51 (s, 1 H), 8.43 (s, 1 H), 8.33-8.28 (m, 2 H), 7.94 (d, J = 7.8 Hz, 1 H), 7.87-7.84 (m, 1 H), 7.78-7.72 (m, 2 H), 7.60-7.53 (m, 3 H), 7.37 (d, J = 8.1 Hz, 1 H), 6.92 (d, J = 8.2 Hz, 1 H), 6.73-6.71 (m, 2 H), 6.03 (s, 2 H), 3.90 (s, 3 H). | 436 (APCI+) | 1.86 |
| 33 | 3-Benzo[1,3]dioxol-5-yl-3-(3'-methoxy-biphenyl-3-yl)-3H-isoindol-1-ylamine trifluoroacetate | 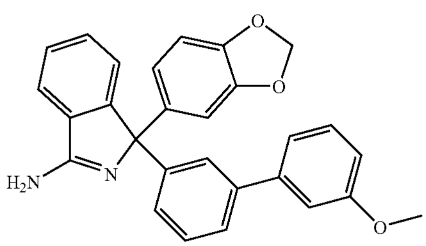 | $^1$H NMR (500 MHz, DMSO-d$_6$) δ 11.71 (s, 1 H), 10.01 (s, 1 H), 9.50 (s, 1 H), 8.29 (d, J = 7.9 Hz, 1 H), 7.91-7.84 (m, 2 H), 7.75-7.72 (m, 1 H), 7.68 (d, J = 7.8 Hz, 1 H), 7.51-7.47 (m, 2 H), 7.39-7.36 (m, 3 H), 7.28 (d, J = 7.8 Hz, 1 H), 7.15-7.11 (m, 2 H), 6.97-6.91 (m, 2 H), 6.79 (s, 1 H), 6.75-6.73 (m, 1 H), 6.03 (s, 2 H), 3.80 (s, 3 H). | 435 (APCI+) | 2.23 |
| 34 | Methanesulfonic acid 3'-(3-amino-1-benzo[1,3]dioxol-5-yl-1H-isoindol-1-yl)-5-methoxy-biphenyl-3-yl ester trifluoroacetate | 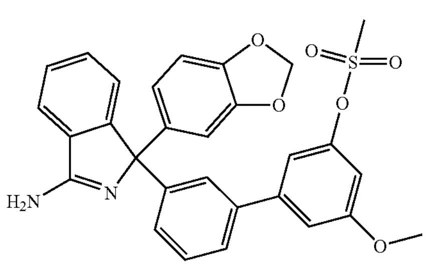 | $^1$H NMR (500 MHz, DMSO-d6) δ 11.70 (s, 1 H), 10.02 (s, 1 H), 9.51 (s, 1 H), 8.29 (d, J = 7.8 Hz, 1 H), 7.92 (d, J = 7.8 Hz, 1 H), 7.87-7.83 (m, 1 H), 7.75-7.70 (m, 2 H), 7.55-7.49 (m, 2 H), 7.33 (d, J = 8.0 Hz, 1 H), 7.17-7.12 (m, 2 H), 6.98-6.96 (m, 1 H), 6.92 (d, J = 8.2 Hz, 1 H), 6.79 (s, 1 H), 6.74-6.71 (m, 1 H), 6.03 (s, 2 H), 3.84 (s, 3 H), 3.41 (s, 3 H). | 529 (APCI+) | 2.24 |

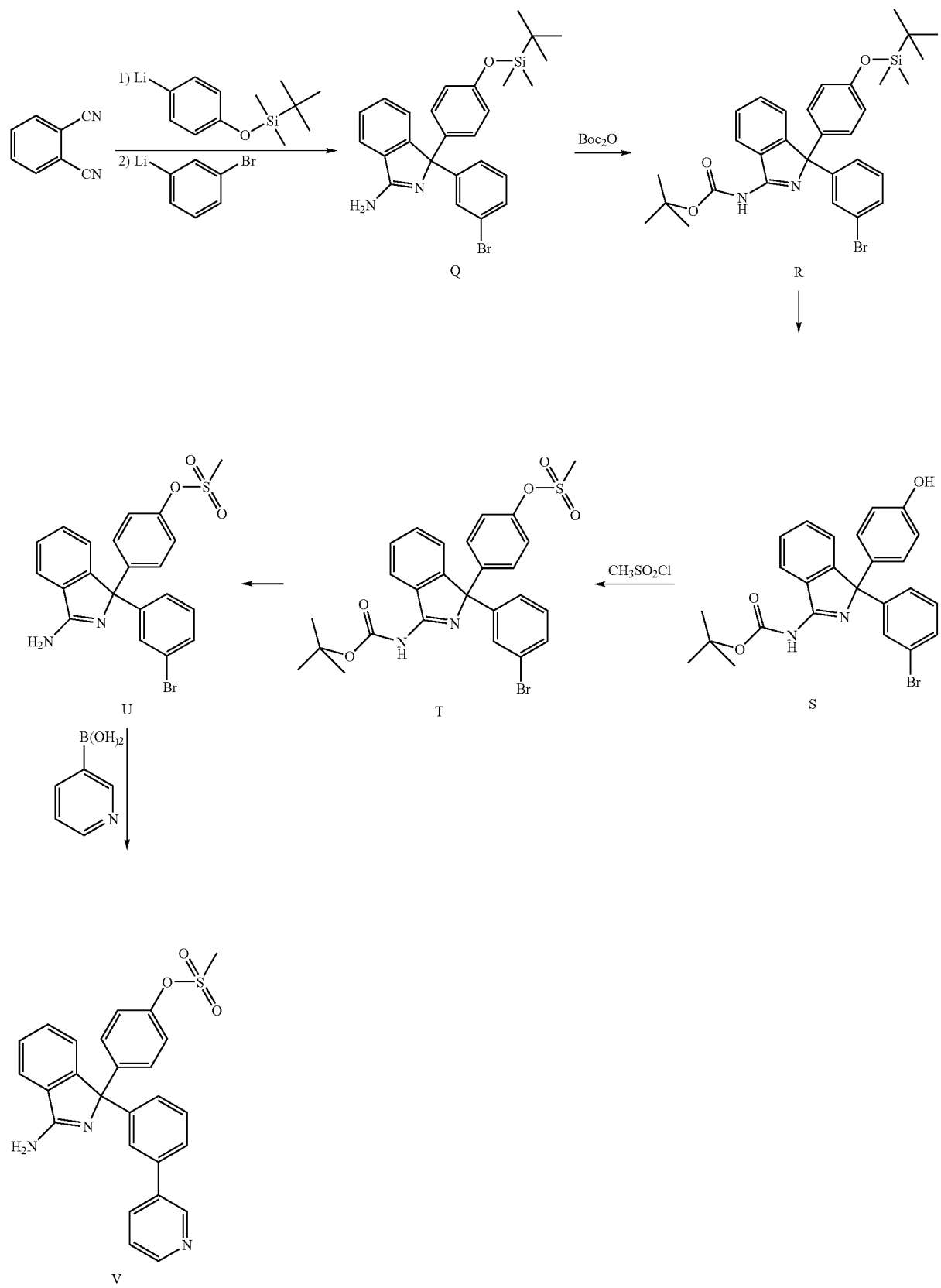

Example 35

Methanesulfonic acid 4-[3-amino-1-(3-pyridin-3-yl-phenyl)-1H-isoindol-1-yl]-phenyl ester trifluoroacatete (Scheme #6, V)

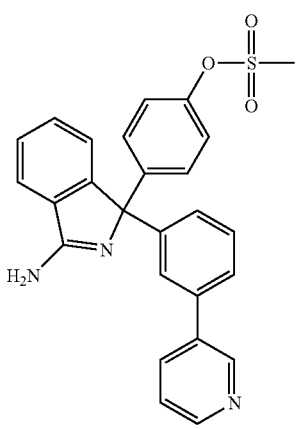

To methanesulfonic acid 4-[3-amino-1-(3-bromo-phenyl)-1H-isoindol-1-yl]-phenyl ester (Scheme #6, U) (100 mg, 0.18 mmol)) was added potassium phosphate (112 mg, 0.53 mmol), 3-pyridyl boronic acid (33 mg, 0.26 mmol), dichlorobis(triphenylphosphine)palladium(II) (12 mg, 0.018 mmol) and 1,2-dimethoxyethane: water:ethanol (7:3:2, 3.0 mL). The reaction was heated in an aluminium block at 100° C. for 15 minutes. The mixture was filtered through a syringe filter and the filtrate was removed of solvent under reduced pressure. The resulting residue was dissolved in acetonitrile/water with trifluoroacetic acid, (75:25:0.1, 4 mL), and purified using RP-HPLC AG2 ($t_R$=10.6 min). The combined purified fractions were lyophilized to give the title compound (52.3 mg, 59%). $^1$H NMR (500 MHz, DMSO-$d_6$/TFA-d) δ 9.23 (d, J=1.6 Hz, 1 H), 8.96 (d, J=5.6 Hz, 1 H), 8.87 (d, J=8.2 Hz, 1 H), 8.37 (d, J=7.8 Hz, 1 H), 8.17 (dd, J=8.2, 5.7 Hz, 1 H), 8.02 (d, J=7.9 Hz, 1 H), 7.90 (dd, J=18.6, 7.8 Hz, 2 H), 7.82 (s, 1 H), 7.77 (t, J=7.6 Hz, 1 H), 7.67 (t, J=7.8 Hz, 1 H), 7.56 (d, J=8.2 Hz, 1 H), 7.41 (s, 4 H), 3.39 (s, 3 H); MS (ES+) m/z 456 [M+1]$^+$; $t_R$=1.42 min.

Example 36

Methanesulfonic acid 4-[3-amino-1-(3-bromo-phenyl)-1H-isoindol-1-yl]-phenyl ester trifluoroacetate (Scheme #6, U)

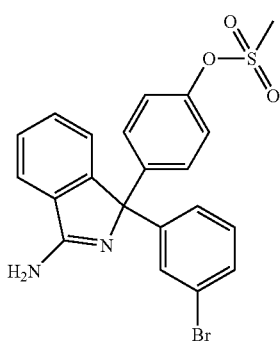

To methanesulfonic acid 4-[1-(3-bromo-phenyl)-3-tert-butoxycarbonylamino-1H-isoindol-1-yl]-phenyl ester (Scheme #6, T) (730 mg, 1.31 mmol) was added 10% trifluoroacetic acid in dichloromethane (10 mL) and the reaction stirred 30 minutes. The solvents were removed under reduced pressure and the resulting oil put under high vacuum. Ether, 20 mL, was added to the gum and the solvent removed under reduced pressure giving the title compound (671 mg, 90%). $^1$H NMR (500 MHz, DMSO-$d_6$) δ 8.32 (d, J=7.9 Hz, 1 H), 7.90-7.86 (m, 2 H), 7.76 (ddd, J=7.9, 6.1, 2.0 Hz, 1 H), 7.63 (d, J=8.0 Hz, 1 H), 7.46 (t, J=1.8 Hz, 1 H), 7.41-7.35 (m, 5 H), 7.31 (d, J=8.5 Hz, 1 H), 3.40 (d, J=4.0 Hz, 3 H); MS (ES+) m/z 457 [M+1]$^+$; $t_R$=1.84 min.

Methanesulfonic acid 4-[1-(3-bromo-phenyl)-3-tert-butoxycarbonylamino-1H-isoindol-1-yl]-phenyl ester (Scheme #6, T)

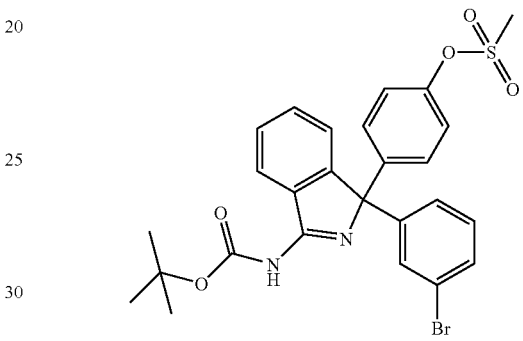

To [3-(3-bromo-phenyl)-3-(4-hydroxy-phenyl)-3H-isoindol-1-yl]-carbamic acid tert-butyl ester (Scheme #6, S) (900 mg, 1.88 mmol) in tetrahydrofuran (10 mL) was added pyridine (306 uL, 3.76 mmol) and methanesulfonyl chloride (218 uL, 2.82 mmol). After stirring over night, additional pyridine (306 uL, 3.76 mmol) and methanesulfonyl chloride (218 uL, 2.82 mmol) were added and the reaction allowed to stir for 8 hours. The solvent was removed under reduced pressure and the resulting oil put under high vacuum. The crude material was chromatographed on 20 g silica gel eluting with 2.5% methanol/dichloromethane and the combined purified fractions removed of solvent to give the title compound as a white solid (734 mg, 70%). $^1$H NMR (500 MHz, DMSO-$d_6$/TFA-d) δ 8.67 (d, J=8.0 Hz, 1 H), 7.92 (t, J=7.6 Hz, 1 H), 7.84 (d, J=7.8 Hz, 1 H), 7.78 (t, J=7.7 Hz, 1 H), 7.62 (d, J=7.6 Hz, 2 H), 7.49 (d, J=8.7 Hz, 2 H), 7.39-7.33 (m, 4 H), 3.40 (s, 3 H), 1.63 (s, 9 H); MS (ES+) m/z 557 [M+1]$^+$; $t_R$=2.29 min.

[3-(3-Bromo-phenyl)-3-(4-hydroxy-phenyl)-3H-isoindol-1-yl]-carbamic acid tert-butyl ester (Scheme #6, S)

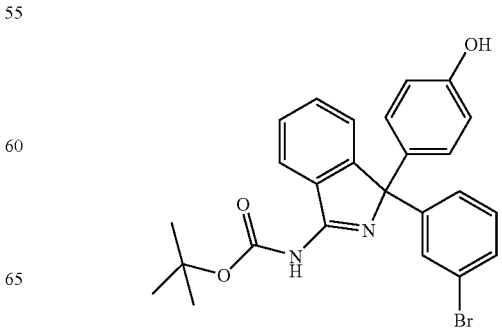

To {3-(3-bromo-phenyl)-3-[4-(tert-butyl-dimethyl-silanyloxy)-phenyl]-3H-isoindol-1-yl}-carbamic acid tert-butyl ester (Scheme #6, R) (1.07 g, 1.80 mmol) in tetrahydrofuran (20 mL) was added 1.0 M tetrabutylammonium fluoride in tetrahydrofuran (1.98 mL, 1.98 mmol). After 10 minutes the reaction was quenched with water (50 mL) and extracted twice with ethyl acetate. The organic layer was washed with aqueous saturated sodium chloride, dried over magnesium sulfate and the solvent removed under reduced pressure to give a yellow oil. This was chromatographed on 20 g silica gel eluting with 40% ethyl acetate/hexanes and the combined purified fractions removed of solvent under reduced pressure to give the title compound as a yellow solid (906 mg, quantitative yield). $^1$H NMR (300 MHz, DMSO-d$_6$/TFA-d) δ 8.64 (d, J=7.7 Hz, 1 H), 7.89 (t, J=7.7 Hz, 1 H), 7.74 (t, J=7.5 Hz, 2 H), 7.61-7.57 (m, 2 H), 7.33 (dd, J=4.7, 1.2 Hz, 2 H), 7.14 (dd, J=6.8, 1.9 Hz, 2 H), 6.78 (d, J=8.9 Hz, 2 H), 1.62 (s, 9 H); MS (APCI+) m/z 479 [M+1]$^+$; t$_R$=2.23 min.

{3-(3-Bromo-phenyl)-3-[4-(tert-butyl-dimethyl-silanyloxy)-phenyl]-3H-isoindol-1-yl}-carbamic acid tert-butyl ester (Scheme #6, R)

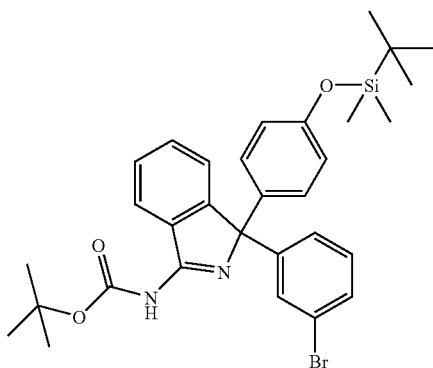

To 3-(3-bromo-phenyl)-3-[4-(tert-butyl-dimethyl-silanyloxy)-phenyl]-3H-isoindol-1-ylamine (Scheme 6, Q) (1.64 g, 3.32 mmol) in dichloromethane was added di-tbutyl dicarbonate (1.09 g, 4.98 mmol). After 30 minutes additional di-tbutyl dicarbonate (0.75 g, 3.44 mmol) was added and the reaction stirred 1 hour. The mixture was poured directly on a silica gel column (20 g) and eluted with dichloromethane and the combined fractions were removed of solvent under reduced pressure to give the product as semi-purified material. This material was then purified on a 20 g silica gel column eluting with a 25% step gradient from hexanes to dichloromethane, 200 mL each wash. The combined purified fractions were removed of solvent under reduced pressure to give the titled compound as a yellow solid (1.07 g, 54%). $^1$H NMR (300 MHz, DMSO-d$_6$) δ 7.86 (d, J=7.4 Hz, 1 H), 7.69-7.42 (m, 5 H), 7.29 (quintet, J=7.9 Hz, 2 H), 7.16 (d, J=8.7 Hz, 2 H), 6.84-6.75 (m, 2 H), 1.50 (d, J=13.7 Hz, 9 H), 0.93 (s, 9 H), 0.17 (d, J=6.7 Hz, 6 H); MS (APCI+) m/z 593 [M+1]$^+$; t$_R$=3.39 min.

3-(3-Bromo-phenyl)-3-[4-(tert-butyl-dimethyl-silanyloxy)-phenyl]-3H-isoindol-1-ylamine (Scheme #6, Q)

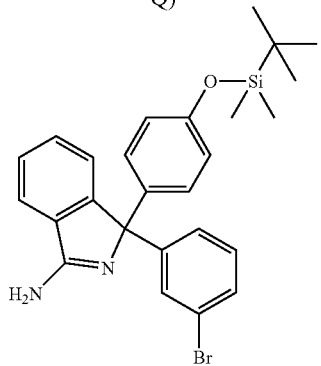

To a −78° C. cooled solution of (4-bromo-phenoxy)-tert-butyl-dimethyl-silane (3.82 mL, 15.61 mmol) in tetrahydrofuran (50 mL) was added 2.5 M n-butyllithium in hexanes (6.2 mL, 15.61 mmol) and the anion stirred 20 minutes. At the same time in a separate round bottom flask containing 1,3-dibromobenzene (2.83 mL, 23.41 mmol) and tetrahydrofuran (50 mL) cooled in a −78° C. bath was added 2.5 M n-butyllithium in hexanes (9.37 mL, 23.41 mmol) and the anion stirred 20 minutes. The first anion was cannulated into a −78° C. solution of 1,2-dicyanobenzene (2.00 g, 15.61 mmol) in tetrahydrofuran (20 mL) and this mixture stirred 10 minutes. The second anion was cannulated into the reaction and the mixture stirred 45 minutes. The reaction was poured into saturated ammonium chloride (100 mL) and extracted twice with ethyl acetate. The combined organic layers were washed with aqueous saturated sodium chloride, dried over magnesium sulfate and removed of solvent under reduced pressure to give an amber foam. The crude material was placed on a 180 g silica gel column and eluted with a gradient of dichloromethane to dichloromethane/methanol (9:1) over 30 minutes at 40 mL/min and the combined purified fractions were removed of solvent under reduced pressure to give the titled compound as a off white solid (1.64 g, 21%). $^1$H NMR (300 MHz, DMSO-d$_6$) δ 7.69 (d, J=7.4 Hz, 1 H), 7.60-7.47 (m, 3 H), 7.42 (s, 2 H), 7.28 (d, J=7.5 Hz, 2 H), 7.14 (d, J=8.6 Hz, 2 H), 6.76 (d, J=8.6 Hz, 2 H), 0.92 (s, 9 H), 0.16 (s, 6 H); MS (APCI+) m/z 493 [M+1]$^+$; t$_R$=2.79 min.

Examples 37-41

Additional compounds in Table 4 were prepared according to Scheme 6 using the appropriate boronic acid starting material.

TABLE 4

| Ex | Compound | Structure | NMR | m/z M + 1 (Ionization) | LC $t_R$ (min) |
|---|---|---|---|---|---|
| 37 | Methanesulfonic acid 4-{3-amino-1-[3-(2-fluoro-pyridin-3-yl)-phenyl]-1H-isoindol-1-yl}-phenyl ester trifluoroacetate | 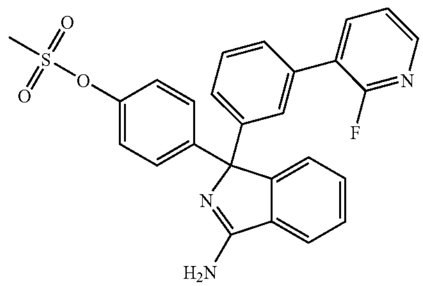 | $^1$H NMR (500 MHz, DMSO-d6/TFA-d) δ 8.36 (d, J = 7.8 Hz, 1 H), 8.25 (d, J = 4.1 Hz, 1 H), 8.08 (ddd, J = 9.8, 7.8, 1.8 Hz, 1 H), 7.93 (d, J = 7.8 Hz, 1 H), 7.88 (t, J = 7.5 Hz, 1 H), 7.76 (t, J = 7.6 Hz, 1 H), 7.67 (d, J = 7.8 Hz, 1 H), 7.61-7.55 (m, 2 H), 7.47-7.40 (m, 6 H), 3.39 (s, 3 H). | 474 (ES+) | 1.75 |
| 38 | Methanesulfonic acid 4-[3-amino-1-(3-pyrimidin-5-yl-phenyl)-1H-isoindol-1-yl]-phenyl ester trifluoroacetate | 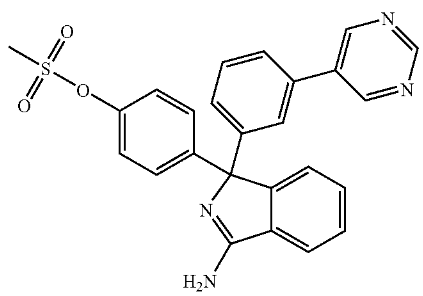 | $^1$H NMR (500 MHz, DMSO-d6/TFA-d) δ 9.23-9.22 (m, 1 H), 9.12 (s, 2 H), 8.35 (d, J = 7.9 Hz, 1 H), 8.01 (d, J = 7.9 Hz, 1 H), 7.90-7.84 (m, 2 H), 7.78-7.75 (m, 2 H), 7.61 (t, J = 7.9 Hz, 1 H), 7.48 (d, J = 8.0 Hz, 1 H), 7.40 (s, 4 H), 3.39 (s, 3 H). | 457 (ES+) | 1.61 |
| 39 | Methanesulfonic acid 4-{3-amino-1-[3-(5-methoxy-pyridin-3-yl)-phenyl]-1H-isoindol-1-yl}-phenyl ester trifluoroacetate | 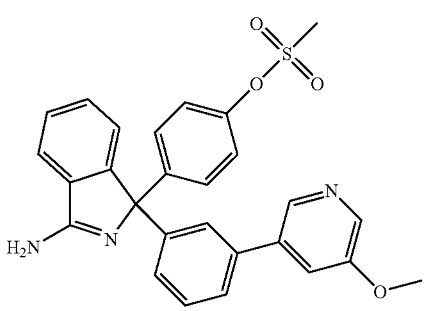 | $^1$H NMR (500 MHz, DMSO-d6/TFA-d) δ 8.82 (s, 1 H), 8.72 (d, J = 2.4 Hz, 1 H), 8.37 (d, J = 7.7 Hz, 2 H), 8.02 (d, J = 7.8 Hz, 1 H), 7.94-7.87 (m, 2 H), 7.80-7.75 (m, 2 H), 7.65 (t, J = 7.8 Hz, 1 H), 7.55 (d, J = 7.7 Hz, 1 H), 7.42-7.37 (m, 4 H), 4.07 (s, 3 H), 3.39 (s, 3 H). | 486 (ES+) | 1.63 |
| 40 | Methanesulfonic acid 4-[3-amino-1-(3'-methoxy-biphenyl-3-yl)-1H-isoindol-1-yl]-phenyl ester trifluoroaceate | 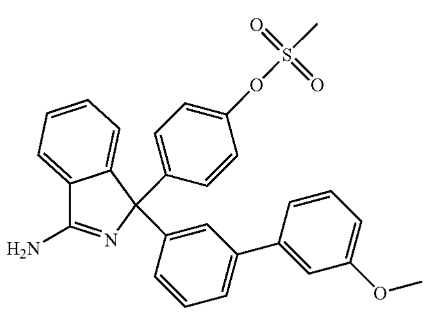 | $^1$H NMR (500 MHz, DMSO-d6/TFA-d) δ 7.95 (d, J = 7.8 Hz, 1 H), 7.89 (t, J = 7.5 Hz, 1 H), 7.76 (t, J = 7.6 Hz, 1 H), 7.71 (d, J = 7.7 Hz, 1 H), 7.56 (s, 1 H), 7.52 (t, J = 7.8 Hz, 1 H), 7.45-7.36 (m, 6 H), 7.32 (d, J = 7.8 Hz, 1 H), 7.17 (d, J = 7.8 Hz, 1 H), 7.14 (s, 1 H), 6.96 (dd, J = 8.2, 2.2 Hz, 1 H), 3.81 (s, 3 H), 3.39 (s, 3 H). | 485 (ES+) | 2.03 |

TABLE 4-continued

| Ex | Compound | Structure | NMR | m/z M + 1 (Ionization) | LC $t_R$ (min) |
|---|---|---|---|---|---|
| 41 | Methanesulfonic acid 4-[3-amino-1-(5'-methane-sulfonyloxy-3'-methoxy-biphenyl-3-yl)-1H-isoindol-1-yl]-phenyl ester trifluoroacetate | 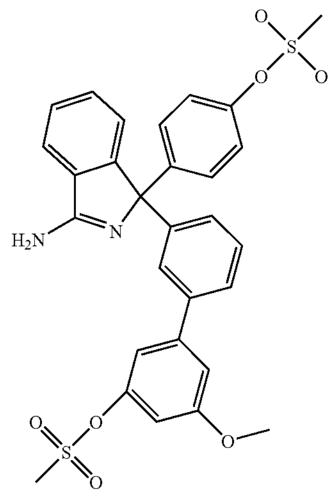 | $^1$H NMR (500 MHz, DMSO-d6/TFA-d) δ 8.35 (d, J = 7.8 Hz, 1 H), 7.96 (d, J = 7.8 Hz, 1 H), 7.89 (t, J = 7.6 Hz, 2 H), 7.76 (t, J = 9.6 Hz, 1 H), 7.59 (s, 1 H), 7.54 (t, J = 7.8 Hz, 1 H), 7.45-7.38 (m, 4 H), 7.16 (d, J = 9.6 Hz, 2 H), 6.98 (s, 1 H), 3.85 (s, 3 H), 3.40 (d, J = 9.2 Hz, 6 H). | 579 (ES+) | 2.02 |

Scheme 7

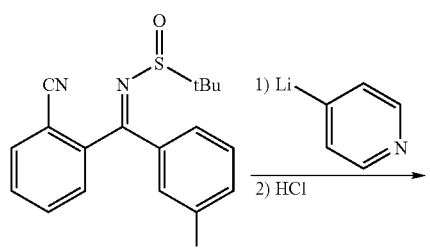

(Scheme 5, Example N)

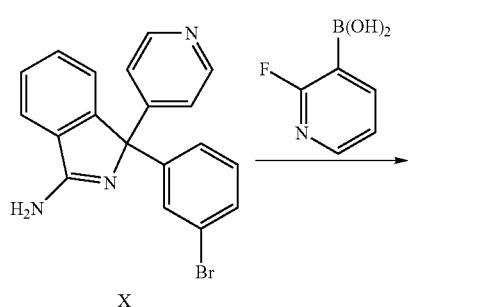

X

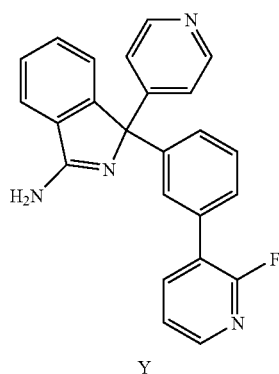

Y

Example 42

3-[3-(2-Fluoro-pyridin-3-yl)-phenyl]-3-pyridin-4-yl-3H-isoindol-1-ylamine trifluoroacetate (Scheme #7, Y)

To 3-(3-bromo-phenyl)-3-pyridin-4-yl-3H-isoindol-1-ylamine (Scheme #7, X) (100 mg, 0.25 mmol) was added potassium phosphate (160 mg, 0.75 mmol), 2-fluoropyridyl-3-boronic acid (53 mg, 0.37 mmol), dichlorobis(triphenylphosphine)palladium(II) (18 mg, 0.025 mmol), and 1,2-dimethoxyethane: water:ethanol (7:3:2, 3.0 mL). The reaction was heated in an aluminium block at 100° C. for 30 minutes. The mixture was filtered through a syringe filter and the filtrate was removed of solvent under reduced pressure. The resulting residue was dissolved in acetonitrile/water with trifluoroacetic acid, (75:25:0.1, 4 mL), and purified using RP-HPLC AG1 ($t_R$=10.6 min). The combined purified fractions were lyophilized and placed under high vacuum over night at 50° C. to give the title compound (43 mg, 35%). $^1$H NMR (500 MHz, DMSO-d$_6$/TFA-d) δ 9.01 (d, J=6.9 Hz, 2 H), 8.41 (d, J=7.8 Hz, 1 H), 8.26 (d, J=4.6 Hz, 1 H), 8.14 (d, J=6.8 Hz, 2 H), 8.12-8.08 (m, 1 H), 8.04 (d, J=7.9 Hz, 1 H), 7.95 (t, J=7.6 Hz, 1 H), 7.84 (t, J=7.6 Hz, 1 H), 7.75 (d, J=7.1

Hz, 1 H), 7.61 (t, J=7.9 Hz, 1 H), 7.51 (s, 1 H), 7.46 (t, J=7.0 Hz, 1 H), 7.34 (d, J=8.9 Hz, 1 H); MS (ES+) m/z 381 [M+1]$^+$; $t_R$=1.37 min.

Example 43

3-(3-Bromo-phenyl)-3-pyridin-4-yl-3H-isoindol-1-ylamine trifluoroacetate (Scheme 7, X)

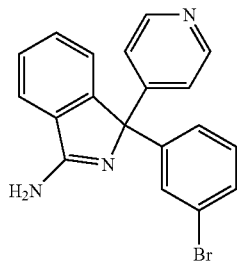

To a vigorously stirred solution of 4-bromopyridine hydrochloride in 20 mL water was added solid sodium bicarbonate until gas evolution stopped. The mixture was washed twice with ether (25 mL each) and the combined organics washed with aqueous saturated sodium chloride, placed in an amber vial and dried over sodium sulfate overnight while in the freezer at −7° C. The drying agent was filtered off and washed with a minimum amount of ether. The ether was removed from the filtrate under a stream of nitrogen. The 4-bromopyridine oil was placed under high vacuum for 10 minutes then stored in the freezer under nitrogen (6.4 g, 79%). $^1$H NMR (500 MHz, DMSO-d$_6$) δ 8.48 (dd, J=4.6, 1.4 Hz, 2 H), 7.68 (dd, J=4.6, 1.5 Hz, 2 H).

To an oven dried, nitrogen purged, 250 mL 3-neck round bottom was added N,N,N',N'-tetramethyl-ethane-1,2-diamine (1.70 mL, 11.30 mmol) followed by anhydrous tetrahydrofuran (40 mL) and the solution cooled in a liquid nitrogen/pentane bath to an internal temperature of −106° C. To this was added 1.7 M t-butyllithium in pentane (13.3 mL, 22.59 mmol) and the yellow solution kept at an internal temperature of −104° C. In a separate dry single neck 50 mL, nitrogen flushed, round bottom was added freshly prepared 4-bromopyridine (1.78 g, 11.30 mmol) and the solution cooled in a −78° C. bath. The 4-bromopyridine solution was cannulated drop wise into the t-butyllithium reaction over 20 minutes carefully maintaining the internal temperature below −78° C. After the addition the reaction was cooled to −98° C. In a separate dry single neck 50 mL nitrogen flushed round bottom was added N-[(3-bromophenyl)(2-cyanophenyl)methylene]-2-methylpropane-2-sulfinamide (Prepared Scheme 5, Example N) (1.50 g, 3.77 mmol) and tetrahydrofuran (20 mL) and the solution cooled in a −78° C. bath. This was cannulated into the 4-lithiopyridine anion reaction over 2 minutes. The reaction was stirred for 15 minutes, quenched with water, warmed to room temperature, and extracted with ethyl acetate. The organic layer was washed with aqueous saturated sodium chloride, dried over sodium sulfate, and removed of solvent under reduced pressure to give a tan solid. The solid chromatographed on 50 g silica gel eluting with 100 mL portions of dichloromethane and dichloromethane with methanol: 2.5%, 5% and 10%. The product was isolated as protected and unprotected material in a 4.5:1 ratio and these combined together and carried directly into the next step (1.82 g).

To the mixture of protected and unprotected material (1.82 g) in 5 mL methanol was added 1.25 M hydrochloric acid in methanol (30 mL) and the reaction stirred 15 minutes. The solvent was removed under reduced pressure to give a tan solid. The solids were triturated with ether (25 mL), filtered off, and transferred to a flask by dissolving in methanol. The solvent was removed under reduced pressure and the material put under high vacuum at 50° C. to give the title compound as a tan solid which was carried forward crude into the next reaction as is (1.91 g). A small portion (100 mg) was purified by RP-HPLC AG1 ($t_R$=11.6 min) to give the purified title compound (70 mg). $^1$H NMR (500 MHz, DMSO-d$_6$/TFA-d) δ 9.02 (d, J=6.9 Hz, 2 H), 8.40 (d, J=7.8 Hz, 1 H), 8.11 (d, J=6.8 Hz, 2 H), 8.00 (d, J=7.8 Hz, 1 H), 7.94 (t, J=7.6 Hz, 1 H), 7.84 (t, J=7.6 Hz, 1 H), 7.70 (d, J=9.1 Hz, 1 H), 7.48 (s, 1 H), 7.43 (t, J=8.0 Hz, 1 H), 7.26 (d, J=8.0 Hz, 1 H); MS (ES+) m/z 364 [M+1]$^+$; $t_R$=1.34 min.

Examples 44-47

Additional compounds in Table 5 were prepared according to Scheme 7 using the appropriate boronic acid starting material.

TABLE 5

| Ex | Compound | Structure | NMR | m/z M + 1 (Ionization) | LC $t_R$ (min) |
|---|---|---|---|---|---|
| 44 | 3-Pyridin-4-yl-3-(3-pyridin-3-yl-phenyl)-3H-isoindol-1-ylamine trifluoroacetate | 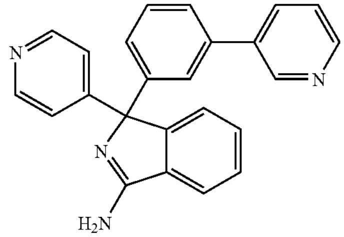 | $^1$H NMR (500 MHz, DMSO-d6/TFA-d) δ 9.26 (d, J = 1.7 Hz, 1 H), 9.03 (d, J = 6.8 Hz, 2 H), 9.00 (d, J = 5.6 Hz, 1 H), 8.90 (d, J = 8.8 Hz, 1 H), 8.43 (d, J = 7.9 Hz, 1 H), 8.20 (dd, J = 8.2, 5.8 Hz, 1 H), 8.11 (d, J = 7.0 Hz, 2 H), 8.08 (d, J = 7.9 Hz, 1 H), 8.00 (d, J = 8.1 Hz, 1 H), 7.95 (t, J = 7.6 Hz, 1 H), 7.84 (t, J = 7.7 Hz, 1 H), 7.77 (s, 1 H), 7.70 (t, J = 7.9 Hz, 1 H), 7.48 (d, J = 8.9 Hz, 1 H). | 363 (ES+) | 1.02 |

TABLE 5-continued

| Ex | Compound | Structure | NMR | m/z M + 1 (Ionization) | LC $t_R$ (min) |
|---|---|---|---|---|---|
| 45 | 3-Pyridin-4-yl-3-(3-pyrimidin-5-yl-phenyl)-3H-isoindol-1-ylamine trifluoroacetate | 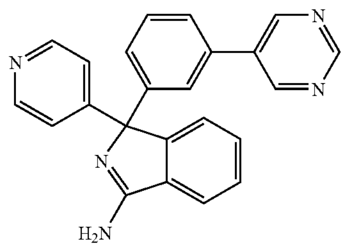 | $^1$H NMR (500 MHz, DMSO-d6/TFA-d) δ 9.23 (s, 1 H), 9.14 (s, 2 H), 9.01 (d, J = 6.8 Hz, 2 H), 8.41 (d, J = 7.8 Hz, 1 H), 8.11 (d, J = 6.8 Hz, 2 H), 8.07 (d, J = 7.9 Hz, 1 H), 7.95 (q, J = 7.1 Hz, 2 H), 7.84 (t, J = 7.7 Hz, 1 H), 7.72 (s, 1 H), 7.64 (t, J = 7.9 Hz, 1 H), 7.38 (d, J = 7.9 Hz, 1 H). | 364 (ES+) | 1.14 |
| 46 | 3-[3-(5-Methoxy-pyridin-3-yl)-phenyl]-3-pyridin-4-yl-3H-isoindol-1-ylamine trifluoroacetate | 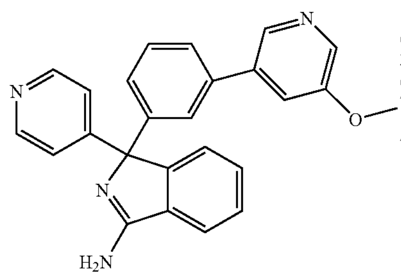 | $^1$H NMR (500 MHz, DMSO-d6/TFA-d) δ 9.02 (d, J = 6.8 Hz, 2 H), 8.85 (s, 1 H), 8.76 (d, J = 2.6 Hz, 1 H), 8.42 (d, J = 7.2 Hz, 2 H), 8.08 (d, J = 6.3 Hz, 3 H), 8.01 (d, J = 8.0 Hz, 1 H), 7.95 (t, J = 7.7 Hz, 1 H), 7.84 (t, J = 7.7 Hz, 1 H), 7.75 (s, 1 H), 7.68 (t, J = 7.9 Hz, 1 H), 7.47 (d, J = 7.9 Hz, 1 H), 4.07 (s, 3 H). | 393 (ES+) | 1.26 |
| 47 | 3-(3'-Methoxy-biphenyl-3-yl)-3-pyridin-4-yl-3H-isoindol-1-ylamine trifluoroacetate | 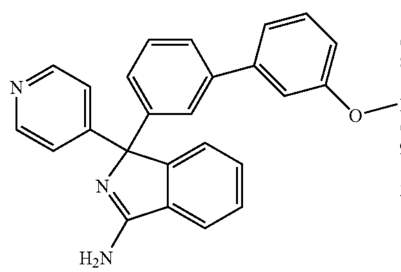 | $^1$H NMR (500 MHz, DMSO-d6/TFA-d) δ 9.00 (d, J = 6.7 Hz, 2 H), 8.41 (d, J = 7.8 Hz, 1 H), 8.14 (d, J = 6.8 Hz, 2 H), 8.06 (d, J = 7.9 Hz, 1 H), 7.95 (t, J = 7.6 Hz, 1 H), 7.84 (t, J = 7.6 Hz, 1 H), 7.79 (d, J = 8.0 Hz, 1 H), 7.57-7.53 (m, 2 H), 7.38 (t, J = 8.0 Hz, 1 H), 7.25 (d, J = 9.0 Hz, 1 H), 7.19 (d, J = 7.8 Hz, 1 H), 7.16 (s, 1 H), 6.98 (dd, J = 8.3, 2.4 Hz, 1 H), 3.81 (s, 3 H). | 392 (ES+) | 1.69 |

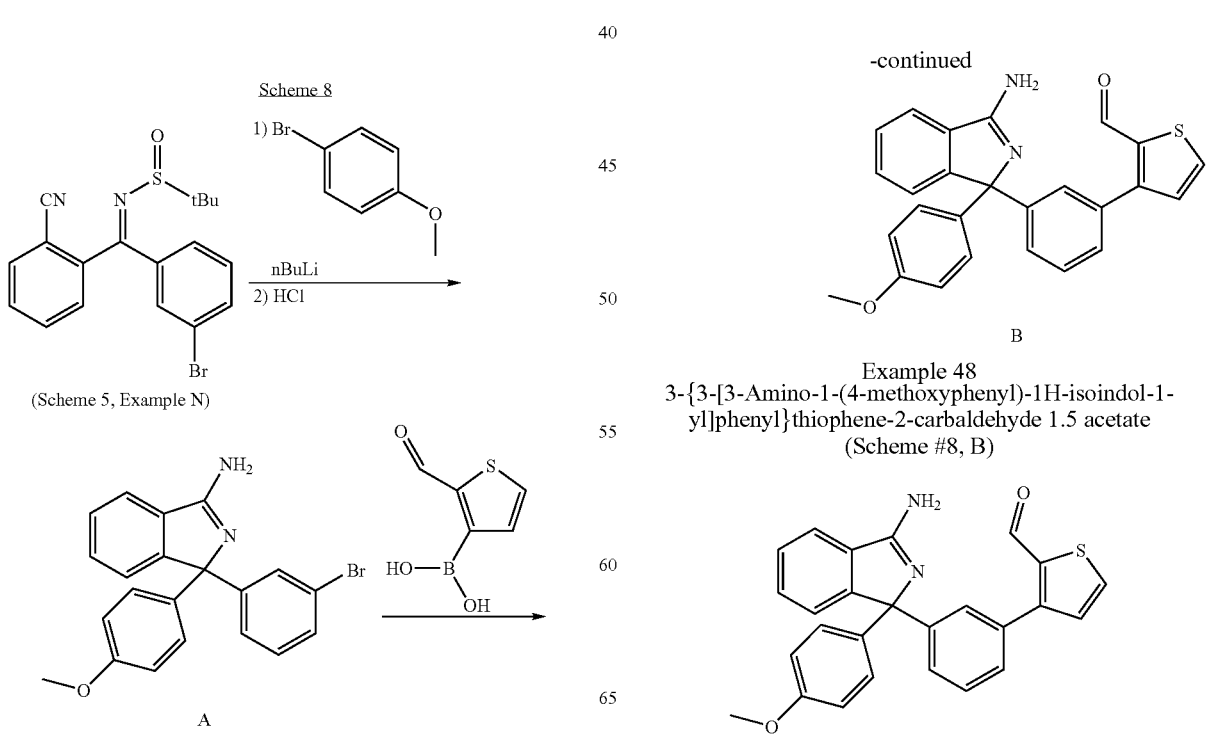

Example 48
3-{3-[3-Amino-1-(4-methoxyphenyl)-1H-isoindol-1-yl]phenyl}thiophene-2-carbaldehyde 1.5 acetate
(Scheme #8, B)

1-(3-Bromophenyl)-1-(4-methoxyphenyl)-1H-isoindol-3-amine (0.079 g, 0.2 mmol) (Scheme #8, A), (2-formyl-3-thienyl)boronic acid (0.047 g, 0.3 mmol), [1,1'-bis(diphenylphosphino)ferrocene]palladium(II) chloride dichloromethane adduct (0.016 g, 0.02 mmol), potassium carbonate (0.083 g, 0.6 mmol) and solvent (3 mL of a mixture of dimethoxyethane, water and ethanol in a ratio of 6:3:1) was irradiated under an argon atmosphere in a microwave at 130° C. for 15 min. When cooled to ambient temperature the mixture was filtered and dimethyl sulfoxide (1.0 mL) was added. The solution was concentrated in vacuo and purified by preparative HPLC to give 0.003 g (4% yield) of the title compound. $^1$H NMR (DMSO-d$_6$) δ 9.68 (s, 1 H), 8.15 (d, J=5.02 Hz, 1 H), 7.79 (dd, J=5.52, 3.01 Hz, 1 H), 7.73 (dd, J=5.52, 2.76 Hz, 1 H), 7.68-7.53 (m, 1 H), 7.50-7.38 (m, 5 H), 7.33 (d, J=5.02 Hz, 1 H), 7.26 (d, J=8.78 Hz, 2 H), 6.83 (d, J=8.78 Hz, 2 H), 3.71 (s, 3 H), 1.91 (s, 3 H); MS (AP) m/z 425 [M+1]$^+$.

1-(3-Bromophenyl)-1-(4-methoxyphenyl)-1H-isoindol-3-amine (Scheme #8, A)

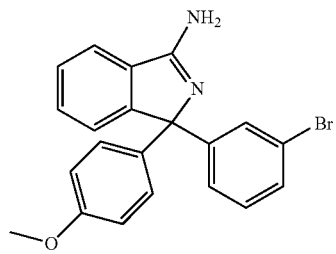

To a −78° C. solution of 4-bromoanisole (0.45 mL, 3.6 mmol) in tetrahydrofuran (15 mL) was n-butyllithium (2.5 M in hexane, 1.3 mL, 3.3 mmol) added, after 0.5 h a solution of N-[(3-bromophenyl)(2-cyanophenyl)methylene]-2-methylpropane-2-sulfinamide (Scheme #5, N) (1.2 g, 3.0 mmol) in tetrahydrofuran (5 mL) was added. The reaction mixture was stirred at −78° C. for 3 h and then quenched by addition of water. Ethyl acetate was added and the mixture was washed with water and brine, dried over magnesium sulfate and concentrated. The residue was dissolved in methanol (25 mL) and treated with hydrochloric acid (2 M in diethyl ether, 3.0 mL, 6.0 mml) over night. The reaction mixture was concentrated and then partitioned between aqueous saturated sodium bicarbonate and chloroform, the organic phase was dried over magnesium sulfate and concentrated. Purification by column chromatography using a gradient of methanol in dichloromethane gave the title compound (0.70 g, 59%). $^1$H NMR (CDCl$_3$) δ 7.57-7.48 (m, 3 H), 7.47-7.41 (m, 1 H), 7.39-7.32 (m, 2 H), 7.32-7.28 (m, 1 H), 7.26-7.20 (m, 2 H), 7.10 (t, J=7.83 Hz, 1 H), 6.83-6.77 (m, 2 H), 5.86 (br s, 2 H), 3.75 (s, 3 H); MS (AP) m/z 393, 395 [M+1]$^+$.

Example 49

1-(3-Bromophenyl)-1-[4-(trifluoromethoxy)phenyl]-1H-isoindol-3-amine

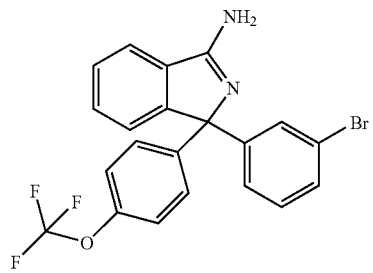

The title compound was synthesized as described in Scheme #8, A starting from 1-bromo-4-(trifluoromethoxy)benzene in 56% yield. $^1$H NMR (DMSO-d$_6$) δ 7.86-7.78 (m, 1 H), 7.78-7.71 (m, 1 H), 7.55-7.36 (m, 6 H), 7.36-7.21 (m, 4 H), 6.89 (br s, 2 H); MS (AP) m/z 447, 449 [M+1]$^+$.

Example 50

4-[3-Amino-1-(3-bromophenyl)-1H-isoindol-1-yl]benzonitrile

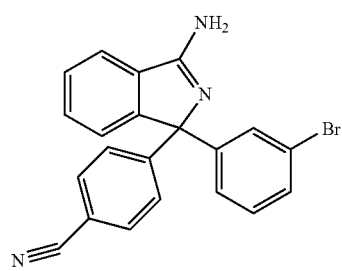

The title compound was synthesized as described in Scheme #8, A starting from 4-bromobenzonitrile in 69% yield. $^1$H NMR (DMSO-d$_6$) δ 7.84-7.79 (m, 1 H), 7.77-7.70 (m, 3 H), 7.51-7.40 (m, 6 H), 7.33-7.28 (m, 1 H), 7.28-7.21 (m, 1 H), 6.95 (br s, 2 H); MS (AP) m/z 387, 389 [M+1]$^+$.

Example 51

1-(3-Bromophenyl)-1-[4-(trifluoromethyl)phenyl]-1H-isoindol-3-amine

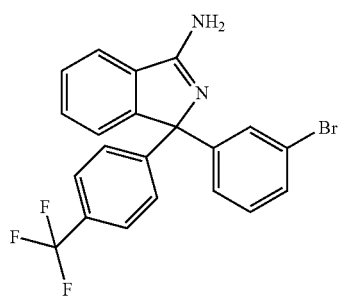

The title compound was synthesized as described in Scheme #8, A starting from 1-bromo-4-trifluoromethylbenzene in 82% yield. $^1$H NMR (DMSO-d$_6$) δ 7.85-7.78 (m, 1 H), 7.77-7.71 (m, 1 H), 7.63 (d, J=8.34 Hz, 2 H), 7.53-7.39 (m, 6 H), 7.35-7.29 (m, 1 H), 7.29-7.20 (m, 1 H), 6.92 (br s, 2 H); MS (AP) m/z 430, 432 [M+1]$^+$.

Example 52

1-(3-Bromophenyl)-1-[6-(trifluoromethyl)pyridin-3-yl]-1H-isoindol-3-amine acetate

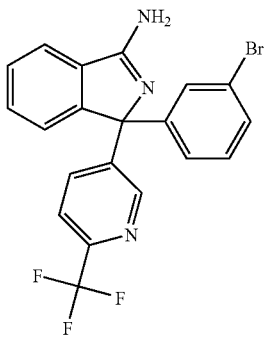

The title compound was prepared as described in Scheme #8, A starting from 5-bromo-2-(trifluoromethyl)pyridine. Purification by column chromatography using gradient eluation from dichloromethane to dichloromethane:3.5 M ammonia in methanol 95:5 and preparative HPLC gave 13% yield: $^1$H NMR (DMSO-d$_6$) δ 8.67 (d, J=2.01 Hz, 1 H), 7.94 (dd, J=8.03, 1.76 Hz, 1 H), 7.89-7.79 (m, 3 H), 7.56-7.42 (m, 4 H), 7.39-7.32 (m, 1 H), 7.32-7.23 (m, 1 H), 7.00 (br s, 2 H), 1.89 (s, 3 H); MS (ES) m/z 432, 434 [M+1]$^+$.

Scheme 9

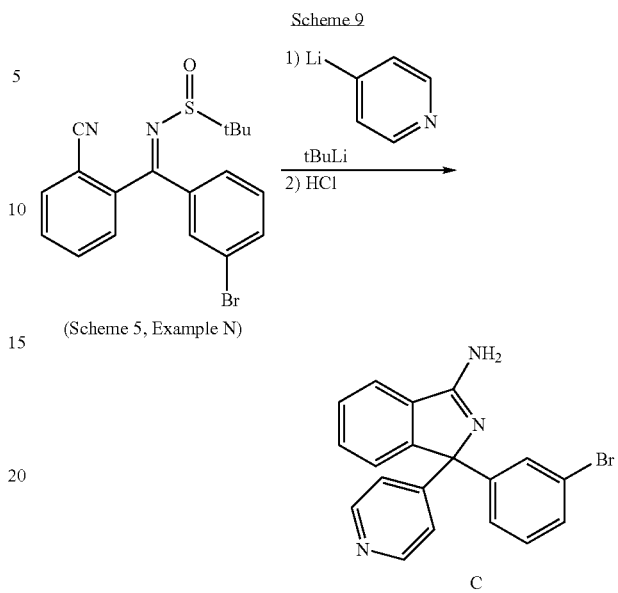

(Scheme 5, Example N)

1-(3-Bromophenyl)-1-pyridin-4-yl-1H-isoindol-3-amine (Scheme #9, C)

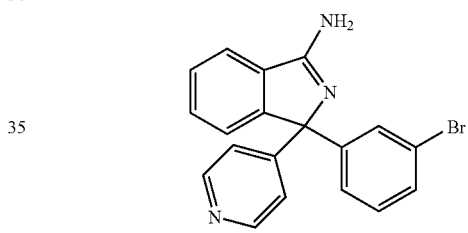

To a solution of tert-butyllithium (1.7 M in pentane, 3.5 mL, 6.0 mmol) in tetrahydrofuran (20 mL) at −105° C. was a solution of 4-iodopyridine (0.68 g, 3.3 mmol) in tetrahydrofuran (10 mL) added drop wise. Next was a solution of N-[(3-bromophenyl)(2-cyanophenyl)methylene]-2-methylpropane-2-sulfinamide (1.2 g, 3.0 mmol) in tetrahydrofuran (10 mL) added. After 1 h at −105° C. was the reaction quenched by addition of water. The resulting mixture was partitioned between ethyl acetate and water, the organic phase was dried over magnesium sulfate and evaporated. The residue was dissolved in methanol (25 mL) and treated with hydrochloric acid (2 M in diethylether, 3.0 mL, 6.0 mml) over night. The reaction mixture was concentrated and then partitioned between aqueous saturated sodium bicarbonate and chloroform, the organic phase was dried over magnesium sulfate and concentrated. Purification by column chromatography using a stepwise gradient of methanol in ethyl acetate (5-10%) with 1% triethylamine afforded the title compound (0.66 g, 61%). $^1$H NMR (CDCl$_3$) δ 8.56-8.48 (m, 2 H), 7.60-7.38 (m, 6 H), 7.27-7.21 (m, 3 H), 7.21-7.14 (m, 1 H), 5.16 (br s, 2 H); MS (AP) m/z 364, 366 [M+1]$^+$.

Examples 53-64

The following compounds were prepared according to Example 48 (Scheme #8, B) using the starting material described above and the appropriate boronic acid or boronic ester.

TABLE 6

| Ex | Compound | Structure | NMR | M/z |
|---|---|---|---|---|
| 53 | 1-[3-(1-Isobutyl-1H-pyrazol-4-yl)phenyl]-1-(4-methoxyphenyl)-1H-isoindol-3-amine 0.5 acetate | 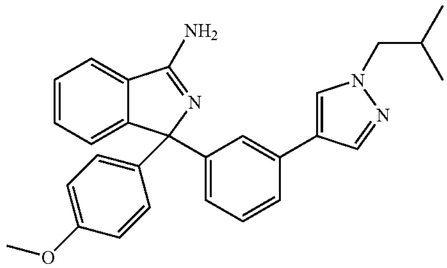 | $^1$H NMR (DMSO-d$_6$) δ 8.00 (s, 1 H), 7.81-7.76 (m, 1 H), 7.74-7.68 (m, 2 H), 7.53-734 (m, 4 H), 7.27-7.12 (m, 4 H), 6.81 (d, J = 9.03 Hz, 2 H), 3.91 (d, J = 7.28 Hz, 2 H), 3.70 (s, 3 H), 2.20-2.02 (m, 1 H), 0.84 (d, 6 H), 1.91 (s, 1.5 H). | 437 (AP+) |
| 54 | 1-(4-Methoxyphenyl)-1-[3-(5-methyl-2-furyl)phenyl]-1H-isoindol-3-amine 0.5 acetate | 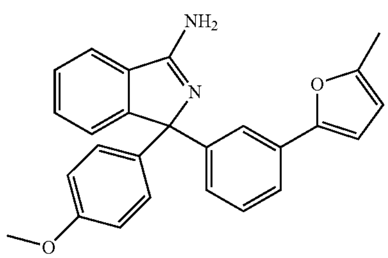 | $^1$H NMR (DMSO-d$_6$) δ 7.78 (dd, J = 5.65, 2.38 Hz, 1 H), 7.66 (dd, J = 5.77, 2.26 Hz, 1 H), 7.61 (s, 1 H), 7.49-7.40 (m, 3 H), 7.26 (t, J = 7.65 Hz, 1 H), 7.22-7.14 (m, 3 H), 6.81 (d, J = 8.78 Hz, 2 H), 6.67 (d, J = 3.26 Hz, 1 H), 6.20-6.13 (m, 1 H), 3.71 (s, 3 H), 2.31 (s, 3 H), 1.91 (s, 1.5 H). | 395 (AP+) |
| 55 | 3'-[3-Amino-1-(4-methoxyphenyl)-1H-isoindol-1-yl]biphenyl-2-carboxamide 0.5 acetate | 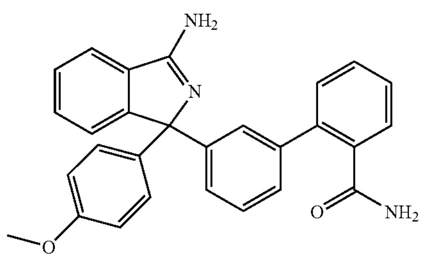 | $^1$NMR (DMSO-d$_6$) δ 7.76 (d, J = 7.28 Hz, 1 H), 7.71 (d, J = 7.28 Hz, 1 H), 7.64 (s, 1 H), 7.49-7.34 (m, 5 H), 7.34-7.18 (m, 6 H), 6.80 (d, J = 8.78 Hz, 2 H), 3.70 (s, 3 H), 1.91 (s, 1.5 H). | 434 (AP+) |
| 56 | 1-[3-(5-Fluoropyridin-3-yl)phenyl]-1-[4-(trifluoromethoxy)phenyl]-1H-isoindol-3-amine 0.75 acetate | 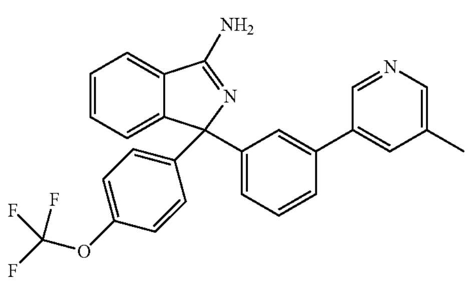 | $^1$H NMR (400 MHz, DMSO-d$_6$) δ 8.64 (s, 1 H), 8.57 (d, J = 2.76 Hz, 1 H), 7.96-7.90 (m, 1 H), 7.88 (d, J = 6.53 Hz, 1 H), 7.82 (d, J = 6.02 Hz, 1 H), 7.70-7.57 (m, 2 H), 7.53-7.37 (m, 6 H), 7.26 (d, J = 8.53 Hz, 2 H), 6.86 (br s, 2 H), 1.91 (s, 2.3 H). | 464 (AP+) |
| 57 | 1-(3-Pyrimidin-5-ylphenyl)-1-[4-(trifluoromethoxy)phenyl]-1H-isoindol-3-amine 0.25 acetate | 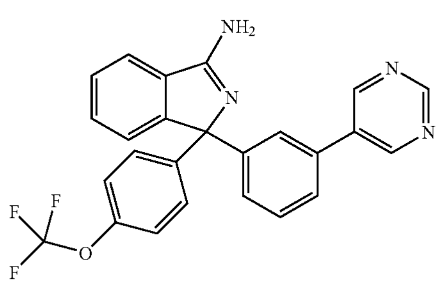 | $^1$H NMR (DMSO-d$_6$) δ 9.18 (s, 1 H), 9.00 (s, 2 H), 7.91-7.87 (m, 1 H), 7.83-7.78 (m, 1 H), 7.69-7.62 (m, 2 H), 7.53-7.41 (m, 6 H), 7.26 (d, J = 8.28 Hz, 2 H), 6.82 (br s, 2 H), 1.91 (s, 0.5 H). | 447 (AP+) |

TABLE 6-continued

| Ex | Compound | Structure | NMR | M/z |
|---|---|---|---|---|
| 58 | 4-[3-Amino-1-(3-pyrimidin-5-ylphenyl)-1H-isoindol-1-yl]benzonitrile 0.25 acetate | 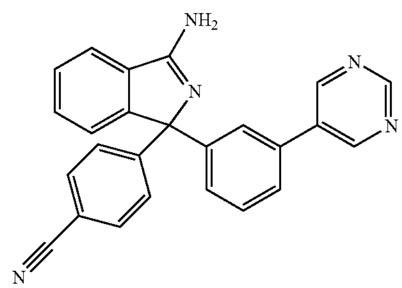 | ¹H NMR (DMSO-d₆) δ 9.18 (s, 1 H), 9.01 (s, 2 H), 7.93-7.88 (m, 1 H), 7.85-7.80 (m, 1 H), 7.73 (d, J = 8.53 Hz, 2 H), 7.69-7.64 (m, 2 H), 7.55-7.44 (m, 6 H), 6.89 (br s, 2 H), 1.91 (s, 0.5 H). | 388 (AP+) |
| 59 | 1-[3-(5-Fluoropyridin-3-yl)phenyl]-1-[4-(trifluoromethyl)phenyl]-1H-isoindol-3-amine 0.25 acetate | 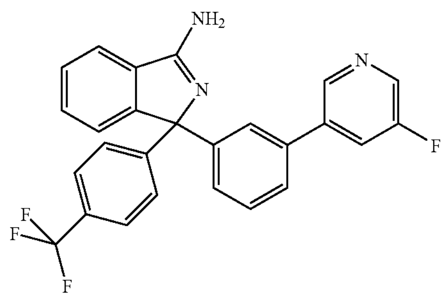 | ¹H NMR (DMSO-d₆) δ 8.65 (s, 1 H), 8.57 (d, J = 2.51 Hz, 1 H), 7.93 (d, J = 10.04 Hz, 1 H), 7.88 (d, J = 6.53 Hz, 1 H), 7.84 (d, 1 H), 7.69-7.60 (m, 4 H), 7.57-7.40 (m, 4 H), 6.87 (br s, 2 H), 1.91 (s, 1.0 H). | 446 (ES−) |
| 60 | 1-(3-Pyrimidin-5-ylphenyl)-1-[4-(trifluoromethyl)phenyl]1H-isoindol-3-amine 0.25 acetate | 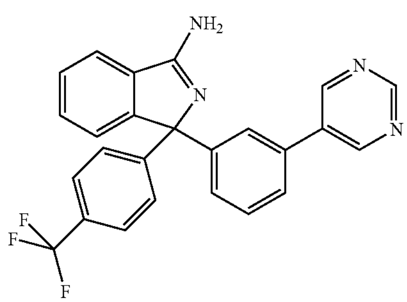 | ¹H NMR (DMSO-d₆) δ 9.18 (s, 1 H), 9.01 (s, 2 H), 7.92-7.87 (m, 1 H), 7.85-7.80 (m, 1 H), 7.71-7.60 (m, 4 H), 7.58-7.44 (m, 6 H), 6.86 (br s, 2 H), 1.91 (s, 0.5 H). | 429 (ES−) |
| 61 | 3-[3-(3-Amino-1-pyridin-4-yl-1H-isoindol-1-yl)phenyl]thiophene-2-carbaldehyde | 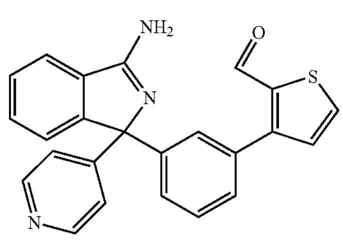 | | 396 (ES+) |
| 62 | 1-[3-(1-Isobutyl-1H-pyrazol-4-yl)phenyl]-1-pyridin-4-yl-1H-isoindol-3-amine 0.25 | 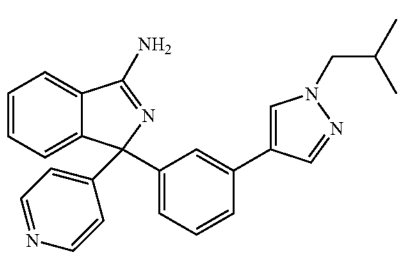 | ¹H NMR (DMSO-d₆) δ 8.44 (dd, J = 4.52, 1.51 Hz, 2 H), 8.03 (s, 1 H), 7.81 (dd, J = 5.14, 3.14 Hz, 2 H), 7.72 (s, 1 H), 7.52-7.46 (m, 3 H), 7.43 (d, J = 7.78 Hz, 1 H), 7.31-7.23 (m, 3 H), 7.21-7.13 (m, 1 H), 6.84 (br s, 2 H), 3.91 (d, J = 7.28 Hz, 2 H), 2.18-2.05 (m, 1 H), 0.85 (d, J = 6.78 Hz, 6 H), 1.91 (s, 1.0 H). | 408 (ES+) |

TABLE 6-continued

| Ex | Compound | Structure | NMR | M/z |
|---|---|---|---|---|
| 63 | 1-[3-(5-Methyl-2-furyl)phenyl]-1-pyridin-4-yl-1H-isoindol-3-amine acetate | 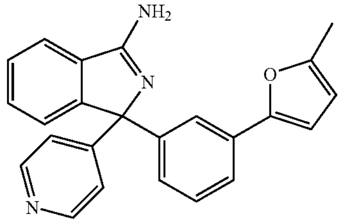 | $^1$H NMR (DMSO-d$_6$) δ 8.45 (dd, J = 4.52, 1.51 Hz, 2 H), 7.87-7.80 (m, 1 H), 7.79-7.73 (m, 1 H), 7.61 (s, 1 H), 7.55-7.45 (m, 3 H), 7.34-7.25 (m, 3 H), 7.20 (d, J = 8.03 Hz, 1 H), 6.88 (br s, 2 H), 6.70 (d, J = 3.26 Hz, 1 H), 6.21-6.12 (m, 1 H), 2.31 (s, 3 H), 1.91 (s, 3.0 H). | 366 (AP+) |
| 64 | 3'-(3-Amino-1-pyridin-4-yl-1H-isoindol-1-yl)biphenyl-2-carboxamide 0.25 acetate | 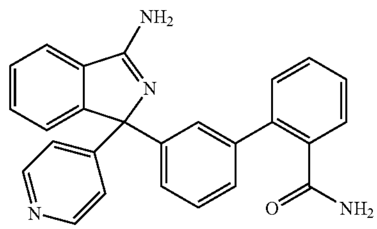 | $^1$H NMR (DMSO-d$_6$) δ 8.49-8.41 (m, 2 H), 7.79 (t, J = 6.90 Hz, 2 H), 7.67 (s, 1 H), 7.53-7.25 (m, 11 H), 6.84 (br s, 2 H), 1.91 (s, 1.0 H). | 405 (ES+) |

Example 65

4-{3-Amino-1-[3-(2-fluoropyridin-3-yl)phenyl]-1H-isoindol-1-yl}benzonitrile

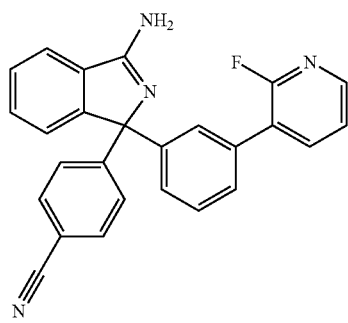

4-[3-Amino-1-(3-bromophenyl)-1H-isoindol-1-yl]benzonitrile (0.086 g, 0.22 mmol) (Example 50), (2-fluoropyridin-3-yl)boronic acid (0.047 g, 0.33 mmol), [1,1'-bis(diphenylphosphino)ferrocene]palladium(II) chloride dichloromethane adduct (0.018 g, 0.022 mmol), potassium carbonate (0.091 g, 0.66 mmol) and solvent (3 mL of a mixture of dimethoxyethene, water and ethanol in a ratio of 6:3:1) was irradiated under argon atmosphere in a microwave at 125° C. for 6 min. When cooled to ambient temperature the mixture was partitioned between ethyl acetate and water; the organic phase was dried over magnesium sulfate and evaporated. Purification by preparative HPLC to give 0.062 g (70% yield) of the title compound. $^1$H NMR (DMSO-d$_6$) δ 8.22 (dd, J=3.28, 1.52 Hz, 1 H), 8.05-7.94 (m, 1 H), 7.84-7.75 (m, 2 H), 7.75-7.69 (m, 2 H), 7.56-7.34 (m, 9 H), 6.90 (br s, 2 H); MS (AP) m/z 405 [M+1]$^+$.

Example 66

1-[3-(2-Fluoropyridin-3-yl)phenyl]-1-[4-(trifluoromethyl)phenyl]-1H-isoindol-3-amine

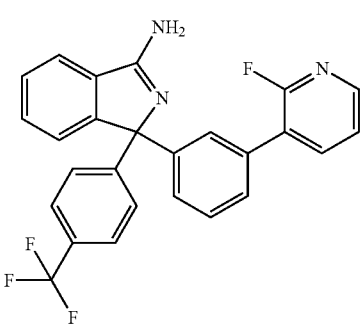

The title compound was synthesized as described in Example 65 starting from 1-(3-bromophenyl)-1-[4-(trifluoromethyl)phenyl]-1H-isoindol-3-amine (Example 51), in 70% yield. $^1$H NMR (DMSO-d$_6$) δ 8.25-8.18 (m, 1 H), 8.05-7.95 (m, 1 H), 7.85-7.73 (m, 2 H), 7.63 (d, J=8.34 Hz, 2H), 7.57-7.37 (m, 9 H), 6.89 (br s, 2 H); MS (AP) m/z 448 [M+1]$^+$.

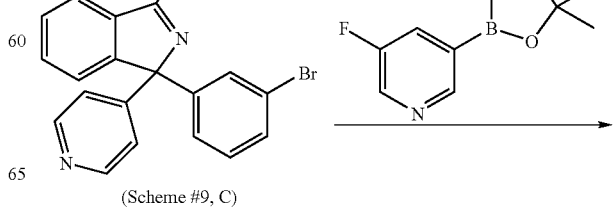

(Scheme #9, C)

87

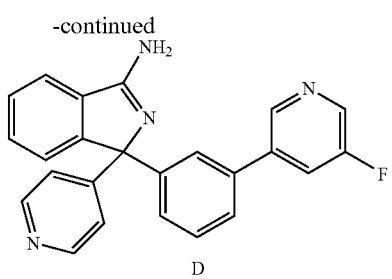

Example 67

1-[3-(5-Fluoropyridin-3-yl)phenyl]-1-pyridin-4-yl-1H-isoindol-3-amine 0.75 acetate (Scheme #10, D)

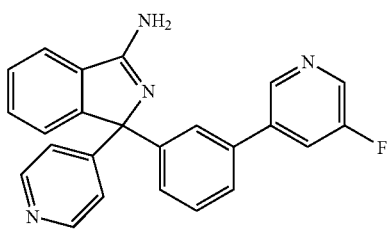

88

A mixture of 1-(3-bromophenyl)-1-pyridin-4-yl-1H-isoindol-3-amine (Scheme #9, C) (0.073 g, 0.20 mmol), 3-fluoro-5-(4,4,5,5-tetramethyl-1,3,2-dioxaborolan-2-yl)pyridine (0.067 g, 0.30 mmol), potassium carbonate (0.055 g, 0.40 mmol), [1,1'-bis(diphenylphosphino)ferrocene]palladium (II) chloride dichloromethane adduct (0.020 g, 0.025 mmol), dimethoxyethane (2 mL), water (1 mL) and ethanol (0.3 mL) under an argon atmosphere was irradiated in a microwave at 100° C. for 15 min. The reaction mixture was filtered and partitioned between water and ethyl acetate, the organic phase was concentrated and the residue was purified by preparative HPLC, which gave the title compound (0.041 g, 54%). $^1$H NMR (DMSO-$d_6$) δ 8.67-8.63 (m, 1 H), 8.57 (d, J=2.78 Hz, 1 H), 8.49-8.42 (m, 2 H), 7.99-7.90 (m, 2 H), 7.85-7.79 (m, 1 H), 7.67-7.62 (m, 2 H), 7.55-7.41 (m, 4 H), 7.37-7.28 (m, 2 H), 6.95 (br s, 2 H), 1.91 (s, 2.2 H); MS (ESI) m/z 381 [M+1]$^+$.

Scheme 11

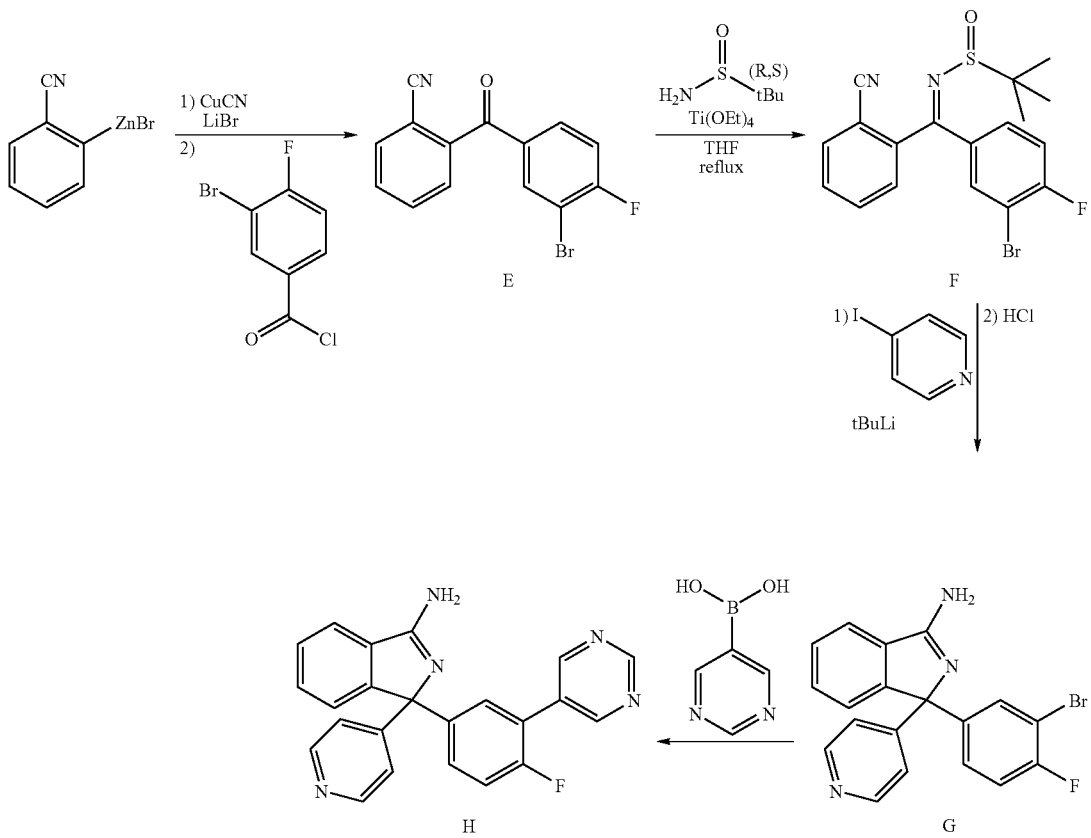

Example 68

1-(4-Fluoro-3-pyrimidin-5-ylphenyl)-1-pyridin-4-yl-1H-isoindol-3-amine 0.5 acetate (Scheme #11, H)

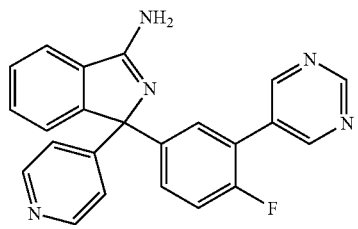

The title compound was synthesized from 1-(3-bromo-4-fluorophenyl)-1-pyridin-4-yl-1H-isoindol-3-amine (Scheme #11, G) as described in Example 67 (Scheme #10, D) in 41% yield using pyrimidin-5-ylboronic acid. $^1$H NMR (DMSO-$d_6$) δ 9.02 (s, 1 H), 8.78-8.72 (m, 2 H), 8.30-8.23 (m, 2 H), 7.78-7.70 (m, 1 H), 7.66-7.58 (m, 1 H), 7.41-7.26 (m, 4 H), 7.20-7.08 (m, 3 H), 6.76 (br s, 2 H), 1.72 (s, 1.9 H); MS (ESI) m/z 382 [M+1]$^+$.

1-(3-Bromo-4-fluorophenyl)-1-pyridin-4-yl-1H-isoindol-3-amine (Scheme #11, G)

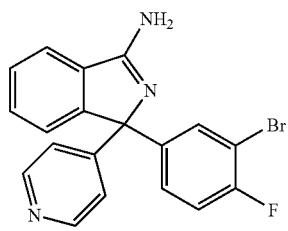

The title compound was synthesized as described in Scheme #9, C in 16% yield starting from N-[(3-bromo-4-fluorophenyl)(2-cyanophenyl)methylene]-2-methylpropane-2-sulfinamide (Scheme #11, F). MS (AP) m/z 382, 384 [M+1]$^+$.

N-[(3-Bromo-4-fluorophenyl)(2-cyanophenyl)methylene]-2-methylpropane-2-sulfinamide (Scheme #11, F)

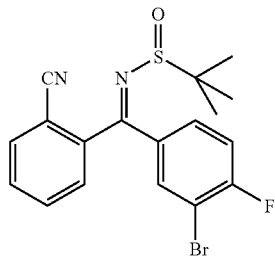

A mixture of 2-(3-bromo-4-fluorobenzoyl)benzonitrile (Scheme #11, E) and tetraethyl orthotitanate (1 M solution in tetrahydrofuran, 18.3 mL, 18.3 mmol) was stirred for 5 minutes, then 2-methyl-2-propanesulfinamide (1.11 g, 9.13 mmol) was added and the resulting mixture was heated to reflux over night. When the reaction had cooled to room temperature methanol, aqueous saturated sodium bicarbonate and ethyl acetate was added. After filtering the reaction mixture through a pad of sodium sulfate, the filtrate was concentrated. Purification of the residue by column chromatography using chloroform as the eluent gave the title compound (1.22 g, 30% over 2 steps). $^1$H NMR (CDCl$_3$) δ 7.90-7.69 (m, 3 H), 7.68-7.39 (m, 3 H), 7.18 (t, J=8.21 Hz, 1 H), 1.38 (br s, 9 H); MS (AP) m/z 407, 409 [M+1]$^+$.

2-(3-Bromo-4-fluorobenzoyl)benzonitrile (Scheme #11, E)

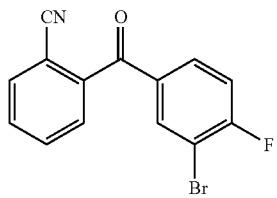

To a −20° C. solution of 2-cyanophenylzinc bromide (0.5 M in tetrahydrofuran, 20 mL, 10 mmol) was a solution of copper cyanide (0.94 g, 10.5 mmol) and lithium bromide (1.82 g, 21.0 mmol) in tetrahydrofuran (15 mL) added, the reaction was slowly allowed to reach room temperature, after 15 minutes the reaction mixture was recooled to −25° C. A solution of 3-bromo-4-fluorobenzoyl chloride (1.45 g, 10.5 mmol) in tetrahydrofuran (10 mL) was added, the reaction mixture was stirred at −25° C. 1 h and at room temperature over night. After partition between aqueous ammonium chloride and diethylether, the organic phase was dried over magnesium sulfate and concentrated to give the crude title product which was used without further purification. MS (ESI) m/z 304, 306 [M+1]$^+$.

Example 69

1-[4-Fluoro-3-(5-fluoro pyridin-3-yl)phenyl]-1-pyridin-4-yl-1H-isoindol-3-amine 0.75 acetate

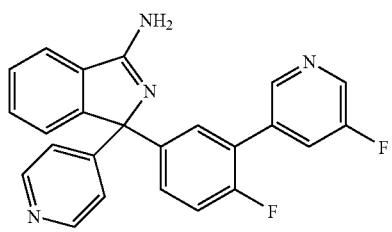

The title compound was synthesized from 1-(3-bromo-4-fluorophenyl)-1-pyridin-4-yl-1H-isoindol-3-amine (Scheme #11, G) as described in Example 67 (Scheme #10, D) in 31% yield using 3-fluoro-5-(4,4,5,5-tetramethyl-1,3,2-dioxaborolan-2-yl)pyridine. $^1$H NMR (DMSO-$d_6$) δ 8.63 (d, J=2.78 Hz, 1 H), 8.57-8.51 (m, 1 H), 8.50-8.42 (m, 2 H), 7.95-7.86 (m, 2 H), 7.85-7.78 (m, 1 H), 7.56-7.46 (m, 4 H), 7.36-7.27 (m, 3 H), 6.96 (br s, 2 H), 1.91 (s, 2.5 H); MS (ESI) m/z 399 [M+1]$^+$.

Scheme 12

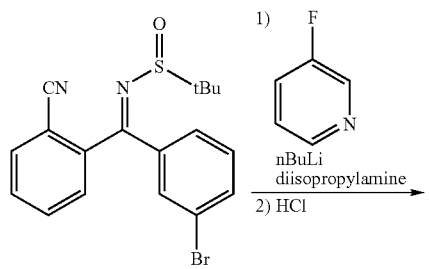

(Scheme 5, Example N)

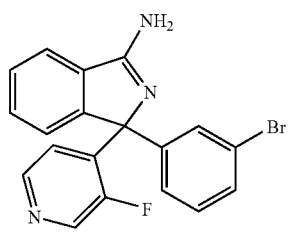

1-(3-Bromophenyl)-1-(3-fluoropyridin-4-yl)-1H-isoindol-3-amine (Scheme #12, I)

To a −78° C. solution of diisopropylamine (0.77 mL, 5.50 mmol) in tetrahydrofuran (10 mL) was n-butyllithium (2.5 M in hexane, 2.20 mL, 5.50 mmol) added, the mixture was stirred 0.5 h and then a solution of 3-fluoropyridine (0.47 mL, 5.50 mmol) in tetrahydrofuran (2 mL) was added and after another 0.5 h N-[(3-bromophenyl)(2-cyanophenyl)methylene]-2-methylpropane-2-sulfinamide (Scheme #5, N) (1.95 g, 5.0 mmol) in tetrahydrofuran (5 mL) was added. After 1.5 h at −78° C. water was added, the mixture was extracted with ethyl acetate, the organic phase was dried over magnesium sulfate and concentrated. The residue was dissolved in methanol (40 mL) and treated with hydrochloric acid (2 M in diethylether, 5 mL, 10.0 mmol) over night. After evaporation, the residue was partitioned between aqueous saturated sodium bicarbonate and chloroform, the organic phase was dried over magnesium sulfate and evaporated. Purification of the residue by column chromatography using a stepwise gradient of methanol in chloroform (0-10%) as the eluent gave the title compound (1.22 g, 64%). $^1$H NMR (CDCl$_3$) δ 8.43 (d, J=2.78 Hz, 1 H), 8.35 (d, J=5.05 Hz, 1 H), 7.76 (d, J=8.08 Hz, 1 H), 7.60-7.50 (m, 3 H), 7.45-7.37 (m, 2 H), 7.37-7.33 (m, 1 H), 7.20-7.13 (m, 2 H), 5.37 (br s, 2 H); MS (AP) m/z 382, 384 [M+1]$^+$.

Example 70

1-(3-Bromo-4-fluorophenyl)-1-(3-fluoropyridin-4-yl)-1H-isoindol-3-amine

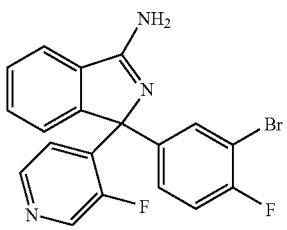

The title compound was synthesized starting from N-[(3-bromo-4-fluorophenyl)(2-cyanophenyl)methylene]-2-methylpropane-2-sulfinamide (Scheme #11, F) as described in Scheme #12, I in 74% yield. $^1$H NMR (DMSO-d$_6$) δ 8.46 (d, J=2.78 Hz, 1 H), 8.38 (d, J=5.05 Hz, 1 H), 7.89-7.71 (m, 2 H), 7.66-7.53 (m, 2 H), 7.44-7.35 (m, 2 H), 7.19-7.13 (m, 1 H), 7.05 (t, J=8.34 Hz, 1 H); MS (ESI) m/z 400, 402 [M+1]$^+$.

Example 71

1-(3-Fluoropyridin-4-yl)-1-[3-(5-fluoropyridin-3-yl)phenyl]-1H-isoindol-3-amine 0.5 acetate

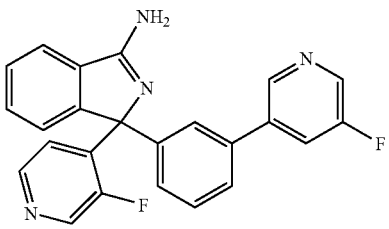

The title compound was synthesized from 1-(3-bromophenyl)-1-(3-fluoropyridin-4-yl)-1H-isoindol-3-amine (Scheme #12, I) as described in Scheme #10, D in 57% yield using 3-fluoro-5-(4,4,5,5-tetramethyl-1,3,2-dioxaborolan-2-yl)pyridine. $^1$H NMR (DMSO-d$_6$) δ 8.58-8.52 (m, 1 H), 8.49 (d, J=2.78 Hz, 1 H), 8.37 (d, J=2.78 Hz, 1 H), 8.27 (d, J=4.80 Hz, 1 H), 7.88-7.82 (m, 1 H), 7.81-7.72 (m, 2 H), 7.60-7.53 (m, 1 H), 7.51-7.40 (m, 3 H), 7.35 (t, J=7.71 Hz, 1 H), 7.30-7.25 (m, 1 H), 7.21 (dd, J=6.82, 5.05 Hz, 1 H), 6.95 (br s, 2 H), 1.84 (s, 1.4 H); MS (ESI) m/z 399 [M+1]$^+$.

Example 72

1-(3-Fluoropyridin-4-yl)-1-(3-pyrimidin-5-ylphenyl)-1H-isoindol-3-amine 1.25 acetate

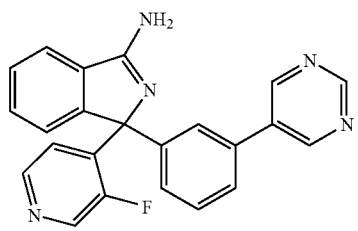

The title compound was synthesized from 1-(3-bromophenyl)-1-(3-fluoropyridin-4-yl)-1H-isoindol-3-amine (Scheme #12, I) as described in Scheme #10, D in 91% yield using pyrimidin-5-ylboronic acid. $^1$H NMR (DMSO-d$_6$) δ 9.10 (s, 1 H), 8.91 (s, 2 H), 8.37 (d, J=2.78 Hz, 1 H), 8.27 (d, J=5.05 Hz, 1 H), 7.81-7.74 (m, 2 H), 7.62-7.56 (m, 1 H), 7.52-7.48 (m, 1 H), 7.46-7.34 (m, 3 H), 7.33-7.27 (m, 1 H), 7.21 (dd, J=6.82, 5.05 Hz, 1 H), 6.95 (br s, 2 H), 1.84 (s, 3.6 H); MS (ESI) m/z 382 [M+1]$^+$.

Example 73

1-(3-Fluoropyridin-4-yl)-1-[3-(2-fluoropyridin-3-yl)phenyl]-1H-isoindol-3-amine 1.25 acetate

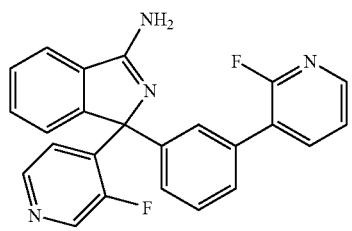

The title compound was synthesized from 1-(3-bromophenyl)-1-(3-fluoropyridin-4-yl)-1H-isoindol-3-amine (Scheme #12, I) as described in Scheme #10, D in 47% yield using (2-fluoropyridin-3-yl)boronic acid. $^1$H NMR (DMSO-d$_6$) δ 8.38 (d, J=2.78 Hz, 1 H), 8.27 (d, J=5.05 Hz, 1 H), 8.17-8.12 (m, 1 H), 7.96-7.88 (m, 1 H), 7.80-7.74 (m, 1 H), 7.71-7.65 (m, 1 H), 7.48-7.31 (m, 6 H), 7.27-7.20 (m, 2 H), 6.93 (br s, 2 H), 1.89 (s, 3.9 H); MS (ESI) m/z 397 [M−1]$^-$.

Example 74

1-(3-Fluoropyridin-4-yl)-1-(4-fluoro-3-pyrimidin-5-ylphenyl)-1H-isoindol-3-amine 1.25 acetate

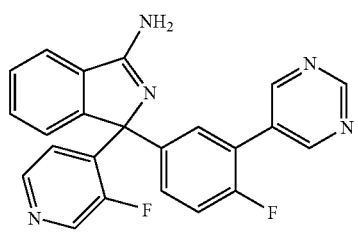

The title compound was synthesized from 1-(3-bromo-4-fluorophenyl)-1-(3-fluoropyridin-4-yl)-1H-isoindol-3-amine (Example 70) as described in Scheme #10, D in 47% yield using pyrimidin-5-ylboronic acid. $^1$H NMR (DMSO-d$_6$) δ 9.00 (s, 1 H), 8.70 (d, J=1.26 Hz, 2 H), 8.24 (d, J=3.03 Hz, 1 H), 8.13 (d, J=5.05 Hz, 1 H), 7.68-7.60 (m, 2 H), 7.35-7.24 (m, 3 H), 7.24-7.18 (m, 1 H), 7.11 (dd, J=10.11, 8.84 Hz, 1 H), 7.05 (dd, J=6.82, 5.05 Hz, 1 H), 6.82 (br s, 2 H), 1.88 (s, 3.8 H); MS (ESI) m/z 400 [M+1]$^+$.

Example 75

1-[4-Fluoro-3-(5-fluoropyridin-3-yl)phenyl]-1-(3-fluoropyridin-4-yl)-1H-isoindol-3-amine 1.5 acetate

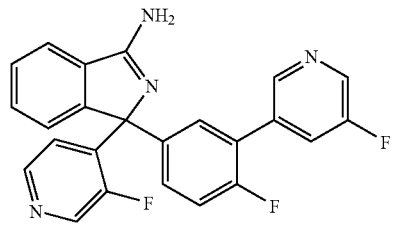

The title compound was synthesized from 1-(3-bromo-4-fluorophenyl)-1-(3-fluoropyridin-4-yl)-1H-isoindol-3-amine (Example 70) as described in Scheme #10, D in 26% yield using 3-fluoro-5-(4,4,5,5-tetramethyl-1,3,2-dioxaborolan-2-yl)pyridine. $^1$H NMR (DMSO-d$_6$) δ 8.41 (d, J=2.78 Hz, 1 H), 8.30 (d, J=1.52 Hz, 1 H), 8.25 (d, J=2.78 Hz, 1 H), 8.13 (d, J=4.80 Hz, 1 H), 7.59-7.70 (m, 3 H), 7.35-7.27 (m, 2 H), 7.25-7.15 (m, 2 H), 7.13-7.03 (m, 2 H), 6.83 (br s, 2 H), 1.89 (s, 4.3 H); MS (ESI) m/z 415 [M−1]$^-$.

Example 76

1-[4-Fluoro-3-(2-fluoropyridin-3-yl)phenyl]-1-(3-fluoropyridin-4-yl)-1H-isoindol-3-amine 1.5 acetate

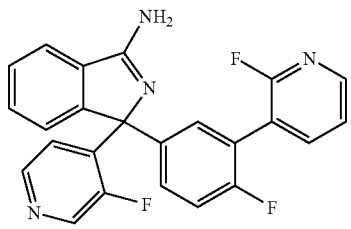

The title compound was synthesized from 1-(3-bromo-4-fluorophenyl)-1-(3-fluoropyridin-4-yl)-1H-isoindol-3-amine (Example 70) as described in Scheme #10, D in 21% yield using (2-fluoropyridin-3-yl)boronic acid. $^1$H NMR (DMSO-d$_6$) δ 8.25 (d, J=2.78 Hz, 1 H), 8.16-8.06 (m, 2 H), 7.79-7.69 (m, 1 H), 7.67-7.60 (m, 1 H), 7.60-7.54 (m, 1 H), 7.36-7.22 (m, 3 H), 7.21-7.11 (m, 2 H), 7.11-7.03 (m, 2 H), 6.82 (br s, 2 H), 1.87 (s, 4.3 H); MS (ESI) m/z 415 [M−1]$^-$.

Scheme 13

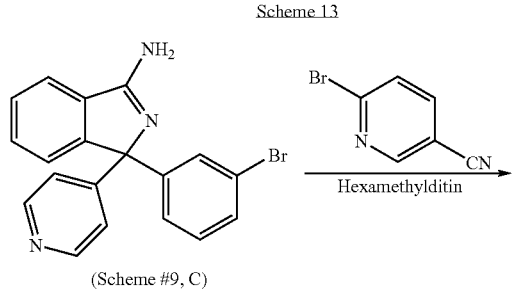

(Scheme #9, C)

Example 77

5-[3-(3-Amino-1-pyridin-4-yl-1H-isoindol-1-yl)phenyl]nicotinonitrile acetate (Scheme #13, J)

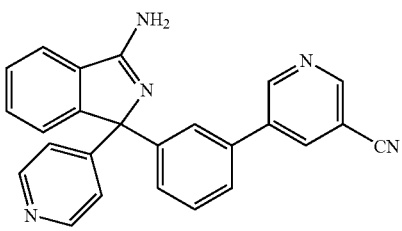

A mixture of 5-bromo-3-cyanopyridine (0.073 g, 0.40 mmol), hexamethylditin (0.13 g, 0.40 mmol), tetrakis(triphenylphosphine)palladium (0.012 g, 0.010 mmol) and dimethoxyethane (2 mL) under an argon atmosphere was irradiated in a microwave at 130° C. for 1 h. 1-(3-Bromophenyl)-1-pyridin-4-yl-1H-isoindol-3-amine (Scheme #9, C) (0.073 g, 0.20 mmol) and tetrakis(triphenylphosphine)palladium (0.012 g, 0.010 mmol) was added to the reaction mixture and heating was continued for 2 h at 100° C. The reaction mixture was filtered and partitioned between water and ethyl acetate, the organic phase was concentrated and the residue was purified by preparative HPLC, which gave the title compound (0.017 g, 23%). $^1$H NMR (DMSO-$d_6$) δ 8.97 (d, J=2.27 Hz, 1 H), 8.93 (d, J=1.77 Hz, 1 H), 8.48 (t, J=2.02 Hz, 1 H), 8.43-8.34 (m, 2 H), 7.91-7.85 (m, 1 H), 7.78-7.73 (m, 1 H), 7.66-7.57 (m, 2 H), 7.48-7.35 (m, 4 H), 7.23 (d, J=6.06 Hz, 2 H), 6.91 (br s, 2 H), 1.83 (s, 2.9 H); MS (ESI) m/z 388 [M+1]$^+$.

Scheme 14

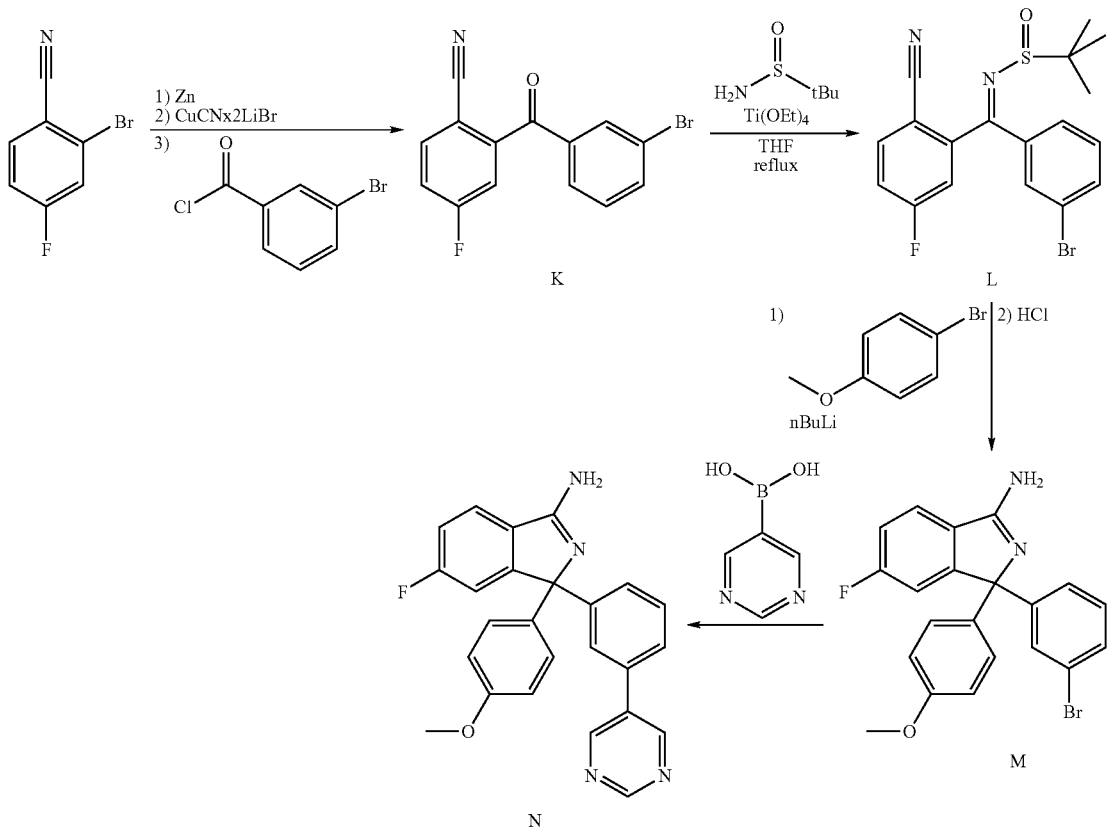

Example 78

6-Fluoro-1-(4-methoxyphenyl)-1-(3-pyrimidin-5-ylphenyl)-1H-isoindol-3-amine (Scheme #14, N)

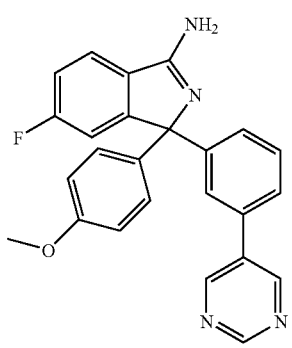

A mixture of 1-(3-bromophenyl)-6-fluoro-1-(4-methoxyphenyl)-1H-isoindol-3-amine (Scheme #14, M) (77 mg, 0.187 mmol), pyrimidin-5-ylboronic acid (30 mg, 0.243 mmol), [1,1'-bis(diphenylphosphino)ferrocene]palladium(II) dichloride dichloromethane adduct (15.5 mg, 0.019 mmol) and cesium carbonate (183 mg, 0.561 mmol) in a mixture of dimethoxyethane, water and ethanol (6:3:1, 5 mL) was irradiated with microwaves at 130° C., under an argon atmosphere for 15 min. After cooling to ambient temperature the mixture was filtered, concentrated in vacuo and purified by preparative HPLC to give 10.3 mg (13.4% yield): $^1$H NMR (CDCl$_3$) δ 9.17 (s, 1 H), 8.87 (s, 2 H), 7.53 (m, 1 H), 7.48-7.37 (m, 4 H), 7.24 (m, 3 H), 7.12 (m, 1 H), 6.82 (m, 2 H), 3.78 (s, 3 H); MS (ESI) m/z 411 [M+1]$^+$.

1-(3-Bromophenyl)-6-fluoro-1-(4-methoxyphenyl)-1H-isoindol-3-amine (Scheme #14, M)

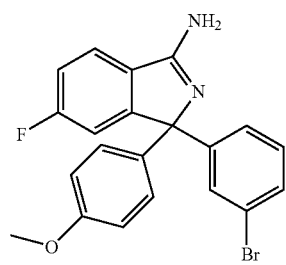

The title compound was prepared as described in Scheme #5, O using N-[(3-bromophenyl) (2-cyano-5-fluorophenyl)methylene]-2-methylpropane-2-sulfinamide (Scheme #14, L) as starting material (73.5% yield): $^1$H NMR (CDCl$_3$) δ 7.45 (t, J=1.77 Hz, 1 H), 7.41 (dd, J=8.21, 4.67 Hz, 1 H), 7.37 (m, 1 H), 7.25-7.17 (m, 4 H), 7.19-7.09 (m, 2 H), 6.81 (m, 2 H), 3.78 (s, 3 H).

N-[(3-bromophenyl)(2-cyano-5-fluorophenyl)methylene]-2-methylpropane-2-sulfinamide (Scheme #14, L)

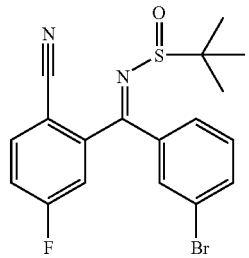

The title compound was prepared as described in Scheme #5, N using 2-(3-bromobenzoyl)-4-fluorobenzonitrile (Scheme #14, K) as starting material (55% yield): $^1$H NMR (CDCl$_3$) δ 7.82-7.72 (m, 2 H), 7.67 (m, 1 H), 7.45 (m, 1 H), 7.30 (m, 2 H), 7.12 (m, 1 H), 1.39 (br s, 9 H).

2-(3-Bromobenzoyl)-4-fluorobenzonitrile (Scheme #14, K)

A 0.1 g/mL suspension of highly activated zinc powder in tetrahydrofuran (33 mL, 50 mmol) was transferred via cannula to a solution of 2-bromo-4-fluorobenzonitrile (5.0 g, 25 mmol) in anhydrous tetrahydrofuran (100 mL) at room temperature under an atmosphere of argon. The mixture was stirred at room temperature for 5 h and then sonicated with ultrasound for 30 min. The excess zinc was allowed to settle over night at −20° C. The solution on top was transferred via cannula to another flask under argon atmosphere and cooled to −20° C. To this was added 1 M CuCNx2LiBr complex solution in tetrahydrofuran (26.3 mL). The resulting solution was stirred at −20° C. for 10 min and at 0° C. for 25 min, then it was cooled to −25° C. and 3-bromobenzoyl chloride was added. The mixture was stirred for 1 h while the temperature was kept between −25° C. and −15° C., and then it was stored in a refrigerator at 0° C. for two and a half days. The reaction was quenched by the addition of saturated ammonium chloride solution. The mixture was diluted with ethyl acetate, the phases were separated and the organic phase was washed with 1 M hydrochloric acid and 1 M sodium carbonate solution, dried over magnesium sulfate and evaporated. Purification by column chromatography using a gradient of gradually increasing concentration of ethyl acetate in heptane (0-40%) gave 5.58 g of the title product (73% yield): $^1$H NMR (CDCl$_3$) δ 7.96 (t, J=1.64 Hz, 1 H), 7.88 (dd, J=8.46, 4.93 Hz, 1 H), 7.80 (m, 1 H), 7.72 (m, 1 H), 7.44-7.37 (m, 2 H), 7.35 (dd, J=8.08, 2.53 Hz, 1 H); MS (EI) m/z 304, 306 [M+1]⁺.

Example 79

6-Fluoro-1-(4-methoxyphenyl)-1-(3-pyridin-3-ylphenyl)-1H-isoindol-3-amine

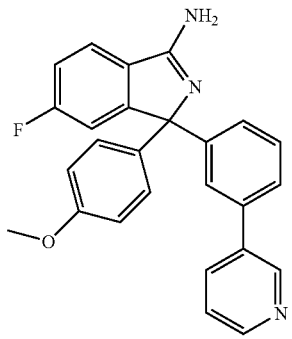

The title compound was prepared as described in Example 78 (Scheme #14, N) using pyridin-3-ylboronic acid (15% yield): ¹H NMR (CDCl₃) δ 8.76 (dd, J=2.40, 0.88 Hz, 1 H), 8.56 (dd, J=4.80, 1.52 Hz, 1 H), 7.80 (m, 1 H) 7.53 (m, 1 H), 7.46 (m, 1 H), 7.42-7.36 (m, 2 H), 7.36-7.30 (m, 2 H), 7.27-7.23 (m, 3 H), 7.12 (m, 1 H), 6.82 (m, 2 H), 3.79 (s, 3 H); MS (ESI) m/z 410 [M+1]⁺.

Example 80

6-Fluoro-1-(3'-methoxybiphenyl-3-yl)-1-(4-methoxyphenyl)-1H-isoindol-3-amine

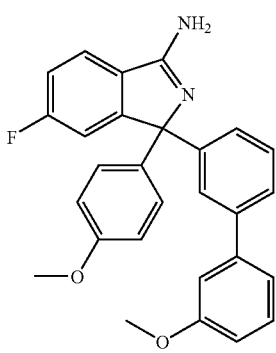

The title compound was prepared as described in Example 78 (Scheme #14, N) using (3-methoxyphenyl)boronic acid (23% yield): ¹H NMR (CDCl₃) δ 7.53 (m, 1 H), 7.46 (m, 1 H), 7.39 (dd, J=8.34, 4.55 Hz, 1 H), 7.28 (m, 6 H), 7.09 (m, 2 H), 7.04 (m, 1 H), 6.87 (m, 1 H), 6.81 (m, 2 H), 3.83 (s, 3 H), 3.78 (s, 3 H); MS (ESI) m/z 439 [M+1]⁺.

Example 81

6-Fluoro-1-(4-methoxyphenyl)-1-[3-(5-methoxypyridin-3-yl)phenyl]-1H-isoindol-3-amine

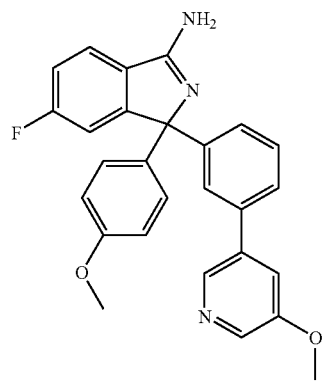

The title compound was prepared as described in Example 78 (Scheme #14, N) using (5-methoxypyridin-3-yl)boronic acid (42% yield): ¹H NMR (CDCl₃) δ 8.36 (d, J=1.77 Hz, 1 H), 8.26 (d, J=2.78 Hz, 1 H), 7.53 (m, 1 H), 7.44 (m, 2 H), 7.38 (m, 1 H), 7.34 (m, 1 H), 7.30 (dd, J=2.78, 1.77 Hz, 1 H), 7.24 (m, 3 H), 7.12 (m, 1 H), 6.82 (m, 2 H), 3.89 (s, 3 H), 3.78 (s, 3 H); MS (ESI) m/z 440 [M+1]⁺.

Example 82

1-(3-Bromophenyl)-6-fluoro-1-pyridin-4-yl-1H-isoindol-3-amine

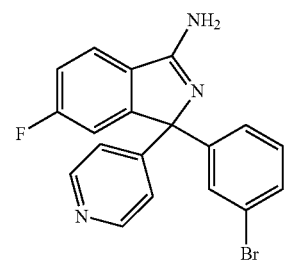

The title compound was prepared as described in Scheme #9, C using N-[(3-bromophenyl)(2-cyano-5-fluorophenyl)methylene]-2-methylpropane-2-sulfinamide (Scheme #14, L) as starting material (90% yield): ¹H NMR (CDCl₃) δ 8.46 (m, 2 H), 7.83 (dd, J=8.46, 4.93 Hz, 1 H), 7.75 (dd, J=8.97, 2.15 Hz, 1 H), 7.47-7.43 (m, 2 H), 7.37-7.31 (m, 2 H), 7.30-7.23 (m, 3 H), 6.98 (br s, 2 H).

Example 83

6-Fluoro-1-pyridin-4-yl-1-(3-pyridin-3-ylphenyl)-1H-isoindol-3-amine

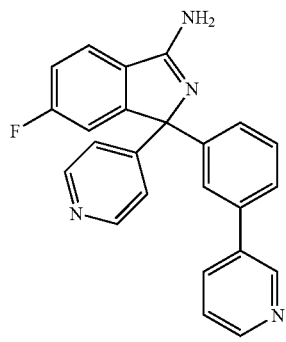

The title compound was prepared as described in Example 78 (Scheme #14, N) using pyridin-3-ylboronic acid and 1-(3-bromophenyl)-6-fluoro-1-pyridin-4-yl-1H-isoindol-3-amine (Example 82) (18.5% yield): $^1$H NMR (DMSO-d$_6$) δ 8.77 (m, 1 H), 8.55 (dd, J=4.80, 1.52 Hz, 1 H), 8.46 (m, 2 H), 7.95 (m, 1 H), 7.87-7.81 (m, 2 H), 7.59 (m, 2 H), 7.47 (m, 1 H), 7.39-7.44 (m, 2 H), 7.37-7.31 (m, 3 H), 6.96 (br s, 2 H); MS (ESI) m/z 381 [M+1]$^+$.

Example 84

6-Fluoro-1-pyridin-4-yl-1-(3-pyrimidin-5-ylphenyl)-1H-isoindol-3-amine

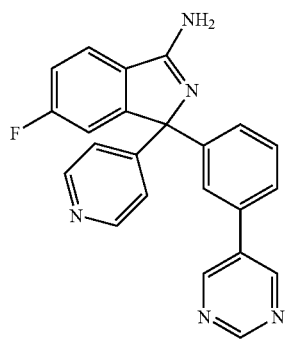

The title compound was prepared as described in Example 78 (Scheme #14, N) using pyrimidin-5-ylboronic acid and 1-(3-bromophenyl)-6-fluoro-1-pyridin-4-yl-1H-isoindol-3-amine (Example 82) (26% yield): $^1$H NMR (CDCl$_3$) δ 9.19 (s, 1 H), 8.87 (s, 2 H), 8.55 (m, 2 H), 7.53-7.45 (m, 4 H), 7.36 (m, 1 H), 7.29-7.25 (m, 3 H), 7.20 (m, 1 H); MS (ESI) m/z 382 [M+1]$^+$.

Example 85

6-Fluoro-1-[3-(5-methoxypyridin-3-yl)phenyl]-1-pyridin-4-yl-1H-isoindol-3-amine

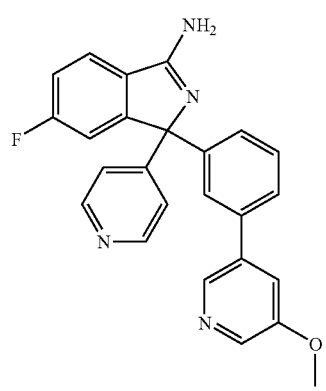

The title compound was prepared as described in Example 78 (Scheme #14, N) using (5-methoxypyridin-3-yl)boronic acid and 1-(3-bromophenyl)-6-fluoro-1-pyridin-4-yl-1H-isoindol-3-amine (Example 82) (16% yield): $^1$H NMR (CDCl$_3$) δ 8.54 (m, 2 H), 8.36 (d, J=1.77 Hz, 1 H), 8.28 (d, J=2.78 Hz, 1 H), 7.52-7.45 (m, 3 H), 7.42 (m, 1 H), 7.32-7.25 (m, 5 H), 7.18 (m, 1 H), 3.90 (s, 3 H); MS (ESI) m/z 411 [M+1]$^+$.

Example 86

6-Fluoro-1-[3-(2-fluoropyridin-3-yl)phenyl]-1-pyridin-4-yl-1H-isoindol-3-amine

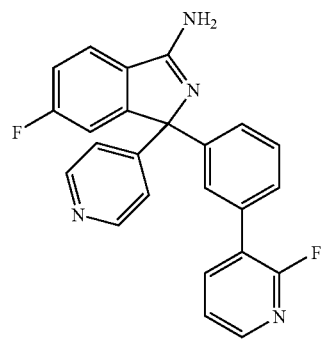

The title compound was prepared as described in Example 78 (Scheme #14, N) using (2-fluoropyridin-3-yl)boronic acid and 1-(3-bromophenyl)-6-fluoro-1-pyridin-4-yl-1H-isoindol-3-amine (Example 82) (22.5% yield): $^1$H NMR (CDCl$_3$) δ 8.54 (m, 2 H), 8.18 (m, 1 H), 7.79 (m, 1 H), 7.50 (m, 1 H), 7.48-7.39 (m, 3 H), 7.32 (m, 1 H), 7.29-7.23 (m, 4 H), 7.18 (m, 1 H); MS (ESI) m/z 399 [M+1]$^+$.

Example 87

1-(3-Bromophenyl)-1-(4-methoxyphenyl)-1H-isoindole-3-amine acetate

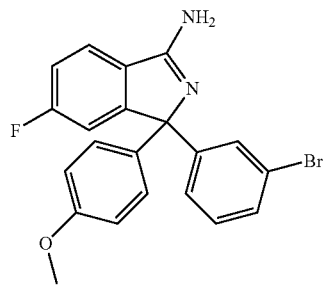

The title compound was prepared in 2.8% yield as described for in Scheme #3, I and purified by column chromatography using 0-10% methanol in dichloromethane followed by column chromatography using ethyl acetate:methanol 4:1+1% acetic acid: $^1$H NMR (400 MHz) δ 7.82-7.58 (m, 3 H), 7.58-7.49 (m, 1 H), 7.45-7.41 (m, 1 H), 7.36-7.24 (m, 3 H), 7.19-7.12 (m, 2 H), 6.96-6.86 (m, 2 H), 3.73 (s, 3 H), 1.91 (s, 3 H); MS (ES) m/z 393, 395 [M+1]$^+$.

Example 88

1-(3',5'-Dichlorobiphenyl-3-yl)-1-(4-methoxyphenyl)-1H-isoindol-3-amine acetate

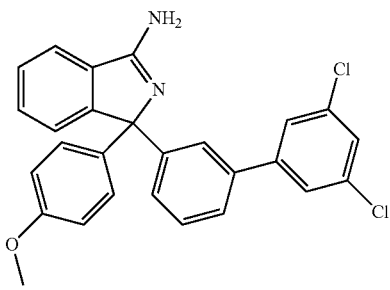

The title compound was prepared as described for Example 78 (Scheme #14, N) starting from 1-(3-bromophenyl)-1-(4-methoxyphenyl)-1H-isoindole-3-amine acetate (Example 87) and (3,5-dichlorophenyl)boronic acid in 28% yield: $^1$H NMR (DMSO-d$_6$) δ 7.78-7.74 (m, 2 H), 7.59-7.52 (m, 5 H), 7.47-7.41 (m, 2 H), 7.41-7.34 (m, 2 H), 7.23-7.18 (m, 2 H), 6.82-6.77 (m, 2 H), 3.69 (s, 3 H), 1.88 (s, 3 H); MS (ES) m/z 459, 461, 463 [M+1]$^+$.

Scheme 15

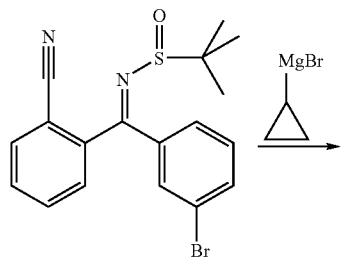

Scheme #5, N

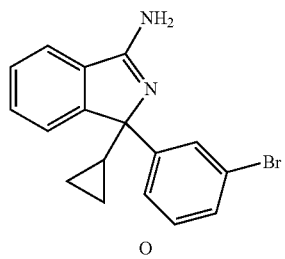

1-(3-Bromophenyl)-1-cyclopropyl-1H-isoindol-3-amine acetate (Scheme 15, O)

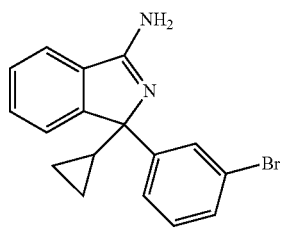

Cyclopropylmagnesium bromide (7.20 mL, 3.60 mmol, 0.5 M in tetrahydrofuran) was added drop wise to N-[(3-bromophenyl)(2-cyanophenyl)methylene]-2-methylpropane-2-sulfinamide (Scheme #5, N) (1.00 g, 2.57 mmol) in dry tetrahydrofuran (10 mL) at room temperature under argon atmosphere. The reaction was heated to 30° C. and stirred for 2.5 h, then cooled to 0° C. The reaction was quenched with methanol (5 mL) and extracted twice with ethyl acetate. The organic phases were pooled, washed (saturated aqueous ammonium chloride and water), dried over magnesium sulfate and concentrated. Column chromatography using gradient solution from dichloromethane to dichloromethane:3.5 M ammonia in methanol 97:3 followed by preparative HPLC (Column: Gemini C8; Mobile phase: 35% acetonitrile in 0.1 M ammonium acetate/water; Flow: 1 mL/min) afforded 0.108 g (11% yield) of the title compound: $^1$H NMR (DMSO-d$_6$) δ 7.72-7.69 (m, 1 H), 7.62-7.57 (m, 3 H), 7.40-7.35 (m, 3 H), 7.25 (t, J=7.78 Hz, 1 H), 1.89 (s, 3 H), 1.86-1.81 (m, 1 H), 0.46-0.35 (m, 2 H), 0.21-0.13 (m, 1 H), -0.09--0.02 (m, 1 H); MS (ES) m/z 327, 329 [M+1]$^+$.

Scheme 16

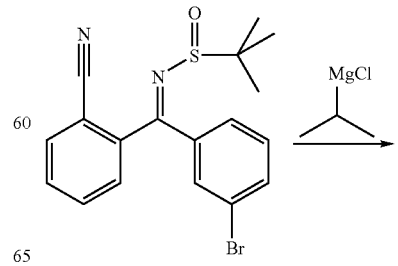

Scheme #5, N

-continued

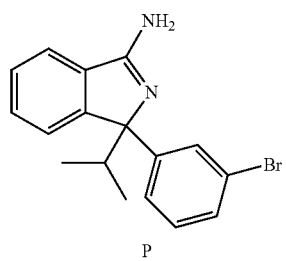

P

Example 89

1-(3-Bromophenyl)-1-isopropyl-1H-isoindol-3-amine hydrochloride (Scheme #16, P)

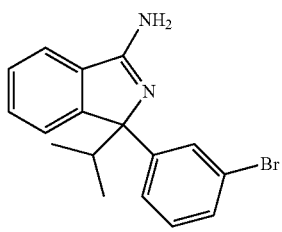

Isopropylmagnesium chloride (1.56 mL, 3.08 mmol, 2 M in tetrahydrofuran) was slowly and drop wise added to N-[(3-bromophenyl)(2-cyanophenyl)methylene]-2-methylpropane-2-sulfinamide (Scheme #5, N) (1.00 g, 2.57 mmol) in dry tetrahydrofuran (15 mL) at room temperature under argon atmosphere. The reaction was heated to 30° C. and stirred for 3 h and then cooled to 0° C. The reaction was quenched with water (5 mL) and extracted twice with ethyl acetate. The organic phases were pooled and washed with saturated aqueous ammonium chloride. The product was extracted five times with 2 M hydrochloric acid and once with 6 M hydrochloric acid. The water phase was neutralized with sodium hydroxide and extracted twice with ethyl acetate. The organic phase was concentrated. Column chromatography using 20-100% chloroform saturated with ammonia in chloroform and 0-100% chloroform saturated with ammonia in chloroform did not yield the pure product. Further purification was made by preparative HPLC using 5-100% acetonitrile in 0.1 M ammonium acetate/water followed by preparative HPLC (Column: Gemini C8) using acetonitrile:water 37:63+1% trifluoroacetic acid. The residue was partitioned between ethyl acetate and sodium bicarbonate. The organic phase was washed (water), dried over magnesium sulfate and concentrated. The residue was dissolved in hydrochloric acid in diethyl ether (0.13 mL, 1 M), stirred for 1 h at ambient temperature and then concentrated to give 30.1 mg (3.2% yield) of the title compound: $^1$H NMR (DMSO-$d_6$) δ 8.27 (d, J=8.03 Hz, 1 H), 7.92 (d, J=7.78 Hz, 1 H), 7.84-7.76 (m, 2 H), 7.70 (d, J=8.03 Hz, 1 H), 7.64 (t, J=7.53 Hz, 1 H), 7.57-7.52 (m, 1 H), 7.39 (t, J=7.91 Hz, 1 H), 3.17-3.07 (m, 1 H), 0.88 (d, J=7.03 Hz, 3 H), 0.51 (d, J=6.78 Hz, 3 H); MS (ES) m/z 329, 331 [M+1]$^+$.

Scheme 17

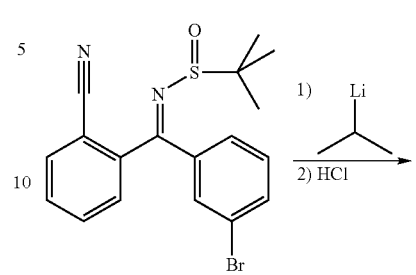

Scheme #5, N

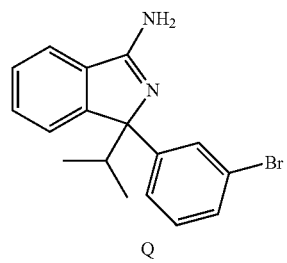

Q 1-(3-Bromophenyl)-1-isopropyl-1H-isoindol-3-amine acetate (Scheme #17, Q)

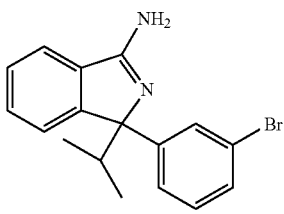

Isopropyllithium (0.88 mL, 0.616 mmol, 0.7 M in pentane) was drop wise added to N-[(3-bromophenyl)(2-cyanophenyl)methylene]-2-methylpropane-2-sulfinamide (Scheme #5, N) (0.200 g, 0.514 mmol) in tetrahydrofuran (5 mL) at −78° C. The temperature was allowed to rise to −25° C. after 2 h of stirring. The reaction was quenched with water (2 mL) and extracted with ethyl acetate. The organic phase was washed (water and brine), dried over magnesium sulfate and concentrated. The residue was dissolved in methanol (5 mL) and hydrochloric acid (1 mL, 1 M in diethyl ether) was added. The reaction mixture was stirred at room temperature for 18 h and was then concentrated. The residue was partitioned between dichloromethane and saturated aqueous sodium bicarbonate. The organic phase was washed (brine), dried over magnesium sulfate and concentrated. Purification by column chromatography using gradient elution from dichloromethane to dichloromethane: 3.5 M ammonia in methanol 90:10 and preparative HPLC gave 9.0 mg (4.5% yield) of the title compound: $^1$H NMR (CDCl$_3$) δ 7.97 (d, J=7.83 Hz, 1 H), 7.69 (t, J=1.89 Hz, 1 H), 7.67-7.63 (m, 1 H), 7.61-7.55 (m, 1 H), 7.55-7.45 (m, 2 H), 7.43-7.35 (m, 1 H), 7.22 (t, J=7.96 Hz, 1

H), 2.92-2.77 (m, 1 H), 2.11 (s, 3 H), 1.02 (d, J=6.82 Hz, 3 H), 0.63 (d, J=6.57 Hz, 3 H); MS (ES) m/z 329, 331 [M+1]+.

Example 90

1-(3-Bromophenyl)-1-methyl-1H-isoindol-3-amine

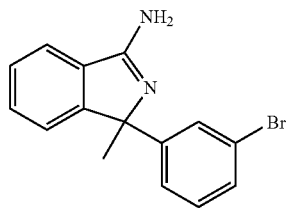

N-[(3-Bromophenyl)(2-cyanophenyl)methylene]-2-methylpropane-2-sulfinamide (Scheme #5, N) (1.00 g, 2.57 mmol) in dry tetrahydrofuran (20 mL) cooled to −78° C. was drop wise added to methyl lithium (1.93 mL, 3.08 mmol, 1.6 M in diethyl ether) in dry tetrahydrofuran (10 mL) at −78° C. under argon atmosphere. The reaction was stirred for 2 h and then the temperature was allowed to rise to −25° C. The reaction was quenched with water (10 mL) and extracted with ethyl acetate. The organic phases were pooled, washed (brine, water), dried over magnesium sulfate and concentrated. Column chromatography using gradient solution from chloroform to chloroform:chloroform saturated with ammonia 0:100 to afford the intermediate, which was then dissolved in methanol (25 mL) and hydrochloric acid (5 mL, 1 M in diethyl ether) was added. The reaction mixture was stirred for 23 h, and then concentrated. The residue was partitioned between dichloromethane and saturated aqueous sodium bicarbonate. The organic phases were pooled, washed (brine), dried over magnesium sulfate and concentrated. Column chromatography using gradient solution from dichloromethane to dichloromethane: 3.5 M ammonia in methanol 95:5 afforded 0.456 g (59% yield) of the title compound: $^1$H NMR (DMSO-$d_6$) δ 7.73-7.68 (m, 1 H), 7.59-7.52 (m, 3 H), 7.39-7.33 (m, 3 H), 7.24 (t, J=8.03 Hz, 1 H), 6.59 (br s, 2 H), 1.66 (s, 3 H); MS (ES) m/z 301, 303 [M+1]+.

Example 91

3'-(3-Amino-1-cyclopropyl-1H-isoindol-1-yl)-5-methoxybiphenyl-2-carbonitrile acetate

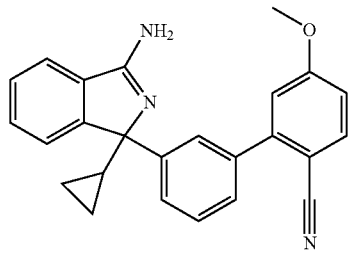

The title compound was prepared in 51% yield as described for Example 78 (Scheme #14, N) starting from 1-(3-bromophenyl)-1-cyclopropyl-1H-isoindol-3-amine acetate (Scheme #15, O) and 4-methoxy-2-(4,4,5,5-tetramethyl-1,3,2-dioxaborolan-2-yl)benzonitrile: $^1$H NMR (DMSO-$d_6$) δ 7.89-7.84 (m, 2 H), 7.75-7.68 (m, 1 H), 7.68-7.63 (m, 1 H), 7.56-7.51 (m, 1 H), 7.43-7.35 (m, 4 H), 7.12 (dd, J=8.66, 2.64 Hz, 1 H), 7.06 (d, J=2.51 Hz, 1 H), 3.89 (s, 3 H), 1.92-1.83 (m, 4 H), 0.49-0.38 (m, 2 H), 0.25-0.16 (m, 1 H), −0.04-0.03 (m, 1 H): MS (ES) m/z 380 [M+1]+.

Example 92

1-Cyclopropyl-1-(3-pyrimidin-5-ylphenyl)-1H-isoindol-3-amine acetate

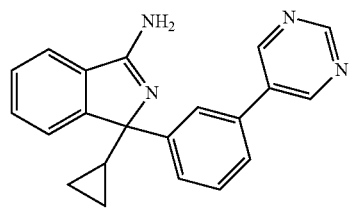

The title compound was prepared in 85% yield as described for Example 78 (Scheme #14, N) starting from 1-(3-bromophenyl)-1-cyclopropyl-1H-isoindol-3-amine acetate (Scheme #15, O) and pyrimidine-5-ylboronic acid: $^1$H NMR (DMSO-$d_6$) δ 9.19 (s, 1 H), 9.10 (s, 2 H), 8.02 (t, J=1.76 Hz, 1 H), 7.77 (t, J=8.03 Hz, 2 H), 7.64 (dd, J=7.78, 1.25 Hz, 1 H), 7.60-7.55 (m, 1 H), 7.47-7.37 (m, 3 H), 2.05-1.94 (m, 1 H), 1.87 (s, 3 H), 0.52-0.41 (m, 2 H), 0.28-0.17 (m, 1 H), −0.04-0.05 (m, 1 H); MS (ES) m/z 327 [M+1]+.

Example 93

3'-(3-Amino-1-methyl-1H-isoindol-1-yl)-5-methoxybiphenyl-2-carbonitrile acetate

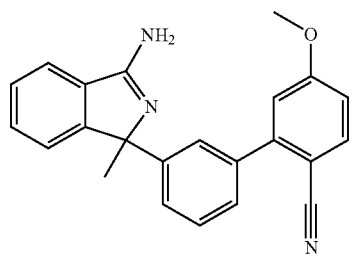

The title compound was prepared in 49% yield as described for Example 78 (Scheme #14, N) starting from 1-(3-bromophenyl)-1-methyl-1H-isoindol-3-amine (Example 90) and 4-methoxy-2-(4,4,5,5-tetramethyl-1,3,2-dioxaborolan-2-yl)benzonitrile: $^1$H NMR (DMSO-$d_6$) δ 7.86 (d, J=8.78 Hz, 1 H), 7.77-7.71 (m, 2 H), 7.66-7.62 (m, 1 H), 7.54-7.50 (m, 1 H), 7.41-7.35 (m, 4 H), 7.12 (dd, J=8.66, 2.64 Hz, 1 H), 7.06 (d, J=2.51 Hz, 1 H), 3.89 (s, 3 H), 1.89 (s, 3 H), 1.73 (s, 3H); MS (ES) m/z 354 [M+1]+.

Example 94

1-(3',5'-Dichlorobiphenyl-3-yl)-1-methyl-1H-isoindol-3-amine hydrochloride

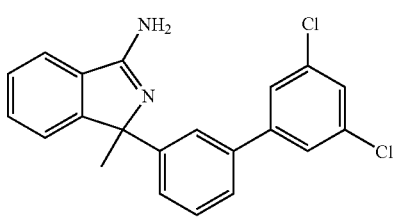

The title compound was prepared as described for Example 78 (Scheme #14, N) starting from 1-(3-bromophenyl)-1-methyl-1H-isoindol-3-amine (Example 90) (71.4 mg, 0.237) and (3,5-dichlorophenyl)boronic acid (47.4 mg, 0.249 mmol) with the exception that the hydrochloride was made by dissolving the product in dichloromethane (1 mL) and adding hydrochloric acid (0.71 mL, 1 M in diethyl ether). The solution was stirred for 1 h and was then concentrated to afford 31.0 mg (32% yield) of the title compound: $^1$H NMR (DMSO-$d_6$) δ 8.23 (d, J=7.78 Hz, 1 H), 7.91-7.87 (m, 1 H), 7.84-7.74 (m, 4 H), 7.71 (d, J=7.78 Hz, 1 H), 7.67-7.62 (m, 2 H), 7.47 (t, J=7.78 Hz, 1 H), 7.43-7.38 (m, 1 H), 2.06 (s, 3 H); MS (ES) m/z 367, 369, 371 [M+1]$^+$.

Example 95

1-Methyl-1-(3-pyrimidin-5-ylphenyl)-1H-isoindol-3-amine acetate

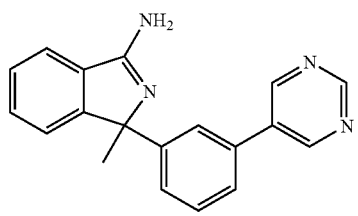

The title compound was prepared in 89% yield as described for Example 78 (Scheme #14, N) starting from 1-(3-bromophenyl)-1-methyl-1H-isoindol-3-amine (Example 90) and pyrimidine-5-ylboronic acid with the exception that the product was purified by column chromatography using gradient solution from dichloromethane to dichloromethane:3.5 M ammonia in methanol 95:5 before purification by preparative HPLC: $^1$H NMR (DMSO-$d_6$) δ 9.19 (s, 1 H), 9.11 (s, 2 H), 7.94 (t, J=1.76 Hz, 1 H), 7.82-7.77 (m, 1 H), 7.70 (dd, J=6.40, 0.88 Hz, 1 H), 7.65-7.61 (m, 1 H), 7.54-7.50 (m, 1 H), 7.47-7.37 (m, 3 H), 1.90 (s, 3 H), 1.80 (s, 3 H); MS (ES) m/z 301 [M+1]$^+$.

Example 96

1-[3-(2-Fluoropyridin-3-yl)phenyl]-1-methyl-1H-isoindol-3-amine acetate

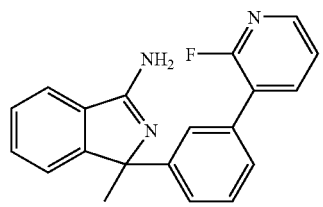

The title compound was prepared in 76% yield as described for Example 78 (Scheme #14, N) starting from 1-(3-bromophenyl)-1-methyl-1H-isoindol-3-amine (Example 90) and (2-fluoropyridine-3-yl)boronic acid: $^1$H NMR (DMSO-$d_6$) δ 8.27-8.20 (m, 1 H), 8.10-8.02 (m, 1 H), 7.80-7.73 (m, 1 H), 7.71 (d, J=1.25 Hz, 1 H), 7.66-7.61 (m, 1 H), 7.59-7.53 (m, 1 H), 7.50-7.35 (m, 5 H), 1.87 (s, 3 H), 1.74 (s, 3 H); MS (ES) m/z 318 [M+1]$^+$.

Example 97

1-Isopropyl-1-(3-pyrimidin-5-ylphenyl)-1H-isoindol-3-amine acetate

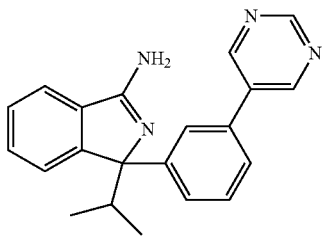

The title compound was prepared as described for Example 78 (Scheme #14, N) starting from 1-(3-bromophenyl)-1-isopropyl-1H-isoindol-3-amine hydrochloride (Example 89, Scheme #16, P) (15.0 mg, 0.0410 mmol), 1-(3-bromophenyl)-1-isopropyl-1H-isoindol-3-amine acetate (Scheme #17, Q) (6.5 mg, 0.0167 mmol) and pyrimidine-5-ylboronic acid (15.9 mg, 0.128 mmol) to give 18.2 mg (81% yield): $^1$H NMR (DMSO-$d_6$) δ 9.19 (d, J=2.14 Hz, 1 H), 9.10 (d, J=2.14 Hz, 2 H), 8.06 (d, J=1.23 Hz, 1 H), 7.85 (d, J=8.58 Hz, 1 H), 7.73 (t, J=9.19 Hz, 2 H), 7.62 (d, J=7.66 Hz, 1 H), 7.48-7.31 (m, 3 H), 3.02-2.91 (m, 1 H), 1.89 (s, 3 H), 0.86 (d, J=6.74 Hz, 3 H), 0.43 (d, J=6.43 Hz, 3H); MS (ES) m/z 329 [M+1]$^+$.

Scheme 18

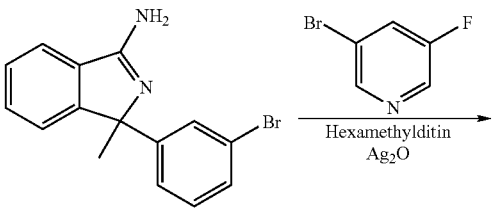

-continued

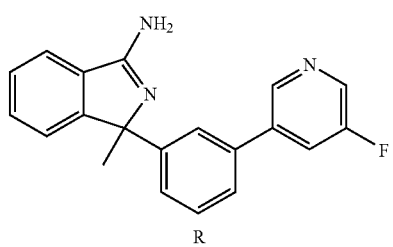

R

Example 98

1-[3-(5-Fluoropyridin-3-yl)phenyl]-1-methyl-1H-isoindol-3-amine acetate (Scheme #18, R)

3-Bromo-5-fluoropyridine (205 mg, 1.17 mmol), hexamethylditin (0.24 mL, 1.17 mmol) and tetrakis(triphenylphosphine)palladium(0) (34.0 mg, 0.0294 mmol) were dissolved in dry tetrahydrofuran (3 mL) and heated to 130° C. for 30 min in a microwave. 1-(3-Bromophenyl)-1-methyl-1H-isoindol-3-amine (Example 90) (82.5 mg, 0.274 mmol) and tetrakis(triphenylphosphine)palladium(0) (13.5 mg, 0.0117 mmol) were added and the reaction mixture was heated to 130° C. for 10 h in a microwave. No product could be detected by LC-MS analysis. Silver oxide (Ag$_2$O) (38.3 mg, 0.274 mmol) and tetrakis(triphenylphosphine)palladium(0) (13.5 mg, 0.0117 mmol) were added and the reaction mixture was heated to 130° C. for 30 min and 150° C. for 2 h in a microwave. When cooled to ambient temperature the mixture was filtered and purified by column chromatography using gradient solution from dichloromethane to dichloromethane:3.5 M ammonia in methanol 95:5 and preparative HPLC to give 20.2 mg (20% yield) of the title compound: $^1$H NMR (DMSO-d$_6$) δ 8.74 (t, J=1.76 Hz, 1H), 8.57 (d, J=2.76 Hz, 1 H), 8.07-7.99 (m, 1 H), 7.90 (t, J=1.63 Hz, 1 H), 7.78-7.72 (m, 1 H), 7.69 (dd, J=6.15, 1.88 Hz, 1 H), 7.62-7.55 (m, 1 H), 7.54-7.47 (m, 1 H), 7.43-7.34 (m, 3 H), 1.87 (s, 3 H), 1.76 (s, 3 H); MS (ES) m/z 318 [M+1]$^+$.

Example 99

1-(2'-Fluoro-5'-methoxybiphenyl-3-yl)-1-(3-fluoropyridin-4-yl)-1H-isoindol-3-amine

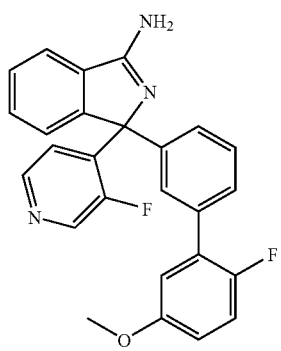

The title compound was synthesized from 1-(3-bromophenyl)-1-(3-fluoropyridin-4-yl)-1H-isoindol-3-amine (Scheme #12, I) as described in Example 67 (Scheme #10, D) in 73% yield using 2-fluoro-5-methoxyphenylboronic acid. $^1$H NMR (DMSO-d$_6$) δ 8.45 (d, J=2.78 Hz, 1 H), 8.34 (d, J=4.80 Hz, 1 H), 7.88-7.82 (m, 1 H), 7.77-7.69 (m, 1 H), 7.54-7.46 (m, 2 H), 7.45-7.30 (m, 4 H), 7.27-7.15 (m, 2 H), 7.04-6.85 (m, 4 H), 3.76 (s, 3 H); MS (ESI) m/z 428 [M+1]$^+$.

Example 100

1-(2'-Fluoro-3'-methoxybiphenyl-3-yl)-1-(3-fluoropyridin-4-yl)-1H-isoindol-3-amine

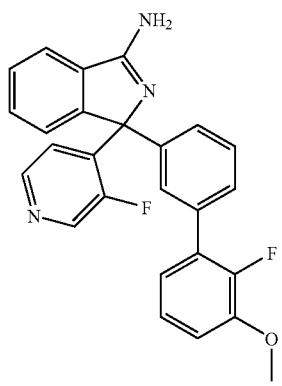

The title compound was synthesized from 1-(3-bromophenyl)-1-(3-fluoropyridin-4-yl)-1H-isoindol-3-amine (Scheme #12, I) as described in Example 67 (Scheme #10, D) in 69% yield using 2-fluoro-3-methoxyphenylboronic acid. $^1$H NMR (DMSO-d$_6$) δ 8.26 (d, J=2.78 Hz, 1 H), 8.14 (d, J=5.05 Hz, 1 H), 7.67-7.61 (m, 1 H), 7.55-7.50 (m, 1 H), 7.34-7.28 (m, 2 H), 7.21-7.10 (m, 4 H), 7.07-6.92 (m, 3 H), 6.77 (br s, 2 H), 6.74-6.68 (m, 1 H), 3.65 (s, 3 H); MS (ESI) m/z 428 [M+1]$^+$.

Example 101

1-(2',6-Difluoro-3'-methoxybiphenyl-3-yl)-1-(3-fluoropyridin-4-yl)-1H-isoindol-3-amine

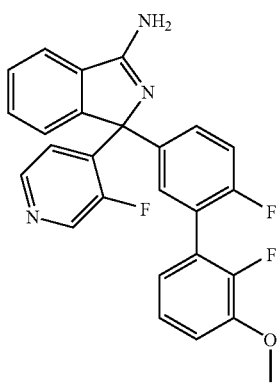

The title compound was synthesized from 1-(3-bromo-4-fluorophenyl)-1-(3-fluoropyridin-4-yl)-1H-isoindol-3-amine (Example 70) as described in Example 67 Scheme #10, D in 25% yield using 2-fluoro-3-methoxyphenyl boronic acid. $^1$H NMR (DMSO-$d_6$) δ 8.39 (d, J=3.03 Hz, 1 H), 8.26 (d, J=5.05 Hz, 1 H), 7.83-7.73 (m, 1 H), 7.71-7.64 (m, 1H), 7.48-7.39 (m, 2 H), 7.29-7.11 (m, 6 H), 6.92 (br s, 2 H), 6.81-6.73 (m, 1 H), 3.79 (s, 3 H); MS (ESI) m/z 446 [M+1]$^+$.

Example 102

5-{3-[3-Amino-1-(3-fluoropyridin-4-yl)-1H-isoindol-1-yl]phenyl}nicotinonitrile

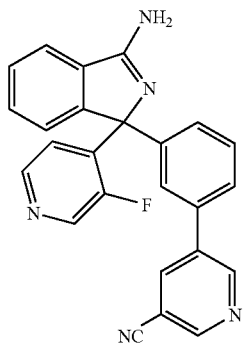

The title compound was synthesized from 1-(3-bromophenyl)-1-(3-fluoropyridin-4-yl)-1H-isoindol-3-amine (Scheme #12, I) as described in Example 77 (Scheme #13, J) in 37% yield. $^1$H NMR (DMSO-$d_6$) δ 8.92 (dd, J=10.74, 2.15 Hz, 2 H), 8.43 (t, J=2.15 Hz, 1 H), 8.34 (d, J=3.03 Hz, 1 H), 8.25 (d, J=5.05 Hz, 1 H), 7.80-7.72 (m, 2 H), 7.61-7.55 (m, 1 H), 7.54-7.50 (m, 1 H), 7.45-7.39 (m, 2 H), 7.38-7.26 (m, 2 H), 7.17 (dd, J=6.82, 5.05 Hz, 1 H), 6.89 (br s, 2 H); MS (ESI) m/z 406 [M+1]$^+$.

Example 103

1-(2'-Fluoro-5'-methoxybiphenyl-3-yl)-1-pyridin-4-yl-1H-isoindol-3-amine

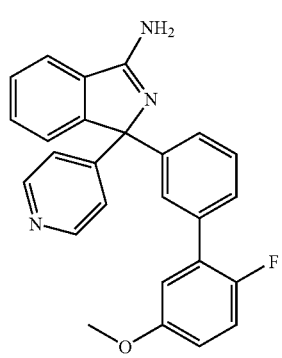

The title compound was synthesized from 1-(3-bromophenyl)-1-pyridin-4-yl-1H-isoindol-3-amine (Scheme #9, C) as described in Example 67 Scheme #10, D in 66% yield using 2-fluoro-3-methoxyphenyl boronic acid. $^1$H NMR (DMSO-$d_6$) δ 8.31-8.23 (m, 2 H), 7.67-7.55 (m, 2 H), 7.34-7.25 (m, 3 H), 7.25-7.10 (m, 5 H), 7.01 (dd, J=10.11, 8.84 Hz, 1 H), 6.62-6.84 (m, 4 H), 3.58 (s, 3 H); MS (ESI) m/z 410 [M+1]$^+$.

Example 104

1-(2'-Fluoro-3'-methoxybiphenyl-3-yl)-1-pyridin-4-yl-1H-isoindol-3-amine

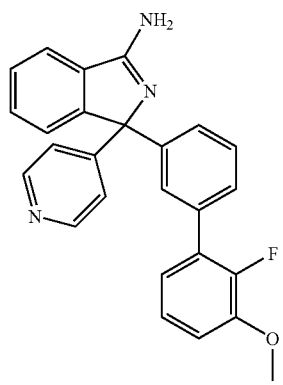

The title compound was synthesized from 1-(3-bromophenyl)-1-pyridin-4-yl-1H-isoindol-3-amine (Scheme #9, C) as described in Example 67 Scheme #10, D in 50% yield using 2-fluoro-3-methoxyphenyl boronic acid. $^1$H NMR (DMSO-$d_6$) δ 8.42-8.32 (m, 2 H), 7.78-7.67 (m, 2 H), 7.44-7.34 (m, 3 H), 7.34-7.20 (m, 5 H), 7.15-7.02 (m, 2 H), 6.92-6.74 (m, 3 H), 3.78 (s, 3 H); MS (ESI) m/z 410 [M+1]$^+$.

Example 105

1-[4-Fluoro-3-(2-fluoropyridin-3-yl)phenyl]-1-pyridin-4-yl-1H-isoindol-3-amine

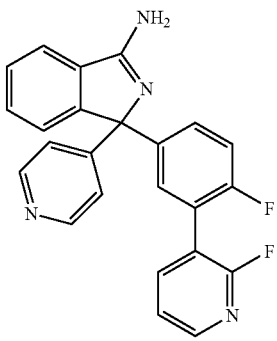

The title compound was synthesized from 1-(3-bromo-4-fluorophenyl)-1-pyridin-4-yl-1H-isoindol-3-amine (Scheme #11, G) as described in Example 67 Scheme #10, D using 2-fluoropyridine-3-boronic acid. $^1$H NMR (DMSO-d$_6$) δ 8.49-8.41 (m, 2 H), 8.32-8.27 (m, 1 H), 8.04-7.95 (m, 1 H), 7.88-7.79 (m, 2 H), 7.55-7.40 (m, 5 H), 7.35-7.25 (m, 3 H), 6.92 (br s, 2 H); MS (ESI) m/z 399 [M+1]$^+$.

Example 106

1-(3-Bromophenyl)-1-(2-methoxypyrimidin-5-yl)-1H-isoindol-3-amine

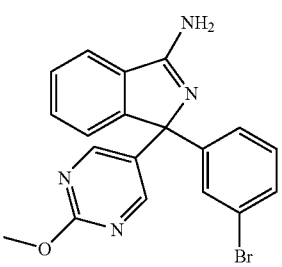

The title compound was synthesized as described in Scheme #8, A starting from 5-bromo-2-methoxypyrimidine at −100° C. in 66% yield. $^1$H NMR (DMSO-d$_6$) δ 8.51 (s, 2 H), 7.99-7.75 (m, 2 H), 7.56-7.41 (m, 4 H), 7.40-7.33 (m, 1 H), 7.26 (t, J=7.83 Hz, 1 H), 6.97 (br s, 2 H), 3.88 (s, 3 H); MS (ESI) m/z 395, 397 [M+1]$^+$.

Example 107

1-[3-(2-Fluoropyridin-3-yl)phenyl]-1-(2-methoxypyrimidin-5-yl)-1H-isoindol-3-amine

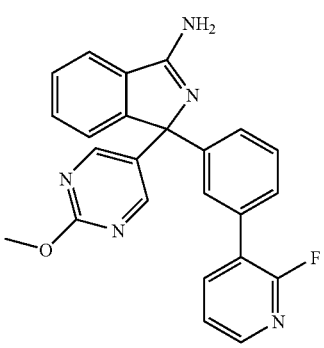

The title compound was synthesized from 1-(3-bromophenyl)-1-(2-methoxypyrimidin-5-yl)-1H-isoindol-3-amine (Example 106) as described in Example 67 Scheme #10, D in 34% yield using 2-fluoropyridine-3-boronic acid. $^1$H NMR (DMSO-d$_6$) δ 8.47 (s, 2 H), 8.19-8.13 (m, 1 H), 8.01-7.91 (m, 1 H), 7.88-7.81 (m, 1 H), 7.77 (d, J=5.56 Hz, 1 H), 7.52-7.48 (m, 1 H), 7.46-7.32 (m, 6 H), 6.88 (br s, 2 H), 3.80 (s, 3 H); MS (ESI) m/z 412 [M+1]$^+$.

Example 108

1-(2-Methoxypyrimidin-5-yl)-1-(3-pyrimidin-5-ylphenyl)-1H-isoindol-3-amine

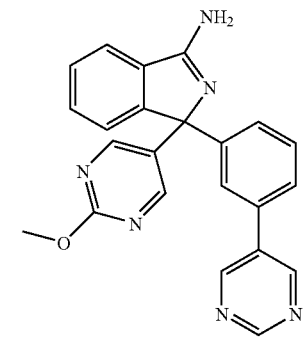

The title compound was synthesized from 1-(3-bromophenyl)-1-(2-methoxypyrimidin-5-yl)-1H-isoindol-3-amine (Example 106) as described in Example 67 Scheme #10, D in 54% yield using pyrimidine-5-boronic acid. $^1$H NMR (DMSO-d$_6$) δ 9.18 (s, 1 H), 9.05 (s, 2H), 8.55 (s, 2 H), 7.98-8.11 (m, 1 H), 7.79-7.88 (m, 1 H), 7.70-7.77 (m, 1 H), 7.67 (d, J=7.58 Hz, 1 H), 7.41-7.57 (m, 4 H), 6.96 (br s, 2 H), 3.87 (s, 3 H); MS (ESI) m/z 395 [M+1]$^+$.

Example 109

1-(2'-Fluoro-3'-methoxybiphenyl-3-yl)-1-(2-methoxypyrimidin-5-yl)-1H-isoindol-3-amine

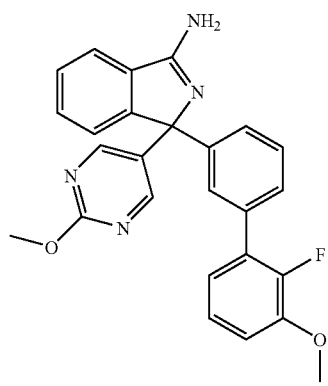

The title compound was synthesized from 1-(3-bromophenyl)-1-(2-methoxypyrimidin-5-yl)-1H-isoindol-3-amine (Example 106) as described in Example 67 Scheme #10, D in 27% yield using 2-fluoro-3-methoxyphenylboronic acid. $^1$H NMR (DMSO-d$_6$) δ 8.55 (s, 2H), 7.96-7.79 (m, 2 H), 7.58-7.43 (m, 3 H), 7.43-7.34 (m, 3 H), 7.24-7.12 (m, 2 H), 7.08-6.83 (m, 3 H), 3.88 (s, 3 H), 3.86 (s, 3 H); MS (ESI) m/z 441 [M+1]$^+$.

Example 110

1-(3-Bromophenyl)-1-(2-ethylpyridin-4-yl)-1H-isoindol-3-amine

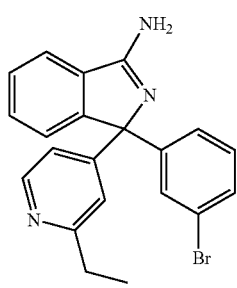

The title compound was synthesized as described in Scheme #9, C starting from 4-bromo-2-ethylpyridine (synthesised according to Comins et al, *J. Org. Chem.* 4410) in 45% yield. $^1$H NMR (DMSO-d$_6$) δ 8.41-8.34 (m, 1 H), 7.92-7.73 (m, 2 H), 7.59-7.38 (m, 4 H), 7.33-7.23 (m, 2 H), 7.18-7.13 (m, 1 H), 7.10 (dd, J=5.18, 1.64 Hz, 1 H), 6.95 (br s, 2 H), 2.68 (q, J=7.58 Hz, 2 H), 1.16 (t, J=7.58 Hz, 3 H); MS (ESI) m/z 392, 394 [M+1]$^+$.

Example 111

1-(2-Ethylpyridin-4-yl)-1-(3-pyrimidin-5-ylphenyl)-1H-isoindol-3-amine

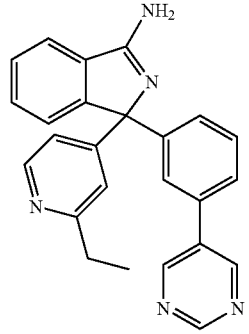

The title compound was synthesized from 1-(3-bromophenyl)-1-(2-ethylpyridin-4-yl)-1H-isoindol-3-amine (Example 110) as described in Example 67 Scheme #10, D in 58% yield using pyrimidine-5-boronic acid. $^1$H NMR (DMSO-d$_6$) δ 9.11 (s, 1 H), 8.93 (s, 2 H), 8.28 (d, J=5.30 Hz, 1 H), 7.86 (dd, J=6.06, 1.77 Hz, 1 H), 7.80-7.68 (m, 1 H), 7.64-7.54 (m, 2 H), 7.47-7.36 (m, 4 H), 7.19-7.10 (m, 1 H), 7.07 (dd, J=5.18, 1.64 Hz, 1 H), 6.85 (br s, 2 H), 2.59 (q, J=7.58 Hz, 2 H), 1.08 (t, J=7.58 Hz, 3 H); MS (ESI) m/z 392 [M+1]$^+$.

Example 112

1-(2-Ethylpyridin-4-yl)-1-[3-(2-fluoropyridin-3-yl)phenyl]-1H-isoindol-3-amine

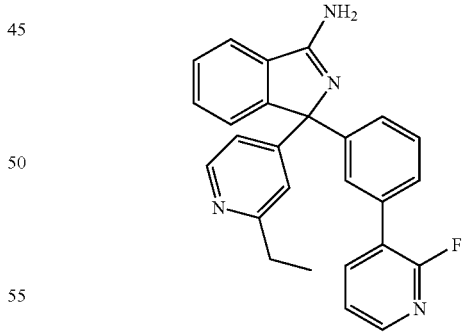

The title compound was synthesized from 1-(3-bromophenyl)-1-(2-ethylpyridin-4-yl)-1H-isoindol-3-amine (Example 110) as described in Example 67 Scheme #10, D in 61% yield using 2-fluoropyridine-3-boronic acid. $^1$H NMR (DMSO-d$_6$) δ 8.28 (d, J=5.31 Hz, 1 H), 8.20-8.11 (m, 1 H), 7.98-7.89 (m, 1 H), 7.79-7.71 (m, 2 H), 7.47-7.28 (m, 7 H), 7.15-7.10 (m, 1 H), 7.06 (dd, J=5.18, 1.64 Hz, 1 H), 6.83 (br s, 2 H), 2.60 (q, J=7.58 Hz, 2 H), 1.08 (t, J=7.58 Hz, 3 H); MS (ESI) m/z 409 [M+1]$^+$.

Example 113

1-(3-Bromophenyl)-1-(2-isopropylpyridin-4-yl)-1H-isoindol-3-amine

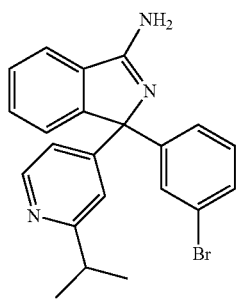

The title compound was synthesized as described in Scheme #9, C starting from 4-bromo-2-isopropylpyridine (obtained according to the procedure described in Comins et al, *J. Org. Chem.* 4410) in 37% yield. $^1$H NMR (DMSO-d$_6$) δ 8.38 (d, J=5.05 Hz, 1 H), 7.88-7.75 (m, 2 H), 7.55-7.38 (m, 4 H), 7.33-7.23 (m, 2 H), 7.17-7.12 (m, 1 H), 7.10 (dd, J=5.31, 1.77 Hz, 1 H), 6.94 (br s, 2 H), 3.01-2.85 (m, 1 H), 1.16 (d, J=6.82 Hz, 6 H); MS (ESI) m/z 406, 408 [M+1]$^+$.

Example 114

1-(2-Isopropylpyridin-4-yl)-1-(3-pyrimidin-5-ylphenyl)-1H-isoindol-3-amine

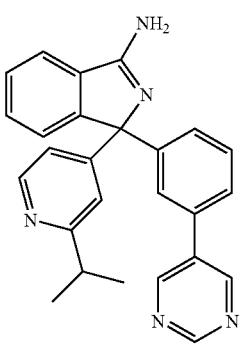

The title compound was synthesized from 1-(3-bromophenyl)-1-(2-isopropylpyridin-4-yl)-1H-isoindol-3-amine (Example 113) as described in Example 67 Scheme #10, D in 58% yield using pyrimidine-5-boronic acid. $^1$H NMR (DMSO-d$_6$) δ 9.11 (s, 1 H), 8.93 (s, 2 H), 8.30 (d, J=5.30 Hz, 1 H), 7.90-7.82 (m, 1 H), 7.81-7.69 (m, 1 H), 7.65-7.53 (m, 2 H), 7.49-7.33 (m, 4 H), 7.17-7.11 (m, 1 H), 7.07 (dd, J=5.31, 1.77 Hz, 1 H), 6.86 (br s, 2 H), 2.97-2.75 (m, 1 H), 1.08 (d, J=6.82 Hz, 6 H); MS (ESI) m/z 406 [M+1]$^+$.

Example 115

1-[3-(2-Fluoropyridin-3-yl)phenyl]-1-(2-isopropylpyridin-4-yl)-1H-isoindol-3-amine

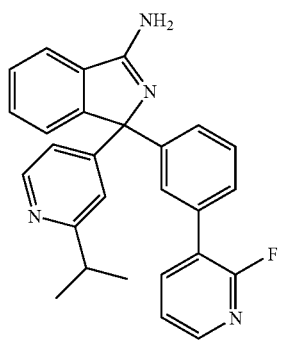

The title compound was synthesized from 1-(3-bromophenyl)-1-(2-isopropylpyridin-4-yl)-1H-isoindol-3-amine (Example 113) as described in Example 67 Scheme #10, D in 42% yield using 2-fluoropyridine-3-boronic acid. $^1$H NMR (DMSO-d$_6$) δ 8.29 (d, J=5.30 Hz, 1 H), 8.19-8.11 (m, 1 H), 7.97-7.90 (m, 1 H), 7.82-7.70 (m, 2 H), 7.49-7.27 (m, 7 H), 7.18-7.11 (m, 1 H), 7.05 (dd, J=5.31, 1.77 Hz, 1 H), 6.84 (br s, 2 H), 2.93-2.77 (m, 1 H), 1.08 (d, J=6.82 Hz, 6 H); MS (ESI) m/z 423 [M+1]$^+$.

Example 116

1-(3-Bromophenyl)-1-(2-fluoropyridin-4-yl)-1H-isoindol-3-amine

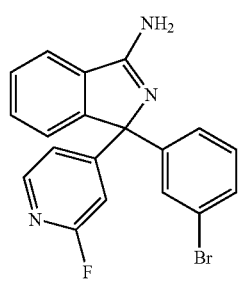

The title compound was synthesized as described in Scheme #9, C starting from 4-bromo-2-fluoropyridine. $^1$H NMR (DMSO-d$_6$) δ 8.15 (d, J=5.05 Hz, 1 H), 7.98-7.78 (m, 2 H), 7.58-7.38 (m, 4 H), 7.37-7.22 (m, 3 H), 7.10-6.92 (m, 3 H); MS (ESI) m/z 382, 384 [M+1]$^+$.

Example 117

1-(2-Fluoropyridin-4-yl)-1-[3-(2-fluoropyridin-3-yl)phenyl]-1H-isoindol-3-amine

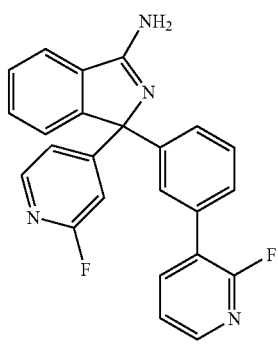

The title compound was synthesized from 1-(3-bromophenyl)-1-(2-fluoropyridin-4-yl)-1H-isoindol-3-amine (Example 116) as described in Example 67 Scheme #10, D in 19% yield using 2-fluoropyridine-3-boronic acid. $^1$H NMR (DMSO-d$_6$) δ 8.26-8.19 (m, 1 H), 8.15 (d, J=5.31 Hz, 1 H), 8.08-7.99 (m, 1 H), 7.95-7.79 (m, 2 H), 7.59-7.38 (m, 7 H), 7.37-7.30 (m, 1 H), 7.18-6.82 (m, 3 H); MS (ESI) m/z 399 [M+1]$^+$.

Example 118

1-(3-Bromophenyl)-1-(2-methoxypyridin-4-yl)-1H-isoindol-3-amine

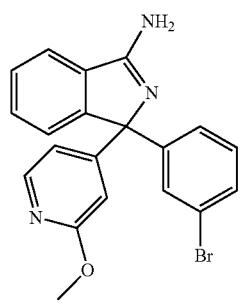

The title compound was obtained as a side-product in the synthesis of 1-(3-bromophenyl)-1-(2-fluoropyridin-4-yl)-1H-isoindol-3-amine (Example 116). $^1$H NMR (DMSO-d$_6$) δ 8.12-8.00 (m, 1 H), 7.91-7.72 (m, 2 H), 7.61-7.36 (m, 3 H), 7.35-7.20 (m, 3 H), 7.05-6.80 (m, 3 H), 6.64 (s, 1 H), 3.80 (s, 3 H); MS (ESI) m/z 394, 396 [M+1]$^+$.

Example 119

1-[3-(2-Fluoropyridin-3-yl)phenyl]-1-(2-methoxypyridin-4-yl)-1H-isoindol-3-amine

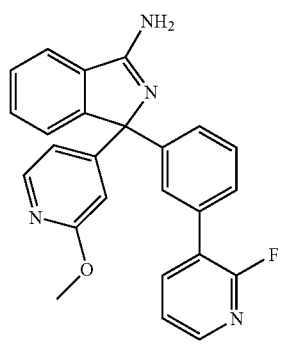

The title compound was synthesized from 1-(3-bromophenyl)-1-(2-methoxypyridin-4-yl)-1H-isoindol-3-amine (Example 118) as described in Example 67 Scheme #10, D in 23% yield using 2-fluoropyridine-3-boronic acid. $^1$H NMR (DMSO-d$_6$) δ 8.20-8.26 (m, 1 H), 7.97-8.09 (m, 2 H), 7.75-7.92 (m, 2 H), 7.37-7.58 (m, 7 H), 6.78-7.10 (m, 3 H), 6.67 (s, 1 H), 3.79 (s, 3 H); MS (ESI) m/z 411 [M+1]$^+$.

Example 120

1-(3-Bromophenyl)-1-(2-chloropyridin-4-yl)-1H-isoindol-3-amine

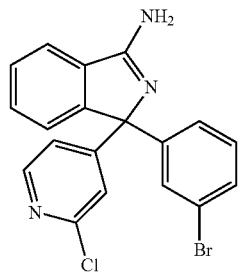

The title compound was synthesized as described in Scheme #9, C starting from 2-chloro-4-iodopyridine in 85% yield. $^1$H NMR (DMSO-d$_6$) δ 8.37-8.28 (m, 1 H), 7.91-7.79 (m, 2 H), 7.59-7.43 (m, 4 H), 7.39-7.23 (m, 4 H), 7.04 (br s, 2 H); MS (ESI) m/z 398, 400 [M+1]$^+$.

Example 121
1-(2-Chloropyridin-4-yl)-1-[3-(2-fluoropyridin-3-yl)phenyl]-1H-isoindol-3-amine

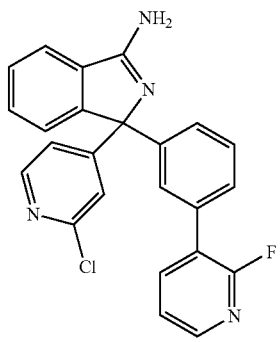

The title compound was synthesized from 1-(3-bromophenyl)-1-(2-chloropyridin-4-yl)-1H-isoindol-3-amine (Example 120) as described in Example 67 Scheme #10, D in 35% yield using 2-fluoropyridine-3-boronic acid. $^1$H NMR (DMSO-$d_6$) δ 8.32 (d, J=5.31 Hz, 1 H), 8.27-8.19 (m, 1 H), 8.08-7.99 (m, 1 H), 7.96-7.81 (m, 2 H), 7.61-7.31 (m, 9 H), 7.01 (br s, 2 H); MS (ESI) m/z 415 [M+1]$^+$.

Example 122
1-(2-Chloropyridin-4-yl)-1-(3-pyrimidin-5-ylphenyl)-1H-isoindol-3-amine

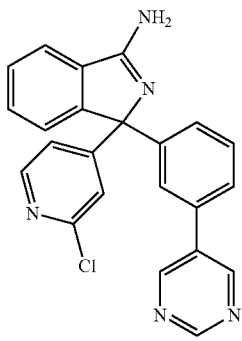

The title compound was synthesized from 1-(3-bromophenyl)-1-(2-chloropyridin-4-yl)-1H-isoindol-3-amine (Example 120) as described in Example 67 Scheme #10, D in 51% yield using pyrimidine-5-boronic acid. $^1$H NMR (DMSO-$d_6$) δ 9.18 (s, 1 H), 9.04 (s, 2 H), 8.31 (d, J=5.30 Hz, 1 H), 8.06-7.94 (m, 1 H), 7.89-7.81 (m, 1 H), 7.72-7.65 (m, 2 H), 7.57-7.45 (m, 4 H), 7.38 (dd, J=5.31, 1.52 Hz, 1 H), 7.36-7.33 (m, 1 H), 7.01 (br s, 2 H); MS (ESI) m/z 398 [M+1]$^+$.

Example 123
1-(3-Bromophenyl)-1-(5-fluoropyridin-3-yl)-1H-isoindol-3-amine

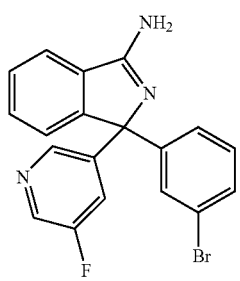

The title compound was synthesized as described in Scheme #9, C starting from 3-bromo-5-fluoropyridine in 80% yield. $^1$H NMR (DMSO-$d_6$) δ 8.52-8.38 (m, 2 H), 7.95-7.79 (m, 2 H), 7.60-7.40 (m, 5 H), 7.39-7.32 (m, 1 H), 7.31-7.21 (m, 1 H), 7.01 (br s, 2 H); MS (ESI) m/z 382, 384 [M+1]$^+$.

Example 124
1-(5-Fluoropyridin-3-yl)-1-[3-(2-fluoropyridin-3-yl)phenyl]-1H-isoindol-3-amine

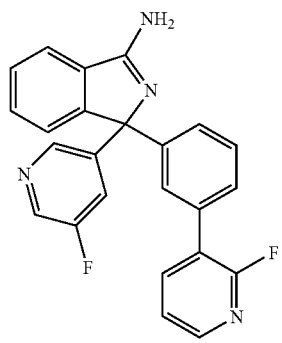

The title compound was synthesized from 1-(3-bromophenyl)-1-(5-fluoropyridin-3-yl)-1H-isoindol-3-amine (Example 123) as described in Example 67 Scheme #10, D in 26% yield using 2-fluoropyridine-3-boronic acid. $^1$H NMR (DMSO-$d_6$) δ 8.35-8.45 (m, 2 H), 8.12-8.21 (m, 1 H), 7.92-8.01 (m, 1 H), 7.83-7.90 (m, 1 H), 7.73-7.82 (m, 1 H), 7.33-7.56 (m, 8 H), 6.91 (br s, 2 H); MS (ESI) m/z 399 [M+1]$^+$.

Example 125
1-(5-Fluoropyridin-3-yl)-1-(3-pyrimidin-5-ylphenyl)-1H-isoindol-3-amine

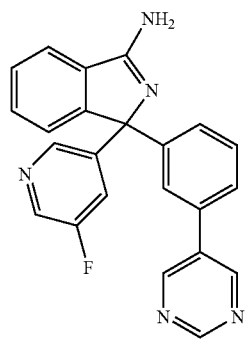

The title compound was synthesized from 1-(3-bromophenyl)-1-(5-fluoropyridin-3-yl)-1H-isoindol-3-amine (Example 123) as described in Example 67 Scheme #10, D in 41% yield using pyrimidine-5-boronic acid. $^1$H NMR (DMSO-$d_6$) δ 9.18 (s, 1 H), 9.04 (s, 2 H), 8.49 (t, J=1.77 Hz, 1 H), 8.45 (d, J=2.53 Hz, 1 H), 8.08-8.02 (m, 1 H), 7.90-7.80 (m, 1 H), 7.74-7.64 (m, 2 H), 7.62-7.43 (m, 5 H), 6.98 (br s, 2 H); MS (ESI) m/z 382 [M+1]$^+$.

Example 126

1-(3-Bromo-4-fluorophenyl)-1-(4-methoxy-3-methylphenyl)-1H-isoindol-3-amine

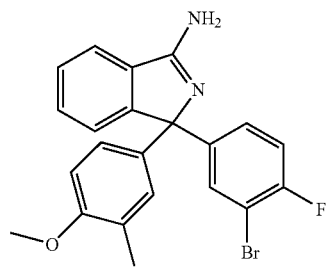

A solution of 4-bromo-1-methoxy-2-methylbenzene (1.21 g, 6.0 mmol) in diethyl ether (10 mL) was added dropwise to magnesium (0.22 g, 9.0 mmol) and iodine. The resulting mixture was heated to reflux for 2 h and was then allowed to cool to room temperature. The prepared reagent was added to a solution of N-((3-bromo-4-fluorophenyl)(2-cyanophenyl)methylene)-2-methylpropane-2-sulfinamide (Scheme #11 F, 0.82 g, 2.0 mmol) in tetrahydrofuran (20 mL) at 0°. The mixture was stirred at 0° C. for 1 h and then quenched by addition of saturated aqueous ammonium chloride. The reaction mixture was partitioned between water and ethyl acetate, the organic phase was dried over magnesium sulfate and evaporated. The residue was dissolved in methanol (20 mL) and was treated with hydrochloric acid (2M in diethyl ether, 2 mL) overnight. The solvent was evaporated and the residue was partitioned between saturated aqueous sodium bicarbonate and chloroform, the organic phase was dried over magnesium sulfate and evaporated. Purification by flash chromatography using chloroform:methanol (9:1) afforded 0.53 g (63% yield) of the title compound. $^1$H NMR (DMSO-$d_6$) δ 7.90-7.74 (m, 1 H), 7.74-7.67 (m, 1 H), 7.59-7.42 (m, 3 H), 7.35-7.21 (m, 2 H), 7.12-7.00 (m, 2 H), 6.97-6.71 (m, 3 H), 3.74 (s, 3 H), 2.06 (s, 3 H); MS (ESI) m/z 425, 427 [M+1]$^+$.

Example 127

1-(4-Fluoro-3-pyrimidin-5-ylphenyl)-1-(4-methoxy-3-methylphenyl)-1H-isoindol-3-amine

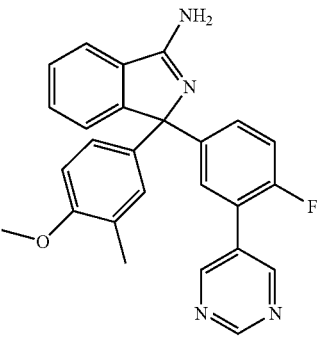

The title compound was synthesized from 1-(3-bromo-4-fluorophenyl)-1-(4-methoxy-3-methylphenyl)-1H-isoindol-3-amine (Example 126) as described in Example 67 Scheme #10, D in 41% yield using pyrimidine-5-boronic acid. $^1$H NMR (DMSO-$d_6$) δ 9.07 (s, 1 H), 8.78 (d, J=1.26 Hz, 2 H), 7.76-7.61 (m, 2 H), 7.43-7.24 (m, 4 H), 7.22-7.11 (m, 1 H), 7.01-6.90 (m, 2 H), 6.88-6.54 (m, 3 H), 3.58 (s, 3 H), 1.92 (s, 3 H); MS (ESI) m/z 425 [M+1]$^+$.

Example 128

1-[4-Fluoro-3-(2-fluoropyridin-3-yl)phenyl]-1-(4-methoxy-3-methylphenyl)-1H-isoindol-3-amine

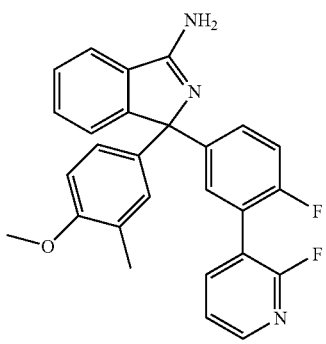

The title compound was synthesized from 1-(3-bromo-4-fluorophenyl)-1-(4-methoxy-3-methylphenyl)-1H-isoindol-3-amine (Example 126) as described in Example 67 Scheme #10, D in 5% yield using 2-fluoropyridine-3-boronic acid. $^1$H NMR (DMSO-$d_6$) δ 8.54-8.46 (m, 1 H), 8.22-8.15 (m, 1 H), 8.05-7.84 (m, 2 H), 7.76-7.55 (m, 5 H), 7.53-7.41 (m, 1 H), 7.32-7.23 (m, 2 H), 7.08-6.78 (m, 3 H), 3.93 (s, 3 H), 2.27 (s, 3 H); MS (ESI) m/z 442 [M+1]$^+$.

Scheme 18

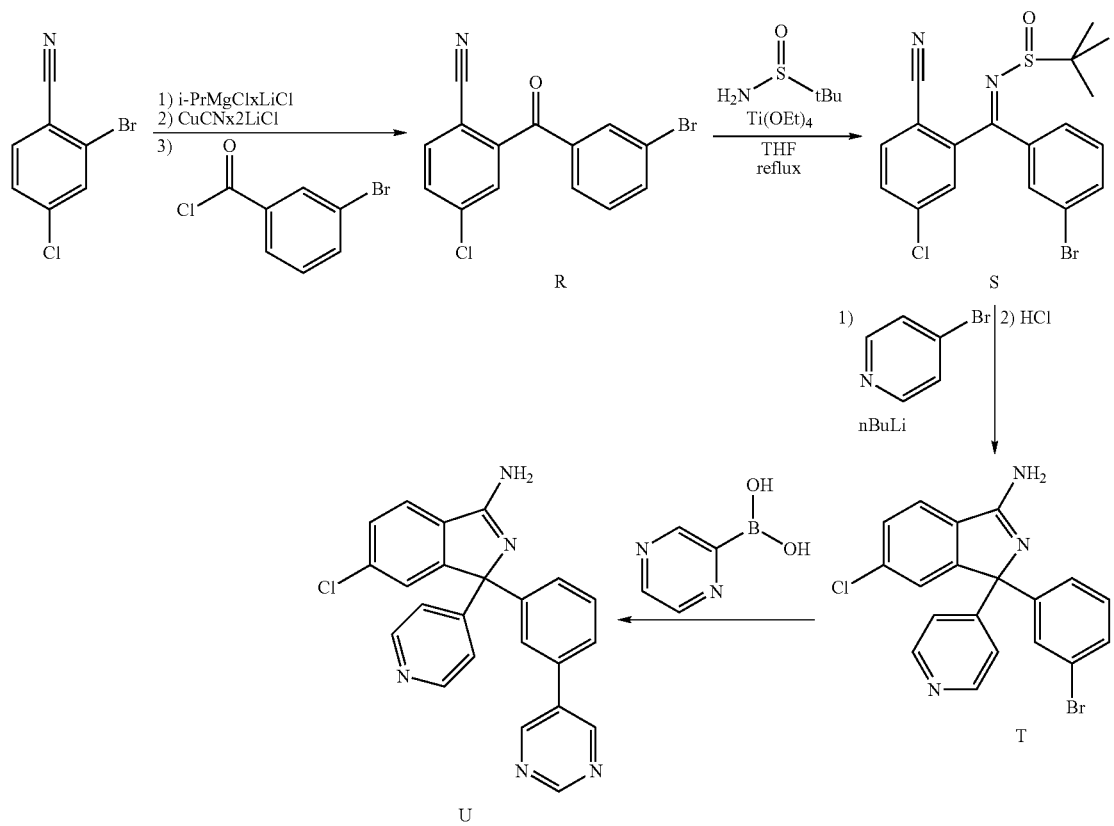

Example 129

6-Chloro-1-pyridin-4-yl-1-(3-pyrimidin-5-ylphenyl)-1H-isoindol-3-amine (Scheme #18, U)

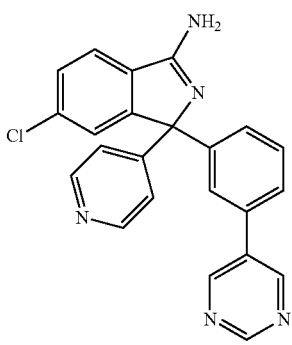

The title compound was synthesized from 1-(3-bromophenyl)-6-chloro-1-pyridin-4-yl-1H-isoindol-3-amine (Scheme #18 T) as described in Example 67 Scheme #10, D in 61% yield using pyrimidine-5-boronic acid. $^1$H NMR (DMSO-$d_6$) δ 9.06 (s, 1 H), 8.93 (s, 2 H), 8.47-8.44 (m, 1 H), 8.37-8.33 (m, 2 H), 7.88 (d, J=1.01 Hz, 2 H), 7.59-7.53 (m, 2 H), 7.43-7.33 (m, 2 H), 7.24-7.19 (m, 2 H), 7.02 (br s, 2 H); MS (ESI) m/z 398 [M+1]$^+$.

1-(3-Bromophenyl)-6-chloro-1-pyridin-4-yl-1H-isoindol-3-amin 0.3 acetate (Scheme #18, T)

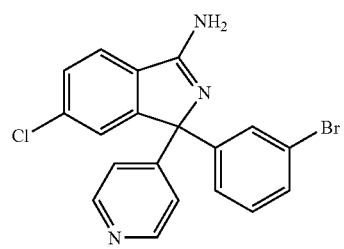

tert-Butyllithium (1.7 M in pentane, 2.20 mL, 3.72 mmol) was added to tetrahydrofuran (15 mL) at −105° C. under argon atmosphere. 4-Iodopyridine in tetrahydrofuran (5 mL) was added over 10 minutes. N-[(1E)-(3-Bromophenyl)(5-chloro-2-cyanophenyl)methylene]-2-methylpropane-2-sulfinamide (Scheme #18 S, 0.789 g, 1.86 mmol) in tetrahydrofuran (5 mL) was added drop wise. The mixture was stirred for 1.5 h at approximately −90° C., then the temperature was allowed to slowly rise to −65° C. The reaction was quenched with water (4 mL) and the reaction mixture was further diluted with water and extracted with ethyl acetate. The organic layers were pooled, washed with brine and concentrated. The residue was dissolved in methanol (15 mL), and hydrochloric acid (1 M in diethyl ether, 2 mL) was added at room temperature under argon atmosphere. The mixture was stirred over weekend, then concentrated. The residue was partitioned between saturated aqueous sodium bicarbonate and dichloromethane. The organic layers were pooled, washed with brine, dried over magnesium sulfate and concentrated. Purification by preparative HPLC afforded 0.249 g (29% yield) of the title compound. $^1$H NMR (DMSO-$d_6$) δ 8.46 (d, J=6.02 Hz, 2 H), 7.92 (d, J=1.51 Hz, 1 H), 7.82 (d, J=8.03 Hz, 1 H), 7.57 (dd, J=8.03, 1.76 Hz, 1 H), 7.52-7.40 (m, 2 H), 7.36-7.22 (m, 4 H), 6.99 (br. s., 2 H), 1.90 (s, 1 H); MS (ES) m/z 398, 400, 402 [M+H]$^+$.

N-[(1E)-(3-Bromophenyl)(5-chloro-2-cyanophenyl) methylene]-2-methylpropane-2-sulfinamide (Scheme #18, S)

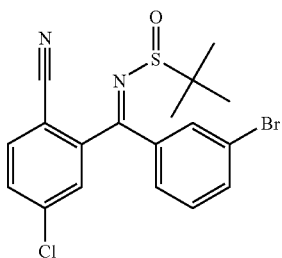

Titanium(IV) ethoxide (1M in tetrahydrofuran, 7.07 mL, 7.07 mmol) was added to 2-(3-bromobenzoyl)-4-chlorobenzonitrile (Scheme #18 R, 1.03 g, 3.21 mmol) at room temperature under argon atmosphere. 2-Methyl-2-propanesulfinamide (0.428 g, 3.53 mmol) was added 2 minutes later. The reaction mixture was refluxed overnight and then stirred at 50° C. for 24 h. The mixture was cooled to ambient temperature and diluted with methanol (7 mL). Saturated aqueous sodium bicarbonate was added and the mixture was diluted with ethyl acetate. The gelatinous precipitate formed was filtered off through a pad of magnesium sulfate (top) and diatomaceous earth (bottom). The filtrate was concentrated and the residue was purified by flash chromatography using ethyl acetate in heptane (0-40%) affording 0.956 g (70% yield) of the title compound. $^1$H NMR (DMSO-$d_6$) δ 8.01 (d, J=6.53 Hz, 1 H), 7.95-7.75 (m, 3 H), 7.71 (s, 1 H), 7.52-7.44 (m, 2 H), 1.28 (s, 9 H).

2-(3-Bromobenzoyl)-4-chlorobenzonitrile (Scheme #18, R)

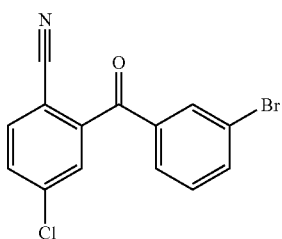

2-Bromo-4-chlorobenzonitrile (1.00 g, 4.62 mmol) was added to isopropylmagnesium chloride×lithium chloride complex (1.05 M in tetrahydrofuran, 4.62 mL, 1.05 mmol) at −15° C. under argon atmosphere. After stirring for 1.5 h 3-bromobenzoyl chloride and CuCN×2LiCl complex solution (1M in tetrahydrofuran, 0.092 mL, 0.0924 mmol) were added and the temperature was raised to 0° C. After 2 h stirring the reaction was quenched with saturated aqueous ammonium chloride (10 mL) and diluted with water. The product was extracted with ethyl acetate and the organic phase was washed with water and concentrated. The residue was purified with flash chromatography using dichloromethane in heptane (0% to 100%) affording 1.03 g (70% yield) of the title compound. $^1$H NMR (DMSO-$d_6$) δ 8.12 (d, J=8.28 Hz, 1 H), 8.00-7.92 (m, 3 H), 7.88 (d, J=2.01 Hz, 1 H), 7.77 (d, J=8.03 Hz, 1 H), 7.60-7.53 (m, 1 H); MS (ES) m/z 320, 322 [M+H]$^+$.

Example 130

1-(3-Pyrimidin-5-ylphenyl)-1-[6-(trifluoromethyl) pyridin-3-yl]-1H-isoindol-3-amine 0.66 acetate

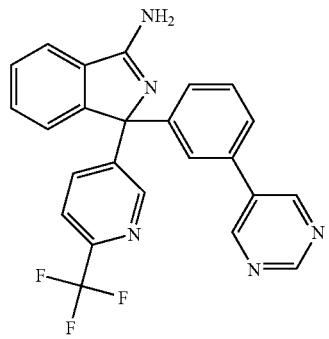

1-(3-Bromophenyl)-1-[6-(trifluoromethyl)pyridin-3-yl]-1H-isoindol-3-amine acetate (Example 52, 0.046 g, 0.09 mmol), pyrimidine-5-boronic acid (0.023 g, 0.186 mmol), [1,1'-bis(diphenylphosphino)ferrocene]palladium(II) chloride dichloromethane adduct (0.004 g, 0.0046 mmol) and cesium carbonate (0.092 g, 0.284 mmol) were dissolved in 1,2-dimethoxyethane:ethanol:water (6:3:1, 2 mL) and heated to 130° C. for 20 minutes in a microwave oven. Additional [1,1'-bis(diphenylphosphino)ferrocene]palladium(II) chloride dichloromethane adduct (0.004 g, 0.0046 mmol) was added and the resulting mixture was heated to 130° C. for additional 20 minutes. After cooled to ambient temperature the mixture was filtered and purified by preparative HPLC to give 0.011 g (26% yield) of the title compound. $^1$H NMR (MeOD) δ 9.12 (s, 1 H), 9.02-8.95 (m, 2 H), 8.64 (d, J=2.02 Hz, 1 H), 8.06-7.92 (m, 2 H), 7.80 (dd, J=7.96, 2.40 Hz, 2 H), 7.76-7.69 (m, 2 H), 7.68-7.61 (m, 2 H), 7.57 (t, J=7.83 Hz, 1 H), 7.49-7.41 (m, 1 H), 1.94 (s, 2 H); MS (ES) m/z 430 [M−H]$^-$, m/z 432 [M+H]$^+$.

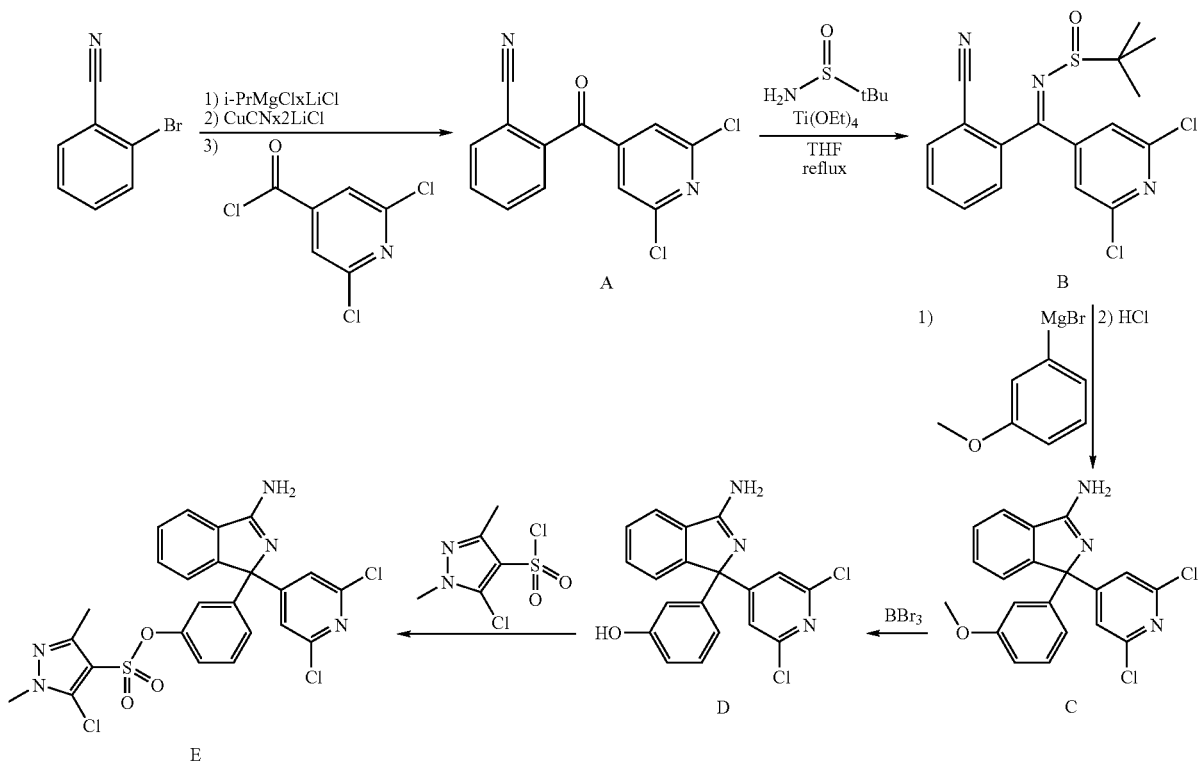

Example 131

3-[3-Amino-1-(2,6-dichloropyridin-4-yl)-1H-isoindol-1-yl]phenyl 5-chloro-1,3-dimethyl-1H-pyrazole-4-sulfonate (Scheme #19, E)

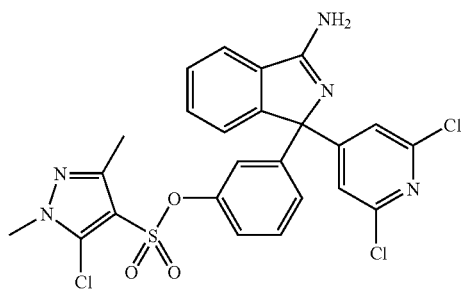

Aqueous sodium hydroxide (2.0 M, 0.559 ml, 1.12 mmol) was added to a solution of 3-(3-amino-1-(2,6-dichloropyridin-4-yl)-1H-isoindol-1-yl)phenol (Scheme #19, D, 0.069 g, 0.19 mmol) in tetrahydrofuran (1 mL) at 0° C. 5-Chloro-1,3-dimethyl-1H-pyrazole-4-sulfonyl chloride (0.051 g, 0.22 mmol) was then added to the reaction mixture. After 30 minutes the reaction mixture was partitioned between ethyl acetate and water. The organic layer was washed with brine, dried over magnesium sulfate and evaporated. Purification by flash chromatography using ethyl acetate followed by purification using preparative HPLC afforded 0.029 g (28% yield) of the title compound. $^1$H NMR (DMSO-d$_6$) δ 7.87-7.77 (m, 2 H), 7.56-7.48 (m, 2 H), 7.41-7.34 (m, 2 H), 7.29 (s, 2 H), 7.12-7.01 (m, 3 H), 6.91 (d, J=1.77 Hz, 1 H), 3.74 (s, 3 H), 1.89 (s, 3 H); MS (AP) m/z 562 [M+1]$^+$.

3-(3-Amino-1-(2,6-dichloropyridin-4-yl)-1H-isoindol-1-yl)phenol (Scheme #19, D)

Boron tribromide (0.229 mL, 2.42 mmol) was added to a solution of 1-(2,6-dichloropyridin-4-yl)-1-(3-methoxyphenyl)-1H-isoindol-3-amine (Scheme #19, C, 0.62 g, 1.61 mmol) in dry dichloromethane (40 mL) at 0° C. The reaction was aloud to reach room temperature and stirred for 6 h. The reaction was quenched by addition of saturated aqueous sodium hydrogen carbonate and extracted with dichloromethane. The organic phase was washed with brine, dried over magnesium sulfate and evaporated. Purification by flash chromatography using ethyl acetate afforded 0.302 g (51% yield) of the title compound. $^1$H NMR (DMSO-d$_6$) δ 7.86-7.77 (m, 2 H), 7.53-7.46 (m, 2 H), 7.37 (s, 2 H), 7.07 (t, J=7.83 Hz, 1 H), 6.96 (br s, 2 H), 6.72-6.58 (m, 3 H); MS (API) m/z 370 [M+1]$^+$.

1-(2,6-Dichloropyridin-4-yl)-1-(3-methoxyphenyl)-1H-isoindol-3-amine (Scheme #19, C)

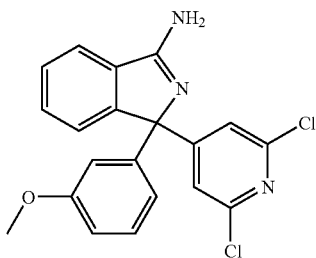

(E)-N-((2-cyanophenyl)(2,6-dichloropyridin-4-yl)methylene)-2-methylpropane-2-sulfinamide (Scheme #19, B, 0.69 g, 1.81 mmol) was dissolved in dry tetrahydrofuran (20 mL) at 0° C. to which a solution of 3-methoxyphenylmagnesium bromide (1.0 M in tetrahydrofuran, 5.44 mL, 5.44 mmol) in tetrahydrofuran was added. The reaction was stirred for 50 minutes and then quenched by addition of saturated aqueous ammonium chloride (25 mL), then further diluted with saturated aqueous sodiumhydrogen carbonate and extracted with ethyl acetate. The organic phase was dried over magnesium sulfate and evaporated. The residue was dissolved in methanol (20 mL) and treated with hydrochloride (1.0 M in diethyl ether, 3.63 mL, 3.63 mmol) for 1.5 h and then treated with saturated aqueous sodiumhydrogen carbonate and washed with ethyl acetate. The organic phase was washed with brine, dried over sodium sulfate and evaporated. Purification by flash chromatography using ethyl acetate afforded 0.621 g (89% yield) of the title compound. $^1$H NMR (CDCl$_3$) δ 7.59-7.43 (m, 4 H), 7.29-7.20 (m, 3 H), 6.89-6.87 (m, 3 H), 3.75 (s, 3 H). MS (AP) m/z 384 [M+1]$^+$.

(E)-N-((2-Cyanophenyl)(2,6-dichloropyridin-4-yl)methylene)-2-methylpropane-2-sulfinamide (Scheme #19, B)

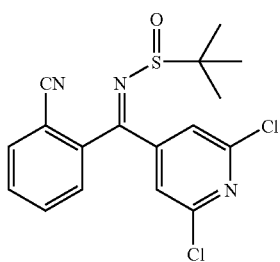

Titanium (IV) ethoxide (1M in tetrahydrofuran, 10.2 mL, 10.2 mmol) was added to a solution of 2-(2,6-dichloroisonicotinoyl)benzonitrile (Scheme #19, A, 1.0 g, 3.3 mmol) in tetrahydrofuran (5 mL) at room temperature. After 5 minutes 2-methyl-propanesulfinamide (0.48 g, 3.96 mmol) was added and the reaction mixture was refluxed over night. Additional amounts of titanium (IV) ethoxide (1M in tetrahydrofuran, 3.0 mL, 3.0 mmol) and 2-methyl-propanesulfinamide (0.2 g, 1.6 mmol) were added and the reaction mixture was refluxed for 5 h. After cooled to room temperature methanol (5 mL) and saturated aqueous sodium hydrogen carbonate (0.1 mL) added to the reaction mixture. A precipitation occurred and the crude was filtered through a pad of sodium sulfate before evaporation. Purification by flash chromatography using a stepwise gradient of ethylacetate in heptane afforded the title compound in 44% yield. $^1$H NMR (CDCl$_3$) δ 7.85-7.78 (m, 1 H), 7.78-7.70 (m, 1 H), 7.68-7.61 (m, 1 H), 7.44-7.35 (m, 1 H), 7.32 (s, 2 H), 1.38 (s, 9 H). MS (API) m/z 380 [M+1]$^+$.

2-(2,6-Dichloroisonicotinoyl)benzonitrile (Scheme #19, A)

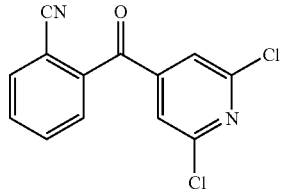

A solution prepared by mixing copper cyanide (0.94 g, 10.05 mmol) and lithium bromide (1.82 g, 21.0 mmol) in tetrahydrofuran (20 mL) was added to a cold (−20° C.) solution of 2-cyanophenylzinc bromide (0.5 M in tetrahydrofuran, 20 mL, 10 mmol) in tetrahydrofuran. The reaction mixture was allowed to reach 0° C. and stirred for 15 minutes. The reaction mixture was then cold to −30° C. before a solution of 2,6-dichloro-isonicotinoyl chloride in tetrahydrofuran (20 mL), formed when 2,6-dichloro-isonicotinic acid (1.9 g, 10 mmol) was refluxed in thionyl chloride (20 ml) for 2 h, followed by co-evaporation with toluene. The reaction mixture was stirred for 4 h and allowed to reach room temperature. The mixture was then treated with saturated aqueous ammonium chloride and extracted with diethylether. The organic phase was dried over magnesium sulfate and evaporated. Purification by flash chromatography using a stepwise gradient of ethylacetate in heptane afforded 1.8 g (65%) of the title compound. $^1$H NMR (CDCl$_3$) δ 7.95-7.91 (m, 1 H), 7.83-7.77 (m, 2 H), 7.69-7.64 (m, 1 H), 7.55 (s, 2 H). MS (AP) m/z 277 [M+1]$^+$.

Example 132

3-[3-Amino-1-(2,6-dichloropyridin-4-yl)-1H-isoindol-1-yl]phenyl 6-chloroimidazo[2,1-b][1,3]thiazole-5-sulfonate

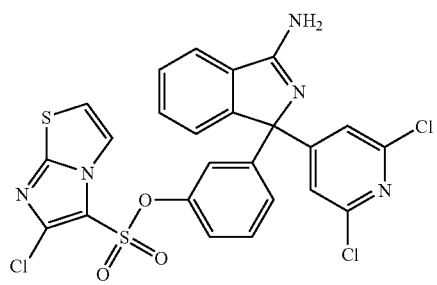

The title compound was synthesized as described in Example 131 (Scheme #19, E) using 6-chloroimidazo[2,1-B][1,3]thiazole-5-sulfonyl chloride in 56% yield. $^1$H NMR (DMSO-d$_6$) δ 7.86-7.76 (m, 2 H), 7.70 (d, J=5.56 Hz, 1 H), 7.64 (d, J=4.55 Hz, 1 H), 7.55-7.45 (m, 2 H), 7.41-7.33 (m, 2 H), 7.22 (s, 2 H), 7.11-7.00 (m, 3 H), 6.82 (s, 1 H); MS (ES) m/z 590 [M+1]+.

Example 133

3-[3-Amino-1-(2,6-dichloropyridin-4-yl)-1H-isoindol-1-yl]phenyl 2,6-difluorobenzenesulfonate

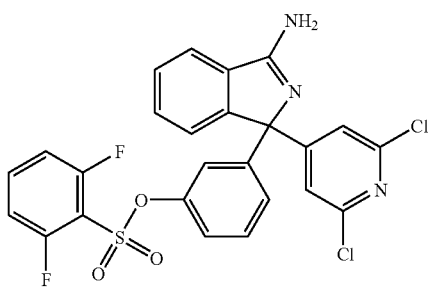

The title compound was synthesized as described in Example 131 (Scheme #19, E) using 2,6-difluorobenzenesulphonyl chloride in 55% yield. ¹H NMR (DMSO-d₆) δ 7.89-7.79 (m, 2 H), 7.77-7.71 (m, 1 H), 7.54-7.46 (m, 2 H), 7.43-7.37 (m, 1 H), 7.35-7.30 (m, 1 H), 7.30-7.22 (m, 4 H), 7.19-7.14 (m, 1 H), 7.05 (br s, 2 H), 6.84 (t, J=2.02 Hz, 1 H); MS (ES) m/z 546 [M+1]+.

Scheme 20

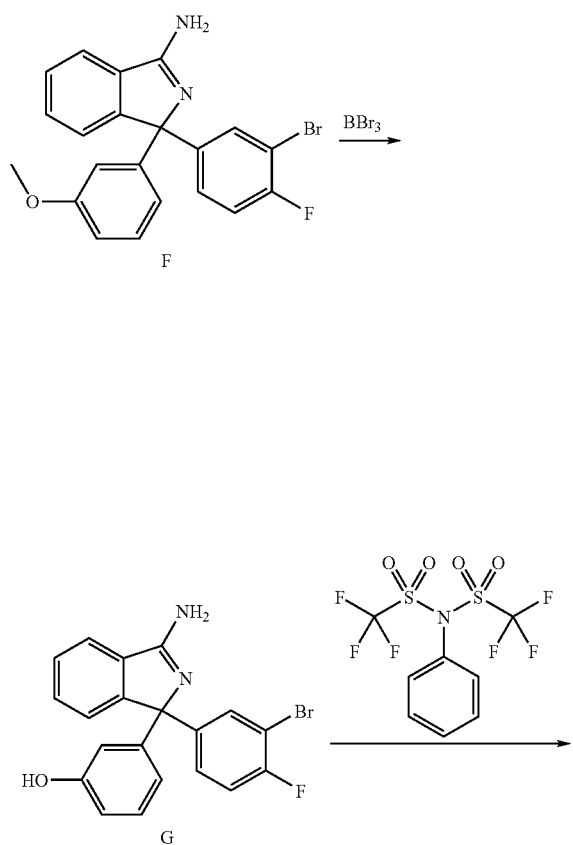

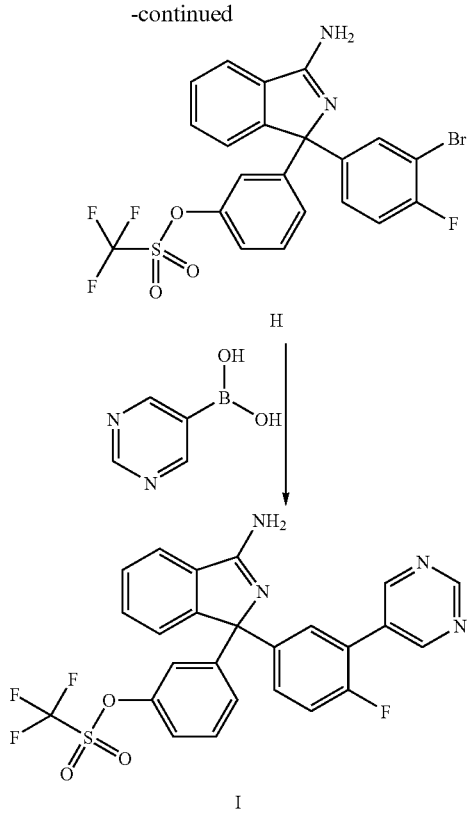

Example 134

3-[3-Amino-1-(4-fluoro-3-pyrimidin-5-ylphenyl)-1H-isoindol-1-yl]phenyl trifluoromethanesulfonate
(Scheme #20, I)

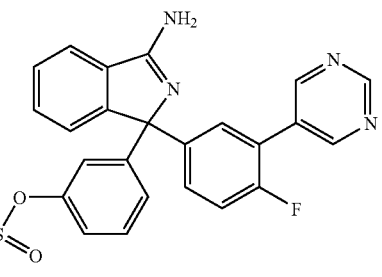

3-(3-Amino-1-(3-bromo-4-fluorophenyl)-1H-isoindol-1-yl)phenyl trifluoromethane-sulfonate (Scheme #20, H, 0.083 g, 0.16 mmol), 5-pyrimidinylboronic acid (0.019 g, 0.16 mmol), potassium acetate (0.031 g, 0.31 mmol), 1,1'-bis(diphenylphosphino)ferrocene-palladium(II) dichloride dichloromethane (0.006 g, 7.84 µmol) and solvent (2 mL of a mixture of dimethoxyethene and water in a ratio of 4:1) was irradiated under argon atmosphere in a microwave at 130° C. for 20 minutes. When cooled to ambient temperature the mixture was partitioned between ethylacetate and water, the organic phase was dried over magnesium sulfate and evaporated. Purification by preparative HPLC afforded 0.031 g (37%) of the title compound. ¹H NMR (CDCl₃) δ 9.18 (s, 1 H), 8.86 (d, J=1.26 Hz, 2 H), 7.58-7.45 (m, 4 H), 7.43-7.31

(m, 4 H), 7.30-7.25 (m, 1 H), 7.19-7.10 (m, 2 H), 5.43 (br s, 2 H); MS (ES) m/z 529 [M+1]+.

3-[3-Amino-1-(3-bromo-4-fluorophenyl)-1H-isoindol-1-yl]phenyl trifluoromethanesulfonate (Scheme #20, H)

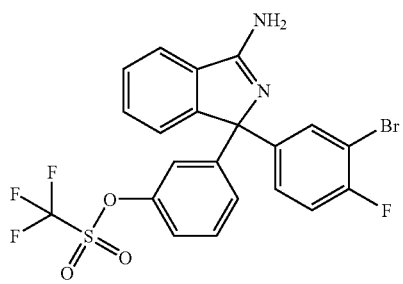

A solution of 3-(3-amino-1-(3-bromo-4-fluorophenyl)-1H-inden-1-yl)phenol (Scheme #20, G, 0.165 g, 0.42 mmol) and N-phenylbis(trifluoromethanesulphonimide) (0.164 g, 0.46 mmol) in anhydrous dichloromethane (10 mL) purged with argon was cooled to 0° C. Triethylamine (0.064 mL, 0.46 mmol) was added dropwise and the temperature was then allowed to reach room temperature. After 2 h more N-phenylbis(trifluoromethanesulphonimide (0.041 g, 0.12 mmol) was added and the reaction was stirred over night. The reaction mixture was washed with brine, dried over sodium sulfate and evaporated. Purification by flash chromatography using ethyl acetate afforded 0.168 g (76% yield) of the title compound. $^1$H NMR (CDCl$_3$) δ 7.64 (d, J=7.33 Hz, 1 H), 7.58-7.51 (m, 1 H), 7.49-7.32 (m, 4 H) 7.29 (t, J=7.96 Hz, 1 H), 7.26-7.20 (m, 1 H), 7.17-7.11 (m, 1 H), 7.11-7.00 (m, 2 H), 6.97-6.81 (m, 2 H); MS (AP) m/z 529 [M+1]+.

3-(3-Amino-1-(3-bromo-4-fluorophenyl)-1H-inden-1-yl)phenol (Scheme #20, G)

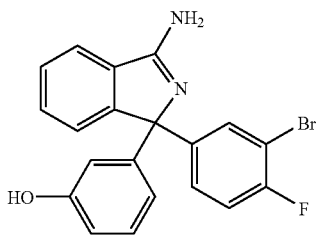

The title compound was synthesized as described in Scheme #19, D using 1-(3-bromo-4-fluorophenyl)-1-(3-methoxyphenyl)-1H-isoindol-3-amine (Scheme #20, F) in 68% yield. $^1$H NMR (CDCl$_3$) δ 7.62-7.54 (m, 1 H), 7.53-7.49 (m, 2 H), 7.48-7.40 (m, 2 H), 7.29-7.20 (m, 1 H), 7.08 (t, J=7.96 Hz, 1 H), 6.98-6.88 (m, 2 H), 6.78-6.70 (m, 1 H), 6.56 (d, J=7.83 Hz, 1 H), 5.89 (br s, 2 H); MS (AP) m/z 397,398 [M+1]+.

1-(3-Bromo-4-fluorophenyl)-1-(3-methoxyphenyl)-1H-isoindol-3-amine (Scheme #20, F)

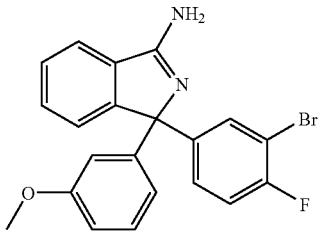

The title compound was synthesized as described in Scheme #19, C using 2-(3-bromo-4-fluorobenzoyl)benzonitrile (Scheme #11, E) in 56% yield. $^1$H NMR (CDCl$_3$) δ 7.57-7.39 (m, 5 H), 7.28-7.16 (m, 2 H), 6.99 (t, J=8.46 Hz, 1 H), 6.89-6.84 (m, 2 H), 6.82-6.74 (m, 1 H), 4.79 (br s, 2 H), 3.73 (s, 3 H); MS (AP) m/z 411 [M+1]+.

Example 135

3-[3-Amino-1-(4-fluoro-3-pyrimidin-5-ylphenyl)-1H-isoindol-1-yl]phenyl trifluoromethanesulfonate

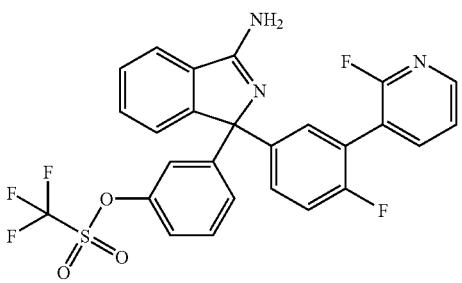

The title compound was synthesized as described in Scheme #20, I using 2-fluoropyridine-3-boronic acid in 29% yield. $^1$H NMR (DMSO-d$_6$) δ 8.29 (d, J=4.80 Hz, 1 H), 8.01-7.91 (m, 1 H), 7.88-7.77 (m, 2 H), 7.53-7.40 (m, 6 H), 7.39-7.32 (m, 3 H), 7.32-7.23 (m, 1 H), 6.92 (br s, 2 H); MS (ES) m/z 546 [M+1]+.

Scheme 21

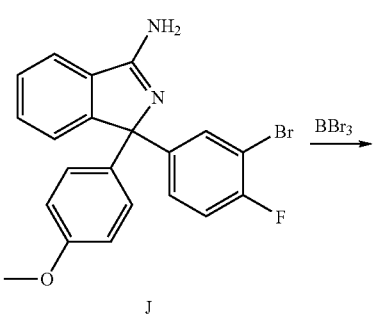

-continued

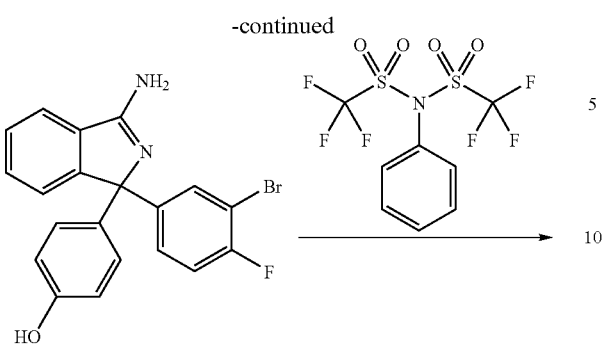

K

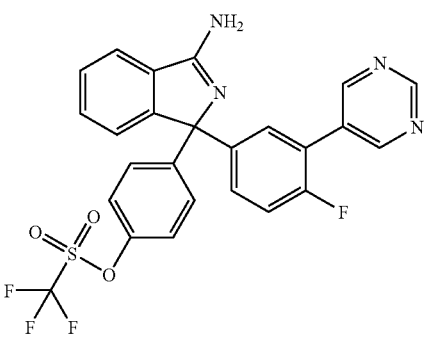

L

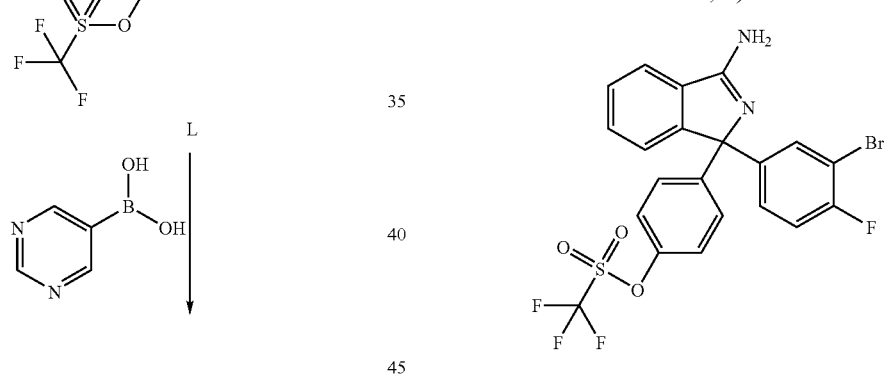

M

Example 136

4-[3-Amino-1-(4-fluoro-3-pyrimidin-5-ylphenyl)-1H-isoindol-1-yl]phenyl trifluoromethanesulfonate (Scheme #21, M)

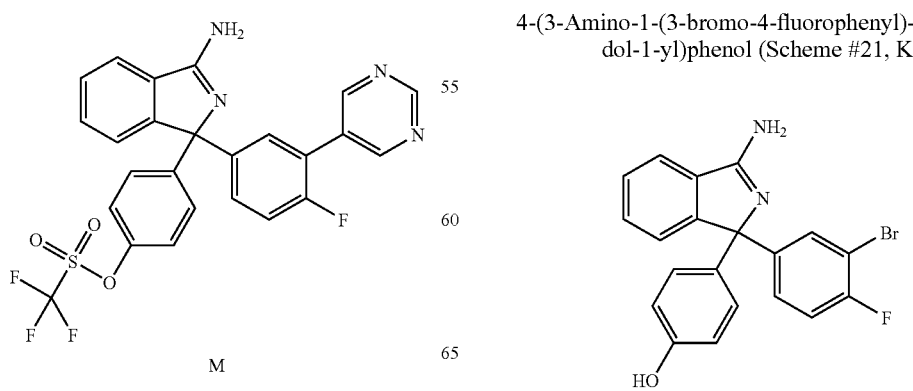

The title compound was synthesized as described in Scheme #20, I using 4-(3-amino-1-(3-bromo-4-fluorophenyl)-1H-isoindol-1-yl)phenyl trifluoromethanesulfonate (Scheme #21, L) in 39% yield. $^1$H NMR (DMSO-$d_6$) δ 9.20 (s, 1 H), 8.92 (d, J=1.52 Hz, 2 H), 7.94-7.88 (m, 1 H), 7.83-7.76 (m, 1 H), 7.59-7.43 (m, 6 H), 7.42-7.28 (m, 3 H), 6.87 (br s, 2 H); MS (ES) m/z 529 [M+1]$^+$.

4-(3-amino-1-(3-bromo-4-fluorophenyl)-1H-isoindol-1-yl)phenyl trifluoromethanesulfonate (Scheme #21, L)

The title compound was synthesized as described in Scheme #20, H using 4-(3-amino-1-(3-bromo-4-fluorophenyl)-1H-isoindol-1-yl)phenol (Scheme #21, K) in 69% yield. $^1$H NMR (CDCl$_3$) δ 7.58-7.42 (m, 5 H), 7.39-7.30 (m, 2 H), 7.22-7.13 (m, 3 H), 7.01 (t, J=8.34 Hz, 1 H), 6.26 (br s, 2 H); MS (AP) m/z 529, 531 [M+1]$^+$.

4-(3-Amino-1-(3-bromo-4-fluorophenyl)-1H-isoindol-1-yl)phenol (Scheme #21, K)

The title compound was synthesized as described in Scheme #20, G starting from 1-(3-bromo-4-fluorophenyl)-1-(4-methoxyphenyl)-1H-isoindol-3-amine (Scheme #21, J) in 70% yield. $^1$H NMR (CDCl$_3$) δ 7.77 (dd, J=5.43, 2.65 Hz, 1 H), 7.69-7.60 (m, 1 H), 7.50 (dd, J=6.82, 2.02 Hz, 1 H), 7.47-7.39 (m, 2 H), 7.35-7.20 (m, 2 H), 7.10-7.01 (m, 2 H), 6.68-6.54 (m, 2 H); MS (API) m/z 397, 399 [M+1]$^+$.

1-(3-Bromo-4-fluorophenyl)-1-(4-methoxyphenyl)-1H-isoindol-3-amine (Scheme #21, J)

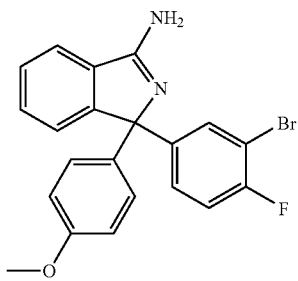

The title compound was synthesized as described in Scheme #20, F starting from 2-(3-bromo-4-fluorobenzoyl)benzonitrile (Scheme #11, E) in 68% yield. $^1$H NMR (CDCl$_3$) δ 7.55-7.50 (m, 2 H), 7.50-7.40 (m, 3 H), 7.28-7.18 (m, 3 H), 6.99 (t, J=8.46 Hz, 1 H), 6.84-6.77 (m, 2 H), 4.90 (br s, 2 H), 3.77 (s, 3 H); MS (AP) m/z 411, 413 [M+1]$^+$.

Assays

Compounds were tested in at least one of the following assays:

β-Secretase Enzyme

The enzyme used in the IGEN Cleavage-, Fluorescent-, TR-FRET- and BiaCore assays is described as follows:

The soluble part of the human β-Secretase (AA 1-AA 460) was cloned into the ASP2-Fc10-1-IRES-GFP-neoK mammalian expression vector. The gene was fused to the Fc domain of IgG1 (affinity tag) and stably cloned into HEK 293 cells. Purified sBACE-Fc is stored in Tris buffer, pH 9.2 and has a purity of 95%.

IGEN Cleavage Assay

The enzyme was diluted to 43 μg/ml in 40 mM MES pH 5.0. The IGEN substrate was diluted to 12 μM in 40 mM MES pH 5.0. Compounds were diluted to the desired concentration in dimethyl sulfoxide (final dimethyl sulfoxide concentration in assay is 5%). The assay was performed in a 96 well PCR plate from Greiner (#650201). Compound in dimethyl sulfoxide (3 μL) and enzyme (27 μL) were added to the plate, and pre-incubated for 10 min. The reaction was started with substrate (30 μL). The final dilution of enzyme was 20 μg/ml and the final concentration of substrate was 6 μM. After 20 minutes reaction at room temperature (RT), the reaction was stopped by removing 10 μL of the reaction mix and diluting it 1:25 in 0.2 M Trizma-HCl, pH 8.0. The product was quantified by adding 50 μL of a 1:5000 dilution of the neoepitope antibody to 50 μL of the 1:25 dilution of the reaction mix (all antibodies and the streptavidin coated beads were diluted in PBS containing 0.5% BSA and 0.5% Tween20). Then, 100 μL of 0.2 mg/mL streptavidin coated beads (Dynabeads M-280) and a 1:5000 dilution of ruthenylated goat anti-rabbit (Ru-GαR) antibody was added. The mixture was measured for electro-chemiluminescence in a BioVeris M8 Analyzer after 2 hours of incubation with shaking at RT. The dimethyl sulfoxide control defined 100% activity level and 0% activity was defined by exclusion of the enzyme (using 40 mM MES pH 5.0 buffer instead).

Fluorescent Assay

The enzyme was diluted to 52 μg/ml in 40 mM MES pH 5.0. The substrate (Dabcyl-Edans) was diluted to 30 μM in 40 mM MES pH 5.0. Compounds were diluted to the desired concentration in dimethyl sulfoxide (final dimethyl sulfoxide concentration in assay is 5%). The assay is done in a Corning 384 well round bottom, low volume, non-binding surface plate (Corning #3676). Enzyme (9 μL) together with 1 μL of compound in dimethyl sulfoxide were added to the plate and pre-incubated for 10 min. Substrate (10 μL) was added and the reaction proceeded in the dark at RT for 25 min. The final dilution of enzyme was 23 μg/ml, and the final concentration of substrate was 15 μM (Km of 25 μM). The fluorescence of the product was measured on a Victor TI plate reader with an excitation wavelength of 360 nm and an emission wavelength of 485 nm using a protocol for labelled Edans peptide. The dimethyl sulfoxide control defined 100% activity level and 0% activity was defined by exclusion of the enzyme (using 40 mM MES pH 5.0 buffer instead).

TR-FRET Assay

Enzyme was diluted to 6 μg/mL and the substrate (Europium)CEVNLDAEFK(Qsy7) to 200 nM in reaction buffer (NaAcetate, chaps, triton x-100, EDTA pH 4.5). Compounds were diluted to the desired concentration in dimethyl sulfoxide (final dimethyl sulfoxide concentration in assay is 5%). The assay was done in a Costar 384 well round bottom, low volume, non-binding surface plate (Corning #3676). Enzyme (9 μL) and 1 μL of compound in dimethyl sulfoxide was added to the plate, mixed and pre-incubated for 10 min. Substrate (10 μL) was added and the reaction proceeded in the dark for 15 min at RT. The reaction was stopped with the addition of 7 μL NaAcetate, pH 9. The fluorescence of the product was measured on a Victor TI plate reader with an excitation wavelength of 340 nm and an emission wavelength of 615 nm. The final concentration of the enzyme was 2.7 μg/ml and the final concentration of the substrate was 100 nM (Km of 290 nM). The dimethyl sulfoxide control defined the 100% activity level and 0% activity was defined by exclusion of the enzyme (using reaction buffer instead).

BACE Biacore Sensor Chip Preparation

BACE was assayed on a Biacore3000 instrument by attaching either a peptidic transition state isostere (TSI) or a scrambled version of the peptidic TSI to the surface of a Biacore CM5 sensor chip. The surface of a CM5 sensor chip has 4 distinct channels that can be used to couple the peptides. The scrambled peptide KFES-statine-ETIAEVENV was coupled to channel 1 and the TSI inhibitor KTEEISEVN-statine-VAEF was coupled to channel 2 of the same chip. The two peptides were dissolved at 0.2 mg/mL in 20 mM sodium acetate pH 4.5, and then the solutions were centrifuged at 14K rpm to remove any particulates. Carboxyl groups on the dextran layer were activated by injecting a one to one mixture of 0.5 M N-ethyl-N'(3-dimethylaminopropyl)-carbodiimide and 0.5 M N-hydroxysuccinimide at 5 μL/min for 7 min. Then the stock solution of the control peptide was injected in channel 1 for 7 min at 5 μL/min., and then the remaining activated carboxyl groups were blocked by injecting 1 M ethanolamine for 7 min at 5 μL/min.

BACE Biacore Assay Protocol

The BACE Biacore assay was done by diluting BACE to 0.5 μM in sodium acetate buffer at pH 4.5 (running buffer minus dimethyl sulfoxide). The diluted BACE was mixed with dimethyl sulfoxide or compound diluted in dimethyl sulfoxide at a final concentration of 5% dimethyl sulfoxide.

The BACE/inhibitor mixture was incubated for 30 minutes at RT before being injected over channel 1 and 2 of the CM5 Biacore chip at a rate of 20 μL/min. As BACE bound to the chip the signal was measured in response units (RU). BACE binding to the TSI inhibitor on channel 2 gave a certain signal. The presence of a BACE inhibitor reduced the signal by binding to BACE and inhibiting the interaction with the peptidic TSI on the chip. Any binding to channel 1 was non-specific and was subtracted from the channel 2 responses. The dimethyl sulfoxide control was defined as 100% and the effect of the compound was reported as percent inhibition of the dimethyl sulfoxide control.

Beta-Secretase Whole Cell Assays

Generation of HEK293-APP695

The pcDNA3.1 plasmid encoding the cDNA of human full-length APP695 was stably transfected into HEK-293 cells using the Lipofectamine transfection reagent according to manufacture's protocol (Invitrogen). Colonies were selected with 0.1-0.5 mg/mL of zeocin. Limited dilution cloning was performed to generate homogeneous cell lines. Clones were characterized by levels of APP expression and Aβ secreted in the conditioned media using an ELISA assay developed in-house.

Cell Culture for HEK293-APP695

HEK293 cells stably expressing human wild-type APP (HEK293-APP695) were grown at 37° C., 5% $CO_2$ in DMEM containing 4500 g/L glucose, GlutaMAX and sodium pyruvate supplemented with 10% FBS, 1% non-essential amino acids and 0.1 mg/mL of the selection antibiotic zeocin.

Aβ40 Release Assay

HEK293-APP695 cells were harvested at 80-90% confluence and seeded at a concentration of $0.2 \times 10^6$ cells/mL, 100 mL cell suspension/well, onto a black clear bottom 96-well poly-D-lysine coated plate. After over night incubation at 37° C., 5% $CO_2$, the cell medium was replaced with cell culture medium with penicillin and streptomycin (100 U/mL, 100 μg/mL, respectively) containing test compounds in a final dimethyl sulfoxide concentration of 1%. Cells were exposed to the test compounds for 24 h at 37° C., 5% $CO_2$ To quantify the amount of released Aβ, 100 μL cell medium was transferred to a round bottom polypropylene 96-well plate (assay plate). The cell plate was saved for the ATP assay, as described below. To the assay plate, 50 μL of primary detection solution containing 0.5 μg/mL of the rabbit anti-Aβ40 antibody and 0.5 μg/mL of the biotinylated monoclonal mouse 6E10 antibody in DPBS with 0.5% BSA and 0.5% Tween-20 was added per well and incubated over night at 4° C. Then, 50 μL of secondary detection solution containing 0.5 g/mL of a ruthenylated goat anti-rabbit antibody and 0.2 mg/mL of streptavidin coated beads (Dynabeads M-280) was added per well. The plate was vigorously shaken at RT for 1-2 hours. The plate was then measured for electro-chemiluminescence in a BioVeris M8 Analyzer.

Cell Culture for SH-SY5Y

SH-SY5Y cells were grown 37° C. with 5% $CO_2$ in DMEM/F-12 1:1 containing GlutaMAX supplemented with 1 mM HEPES, 10% FBS and 1% non-essential amino acids.

sAPPβ Release Assay

SH-SY5Y cells were harvested at 80-90% confluence and seeded at a concentration of $1.5 \times 10^6$ cells/mL, 100 mL cell suspension/well, onto a black clear flat bottom 96-well tissue culture plate. After 7 hours of incubation at 37° C., 5% $CO_2$, the cell medium was replaced with 90 μl cell culture medium with penicillin and streptomycin (100 U/mL, 100 μg/mL, respectively) containing test compounds in a final dimethyl sulfoxide concentration of 1%. Cells were exposed to the test compounds for 18 h at 37° C., 5% $CO_2$. To measure sAPPβ released into the cell medium, sAPPβ microplates from Meso Scale Discovery (MSD) were used and the assay was performed according to the manufacture's protocol. Briefly, 25 μL cell medium was transferred to a previously blocked MSD sAPPβ microplate. The cell plate was saved for the ATP assay, as described below. The sAPPβ was captured during shaking at RT for 1 hour, by antibodies spotted in the wells of the microplate. After multiple washes, SULFO-TAG labeled detection antibody was added (25 μL/well, final concentration 1 nM) to the assay plate and the plate was incubated with shaking at RT for 1 hour. Following multiple washes, 150 μl/well of Read Buffer T was added to the plate. After 10 minutes at RT the plate was read in the SECTOR™ Imager for electro-chemiluminescence.

ATP assay

As indicated above, after transferring medium for analysis of Aβ40 or sAPPβ from the cell plate, the plate was used to analyze cytotoxicity using the ViaLight™ Plus cell proliferation/cytotoxicity kit from Cambrex BioScience that measures total cellular ATP. The assay was performed according to the manufacture's protocol. Briefly, 50 μL cell lysis reagent was added per well. The plates were incubated at RT for 10 min. Two min after addition of 100 μL reconstituted ViaLight™ Plus ATP reagent, the luminescence was measured in a Wallac Victor² 1420 multilabel counter.

hERG Assay

Cell Culture

The hERG-expressing Chinese hamster ovary K1 (CHO) cells described by (Persson, Carlsson, Duker, & Jacobson, 2005) were grown to semi-confluence at 37° C. in a humidified environment (5% $CO_2$) in F-12 Ham medium containing L-glutamine, 10% foetal calf serum (FCS) and 0.6 mg/ml hygromycin (all Sigma-Aldrich). Prior to use, the monolayer was washed using a pre-warmed (37° C.) 3 ml aliquot of Versene 1:5,000 (Invitrogen). After aspiration of this solution the flask was incubated at 37° C. in an incubator with a further 2 ml of Versene 1:5,000 for a period of 6 minutes. Cells were then detached from the bottom of the flask by gentle tapping and 10 ml of Dulbecco's Phosphate-Buffered Saline containing calcium (0.9 mM) and magnesium (0.5 mM) (PBS; Invitrogen) was then added to the flask and aspirated into a 15 ml centrifuge tube prior to centrifugation (50 g, for 4 mins). The resulting supernatant was discarded and the pellet gently re-suspended in 3 ml of PBS. A 0.5 ml aliquot of cell suspension was removed and the number of viable cells (based on trypan blue exclusion) was determined in an automated reader (Cedex; Innovatis) so that the cell re-suspension volume could be adjusted with PBS to give the desired final cell concentration. It is the cell concentration at this point in the assay that is quoted when referring to this parameter. CHO-Kv1.5 cells, which were used to adjust the voltage offset on IonWorks™ HT, were maintained and prepared for use in the same way.

Electrophysiology

The principles and operation of this device have been described by (Schroeder, Neagle, Trezise, & Worley, 2003). Briefly, the technology is based on a 384-well plate (Patch-Plate™) in which a recording is attempted in each well by using suction to position and hold a cell on a small hole separating two isolated fluid chambers. Once sealing has taken place, the solution on the underside of the PatchPlate™ is changed to one containing amphotericin B. This permeabilises the patch of cell membrane covering the hole in each well and, in effect, allows a perforated, whole-cell patch clamp recording to be made.

A β-test IonWorks™ HT from Essen Instrument was used. There is no capability to warm solutions in this device hence it was operated at room temperature (~21° C.), as follows.

The reservoir in the "Buffer" position was loaded with 4 ml of PBS and that in the "Cells" position with the CHO-hERG cell suspension described above. A 96-well plate (V-bottom, Greiner Bio-one) containing the compounds to be tested (at 3-fold above their final test concentration) was placed in the "Plate 1" position and a PatchPlate™ was clamped into the PatchPlate™ station. Each compound plate was laid-out in 12 columns to enable ten, 8-point concentration-effect curves to be constructed; the remaining two columns on the plate were taken up with vehicle (final concentration 0.33% DMSO), to define the assay baseline, and a supra-maximal blocking concentration of cisapride (final concentration 10 μM) to define the 100% inhibition level. The fluidics-head (F-Head) of IonWorks™ HT then added 3.5 μl of PBS to each well of the PatchPlate™ and its underside was perfused with "internal" solution that had the following composition (in mM): K-Gluconate 100, KCl 40, $MgCl_2$ 3.2, EGTA3 and HEPES 5 (all Sigma-Aldrich; pH 7.25-7.30 using 10 M KOH). After priming and de-bubbling, the electronics-head (E-head) then moved round the PatchPlate™ performing a hole test (i.e. applying a voltage pulse to determine whether the hole in each well was open). The F-head then dispensed 3.5 μl of the cell suspension described above into each well of the PatchPlate™ and the cells were given 200 seconds to reach and seal to the hole in each well. Following this, the E-head moved round the PatchPlate™ to determine the seal resistance obtained in each well. Next, the solution on the underside of the PatchPlate™ was changed to "access" solution that had the following composition (in mM): KCl 140, EGTA 1, $MgCl_2$ 1 and HEPES 20 (pH 7.25-7.30 using 10 M KOH) plus 100 μg/ml of amphotericin B (Sigma-Aldrich). After allowing 9 minutes for patch perforation to take place, the E-head moved round the PatchPlate™ 48 wells at a time to obtain pre-compound hERG current measurements. The F-head then added 3.5 □l of solution from each well of the compound plate to 4 wells on the PatchPlate™ (the final DMSO concentration was 0.33% in every well). This was achieved by moving from the most dilute to the most concentrated well of the compound plate to minimise the impact of any compound carry-over. After approximately 3.5 mins incubation, the E-head then moved around all 384-wells of the PatchPlate™ to obtain post-compound hERG current measurements. In this way, non-cumulative concentration-effect curves could be produced where, providing the acceptance criteria were achieved in a sufficient percentage of wells (see below), the effect of each concentration of test compound was based on recording from between 1 and 4 cells.

The pre- and post-compound hERG current was evoked by a single voltage pulse consisting of a 20 s period holding at −70 mV, a 160 ms step to −60 mV (to obtain an estimate of leak), a 100 ms step back to −70 mV, a 1 s step to +40 mV, a 2 s step to −30 mV and finally a 500 ms step to −70 mV. In between the pre- and post-compound voltage pulses there was no clamping of the membrane potential. Currents were leak-subtracted based on the estimate of current evoked during the +10 mV step at the start of the voltage pulse protocol. Any voltage offsets in IonWorks™ HT were adjusted in one of two ways. When determining compound potency, a depolarising voltage ramp was applied to CHO-Kv1.5 cells and the voltage noted at which there was an inflection point in the current trace (i.e. the point at which channel activation was seen with a ramp protocol). The voltage at which this occurred had previously been determined using the same voltage command in conventional electrophysiology and found to be −15 mV (data not shown); thus an offset potential could be entered into the IonWorks™ HT software using this value as a reference point. When determining the basic electrophysiological properties of hERG, any offset was adjusted by determining the hERG tail current reversal potential in IonWorks™ HT, comparing it with that found in conventional electrophysiology (−82 mV) and then making the necessary offset adjustment in the IonWorks™ HT software. The current signal was sampled at 2.5 kHz.

Pre- and post-scan hERG current magnitude was measured automatically from the leak subtracted traces by the IonWorks™ HT software by taking a 40 ms average of the current during the initial holding period at −70 mV (baseline current) and subtracting this from the peak of the tail current response. The acceptance criteria for the currents evoked in each well were: pre-scan seal resistance>60 MΩ, pre-scan hERG tail current amplitude>150 pA; post-scan seal resistance>60 MΩ. The degree of inhibition of the hERG current was assessed by dividing the post-scan hERG current by the respective pre-scan hERG current for each well.

Results

Typical IC50 values for the compounds of the present invention are in the range of about 1 to about 100,000 nM. Biological data on exemplified final compounds is given below in Table 1.

TABLE 1

| Example No. | IC50 in TR-FRET assay (nM) |
| --- | --- |
| 1 | 9139 |
| 2 | 110 |
| 3 | 12006 |
| 4 | 67 |
| 6 | 3516 |
| 7 | 86 |
| 8 | 40 |
| 9 | 154 |
| 10 | 78 |
| 12 | 68 |
| 13 | 106 |
| 14 | 153 |
| 15 | 748 |
| 16 | 425 |
| 17 | 1523 |
| 18 | 593 |
| 19 | 1360 |
| 20 | 101 |
| 21 | 42 |
| 22 | 145 |
| 23 | 88 |
| 24 | 54 |
| 25 | 86 |
| 26 | 1278 |
| 27 | 1059 |
| 28 | 1609 |
| 30 | 942 |
| 31 | 768 |
| 32 | 708 |
| 33 | 1331 |
| 34 | 1089 |
| 35 | 950 |
| 37 | 569 |
| 38 | 706 |
| 39 | 350 |
| 40 | 570 |
| 41 | 575 |
| 42 | 110 |
| 44 | 213 |
| 45 | 501 |
| 46 | 98 |
| 47 | 55 |
| 48 | 300 |
| 53 | 3100 |
| 54 | 1000 |

TABLE 1-continued

| Example No. | IC50 in TR-FRET assay (nM) |
|---|---|
| 55 | 2000 |
| 56 | 200 |
| 57 | 180 |
| 58 | 710 |
| 59 | 630 |
| 60 | 570 |
| 61 | 2000 |
| 62 | >10000 |
| 63 | 1100 |
| 64 | >3100 |
| 65 | 400 |
| 66 | 520 |
| 67 | 92 |
| 68 | 81 |
| 69 | 99 |
| 71 | 190 |
| 72 | 250 |
| 73 | 130 |
| 74 | 150 |
| 75 | 280 |
| 76 | 100 |
| 77 | 150 |
| 78 | 28 |
| 79 | 54 |
| 80 | 84 |
| 81 | 26 |
| 83 | 75 |
| 84 | 94 |
| 85 | 45 |
| 86 | 47 |
| 88 | 65 |
| 91 | 413 |
| 92 | 270 |
| 93 | 4351 |
| 94 | 880 |
| 95 | 2010 |
| 96 | 2200 |
| 97 | 1000 |
| 98 | 2000 |
| 99 | 220 |
| 100 | 220 |
| 101 | 230 |
| 102 | 310 |
| 103 | 110 |
| 104 | 59 |
| 105 | 29 |
| 107 | 440 |
| 108 | 970 |
| 109 | 750 |
| 111 | 95 |
| 112 | 96 |
| 114 | 300 |
| 115 | 210 |
| 117 | 100 |
| 119 | 110 |
| 121 | 80 |
| 122 | 160 |
| 124 | 560 |
| 125 | 810 |
| 127 | 33 |
| 128 | 40 |
| 129 | 85 |
| 130 | 1300 |
| 131 | 1071 |
| 132 | No value yet |
| 133 | 3236 |
| 134 | 347 |
| 135 | 269 |
| 136 | 457 |

The invention claimed is:

1. A compound or a pharmaceutically acceptable salt thereof, wherein:

the compound corresponds to Formula I:

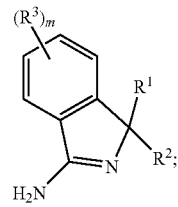

I $R^1$ is selected from aryl and heteroaryl, wherein:
the aryl or heteroaryl is optionally substituted by one, two, or three $R^7$;

$R^3$ is independently selected from halogen, $C_{1-6}$alkyl, $C_{3-6}$alkenyl, $C_{3-6}$alkynyl, $C_{3-6}$cycloalkyl, $C_{5-7}$cycloalkenyl, aryl, heteroaryl, heterocyclyl, —$C_{1-6}$alkyl$C_{3-6}$cycloalkyl, —$C_{1-6}$alkylaryl, —$C_{1-6}$alkylheteroaryl, and —$C_{1-6}$alkylheterocyclyl;

$R^2$ is selected from aryl and heteroaryl, wherein:
the aryl or heteroaryl is optionally substituted with one, two, three, or four $R^7$, and
the aryl or heteroaryl may be optionally fused with a 4, 5, 6, or 7 membered cycloalkyl, cycloalkenyl, or heterocyclyl group to form a bicyclic ring system;

$R^7$ is independently selected from halogen, —$C_{0-6}$alkylOR$^8$, —OSO$_2$R$^8$, $C_{1-6}$alkyl, —$C_{0-6}$alkylaryl, and —$C_{0-6}$alkylheteroaryl, wherein:
any $C_{1-6}$alkyl, —$C_{0-6}$alkylaryl, and —$C_{0-6}$alkylheteroaryl may be optionally substituted by one or more $R^{14}$;

$R^{14}$ is selected from halogen, —OSO$_2$R$^8$, and —$C_{0-6}$alkylOR$^8$;

$R^8$ is independently selected from hydrogen, $C_{1-6}$alkyl, and trifluoromethyl; and m is 1, 2, or 3.

2. A compound or a pharmaceutically acceptable salt thereof, wherein:

the compound corresponds to Formula I:

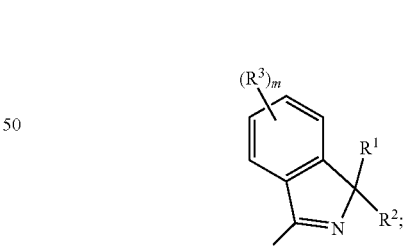

I $R^1$ is selected from aryl and heteroaryl, wherein:
the aryl or heteroaryl is optionally substituted by one, two, or three $R^7$;

$R^3$ is halogen;

$R^2$ is selected from aryl and heteroaryl, wherein:
the aryl or heteroaryl is optionally substituted with one, two, three, or four $R^7$;

$R^7$ is independently selected from halogen, —$C_{0-6}$alkylCN, —$C_{0-6}$alkylOR$^8$, trifluoromethyl, trifluoromethoxy, —$C_{0-6}$alkylaryl, and —$C_{0-6}$alkylheteroaryl, wherein:
the —C$_{0-6}$alkylaryl or —C$_{0-6}$alkylheteroaryl is optionally substituted by one or more R$^{14}$;
R$^{14}$ is selected from halogen, CHO, —C$_{0-6}$alkylCN, —C$_{0-6}$ alkylOR$^8$, —C$_{0-6}$alkylCONR$^8$R$^9$, —(CO)R$^9$, and C$_{1-6}$alkyl;
R$^8$ and R$^9$ are independently selected from hydrogen and C$_{1-6}$alkyl; and
m is 1.

3. A compound or a pharmaceutically acceptable salt thereof, wherein the compound is selected from:
3,3-Diphenyl-3H-isoindol-1-ylamine;
3-(3'-Methoxy-biphenyl-3-yl)-3-(4-methoxy-phenyl)-3H-isoindol-1-ylamine;
Trifluoro-methanesulfonic acid 5-[3-amino-1-(4-methoxy-phenyl)-1H-isoindol-1-yl]-3'-methoxy-biphenyl-2-yl ester;
5-[3-Amino-1-(4-methoxy-phenyl)-1H-isoindol-1-yl]-3'-methoxy-biphenyl-2-ol;
4-[3-Amino-1-(4-methoxy-phenyl)-1H-isoindol-1-yl]-2-pyridin-3-yl-phenol;
4-[3-Amino-1-(4-methoxy-phenyl)-1H-isoindol-1-yl]-2-pyrimidin-5-yl-phenol;
3-(4-Methoxy-phenyl)-3-(3-pyridin-3-yl-phenyl)-3H-isoindol-1-ylamine;
3-[3-(2-Fluoro-pyridin-3-yl)-phenyl]-3-(4-methoxy-phenyl)-3H-isoindol-1-ylamine;
3-(3-Bromo-phenyl)-3-(4-methoxy-phenyl)-3H-isoindol-1-ylamine;
3-(4-Methoxy-phenyl)-3-[3-(5-methoxy-pyridin-3-yl)-phenyl]-3H-isoindol-1-ylamine;
3-(4-Methoxy-phenyl)-3-(3-pyrimidin-5-yl-phenyl)-3H-isoindol-1-ylamine;
Methanesulfonic acid 3'-[3-amino-1-(4-methoxy-phenyl)-1H-isoindol-1-yl]-5-methoxy-biphenyl-3-yl ester;
3-(2,3-Dihydrobenzo[b][1,4]dioxin-6-yl)-3-(3-(2-fluoropyridin-3-yl)phenyl)-3H-isoindol-1-amine;
3-(2,3-Dihydrobenzo[b][1,4]dioxin-6-yl)-3-(3-(5-methoxypyridin-3-yl)phenyl)-3H-isoindol-1-amine;
3-(2,3-Dihydrobenzo[b][1,4]dioxin-6-yl)-3-(3-(pyridin-3-yl)phenyl)-3H-isoindol-1-amine;
3-(2,3-Dihydrobenzo[b][1,4]dioxin-6-yl)-3-(3-(pyrimidin-5-yl)phenyl)-3H-isoindol-1-amine;
3-(3'-Methoxy-biphenyl-3-yl)-3-(4-methoxy-3-methyl-phenyl)-3H-isoindol-1-ylamine;
3-(4-Methoxy-3-methyl-phenyl)-3-[3-(5-methoxy-pyridin-3-yl)-phenyl]-3H-isoindol-1-ylamine;
3-(4-Methoxy-3-methyl-phenyl)-3-(3-pyridin-3-yl-phenyl)-3H-isoindol-1-ylamine;
3-(4-Methoxy-3-methyl-phenyl)-3-(3-pyrimidin-5-yl-phenyl)-3H-isoindol-1-ylamine;
3-[3-(2-Fluoro-pyridin-3-yl)-phenyl]-3-(4-methoxy-3-methyl-phenyl)-3H-isoindol-1-ylamine;
Methanesulfonic acid 3'-[3-amino-1-(4-methoxy-3-methyl-phenyl)-1H-isoindol-1-yl]-5-methoxy-biphenyl-3-yl ester;
5'-(3-Amino-1-(2,3-dihydrobenzo[b][1,4]dioxin-6-yl)-1H-isoindol-1-yl)-5-methoxy-biphenyl-3-yl methanesulfonate;
3-(2,3-Dihydrobenzo[b][1,4]dioxin-6-yl)-3-(3'-methoxy-biphenyl-3-yl)-3H-isoindol-1-amine;
3-Benzo[1,3]dioxol-5-yl-3-(3-pyridin-3-yl)-3H-isoindol-1-ylamine;
3-Benzo[1,3]dioxol-5-yl-3-(3-bromophenyl)-3H-isoindol-1-ylamine;
3-Benzo[1,3]dioxol-5-yl-3-(3-pyrimidin-5-ylphenyl)-3H-isoindol-1-ylamine;
3-Benzo[1,3]dioxol-5-yl-3-[3-(2-fluoropyridin-3-yl)-phenyl]-3H-isoindol-1-ylamine; and
3-Benzo[1,3]dioxol-5-yl-3-[3-(5-methoxypyridin-3-yl)-phenyl]3H isoindol-1-ylamine.

4. A compound or a pharmaceutically acceptable salt thereof, wherein the compound is selected from:
3-Benzo[1,3]dioxol-5-yl-3-(3'-methoxy-biphenyl-3-yl)-3H-isoindol-1-ylamine;
Methanesulfonic acid 3'-(3-amino-1-benzo[1,3]dioxol-5-yl-1H-isoindol-1-yl)-5-methoxy-biphenyl-3-yl ester;
Methanesulfonic acid 4-[3-amino-1-(3-pyridin-3-yl-phenyl)-1H-isoindol-1-yl]-phenyl ester;
Methanesulfonic acid 4-[3-amino-1-(3-bromo-phenyl)-1H-isoindol-1-yl]-phenyl ester;
Methanesulfonic acid 4-{3-amino-1-[3-(2-fluoro-pyridin-3-yl)-phenyl]-1H-isoindol-1-yl}-phenyl ester;
Methanesulfonic acid 4-[3-amino-1-(3-pyrimidin-5-yl-phenyl)-1H-isoindol-1-yl]-phenyl ester;
Methanesulfonic acid 4-{3-amino-1-[3-(5-methoxy-pyridin-3-yl)-phenyl]-1H-isoindol-1-yl}-phenyl ester;
Methanesulfonic acid 4-[3-amino-1-(3'-methoxy-biphenyl-3-yl)-1H-isoindol-1-yl]-phenyl ester;
Methanesulfonic acid 4-[3-amino-1-(5'-methanesulfonyloxy-3'-methoxy-biphenyl-3-yl)-1H-isoindol-1-yl]-phenyl ester;
3-[3-(2-Fluoro-pyridin-3-yl)-phenyl]-3-pyridin-4-yl-3H-isoindol-1-ylamine;
3-Pyridin-4-yl-3-(3-pyridin-3-yl-phenyl)-3H-isoindol-1-ylamine;
3-Pyridin-4-yl-3-(3-pyrimidin-5-yl-phenyl)-3H-isoindol-1-ylamine;
3-[3-(5-Methoxy-pyridin-3-yl)-phenyl]-3-pyridin-4-yl-3H-isoindol-1-ylamine;
3-(3'-Methoxy-biphenyl-3-yl)-3-pyridin-4-yl-3H-isoindol-1-ylamine;
3-{3-[3-Amino-1-(4-methoxyphenyl)-1H-isoindol-1-yl]phenyl}thiophene-2-carbaldehyde;
4-[3-Amino-1-(3-bromophenyl)-1H-isoindol-1-yl]benzonitrile;
1-[3-(1-Isobutyl-1H-pyrazol-4-yl)phenyl]-1-(4-methoxyphenyl)-1H-isoindol-3-amine;
1-(4-Methoxyphenyl)-1-[3-(5-methyl-2-furyl)phenyl]-1H-isoindol-3-amine;
3'-[3-Amino-1-(4-methoxyphenyl)-1H-isoindol-1-yl]biphenyl-2-carboxamide;
1-[3-(5-Fluoropyridin-3-yl)phenyl]-1-[4-(trifluoromethoxy)phenyl]-1H-isoindol-3-amine;
1-(3-Pyrimidin-5-ylphenyl)-1-[4-(trifluoromethoxy)phenyl]-1H-isoindol-3-amine;
4-[3-Amino-1-(3-pyrimidin-5-ylphenyl)-1H-isoindol-1-yl]benzonitrile;
1-[3-(5-Fluoropyridin-3-yl)phenyl]-1-[4-(trifluoromethyl)phenyl]-1H-isoindol-3-amine;
1-(3-Pyrimidin-5-ylphenyl)-1-[4-(trifluoromethyl)phenyl]-1H-isoindol-3-amine;
3-[3-(3-Amino-1-pyridin-4-yl-1H-isoindol-1-yl)phenyl]thiophene-2-carbaldehyde;
1-[3-(1-Isobutyl-1H-pyrazol-4-yl)phenyl]-1-pyridin-4-yl-1H-isoindol-3-amine;
1-[3-(5-Methyl-2-furyl)phenyl]-1-pyridin-4-yl-1H-isoindol-3-amine;
3'-(3-Amino-1-pyridin-4-yl-1H-isoindol-1-yl)biphenyl-2-carboxamide;
4-{3-Amino-1-[3-(2-fluoropyridin-3-yl)phenyl]-1H-isoindol-1-yl}benzonitrile;
1-[3-(2-Fluoropyridin-3-yl)phenyl]-1-[4-(trifluoromethyl)phenyl]-1H-isoindol-3-amine;

1-[3-(5-Fluoropyridin-3-yl)phenyl]-1-pyridin-4-yl-1H-isoindol-3-amine;
1-(4-Fluoro-3-pyrimidin-5-ylphenyl)-1-pyridin-4-yl-1H-isoindol-3-amine;
1-[4-Fluoro-3-(5-fluoropyridin-3-yl)phenyl]-1-pyridin-4-yl-1H-isoindol-3-amine;
1-(3-Fluoropyridin-4-yl)-1-[3-(5-fluoropyridin-3-yl)phenyl]-1H-isoindol-3-amine;
1-(3-Fluoropyridin-4-yl)-1-(3-pyrimidin-5-ylphenyl)-1H-isoindol-3-amine;
1-(3-Fluoropyridin-4-yl)-1-[3-(2-fluoropyridin-3-yl)phenyl]-1H-isoindol-3-amine;
1-(3-Fluoropyridin-4-yl)-1-(4-fluoro-3-pyrimidin-5-ylphenyl)-1H-isoindol-3-amine;
1-[4-Fluoro-3-(5-fluoropyridin-3-yl)phenyl]-1-(3-fluoropyridin-4-yl)-1H-isoindol-3-amine;
1-[4-Fluoro-3-(2-fluoropyridin-3-yl)phenyl]-1-(3-fluoropyridin-4-yl)-1H-isoindol-3-amine;
5-[3-(3-Amino-1-pyridin-4-yl-1H-isoindol-1-yl)phenyl]nicotinonitrile;
6-Fluoro-1-(4-methoxyphenyl)-1-(3-pyrimidin-5-ylphenyl)-1H-isoindol-3-amine;
6-Fluoro-1-(4-methoxyphenyl)-1-(3-pyridin-3-ylphenyl)-1H-isoindol-3-amine;
6-Fluoro-1-(3'-methoxybiphenyl-3-yl)-1-(4-methoxyphenyl)-1H-isoindol-3-amine;
6-Fluoro-1-(4-methoxyphenyl)-1-[3-(5-methoxypyridin-3-yl)phenyl]-1H-isoindol-3-amine;
6-Fluoro-1-pyridin-4-yl-1-(3-pyridin-3-ylphenyl)-1H-isoindol-3-amine;
6-Fluoro-1-pyridin-4-yl-1-(3-pyrimidin-5-ylphenyl)-1H-isoindol-3-amine;
6-Fluoro-1-[3-(5-methoxypyridin-3-yl)phenyl]-1-pyridin-4-yl-1H-isoindol-3-amine;
6-Fluoro-1-[3-(2-fluoropyridin-3-yl)phenyl]-1-pyridin-4-yl-1H-isoindol-3-amine;
1-(3',5'-Dichlorobiphenyl-3-yl)-1-(4-methoxyphenyl)-1H-isoindol-3amine;
3'-(3-Amino-1-cyclopropyl-1H-isoindol-1-yl)-5-methoxybiphenyl-2-carbonitrile;
1-Cyclopropyl-1-(3-pyrimidin-5-ylphenyl)-1H-isoindol-3-amine;
3'-(3-Amino-1-methyl-1H-isoindol-1-yl)-5-methoxybiphenyl-2-carbonitrile;
1-(3',5'-Dichlorobiphenyl-3-yl)-1-methyl-1H-isoindol-3-amine;
1-Methyl-1-(3-pyrimidin-5-ylphenyl)-1H-isoindol-3-amine;
1-[3-(2-Fluoropyridin-3-yl)phenyl]-1-methyl-1H-isoindol-3-amine;
1-Isopropyl-1-(3-pyrimidin-5-ylphenyl)-1H-isoindol-3-amine; and
1-[3-(5-Fluoropyridin-3-yl)phenyl]-1-methyl-1H-isoindol-3-amine.

5. A compound or a pharmaceutically acceptable salt thereof, wherein the compound is selected from:
1-(2'-Fluoro-5'-methoxybiphenyl-3-yl)-1-(3-fluoropyridin-4-yl)-1H-isoindol-3-amine;
1-(2'-Fluoro-3'-methoxybiphenyl-3-yl)-1-(3-fluoropyridin-4-yl)-1H-isoindol-3-amine;
1-(2',6-Difluoro-3'-methoxybiphenyl-3-yl)-1-(3-fluoropyridin-4-yl)-1H-isoindol-3-amine;
5-{3-[3-Amino-1-(3-fluoropyridin-4-yl)-1H-isoindol-1-yl]phenyl}nicotinonitrile;
1-(2'-Fluoro-5'-methoxybiphenyl-3-yl)-1-pyridin-4-yl-1H-isoindol-3-amine;
1-(2'-Fluoro-3'-methoxybiphenyl-3-yl)-1-pyridin-4-yl-1H-isoindol-3-amine;
1-[4-Fluoro-3-(2-fluoropyridin-3-yl)phenyl]-1-pyridin-4-yl-1H-isoindol-3-amine;
1-[3-(2-Fluoropyridin-3-yl)phenyl]-1-(2-methoxypyrimidin-5-yl)-1H-isoindol-3-amine;
1-(2-Methoxypyrimidin-5-yl)-1-(3-pyrimidin-5-ylphenyl)-1H-isoindol-3-amine;
1-(2'-Fluoro-3'-methoxybiphenyl-3-yl)-1-(2-methoxypyrimidin-5-yl)-1H-isoindol-3-amine;
1-(2-Ethylpyridin-4-yl)-1-(3-pyrimidin-5-ylphenyl)-1H-isoindol-3-amine;
1-(2-Ethylpyridin-4-yl)-1-[3-(2-fluoropyridin-3-yl)phenyl]-1H-isoindol-3-amine;
1-(2-Isopropylpyridin-4-yl)-1-(3-pyrimidin-5-ylphenyl)-1H-isoindol-3-amine;
1-[3-(2-Fluoropyridin-3-yl)phenyl]-1-(2-isopropylpyridin-4-yl)-1H-isoindol-3-amine;
1-(2-Fluoropyridin-4-yl)-1-[3-(2-fluoropyridin-3-yl)phenyl]-1H-isoindol-3-amine;
1-[3-(2-Fluoropyridin-3-yl)phenyl]-1-(2-methoxypyridin-4-yl)-1H-isoindol-3-amine;
1-(2-Chloropyridin-4-yl)-1-[3-(2-fluoropyridin-3-yl)phenyl]-1H-isoindol-3-amine;
1-(2-Chloropyridin-4-yl)-1-(3-pyrimidin-5-ylphenyl)-1H-isoindol-3-amine;
1-(5-Fluoropyridin-3-yl)-1-[3-(2-fluoropyridin-3-yl)phenyl]-1H-isoindol-3-amine;
1-(5-Fluoropyridin-3-yl)-1-(3-pyrimidin-5-ylphenyl)-1H-isoindol-3-amine;
1-(4-Fluoro-3-pyrimidin-5-ylphenyl)-1-(4-methoxy-3-methylphenyl)-1H-isoindol-3-amine;
1-[4-Fluoro-3-(2-fluoropyridin-3-yl)phenyl]-1-(4-methoxy-3-methylphenyl)-1H-isoindol-3-amine;
6-Chloro-1-pyridin-4-yl-1-(3-pyrimidin-5-ylphenyl)-1H-isoindol-3-amine;
1-(3-Pyrimidin-5-ylphenyl)-1-[6-(trifluoromethyl)pyridin-3-yl]-1H-isoindol-3-amine;
3-[3-Amino-1-(2,6-dichloropyridin-4-yl)-1H-isoindol-1-yl]phenyl 5-chloro-1,3-dimethyl-1H-pyrazole-4-sulfonate;
3-[3-Amino-1-(2,6-dichloropyridin-4-yl)-1H-isoindol-1-yl]phenyl 6-chloroimidazo[2,1-b][1,3]thiazole-5-sulfonate;
3-[3-Amino-1-(2,6-dichloropyridin-4-yl)-1H-isoindol-1-yl]phenyl 2,6-difluorobenzenesulfonate;
3-[3-Amino-1-(4-fluoro-3-pyrimidin-5-ylphenyl)-1H-isoindol-1-yl]phenyl trifluoromethanesulfonate;
3-[3-Amino-1-(4-fluoro-3-pyrimidin-5-ylphenyl)-1H-isoindol-1-yl]phenyl trifluoromethanesulfonate; and
4-[3-Amino-1-(4-fluoro-3-pyrimidin-5-ylphenyl)-1H-isoindol-1-yl]phenyl trifluoromethanesulfonate.

6. A pharmaceutical formulation, wherein the formulation comprises:
a therapeutically effective amount of a compound or pharmaceutically acceptable salt thereof according to claim 1; and
one or more pharmaceutically acceptable excipients, carriers, or diluents.

7. A pharmaceutical formulation, wherein the formulation comprises:
a therapeutically effective amount of a compound or pharmaceutically acceptable salt thereof according to claim 2; and
one or more pharmaceutically acceptable excipients, carriers, or diluents.

8. A pharmaceutically acceptable salt according to claim 3, wherein the salt comprises a trifluoroacetate salt.

9. A pharmaceutical formulation, wherein the formulation comprises:
- a therapeutically effective amount of a compound or pharmaceutically acceptable salt thereof according to claim 3; and
- one or more pharmaceutically acceptable excipients, carriers, or diluents.

10. A compound or pharmaceutically acceptable salt thereof according to claim 4, wherein the compound is 6-Fluoro-1-(4-methoxyphenyl)-1-(3-pyrimidin-5-ylphenyl)-1H-isoindol-3-amine.

11. A pharmaceutically acceptable salt according to claim 4, wherein the salt comprises a trifluoroacetate salt.

12. A pharmaceutically acceptable salt according to claim 4, wherein the salt comprises an acetate salt.

13. A pharmaceutically acceptable salt according to claim 4, wherein the salt comprises a hydrochloride salt.

14. A pharmaceutical formulation, wherein the formulation comprises:
- a therapeutically effective amount of a compound or pharmaceutically acceptable salt thereof according to claim 4; and
- one or more pharmaceutically acceptable excipients, carriers, or diluents.

15. A pharmaceutically acceptable salt according to claim 5, wherein the salt comprises an acetate salt.

16. A pharmaceutical formulation, wherein the formulation comprises:
- a therapeutically effective amount of a compound or pharmaceutically acceptable salt thereof according to claim 5; and
- one or more pharmaceutically acceptable excipients, carriers, or diluents.

\* \* \* \* \*